US008741581B2

(12) United States Patent
Admon et al.

(10) Patent No.: US 8,741,581 B2
(45) Date of Patent: Jun. 3, 2014

(54) MARKERS FOR CANCER DETECTION

(75) Inventors: Arie Admon, Tivon (IL); Eilon Barnea, Nesher (IL); Ilan Beer, Haifa (IL); Tamar Ziv, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 13/266,567

(22) PCT Filed: Apr. 27, 2010

(86) PCT No.: PCT/IL2010/000342

§ 371 (c)(1), (2), (4) Date: Oct. 27, 2011

(87) PCT Pub. No.: WO2010/125566

PCT Pub. Date: Nov. 4, 2010

(65) Prior Publication Data

US 2012/0039811 A1 Feb. 16, 2012

Related U.S. Application Data

(60) Provisional application No. 61/172,800, filed on Apr. 27, 2009.

(51) Int. Cl.
*G01N 33/53* (2006.01)

(52) U.S. Cl.
USPC .......................................................... 435/7.1

(58) Field of Classification Search
CPC combination set(s) only.
See application file for complete search history.

(56) References Cited

U.S. PATENT DOCUMENTS

| | | | |
|---|---|---|---|
| 4,816,397 | A | 3/1989 | Boss |
| 4,816,567 | A | 3/1989 | Cabilly |
| 4,946,778 | A | 8/1990 | Ladner |
| 5,242,974 | A | 9/1993 | Holmes |
| 5,384,261 | A | 1/1995 | Winkler |
| 5,405,783 | A | 4/1995 | Pirrung |
| 5,412,087 | A | 5/1995 | McGall |
| 5,424,186 | A | 6/1995 | Fodor |
| 5,429,807 | A | 7/1995 | Matson |
| 5,436,327 | A | 7/1995 | Southern |
| 5,445,934 | A | 8/1995 | Fodor |
| 5,449,754 | A | 9/1995 | Nishioka |
| 5,472,672 | A | 12/1995 | Brennan |
| 5,527,681 | A | 6/1996 | Holmes |
| 5,529,756 | A | 6/1996 | Brennan |
| 5,532,128 | A | 7/1996 | Eggers |
| 5,545,531 | A | 8/1996 | Rava |
| 5,554,501 | A | 9/1996 | Coassin |
| 5,556,752 | A | 9/1996 | Lockhart |
| 5,561,071 | A | 10/1996 | Hollenberg |
| 5,571,639 | A | 11/1996 | Hubbell |
| 5,578,832 | A | 11/1996 | Trulson |
| 5,593,839 | A | 1/1997 | Hubbell |
| 5,599,695 | A | 2/1997 | Pease |
| 5,604,531 | A | 2/1997 | Iddan |
| 5,624,711 | A | 4/1997 | Sundberg |
| 5,631,734 | A | 5/1997 | Stern |
| 5,658,734 | A | 8/1997 | Brock |
| 5,693,762 | A | 12/1997 | Queen |
| 5,700,637 | A | 12/1997 | Southern |
| 5,712,120 | A | 1/1998 | Rodriguez |
| 5,965,405 | A | 10/1999 | Winter |
| 5,969,108 | A | 10/1999 | McCafferty |
| 6,004,755 | A | 12/1999 | Wang |
| 6,033,916 | A | 3/2000 | Sieben |
| 6,475,809 | B1 | 11/2002 | Wagner |
| 6,919,176 | B2 | 7/2005 | Yang |
| 6,949,339 | B1 | 9/2005 | Macina |
| 7,078,180 | B2 | 7/2006 | Genetta |
| 7,098,008 | B2 | 8/2006 | Park |
| 7,115,368 | B2 | 10/2006 | Powers |
| 7,129,043 | B1 | 10/2006 | Boustany |
| 7,344,840 | B2 | 3/2008 | Cohen |
| 7,402,403 | B1 | 7/2008 | Robertson |
| 7,452,727 | B2 | 11/2008 | Henning |
| 7,468,044 | B2 | 12/2008 | Iddan |
| 7,501,242 | B2 | 3/2009 | Reinhard |
| 7,507,541 | B2 | 3/2009 | Raitano |
| 7,515,953 | B2 | 4/2009 | Madar |
| 2005/0208472 | A1 | 9/2005 | Xu |
| 2007/0037204 | A1 | 2/2007 | Aburatani |
| 2008/0146896 | A1 | 6/2008 | Rabinowitz |
| 2008/0260742 | A1 | 10/2008 | Sato |
| 2009/0216082 | A1 | 8/2009 | Rabinovitz |

FOREIGN PATENT DOCUMENTS

| | | |
|---|---|---|
| WO | 91/17271 | 11/1991 |
| WO | 92/01047 | 1/1992 |
| WO | 2006/014999 | 2/2006 |
| WO | 2008/086182 | 7/2008 |

OTHER PUBLICATIONS

Gerard et al (Anticancer Research, 1989, 9(4): Abstract).*
Crawford et al (Journal of Surgical Oncology, 2003, 84: 239-248).*
Beijnum et al (International Journal of Cancer, 2002, 101: 118-127).*
Sharkey et al (Nature Medicine, 2005, 11(11): 1250-1255).*
Imamura et al (Gastoenterol Jpn, 1990, 25(2): Abstract).*
Gerard et al (Anticancer Research, 1989, 9(4): 1033-1035).*
Folli et al (PNAS, 1992, 89(17): 7973-7977).*
Alencar et al., (2007) Colonic adenocarcinomas: near-infrared microcatheter imaging of smart probes for early detection—study in mice. Radiology 244(1): 232-238.

(Continued)

*Primary Examiner* — Sean Aeder
(74) *Attorney, Agent, or Firm* — Browdy and Neimark, PLLC

(57) ABSTRACT

The present invention relates to methods for detecting, prognosing and staging cancers, in particular cancers of the gastrointestinal tract. The methods of the invention comprise detecting specific protein markers in a tissue of interest, wherein the detected levels thereof may be indicative of precancerous or cancerous tissue, or the stage or prognosis of a cancer. Further provided are methods of treating cancer, and cancer detection kits.

13 Claims, 3 Drawing Sheets

(56) References Cited

OTHER PUBLICATIONS

Blumenthal et al., (2007) Expression patterns of CEACAM5 and CEACAM6 in primary and metastatic cancers. BMC Cancer 7: 2.
Conrotto et al., (2008) Identification of new accessible tumor antigens in human colon cancer by ex vivo protein biotinylation and comparative mass spectrometry analysis. Int J Cancer 123(12): 2856-2864.
Govindan et al., (2009) CEACAM5-targeted therapy of human colonic and pancreatic cancer xenografts with potent labetuzumab-SN-38 immunoconjugates. Clin Cancer Res 15(19): 6052-6061.
Koshida et al., (2007) Specific overexpression of OLFM4(GW112/HGC-1) mRNA in colon, breast and lung cancer tissues detected using quantitative analysis. Cancer Sci 98(3): 315-320.
Maxwell et al., (2009) An improved cell-penetrating, caspase-activatable, near-infrared fluorescent peptide for apoptosis imaging. Bioconjug Chem 20(4): 702-709.
McCaffrey et al., (2008) Swallowable-capsule technology. Pervasive Computing, IEEE 7(1): 23-29.
McDermott et al., (2010) Fluorescence Imaging of Cancer in Live Animals: Time to Get Excited? Microscopy & Imaging Focus (2 pages).
McIntyre and Matrisian (2009) Optical proteolytic beacons for in vivo detection of matrix metalloproteinase activity. Methods Mol Biol 539: 155-174.
Moglia et al., (2008) Recent patents on wireless capsule endoscopy. Recent Patents on Biomedical Engineering 1: 24-33.
Saitoh et al., (2000) Comparison of tests for fecal lactoferrin and fecal occult blood for colorectal diseases: a prospective pilot study. Intern Med 39(10): 778-782.
Stulík et al., (1999) The analysis of S100A9 and S100A8 expression in matched sets of macroscopically normal colon mucosa and colorectal carcinoma: the S100A9 and S100A8 positive cells underlie and invade tumor mass. Electrophoresis 20(4-5): 1047-1054.

* cited by examiner

MARKERS FOR CANCER DETECTION

FIELD OF THE INVENTION

The present invention relates to methods for detecting, prognosing and staging cancers, in particular cancers of the gastrointestinal tract. The methods of the invention comprise detecting specific protein markers in a tissue of interest, wherein the detected levels thereof may be indicative of pre-cancerous or cancerous tissue, or the stage or prognosis of a cancer. Further provided are methods of using the markers for treating cancer, and cancer detection kits.

BACKGROUND OF THE INVENTION

Colorectal cancer, also referred to as colon cancer or large bowel cancer, is a malignant neoplastic disease associated with tumors in the colon, rectum and appendix. With 655,000 deaths worldwide per year, it is the third most common form of cancer and the second leading cause of cancer-related death in the Western world.

Colorectal cancers originate in the colorectal epithelium and typically are not extensively vascularized (and therefore not invasive) during the early stages of development. The transition to a highly vascularized, invasive and ultimately metastatic cancer, which spreads throughout the body, commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. For example, patients diagnosed with early colon cancer generally have a much greater, five-year survival rate as compared to the survival rate for patients diagnosed with distant metastasized colon cancer. Accordingly, early detection of colorectal cancer is of critical importance for reducing its morbidity.

Diagnostic methods for colon cancer most frequently depend on direct visual inspection of the gastrointestinal (GI) tract. Endoscopy involves inspection with a miniaturized light source at a probe end of a coherent bundle fiber optic cable. Reflected light beam images are returned through the fiber optic cable for detection by an external digital camera and display on an external monitor or for recording on an external video recorder or both. While this technique allows for identification, removal, and biopsy of potentially cancerous growths such as polyps, its use is associated with certain disadvantages, such as being expensive, uncomfortable, inherently risky due to its invasive nature, and the inability to access some portions of the large intestine and most of the small intestine.

Swallowable endoscopy capsules containing miniaturized optical, digital camera and radio transmission systems have been subsequently developed along with complementary external monitoring systems for inspecting the GI tract. For example, the capsule marketed under the trade name PillCam® SB was initially approved by the U.S. Food and Drug Administration in 2001 for detection and diagnosis of disorders of the small intestine. U.S. Pat. No. 5,604,531 discloses an in vivo video camera system comprising a swallowable capsule. The transit of endoscopy capsules through the small intestine is dependent on peristalsis, meaning that some areas with lesions may be missed if the capsule is not retained in that area for a sufficient amount of time. Further, the endoscopy capsules in current use are not capable of identifying molecular markers, which may be early indicators of colorectal cancer, even prior to the development of pre-cancerous polyps.

U.S. Pat. No. 7,468,044 discloses a system and method for in vivo and in situ detection of body lumen conditions, such as in the GI tract. The system comprises an interaction chamber comprising an indicator; a light source for illuminating the interaction chamber; and an optical detector for detecting in vivo optical changes occurring in the interaction chamber upon reaction of the indicator with an endo-luminal sample.

U.S. Pat. No. 7,515,953 discloses a method for detecting fluorescence emitted by cells in a wall of a body lumen, such as an intestinal wall, the method comprising use of a swallowable capsule, the capsule comprising a light source and a fluorescent-labeled probe, which is released from a reservoir in the capsule. According to the disclosure, an electric field generated from an electrode in the capsule enhances uptake of the probe, and a detector in the capsule detects the fluorescent signal emitted. By determining the intensity and/or position in the lumen wall of the fluorescent signal, a drug for killing abnormal cells is released from a second reservoir in the capsule. According to the disclosure, the abnormal cells may be cancer cells, colon polyps or precancerous cells.

U.S. Patent Application Publication No. 2008/0146896 discloses a device, such as an autonomous capsule, for in vivo analysis which includes a reaction chamber to store a detecting reagent able to react with a sample collected in vivo; and optionally a labeled-substance chamber to store a labeled substance able to bind to a compound resulting from a reaction of the detecting reagent and the sample. According to the disclosure, the detecting reagent may be an antibody.

U.S. Patent Application Publication No. 2009/0216082 discloses a device system for in vivo detection of target molecules in an endo-luminal sample, and a method for in vivo magnetic immunoassay, which may be used for the detection of cancer in the gastrointestinal tract.

Yet other methods of colon cancer detection are based on detection of particular proteins or genes which are considered to be specifically or differentially expressed in colon cancer.

U.S. Pat. No. 7,507,541 discloses a method of detecting the presence of inter alia colon cancer that is based on determining the level of 36P6D5 protein expressed by cells in a test tissue sample from an individual, and comparing the level to that expressed in a corresponding normal tissue sample.

U.S. Pat. No. 7,501,242 discloses a method of detecting colon cancer that is based on detecting levels of expression of tyrosine threonine kinase (TTK) in a test sample, such as a colon sample, that are increased by at least two fold relative to the level of expression in a normal non-cancer sample of the same type.

U.S. Pat. No. 7,452,727 discloses a automatable method for identifying cancer cells and their precursor cells that is based on detecting at least two molecular markers, wherein the detection of each marker alone is not a reliable indicator of the presence of cancer cells and their precursor cells. According to the disclosure, the molecular markers may be selected from her2/neu, Ki67, p53, her2/neu, bcl-2, MN, mdm-2, EGF receptor, bcl-2 and p16.

U.S. Pat. No. 7,402,403 discloses a method for the detection of cancer or early neoplastic change that is based on detecting autoantibodies directed to tumor marker antigens in a sample of bodily fluids, wherein the tumor marker antigens are selected from MUC1, p53, c-erbB2, Ras, c-myc, BRCA1, BRCA2, PSA, APC and CA125.

U.S. Pat. No. 7,129,043 discloses a method of identifying a human subject having an increased risk of developing colon cancer that is based on detecting upregulation of the CLN3 gene.

U.S. Pat. No. 7,115,368 relates to a method of detecting epithelial cancer cells inter alia colon cancer that is based on detection of expression in a biological sample of pellino proteins.

U.S. Pat. No. 7,098,008 relates to a method for detection of cancer inter alia colon cancer that is based on detecting expression of melanoma antigen gene (MAGE).

U.S. Pat. No. 7,078,180 relates to a method of diagnosing a cancer inter alia colon cancer that is based on detection of a ZEB (zfh-1/delta EF1) polypeptide.

U.S. Pat. No. 6,949,339 relates to methods for detecting, diagnosing, monitoring, staging, and prognosticating colon cancers, based on detection of Colon Specific Genes.

U.S. Pat. No. 6,919,176 discloses a method of detecting cancer inter alia colon cancer that is based on detection of expression of specific G-protein coupled receptors.

There remains an unmet need for methods of early detection, prognosis and treatment of colon cancer.

SUMMARY OF THE INVENTION

The present invention provides methods of detecting cancer that are based on the qualitative or quantitative identification of particular proteins, also referred to herein as molecular markers. Further provided are methods of cancer prevention, prognosis and treatment.

Disclosed herein for the first time is a specific group of protein markers which are indicative of both pre-cancerous and cancerous lesions. Further disclosed herein for the first time is an additional specific group of protein markers which are primarily indicative of pre-cancerous lesions.

The invention is based in part, on the unexpected discovery that the level of expression within the gastrointestinal tract of certain proteins is significantly increased in both pre-cancerous and cancerous tissue relative to the level of expression of the same proteins in healthy tissue of the same type Surprisingly, the expression of these markers is elevated, even compared to healthy tissue bordering tumor growth. It has also been surprisingly found that the expression of yet other markers is significantly increased in early stage cancer, and significantly decreased in later stages of cancer Without wishing to be bound by any particular theory or mechanism of action, the invention enables identification of individuals at risk of developing cancer, in particular colorectal cancer, even prior to observable histological changes in affected tissue. Since the methods of the invention are based on changes in protein expression patterns in cells, rather than later occurring pathological changes in tissue, a level of sensitivity is obtained that is greater by many orders of magnitude than current techniques of cancer detection. Thus, in the case of colorectal cancer, the invention provides a means of predicting the disease well in advance of the possibility of detecting potentially cancerous polyps by conventional endoscopic examination, the latter being the current yet inadequate standard for early detection.

The principles of the current invention are exemplified herein by quantitative mass spectroscopy analysis of healthy, pre-cancerous and cancerous tissue obtained from the gastrointestinal tract of patients during surgical excision of early stage (e.g. polyps) or more advanced stage tumors, which has resulted in the identification of a specific group of proteins, the expression of each of which is significantly increased in diseased colon tissue, as compared to healthy colon tissue. This group of proteins, which includes KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20), has not been previously disclosed, either in part or as a whole, to be useful for detection of colorectal cancer at any stage of the disease.

It is to be specifically understood however, that the current method of the invention need not be limited to examination of colon tissue obtained by surgical means, nor should it be limited to detection and quantification of the subject molecular markers using mass spectrometry techniques. Rather, the invention may be advantageously practiced using for example immunological techniques and reagents for detection of the subject molecular markers, either in vivo or ex vivo. For example, labeled monoclonal antibodies can be used for in vivo detection and quantitation of such proteins in different tissue compartments and regions. The detection may be accomplished for example, using pharmaceutical compositions or endoscopy probes which incorporate specifically designed chemical, immunological or nucleic acid reagents. Advantageously, labeled reagents such as antibodies, which specifically interact with the subject molecular markers may be prepared as injectable or ingestible pharmaceutical compositions and following administration the interaction with their molecular targets may be externally monitored. Alternately or in addition, the invention may be practiced by analysis of biological samples obtained from a subject, such as biopsy tissue.

In a first aspect, the invention provides a method of detecting cancer in a subject, the method comprising: (i) detecting in a biological sample from the subject at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20), so as to determine the level of the at least one protein; and (ii) comparing the level determined in (i) to a reference level of the same at least one protein, wherein detection of a level of said at least one protein in the biological sample which is significantly different from the reference level, is indicative of cancer in the subject.

Each of the aforementioned proteins represents a separate embodiment of the invention and may be used independently from or in combination with any of the others.

In another aspect, the invention provides a method for determining the stage of a cancerous or pre-cancerous growth in a subject, the method comprising: (i) detecting in a test sample from the subject at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20), so as to determine the level of the at least one protein; and (ii) comparing the level determined in (i) to a reference level of the same at least one protein; wherein the level detected in the test sample is indicative of the stage of the growth.

Each of the aforementioned proteins represents a separate embodiment of the invention and may be used independently from or in combination with any of the others.

In another aspect, the invention provides a method for determining the prognosis of a cancerous disease in a subject, the method comprising: (i) detecting in a test sample from the subject at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20), so as to determine the level of the at least one protein; and (ii) comparing the level determined in (i) to a reference level of the same at least one protein; wherein the level detected in the test sample is indicative of the prognosis of the cancerous disease.

Each of the aforementioned proteins represents a separate embodiment of the invention and may be used independently from or in combination with any of the others.

In particular embodiments, the biological sample is selected from the group consisting of blood, serum, nipple aspirate fluid, lymph node aspirate, a biopsy sample, a tumor sample, a tissue sample, mucosal fluid, cervical wash, lacrimal duct fluid, urine, saliva, pleural effusion and sputum. Each of the aforementioned materials represents a separate embodiment of the invention and may be used independently from or in combination with any of the others.

In currently preferred embodiments, the biological sample comprises a tissue sample. In currently preferred embodiments, the tissue sample comprises gastrointestinal tissue, particularly colorectal tissue or pre-cancerous tissue such as polyps. In currently preferred embodiments, the biological sample is selected from a tumor within the gastrointestinal tract, particularly a colorectal tumor. In particular embodiments, the gastrointestinal tissue is from an area or organ selected from the group consisting of the esophagus, the stomach, the small intestine, the large intestine (colon), the rectum, the appendix and a combination thereof.

In particular embodiments, the cancer being detected is selected from the group consisting of adrenal cancer, bladder cancer, bone cancer, brain cancer, breast cancer, cervical cancer, colorectal cancer, fallopian tube cancer, gastric cancer, head and neck cancer, hepatic cancer, lung cancer including small cell lung cancer and non-small cell lung cancer, melanoma, neuroblastoma, oral cancer, ovarian cancer, pancreatic cancer, prostate cancer, thyroid and parathyroid cancer, renal cancer, sarcoma, thymoma, hematological malignancies and germ cell tumors. In a currently preferred embodiment, the cancer is colorectal cancer. Each of the aforementioned cancers represents a separate embodiment of the invention and may be used independently from any of the others.

In a particular embodiment, the at least one protein detected is indicative of a disorder selected from the group consisting of pre-cancerous polyps, early stage colorectal cancer and advanced stage colorectal cancer. In particular embodiments, a method of detecting pre-cancerous polyps or early stage colorectal cancer comprises detecting at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20); and further comprises detecting at least one protein selected from the group consisting of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). Each of the aforementioned proteins represents a separate embodiment of the invention and may be used independently from or in combination with any of the others.

In particular embodiments, a method of detecting pre-cancerous polyps or early stage colorectal cancer comprises detecting at least one of KIAA0152 (SEQ ID NO:1) and NAMPT (SEQ ID NO:2); and further comprises detecting at least one protein selected from the group consisting of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). Each of the aforementioned proteins represents a separate embodiment of the invention and may be used independently from or in combination with any of the others.

In particular embodiments, a method of the invention comprises use of at least one reagent suitable for detecting the level of at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20).

In particular embodiments, said reagent is suitable for detecting the level of at least one of KIAA0152 (SEQ ID NO:1) and NAMPT (SEQ ID NO:2). Each of the aforementioned reagents represents a separate embodiment of the invention and may be used independently from or in combination with any of the others.

In particular embodiments, a method of the invention further comprises use of at least one reagent suitable for detecting the level of at least one protein selected from the group consisting of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). Each of the aforementioned reagents represents a separate embodiment of the invention and may be used independently from or in combination with any of the others.

In particular embodiments, the biological sample or test sample is obtained from the subject by a procedure selected from the group consisting of biopsy, flexible endoscopy, double balloon endoscopy and surgical colorectal re-sectioning.

In particular embodiments, the biological sample or test sample is assessed in vivo in the subject. In particular embodiments, the method comprises contacting a body tissue, cavity or fluid with at least one of a pharmaceutical composition and an endoscopy apparatus.

In particular embodiments, the method comprises contacting a body tissue, cavity or fluid with at least one reagent suitable for detecting the level of at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20)$_4$. In particular embodiments, the body tissue, cavity or fluid is contacted with a reagent is suitable for detecting the level of at least one of KIAA0152 (SEQ ID NO:1) and NAMPT (SEQ ID NO:2). Each of the aforementioned reagents represents a separate embodiment of the invention and may be used independently from or in combination with any of the others.

In particular embodiments, the method further comprises contacting a body tissue, cavity or fluid with at least one reagent suitable for detecting the level of at least one protein selected from the group consisting of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). Each of the aforementioned reagents represents a separate embodiment of the invention and may be used independently from or in combination with any of the others.

In particular embodiments, the method comprises administering a diagnostic pharmaceutical composition. In particular embodiments, the administering of the pharmaceutical composition is by a route selected from the group consisting of oral, parenteral, subcutaneous, intramuscular, intrathoracic and intraarticular.

In particular embodiments, the pharmaceutical composition or the endoscopy apparatus comprise at least one reagent suitable for detecting the level of at least one of the aforementioned proteins. In particular embodiments, the pharmaceutical composition or the endoscopy apparatus comprise at least one reagent suitable for detecting the level of at least one of KIAA0152 (SEQ ID NO:1) and NAMPT (SEQ ID NO:2).

In particular embodiments, the reagent specifically interacts with at least one of the aforementioned proteins or with nucleic acid encoding at least one of the aforementioned proteins, or a fragment of said protein. In particular embodiments, the pharmaceutical composition or the endoscopy apparatus comprises a multiplicity of reagents, wherein each reagent of the multiplicity specifically interacts with one distinct protein or with nucleic acid encoding one distinct protein or a fragment thereof. In particular embodiments, the reagent is selected from an antibody, an antibody mimetic and a nucleic acid. In particular embodiments, the antibody is selected from a monoclonal antibody, a humanized antibody, a single chain antibody, an antibody fragment and combinations thereof. In particular embodiments, the pharmaceutical composition or the endoscopy apparatus comprise a multiplicity of antibody mimetics, wherein each antibody mimetic of the multiplicity specifically interacts with one of the aforementioned proteins.

In particular embodiments, the reagent comprises a detectable label, such as a fluorescent label, a radiolabel or an enzymatic label.

In particular embodiments, the pharmaceutical composition or the endoscopy apparatus comprise at least one least one nucleic acid, wherein the at least one nucleic acid is complementary to a nucleic acid encoding at least one of the aforementioned proteins, or a fragment of said protein. In particular embodiments, the at least one nucleic acid comprises a multiplicity of nucleic acids, wherein each nucleic acid of the multiplicity is complementary to a nucleic acid encoding one distinct protein of the aforementioned proteins, or a fragment of said protein. In particular embodiments, the nucleic acid comprises a detectable label, such as a fluorescent label, a radiolabel or an enzymatic label.

In particular embodiments, the detecting in step (i) comprises use of an assay system. In particular embodiments, the assay system comprises an immunoassay, a nucleic acid hybridization assay, a binding assay, an array, a phage display library or combinations thereof. In particular embodiments, the array is a protein array, or a phage display library array. In particular embodiments, the assay system comprises at least one reagent suitable for detecting the level of at least one of the aforementioned proteins, as described herein. In particular embodiments, the assay system comprises a multiplicity of such reagents, for example antibodies, wherein each reagent in the multiplicity specifically interacts with one of the aforementioned proteins.

In particular embodiments, the detecting comprises use of an external monitoring system. In particular embodiments, the external monitoring system is configured to display the level of the at least one protein detected.

In particular embodiments, a method of the invention further comprises detecting in the sample at least one protein selected from the group consisting of FAM62B (SEQ ID NO:51), SLC1A5 (SEQ ID NO:52), RSL1D1 (SEQ ID NO:53), LYZ (SEQ ID NO:54), THBS1 (SEQ ID NO:55), LMO7 (SEQ ID NO:56), TNC (SEQ ID NO:57), RBM39 (SEQ ID NO:58), ILVBL (SEQ ID NO:59), ERO1L (SEQ ID NO:60), LOC442497 (SEQ ID NO:61), TCOF1 (SEQ ID NO:62), SERPINB9 (SEQ ID NO:63), HSDL2 (SEQ ID NO:64), ADAMDEC1 (SEQ ID NO:65), AMACR (SEQ ID NO:66), AMACR;C1QTNF3 (SEQ ID NO:67), ARID1A (SEQ ID NO:68), CEBPZ (SEQ ID NO:69), COL5A1 (SEQ ID NO:70), EFEMP2 (SEQ ID NO:71), FAM84B (SEQ ID NO:72), FKBP10 (SEQ ID NO:73), FKBP9 (SEQ ID NO:74), GPRC5A (SEQ ID NO:75), KPNA2 (SEQ ID NO:76), MMP1 (SEQ ID NO:77), PNMA5 (SEQ ID NO:78), POLR1C (SEQ ID NO:79), SPARC (SEQ ID NO:80), UBAP2 (SEQ ID NO:81), UCK2 (SEQ ID NO:82) and WDR74 (SEQ ID NO:83). Each of the aforementioned proteins represents a separate embodiment of the invention and may be used independently from or in combination with any of the others.

In particular embodiments, a method of the invention further comprises use of at least one reagent suitable for detecting the level of at least one protein selected from the group consisting of FAM62B (SEQ ID NO:51), SLC1A5 (SEQ ID NO:52), RSL1D1 (SEQ ID NO:53), LYZ (SEQ ID NO:54), THBS1 (SEQ ID NO:55), LMO7 (SEQ ID NO:56), TNC (SEQ ID NO:57), RBM39 (SEQ ID NO:58), ILVBL (SEQ ID NO:59), ERO1L (SEQ ID NO:60), LOC442497 (SEQ ID NO:61), TCOF1 (SEQ ID NO:62), SERPINB9 (SEQ ID NO:63), HSDL2 (SEQ ID NO:64), ADAMDEC1 (SEQ ID NO:65), AMACR (SEQ ID NO:66), AMACR; C1QTNF3 (SEQ ID NO:67), ARID (SEQ ID NO:68), CEBPZ (SEQ ID NO:69), COL5A1 (SEQ ID NO:70), EFEMP2 (SEQ ID NO:71), FAM84B (SEQ ID NO:72), FKBP10 (SEQ ID NO:73), FKBP9 (SEQ ID NO:74), GPRC5A (SEQ ID NO:75), KPNA2 (SEQ ID NO:76), MMP1 (SEQ ID NO:77), PNMA5 (SEQ ID NO:78), POLR1C (SEQ ID NO:79), SPARC (SEQ ID NO:80), UBAP2 (SEQ ID NO:81), UCK2 (SEQ ID NO:82) and WDR74 (SEQ ID NO:83). Each of the aforementioned reagents represents a separate embodiment of the invention and may be used independently from or in combination with any of the others.

In particular embodiments, the cancer is a cancer other than colorectal cancer and the at least one protein includes at least one of FAM62B (SEQ ID NO:51), SLC1A5 (SEQ ID NO:52), RSL1D1 (SEQ ID NO:53), LYZ (SEQ ID NO:54), TNC(SEQ ID NO:57), RBM39 (SEQ ID NO:58), ERO1L (SEQ ID NO:60), LOC442497 (SEQ ID NO:61), TCOF1 (SEQ ID NO:62), NAMPT (SEQ ID NO:2), SERPINB9 (SEQ ID NO:63), HSDL2 (SEQ ID NO:64).

In particular embodiments, the level of the at least one protein in the biological or test sample is increased by at least 2-fold, or at least 3-fold, or at least 5-fold, or at least 10-fold, or at least 20-fold, or at least 50-fold, relative to the reference level. In particular embodiments, the reference level is representative of the level of the same protein in non-diseased tissue. In particular embodiments, the reference level is representative of the level of the same protein in a particular stage or form of cancer. In particular embodiments, the reference level is representative of the level of the same protein in a cancer having a known prognosis.

In another aspect, the invention provides a method of treating cancer, the method comprising administering to a subject in need thereof at least one pharmaceutical agent, wherein the pharmaceutical agent specifically interacts with at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19), CCT4 (SEQ ID NO:20), CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49), CISD1 (SEQ ID NO:50), LYZ (SEQ ID NO:54), LOC442497; SLC3A2 (SEQ ID NO:61), DMBT1 (SEQ ID NO:84), NUCB1 (SEQ ID NO:85), GGH (SEQ ID NO:86), AGR3 (SEQ ID NO:87), TM9SF2 (SEQ ID NO:88), SYK (SEQ ID NO:89), GCA (SEQ ID NO:90), HDLBP (SEQ ID NO:91), C1QBP (SEQ ID NO:92) and CLIC1 (SEQ ID NO:93). Each of the aforementioned agents represents a separate embodiment of the invention and may be used independently from or in combination with any of the others.

In a particular embodiment, the at least one protein is selected from the group consisting of KIAA0152 (SEQ ID NO:1), LYZ (SEQ ID NO:54), LOC442497; SLC3A2 (SEQ ID NO:61), DMBT1 (SEQ ID NO:84), NUCB1 (SEQ ID NO:85), GGH (SEQ ID NO:86), AGR3 (SEQ ID NO:87), TM9SF2 (SEQ ID NO:88), SYK (SEQ ID NO:89), GCA (SEQ ID NO:90), HDLBP (SEQ ID NO:91), C1QBP (SEQ ID NO:92) and CLIC1 (SEQ ID NO:93). In particular embodiments, the pharmaceutical agent specifically interacts with KIAA0152 (SEQ ID NO:1). Each of the aforementioned reagents represents a separate embodiment of the invention and may be used independently from or in combination with any of the others.

In particular embodiments, the pharmaceutical agent is selected from an antibody and an antibody mimetic. In particular embodiments, the pharmaceutical agent further comprises a cytotoxic moiety, such as a plant toxin, a bacterial toxin, a radioactive moiety or a chemotherapeutic agent. In particular embodiments, the pharmaceutical agent is selected from a chemical conjugate and fusion protein.

In another aspect, the invention provides an antigen composition comprising at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19), CCT4 (SEQ ID NO:20), CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49), CISD1 (SEQ ID NO:50), LYZ (SEQ ID NO:54), LOC442497; SLC3A2 (SEQ ID NO:61), DMBT1 (SEQ ID NO:84), NUCB1 (SEQ ID NO:85), GGH (SEQ ID NO:86), AGR3 (SEQ ID NO:87), TM9SF2 (SEQ ID NO:88), SYK (SEQ ID NO:89), GCA (SEQ ID NO:90), HDLBP (SEQ ID NO:91), C1QBP (SEQ ID NO:92) and CLIC1 (SEQ ID NO:93), or an immunogenic fragment of said at least one protein. Each of the aforementioned proteins represents a separate embodiment of the invention and may be used independently from or in combination with any of the others.

In a particular embodiment, the composition comprises at least one of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50), or an immunogenic fragment thereof. Each of the aforementioned proteins represents a separate embodiment of the invention and may be used independently from or in combination with any of the others.

In a particular embodiment, the composition comprises KIAA0152 (SEQ ID NO:1) or an immunogenic fragment thereof. In a particular embodiment, a method of preventing or treating cancer in a subject in need thereof comprises administering to the subject an effective amount of said antigen composition. Further provided is an antigen composition as previously specified; for use in preventing or treating cancer.

In another aspect, the invention provides a kit for detecting, staging or prognosing cancer, the kit comprising at least one reagent suitable for detecting the level of at least one protein selected from the group consisting of KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19), CCT4 (SEQ ID NO:20); CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). Each of the aforementioned proteins represents a separate embodiment of the invention and may be used independently from or in combination with any of the others.

In particular embodiments, the kit is for detecting precancerous polyps or early stage colorectal cancer and comprises at least one reagent suitable for detecting the level of at least one protein selected from the group consisting of CPT2 (SEQ ID NO:21), ARL1 (SEQ ID NO:22), PFKL (SEQ ID NO:23), GOT2 (SEQ ID NO:24), AP1G1 (SEQ ID NO:25), STRBP (SEQ ID NO:26), CLCA1 (SEQ ID NO:27), CYFIP1 (SEQ ID NO:28), COQ9 (SEQ ID NO:29), NDUFA9 (SEQ ID NO:30), ALDH7A1 (SEQ ID NO:31), HMGCS1 (SEQ ID NO:32), NNT (SEQ ID NO:33), PRDX5 (SEQ ID NO:34), PCCB (SEQ ID NO:35), COPZ1 (SEQ ID NO:36), BAX (SEQ ID NO:37), ACAD9 (SEQ ID NO:38), UBXD8 (SEQ ID NO:39), HMGCS2 (SEQ ID NO:40), SLC25A3 (SEQ ID NO:41), SLC25A11 (SEQ ID NO:42), PDCD6 (SEQ ID NO:43), UCRC (SEQ ID NO:44), DEFA6 (SEQ ID NO:45), DYNC1H1 (SEQ ID NO:46), HK1 (SEQ ID NO:47), CYFIP2 (SEQ ID NO:48), DCI (SEQ ID NO:49) and CISD1 (SEQ ID NO:50). In particular embodiments, the kit comprises a reagent suitable for detecting the level of KIAA0152 (SEQ ID NO:1).

According to some embodiments the present invention excludes proteins known to be associated with colorectal cancers. According to other embodiments the methods of the present invention exclude proteins that were known to be associated with other types of cancers.

Other objects, features and advantages of the present invention will become clear from the following description and examples.

DETAILED DESCRIPTION OF THE INVENTION

The present invention provides methods of identification of cancerous cells by detection of levels of particular proteins, also referred to herein as "cancer-associated proteins or "molecular markers", which have been found to be differentially expressed in cancer tissue, in particular, colorectal cancer tissue. Details of the subject cancer-associated proteins disclosed herein are provided in Tables 1 and 3-7. Some of the identified proteins for which significantly elevated levels were detected in colorectal cancer tissue as compared to normal colorectal tissue have not been previously disclosed to be associated with cancerous disease. Examples of such proteins are indicated in Table 1 as denoted by the symbol "+" in the column labeled "Newly identified as cancer-associated" and include the proteins FAM62B, SLC1A5. RSL1D1, LYZ, TNC, RBM39, ILVBL, ERO1L, LOC442497, TCOF1, NAMPT, SERPINB9 and HSDL2. Yet other proteins, in particular THBS1 and LMO7, have been disclosed in the prior art to be down-regulated in cancerous conditions, whereas the inventors of the present invention now disclose significantly increased levels of these proteins in cancer tissue, indicative of up-regulation. These proteins are indicated in Table 1 as denoted by the symbol "UR" in the column labeled "Newly identified as cancer-associated". Yet other proteins were detected at significant levels in colorectal cancer tissue but were completely absent from healthy colorectal tissue in the same patients. Such proteins are indicated in Table 1 as denoted by the symbol "+" in the column labeled "Detected in cancerous but not healthy" and include the proteins AMACR, AMACR; C1 QTNF3, COL5A1, FKBP10, FKBP9, GPRC5A, POLR1c, SPARC and UBAP2.

Table 3 list proteins which are highly expressed in colorectal cancer, both in pre-cancerous polyps and in more advanced stages of the disease. Accordingly, any of the proteins listed in Table 3 represent candidates for use as diagnostic markers of colorectal cancer, which can be indicative of any of pre-cancerous lesions, early stage or late stage forms of the disease. Two currently preferred protein markers are KIAA0152 and NAMPT.

Figure 1:
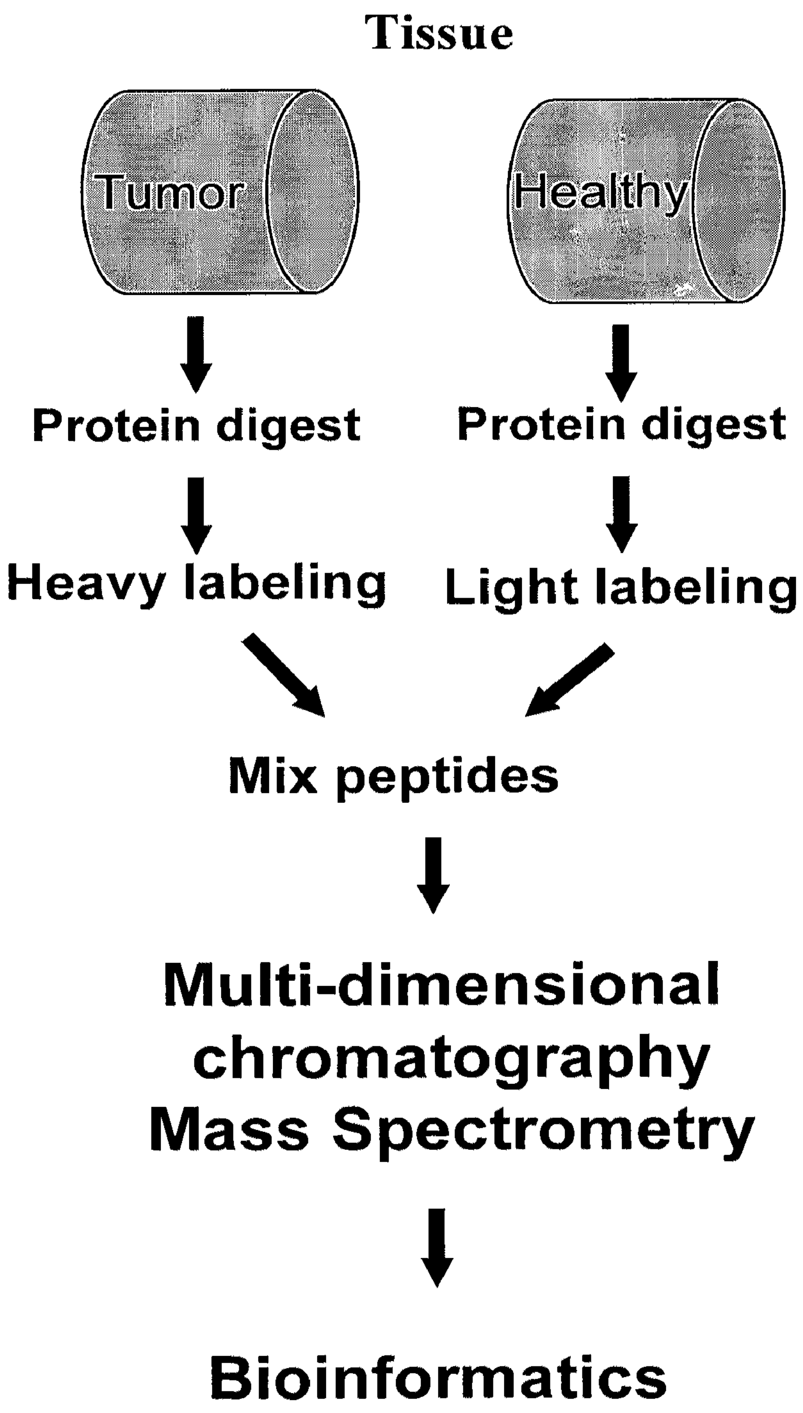
FIG. 1 illustrates methods used for the identification of the protein diagnostic markers of cancer according to the invention.
Figure 2:
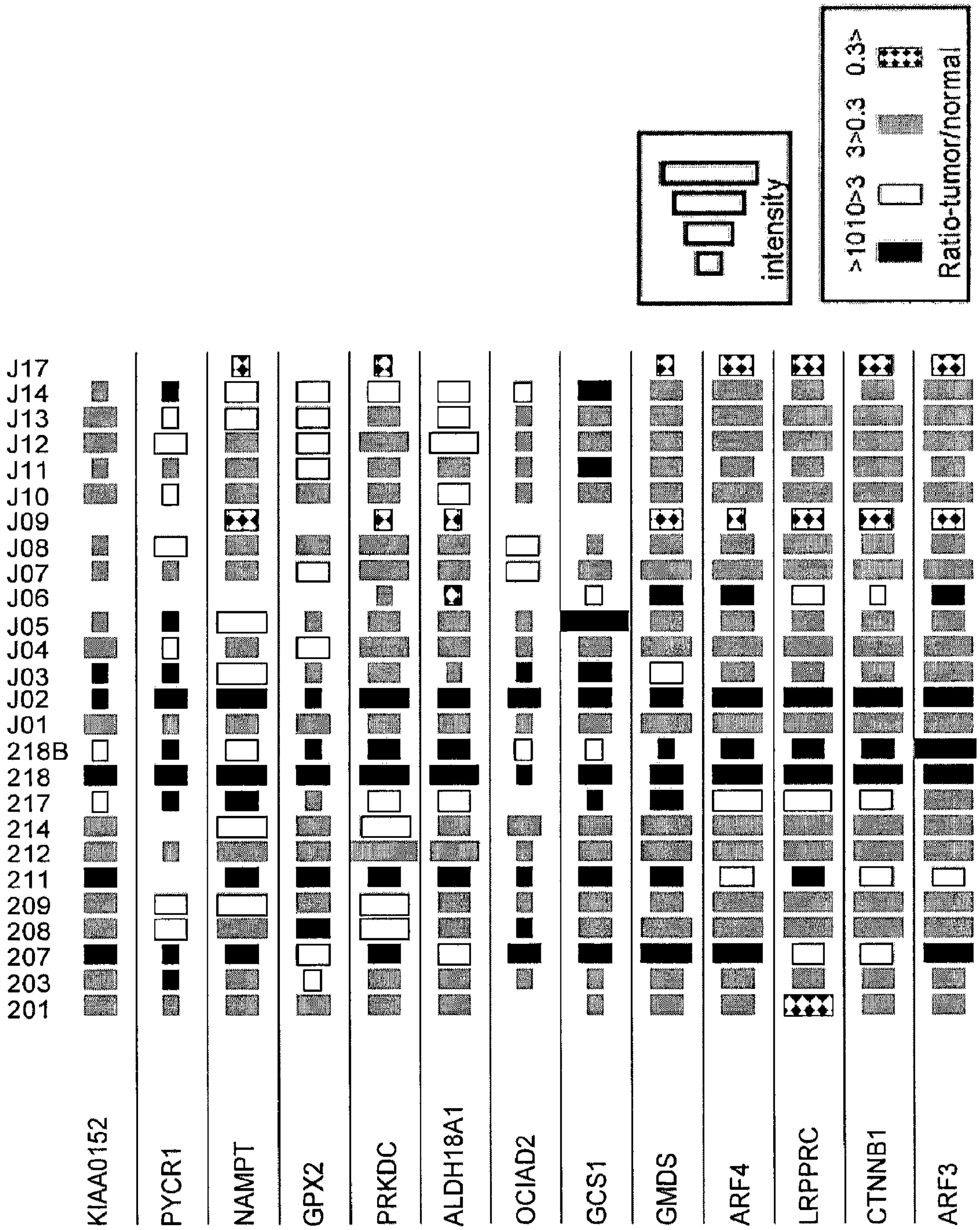
FIG. 2 illustrates quantitative data analysis of protein markers identified in diseased and non-diseased tissues from human subjects with colorectal cancer, including patients with polyps. Sample numbers indicated along the top of the figure correspond to different patients, and in some cases different samples from a single patient. Proteins are indicated along the left side. The height of each rectangle corresponds to the relative signal intensity, and the shading corresponds to the quantitative ratio (protein in diseased tissue:protein in non-diseased tissue) from the same patient. Black shaded rectangles, ratio>10; white rectangles, ratio in the range 3-10; gray shaded rectangles, ratio in the range 0.3-3; diamond filled rectangles, ratio<0.3.
Figure 2:
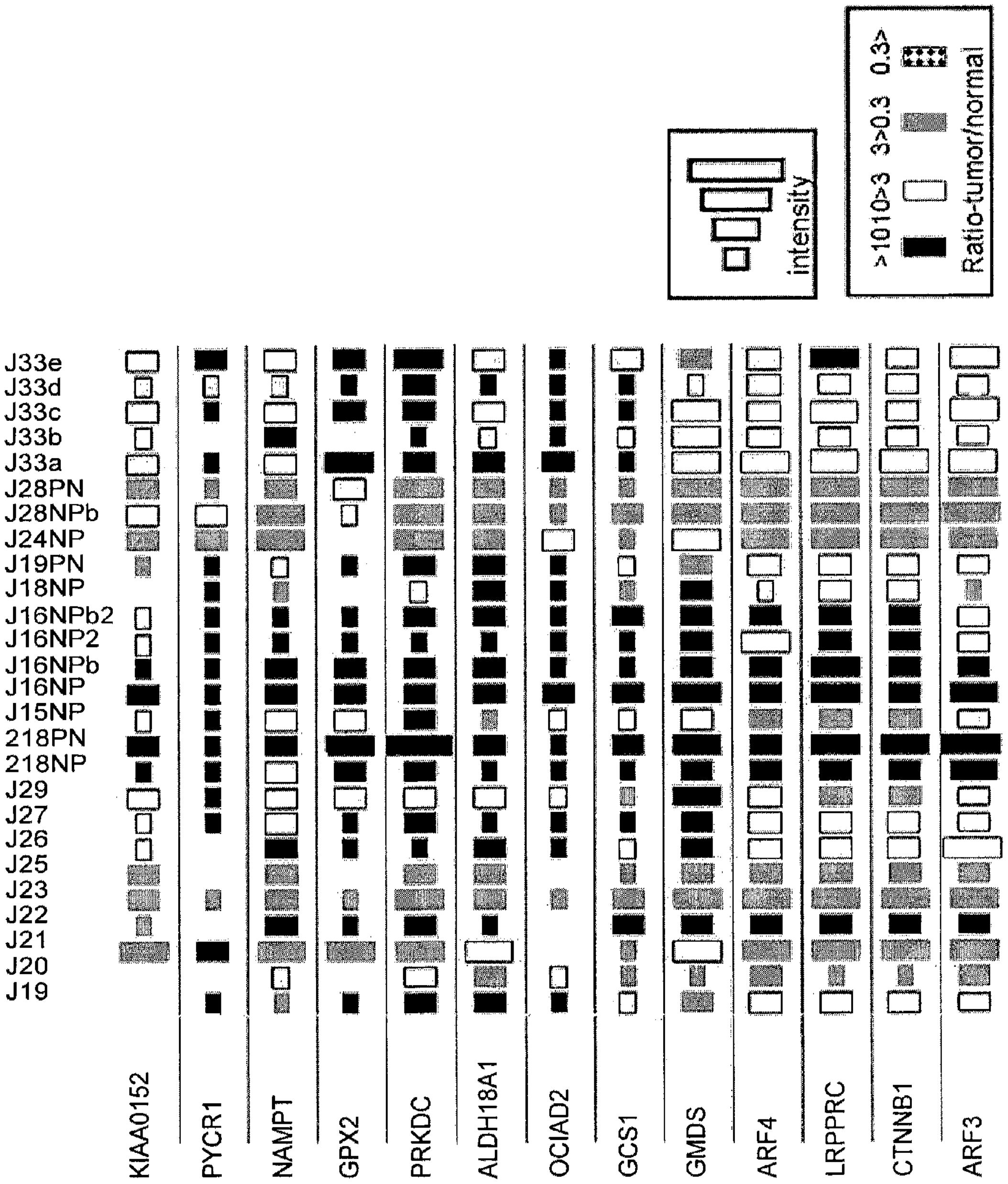

A quantitative analysis of some of the proteins listed in Table 3 is shown in FIG. 2. The analysis shows that in a large number of the patients examined, the quantitative ratio of protein in diseased tissue (i.e. polyps and/or cancer): protein in non-diseased tissue from the same patient, is 3 or greater.

Table 4 lists proteins which appear to be highly expressed in pre-cancerous polyps, yet their expression tends to be diminished in more advanced stages of the disease. Accordingly, proteins listed in Table 4 represent promising candidates for use as very early diagnostic markers to identify individuals at risk of developing colorectal cancer.

Identification and quantification of a panel of tumor-associated proteins such as those listed in Tables 1 and 3-6, provides a specific means of detecting colorectal cancer in a subject, as well as means of prognosing and staging previously diagnosed colorectal cancers. Such methods can conveniently be carried out using detectably-labeled reagents which specifically bind the selected target proteins. Typically such reagents comprise monoclonal antibodies or small chemical mimetics thereof. In some cases however, it may be advantageous to employ nucleic acids complementary to mRNA species encoding the target proteins so as to quantitate expression activity which may be correlated with the corresponding protein levels. Furthermore, therapeutic pharmaceutical agents directed against tumor-associated proteins, for example, those disclosed in Table 7 herein, may be prepared, for example monoclonal antibodies conjugated to cytotoxic moieties, for use in targeted therapy of colorectal cancer.

TABLE 1

| Protein Name | IPI Acc. No. | Newly identified as cancer-associated | Detected in cancerous but not healthy |
|---|---|---|---|
| ABCF2 ATP-binding cassette, sub-family F, member 2 isoform b | 68506 | | |
| ACIN1 Isoform 1 of Apoptotic chromatin condensation inducer in the nucleus | 7334 | | |
| ACOT7 Isoform 1 of Cytosolic acyl coenzyme A thioester hydrolase | 10415 | | |
| ADAMDEC1 ADAM DEC1 precursor | 4480 | | + |
| ADO 2-aminoethanethiol dioxygenase | 45939 | | |
| ADSS Adenylosuccinate synthetase isozyme 2 | 26833 | | |
| AK3 GTP:AMP phosphotransferase mitochondrial | 465256 | | |
| ALG5 Dolichyl-phosphate beta-glucosyltransferase | 2506 | | |
| AMACR Alpha-methylacyl-CoA racemase | 847727 | | + |
| AMACR; C1QTNF3 alpha-methylacyl-CoA racemase isoform 1 | 5918 | | + |
| ANXA3 Annexin A3 | 24095 | | |
| ARHGEF1 Isoform 1 of Rho guanine nucleotide exchange factor 1 | 647786 | | |
| ARID1A Isoform 1 of AT-rich interactive domain-containing protein 1A | 643722 | | + |
| ARRDC1 Arrestin domain containing 1 | 514937 | | |
| ATAD3A Isoform 2 of ATPase family AAA domain-containing protein 3A | 295992 | | |
| ATP6AP2 Renin receptor precursor | 168884 | | |
| ATP6V0A1 97 kDa protein | 892784 | | |
| ATP6V1E1 vacuolar H+ ATPase E1 isoform b | 719806 | | |
| BMS1 Ribosome biogenesis protein BMS1 homolog | 6099 | | |
| BPI Bactericidal/permeability-increasing protein | 552280 | | |
| BUD31 Protein BUD31 homolog | 13180 | | |
| BXDC1 Brix domain containing 1 | 644504 | | |
| C14orf21 Pumilio domain-containing protein C14orf21 | 216999 | | |
| C1orf116 Isoform 1 of Specifically androgen-regulated gene protein | 28392 | | |
| C1R; ACYP1; C17orf13 Complement C1r subcomponent precursor | 296165 | | |
| C20orf43 UPF0549 protein C20orf43 | 297121 | | |
| C2orf47 Uncharacterized protein C2orf47, mitochondrial precursor | 291751 | | |
| C3orf64 Isoform 1 of Uncharacterized glycosyltransferase AER61 precursor | 396231 | | |
| C7orf24 Uncharacterized protein C7orf24 | 31564 | | |
| C8orf55 Uncharacterized protein C8orf55 precursor | 171421 | | |
| CAD Putative uncharacterized protein CAD | 893035 | | |
| CASP8 Uncharacterized protein CASP8 | 220725 | | |
| CBFB Core-binding factor subunit beta | 16746 | | |
| CEACAM5 Carcinoembryonic antigen-related cell adhesion molecule 5 precursor | 27486 | | |
| CEBPZ CCAAT/enhancer-binding protein zeta | 306723 | | + |
| CHD4 Isoform 2 of Chromodomain-helicase-DNA-binding protein 4 | 455210 | | |
| CLPB Isoform 2 of Caseinolytic peptidase B protein homolog | 216192 | | |
| COL12A1 Isoform 1 of Collagen alpha-1(XII) chain precursor | 329573 | | |

TABLE 1-continued

| Protein Name | IPI Acc. No. | Newly identified as cancer-associated | Detected in cancerous but not healthy |
|---|---|---|---|
| COL5A1 Collagen alpha-1(V) chain precursor | 844090 | | + |
| COMT Isoform Soluble of Catechol O-methyltransferase | 375513 | | |
| CSTF1 Cleavage stimulation factor 50 kDa subunit | 11528 | | |
| CTSG Cathepsin G precursor | 28064 | | |
| DCK Deoxycytidine kinase | 20454 | | |
| DDX18 ATP-dependent RNA helicase DDX18 | 301323 | | |
| DEK 48 kDa protein | 871695 | | |
| DHCR7 7-dehydrocholesterol reductase | 294501 | | |
| DHODH Dihydroorotate dehydrogenase, mitochondrial precursor | 24462 | | |
| DHX30 DEAH (Asp-Glu-Ala-His) box polypeptide 30 isoform 2 | 477295 | | |
| DIAPH1 Diaphanous homolog 1 | 884341 | | |
| DMBT1 Isoform 1 of Deleted in malignant brain tumors 1 protein precursor | 99110 | | |
| DNAJA3 Isoform 2 of DnaJ homolog subfamily A member 3, mitochondrial precursor | 179187 | | |
| DNAJC19 10 kDa protein | 795263 | | |
| DPEP1 Dipeptidase 1 precursor | 59476 | | |
| EFEMP2 Mutant p53 binding protein 1 variant (Fragment) | 556657 | | + |
| EI24 Isoform 2 of Etoposide-induced protein 2.4 homolog | 23185 | | |
| EIF2B3 Isoform 1 of Translation initiation factor eIF-2B subunit gamma | 6504 | | |
| EIF2S2 Eukaryotic translation initiation factor 2 subunit 2 | 21728 | | |
| ERO1L ERO1-like protein alpha precursor | 386755 | + | |
| EXOC2 Exocyst complex component 2 | 783559 | | |
| F11R Junctional adhesion molecule A precursor | 1754 | | |
| FAM62B Isoform 2 of Extended synaptotagmin-2 | 409635 | + | |
| FAM84B Protein FAM84B | 64666 | | + |
| FAP Isoform 1 of Seprase | 295461 | | |
| FASN Fatty acid synthase | 26781 | | |
| FASTKD5 FAST kinase domain-containing protein 5 | 414973 | | |
| FDFT1 Squalene synthetase | 20944 | | |
| FERMT1 Isoform 1 of Fermitin family homolog 1 | 304754 | | |
| FKBP10 FK506-binding protein 10 precursor | 303300 | | + |
| FKBP9 FK506-binding protein 9 precursor | 182126 | | + |
| FOXK1 Isoform 1 of Forkhead box protein K1 | 556645 | | |
| FRG1 Protein FRG1 | 4655 | | |
| FYB FYN binding protein (FYB-120/130) isoform 1 | 73110 | | |
| GCA Grancalcin | 4524 | | |
| GEMIN5 Gem-associated protein 5 | 291783 | | |
| GGH Gamma-glutamyl hydrolase precursor | 23728 | | |
| GLRX3 Glutaredoxin-3 | 8552 | | |
| GLT25D1 Glycosyltransferase 25 family member 1 precursor | 168262 | | |
| GMPS GMP synthase | 29079 | | |
| GNL3 Isoform 1 of Guanine nucleotide-binding protein-like 3 | 306380 | | |
| GPR89B; GPR89A Isoform 1 of Protein GPR89 | 472858 | | |
| GPRC5A Retinoic acid-induced protein 3 | 22624 | | + |
| GPX2 Glutathione peroxidase 2 | 298176 | | |
| GTF2F1 General transcription factor IIF subunit 1 | 17450 | | |
| GTF2I Isoform 2 of General transcription factor II-I | 293242 | | |
| HCFC1 Uncharacterized protein HCFC1 | 641743 | | |
| HM13 Isoform 1 of Minor histocompatibility antigen H13 | 152441 | | |
| HSDL2 Isoform 1 of Hydroxysteroid dehydrogenase-like protein 2 | 414384 | + | |
| HSPH1 Isoform Beta of Heat shock Protein 105 kDa | 218993 | | |
| ICAM1 Intercellular adhesion molecule 1 precursor | 8494 | | |
| IGFBP7 Insulin-like growth factor-binding protein 7 precursor | 16915 | | |
| IKIP IKIP2 | 401791 | | |
| ILVBL Isoform 1 of Acetolactate synthase-like protein | 554541 | | |
| IPO7 Importin-7 | 7402 | | |
| ISLR Immunoglobulin superfamily containing leucine-rich repeat protein precursor | 23648 | | |
| KIAA0020 Pumilio domain-containing protein KIAA0020 | 791325 | | |
| KIAA0241 Isoform 1 of Protein KIAA0241 | 397348 | | |
| KIAA1219 Isoform 3 of Protein KIAA1219 | 410120 | | |
| KPNA2 Karyopherin alpha 2 | 789457 | | + |
| LACTB2 Beta-lactamase-like protein 2 | 6952 | | |
| LCN2 Lipocalin 2 | 643623 | | |
| LEPRE1 Isoform 3 of Prolyl 3-hydroxylase 1 precursor | 45839 | | |
| LMO7 Isoform 3 of LIM domain only protein 7 | 291802 | UR | |
| LOC442497; SLC3A2 solute carrier family 3 (activators of dibasic and neutral amino acid transport), member 2 isoform e | 554722 | + | |
| LOC731605 similar to BCL2-associated transcription factor 1 isoform 2 | 886854 | | |
| LTBP2 Latent-transforming growth factor beta-binding protein 2 precursor | 292150 | | |
| LTF Lactotransferrin precursor | 848342 | | |
| LYZ Lysozyme C precursor | 19038 | + | |
| MAN1A2 Uncharacterized protein MAN1A2 | 743100 | | |
| MCM2 DNA replication licensing factor MCM2 | 184330 | | |
| MCM3 DNA replication licensing factor MCM3 | 13214 | | |
| MCM5 DNA replication licensing factor MCM5 | 18350 | | |
| MCM6 DNA replication licensing factor MCM6 | 31517 | | |
| MCM7 Isoform 1 of DNA replication licensing factor MCM7 | 299904 | | |
| MMP1 Interstitial collagenase precursor | 8561 | | + |
| MMP2 72 kDa type IV collagenase precursor | 27780 | | |
| MMP9 Matrix metalloproteinase-9 precursor | 27509 | | |
| MOCS3 Molybdenum cofactor synthesis protein 3 | 4489 | | |
| MPO Isoform H7 of Myeloperoxidase precursor | 236556 | | |
| MRPS6 Mitochondrial 28S ribosomal protein S6 | 305668 | | |

TABLE 1-continued

| Protein Name | IPI Acc. No. | Newly identified as cancer-associated | Detected in cancerous but not healthy |
|---|---|---|---|
| MTA2 Metastasis-associated protein MTA2 | 171798 | | |
| MUC16 Mucin-16 | 103552 | | |
| NAMPT Isoform 1 of Nicotinamide phosphoribosyltransferase | 18873 | + | |
| NAT10 N-acetyltransferase 10 | 300127 | | |
| NCBP1 Nuclear cap-binding protein subunit 1 | 19380 | | |
| NCF4 Isoform 1 of Neutrophil cytosol factor 4 | 14338 | | |
| NEBL Nebulette variant 4 | 872370 | | |
| NIP7 Isoform 1 of 60S ribosome subunit biogenesis protein NIP7 homolog | 7175 | | |
| NOC2L Nucleolar complex protein 2 homolog | 411886 | | |
| NOC4L Nucleolar complex protein 4 homolog | 31661 | | |
| NOL10 Isoform 1 of Nucleolar protein 10 | 29513 | | |
| NQO1 NAD | 12069 | | |
| NUDCD1 Isoform 2 of NudC domain-containing protein 1 | 306398 | | |
| NUP188 Isoform 1 of Nucleoporin NUP188 homolog | 477040 | | |
| NUP210 Isoform 1 of Nuclear pore membrane glycoprotein 210 precursor | 291755 | | |
| NXF1 Nuclear RNA export factor 1 | 33153 | | |
| OCIAD2 Isoform 1 of OCIA domain-containing protein 2 | 555902 | | |
| OLFM4 Olfactomedin-4 precursor | 22255 | | |
| OSBPL2 Isoform 1 of Oxysterol-binding protein-related protein 2 | 14137 | | |
| OTUD6B OTU domain containing 6B | 182180 | | |
| PAICS Multifunctional protein ADE2 | 217223 | | |
| PARP14 poly (ADP-ribose) polymerase family, member 14 | 291215 | | |
| PCNA Proliferating cell nuclear antigen | 21700 | | |
| PEX14 Peroxisomal membrane protein PEX14 | 25346 | | |
| PHF6 Isoform 1 of PHD finger protein 6 | 395568 | | |
| PKP3 Plakophilin-3 | 26952 | | |
| PLOD3 Procollagen-lysine, 2-oxoglutarate 5-dioxygenase 3 precursor | 30255 | | |
| PNMA5 Paraneoplastic antigen-like protein 5 | 514588 | | + |
| POLR1C Isoform 1 of DNA-directed RNA polymerases I and III subunit RPAC1 | 5179 | | + |
| PROM1 Prominin-1 precursor | 12540 | | |
| PSAT1 Isoform 1 of Phosphoserine aminotransferase | 1734 | | |
| PTDSS1 Phosphatidylserine synthase 1 | 10746 | | |
| PTK7 Tyrosine-protein kinase-like 7 precursor | 298292 | | |
| PUF60 Isoform 5 of Poly | 856076 | | |
| PYCR1 pyrroline-5-carboxylate reductase 1 isoform 2 | 376503 | | |
| PYCR2 Pyrroline-5-carboxylate reductase 2 | 470610 | | |
| RAD21 Double-strand-break repair protein rad21 homolog | 6715 | | |
| RANBP3 Isoform 2 of Ran-binding protein 3 | 456728 | | |
| RBM12 RNA-binding protein 12 | 550308 | | |
| RBM39 Isoform 2 of RNA-binding protein 39 | 215801 | + | |
| RCC1 regulator of chromosome condensation 1 isoform b | 787306 | | |
| RCC2 Protein RCC2 | 465044 | | |

TABLE 1-continued

| Protein Name | IPI Acc. No. | Newly identified as cancer-associated | Detected in cancerous but not healthy |
|---|---|---|---|
| RCN1 Reticulocalbin-1 precursor | 15842 | | |
| RDBP Negative elongation factor E | 858 | | |
| REEP6 Receptor expression-enhancing protein 6 | 647161 | | |
| REG1A Lithostathine-1-alpha precursor | 9027 | | |
| REG1B Lithostathine-1-beta precursor | 9197 | | |
| RFC2 Isoform 2 of Replication factor C subunit 2 | 218280 | | |
| RFC5 Replication factor C subunit 5 | 31514 | | |
| RRM1 Ribonucleoside-diphosphate reductase large subunit | 13871 | | |
| RRP1 RRP1-like protein | 550766 | | |
| RRS1 Ribosome biogenesis regulatory protein homolog | 14253 | | |
| RSL1D1 RSL1D1 protein | 642046 | + | |
| S100A11 Protein S100-A11 | 13895 | | |
| S100A12 Protein S100-A12 | 218131 | | |
| S100A8 Protein S100-A8 | 7047 | | |
| S100A9 Protein S100-A9 | 27462 | | |
| SAE1 SUMO-activating enzyme subunit 1 | 33130 | | |
| SDCCAG10 Isoform 1 of Peptidyl-prolyl cis-trans isomerase SDCCAG10 | 25174 | | |
| SERPINB5 Serpin B5 precursor | 783625 | | |
| SERPINB9 Serpin B9 | 32139 | + | |
| SERPINH1 Serpin H1 precursor | 32140 | | |
| SET Isoform 2 of Protein SET | 301311 | | |
| SLC1A5 Neutral amino acid transporter B | 19472 | + | |
| SLC25A15 Mitochondrial ornithine transporter 1 | 3389 | | |
| SLC2A1 Solute carrier family 2, facilitated glucose transporter member 1 | 220194 | | |
| SORD 11 kDa protein | 791243 | | |
| SPARC SPARC precursor | 14572 | | + |
| SQSTM1 Isoform 1 of Sequestosome-1 | 179473 | | |
| SRM Spermidine synthase | 292020 | | |
| SRRM2 Isoform 1 of Serine/arginine repetitive matrix protein 2 | 782992 | | |
| SSBP1 Single-stranded DNA-binding protein, mitochondrial precursor | 29744 | | |
| SYK Isoform Long of Tyrosine-protein kinase SYK | 18597 | | |
| TBC1D2B Isoform 1 of TBC1 domain family member 2B | 550733 | | |
| TCOF1 Isoform 2 of Treacle protein | 298696 | + | |
| TFRC Transferrin receptor protein 1 | 22462 | | |
| TH1L Isoform NELF-D of Negative elongation factor C/D | 759539 | | |
| THBS1 Thrombospondin-1 precursor | 296099 | UR | |
| THBS2 Thrombospondin-2 precursor | 18769 | | |
| THOC6 Isoform 1 of THO complex subunit 6 homolog | 328985 | | |
| TIMP1 TIMP metallopeptidase inhibitor 1 | 642739 | | |
| TJP2 Isoform A1 of Tight junction protein ZO-2 | 3843 | | |
| TM9SF4 Isoform 2 of Transmembrane 9 superfamily member 4 precursor | 885106 | | |
| TNC Isoform 1 of Tenascin precursor | 31008 | + | |
| TOMM34 Mitochondrial import receptor subunit TOM34 | 9946 | | |
| TOP1 DNA topoisomerase 1 | 413611 | | |
| TOP2A Isoform 2 of DNA topoisomerase 2-alpha | 414101 | | |
| TPR nuclear pore complex-associated protein TPR | 742682 | | |
| TRMT6 Isoform 1 of tRNA | 99311 | | |

TABLE 1-continued

| Protein Name | IPI Acc. No. | Newly identified as cancer-associated | Detected in cancerous but not healthy |
|---|---|---|---|
| UBAP2 Ubiquitin-associated protein 2 | 171127 | | + |
| UBE2O Ubiquitin-conjugating enzyme E2 O | 783378 | | |
| UCK2 Isoform 1 of Uridine-cytidine kinase 2 | 65671 | | + |
| UQCC 34 kDa protein | 872061 | | |
| URB1 Nucleolar pre-ribosomal-associated protein 1 | 297241 | | |
| UTP20 Small subunit processome component 20 homolog | 4970 | | |
| VAMP7 Isoform 3 of Vesicle-associated membrane protein 7 | 401804 | | |
| WDR43 WD repeat-containing protein 43 | 55954 | | |
| WDR74 Isoform 1 of WD repeat-containing protein 74 | 18192 | | + |
| XPO5 Isoform 1 of Exportin-5 | 640703 | | |
| XPOT Exportin-T | 306290 | | |
| YLPM1 YLP motif containing 1 | 165434 | | |

DEFINITIONS

The terms "subject" and "patient" as used herein refer to any single subject for which cancer detection, prognosis, staging or therapy is desired, including humans and non-human mammals, such as primate, bovine, ovine, canine, feline and rodent mammals. Also included are subjects involved in clinical research trials not showing any clinical sign of disease, or subjects involved in epidemiological studies, or subjects used as controls.

The terms "cancer detection" and "cancer diagnosis" and related grammatical terms, such as "detecting cancer" and "diagnosing cancer", respectively, are used herein interchangeably to refer to any of determination of a subject's susceptibility to a malignant cancer disease; determination as to whether a subject is presently affected by a malignant cancer disease; determination of a subject's stage of cancer, determination of and monitoring the effect on the cancer in response to anti-cancer therapy.

The term "characteristics of a cancerous or pre-cancerous growth" as used herein refers to one or more molecular, physiological, histological, clinical or other properties which may be used to define the nature and behavior of the growth.

The terms "cancer", "neoplasm", "tumor", "growth" and the like are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-malignant (e.g., benign hyperplasic), malignant, metastatic, and non-metastatic cells.

The term "prognosis" as used herein refers to the expected or predicted outcome of a disease, such as a cancer, in a patient following diagnosis. A prognosis may predict the relative chance of disease progression, arrest or cure. A prognosis may be established on the basis of prognostic indicators specific for a particular disease. Prognostic indicators in cancer may include for example, the grade and stage of cancer at initial diagnosis, the genetic make-up of the patient, the presence and level of cancer-associated antigens in the tumor, and patient responsiveness to a particular therapy.

The terms "biological sample" and "test sample" as used herein encompass a variety of types of biological materials that can be used in the methods of the invention. The sample may be procured from the body of an individual or investigated without removal from the body of an individual. The term encompasses solid tissue samples, such as from biopsy specimens, tumors or tumor metastases, or tissue cultures or cells derived there from and the progeny thereof. The terms also encompass blood and other liquid samples of biological origin, such as nipple aspirate fluid, lymph node aspirate, mucosal fluid, cervical wash, lacrimal duct fluid, urine, saliva, pleural effusion and sputum. The terms encompass samples that have been manipulated in any way after their procurement, such as by lysis, treatment with reagents, solubilization, or enrichment for certain components. Also included are clinical samples, cells in cell culture, cell supernatants and cell lysates. It is to be explicitly understood that in accordance with the invention, a biological or test sample may be obtained i.e. removed, from the body of a subject, or accessed in vivo, for example by contacting with a specific reagent or apparatus.

As used herein, a biological or test sample that is "obtained from a subject", means that the sample is removed from the body of the subject, and any subsequent analysis thereof may be performed outside the body for example under in vitro or ex vivo conditions. When however, a biological or test sample is "assessed in vivo" or "accessed in vivo" it means that the sample is maintained within the body of the subject and direct or indirect contact is established using any suitable means, such as via a reagent, composition, device or apparatus. Subsequent analysis of the accessed sample is performed under in vivo conditions, which can include conditions of local or general anaesthesia. Means of accessing and assessing a sample in vivo include for example, contacting the tissue or organ or region thereof of interest with a pharmaceutical composition, a swallowable endoscopy capsule or an endoscopy probe.

The term "a normal biological sample of the same type" as used herein refers to a non-diseased sample consisting of the same biological material or type of tissue and/or cells e.g. blood, colorectal tissue, as that of the test sample. The normal biological sample may be that from a single individual, including the subject in which cancer detection, prognosing or characterizing is performed, or from a group of individuals of known healthy status. Accordingly, the level of a protein in a normal biological sample may be obtained from a single determination or may advantageously represent a statistical average of multiple determinations, such as from a group of healthy individuals or from multiple healthy tissue sites in a single individual.

The term "a control sample" as used herein refers to the standard provided by either a normal i.e. non-diseased sample or group of samples, or a sample or group of samples corresponding to an established form, type, stage or grade of a disease, in particular a cancer disease. Accordingly, the level of a protein in a control sample may be obtained from a single determination or may advantageously represent a statistical average of multiple determinations, for example from a group of healthy individuals, or from a group of diseased individuals established to have the same form, type, stage or grade of a cancer disease.

The term "non-diseased tissue" as used herein refers to tissue which is determined to be free of a cancer disease, on the basis of any technique known in the art, for example, histological and immuno-histochemical investigation. It is to be understood that diseased and non-diseased tissue of the same tissue type may be present in close proximity in a individual patient.

The term "immunogenic fragment" as used herein in reference to a protein refers to a portion of the protein which is capable of inducing an immune response, such as antibody production, following administration to an individual.

As used herein, the terms "a protein associated with cancer", "tumor associated protein", "molecular marker" and the like, interchangeably refer to a protein that is present at relatively higher or lower levels in a cancer cell relative to a normal cell of the same type (e.g., as in protein associated with colon cancer).

As used herein the terms "nucleic acid encoding a protein," encompass polynucleotides and polypeptides respectively having sequence similarity or sequence identity to the respective gene and gene products having the accession numbers of the particular protein referred to, of at least about 65%, preferably at least about 80%, more preferably at least about 85%, and can be about 90%, 91%, 92%, 93%, 94%, 95%, 96%, 97%, 98%, 99% or more. Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment, as is known in the art. Algorithms for computer-based sequence analysis are known in the art, such as BLAST (see, e.g., Altschul et al., J. Mol. Biol., 215:403-10 (1990)), particularly the Smith-Waterman homology search algorithm as implemented in MPSRCH program (Oxford Molecular).

The terms "protein" and "polypeptide" are used interchangeably herein to refer to polymeric forms of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, a "fusion protein" or "chimeric peptide" refers to a protein or polypeptide which comprises at least a portion of a first naturally occurring protein or polypeptide fused to least a portion of a second protein or polypeptide. For example, a fusion protein for targeting FAM62B may include a portion or all of an anti-FAM62B antibody fused with another peptide or polypeptide such as a protein label moiety or a cytotoxic protein.

The term "antibody" as used herein is used in the broadest sense and specifically encompasses monoclonal antibodies, humanized antibodies, polyclonal antibodies, multispecific antibodies (e.g., bispecific antibodies), single chain antibodies and antibody fragments (e.g., $F(ab')_2$, Fab', Fab, Fv) so long as they bind specifically to a target antigen or epitope of interest.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al., Nature 352:624-628 (1991) and Marks et al., J. Mol. Biol. 222:581-597 (1991).

Furthermore, monoclonal antibodies specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for example U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

The term "reagent suitable for detecting the level of a protein" as used herein refers to a reagent which either specifically binds the protein itself or is complementary to a nucleic acid molecule that is involved in expression of the protein. Particularly suitable examples of reagents which specifically bind to proteins are antibodies and chemical mimetics thereof having similar level of binding affinity and/or avidity. Nucleic acid reagents which are complementary to mRNA encoding a protein of interest are suitable for determining the level of the protein, typically by correlating the amount of mRNA detected with the corresponding level of protein product produced in a suitable translation system.

The terms "specifically interacts" and "specifically binds" are used herein interchangeably to refer to high avidity and/or high affinity binding of a reagent, such as an antibody to a specific polypeptide or epitope thereof, such as for example, an epitope of any of the proteins FAM62B, SLC1A5, RSL1D1, LYZ, RBM39 and TCOF1. Antibody binding to its epitope is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

The term "primary antibody" as used herein refers to an antibody which binds specifically to the target protein antigen in a biological or test sample. A primary antibody is generally the first antibody used in an immunoassay procedure. In some embodiments, the primary antibody is the only antibody used in an immunoassay procedure.

The term "secondary antibody" as used herein refers to an antibody which binds specifically to a primary antibody, thereby forming a bridge between the primary antibody and a subsequent reagent, if any. The secondary antibody is typically directed against the Fc portion of the immunoglobulin type of the primary antibody (e.g., anti-mouse Fc antibody).

The terms "polynucleotide" and "nucleic acid" are used interchangeably herein to refer to polymeric forms of nucleotides of any length, either ribonucleotides or deoxynucleotides, including but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Further include are mRNA or cDNA that comprise intronic sequences (see, e.g., Niwa et al. (1999) Cell 99(7):691-702). The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

The term "complementary" as used herein refers to the broad concept of subunit sequence complementarity between two nucleic acids, e.g., two DNA molecules or a DNA/RNA hybrid. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

The term "hybridization" as used herein encompasses any process by which a strand of nucleic acid joins with a complementary strand through base pairing (see for example, Coombs, Dictionary of Biotechnology, Stockton Press, New York N.Y. (1994)). Accordingly, a hybridization assay is a quantitative means of determining the extent of hybridization between a nucleic acid in a test sample, such as a tissue sample, and a nucleic acid probe corresponding to at least a fragment of a gene (DNA or RNA) encoding a protein of interest, such as a cancer associated protein. "Stringency" typically occurs in a range from about Tm −5° C. (5° C. below the Tm of the nucleic acid probe) to about 20° C. to 25° C. below Tm. As will be understood by those of skill in the art, a stringency hybridization can be used to identify or detect identical polynucleotide sequences or to identify or detect similar or related polynucleotide sequences.

Amplification as carried out in the polymerase chain reaction technologies is described in Dieffenbach et al., PCR Primer, a Laboratory Manual, Cold Spring Harbor Press, Plainview N.Y. (1995), and may be performed prior to or as part of a hybridization assay.

As used herein, the term "differentially expressed" generally refers to a polynucleotide and/or the corresponding protein that is expressed at levels in a test cell that differ significantly from levels in a reference or control cell, e.g., a cancer-associated protein as disclosed herein is found at levels at least about 50% to about 100% increased, generally at least about 1.5-fold, at least about 2-fold, at least about 3-fold, at least about 5-fold, at least about 10-fold, at least about 20-fold, or at least about 30-fold or more increased in a cancerous cell when compared with a cell of the same type that is not cancerous. The comparison can be made between two tissues, for example, if one is using in situ hybridization or another assay method that allows some degree of discrimination among cell types in the tissue. The comparison may also be made between cells removed from their tissue source, or cells maintained in their native state in vivo. "Differential expression" refers to both quantitative, as well as qualitative, differences in the genes' temporal and/or cellular expression patterns among, for example, normal and neoplastic tumor cells, and/or among tumor cells which have undergone different tumor progression events.

The terms "correspond to" or "represents" as used in, for example, the phrase "polynucleotide corresponds to a differentially expressed gene" are used to refer to the relationship between a given polynucleotide and the gene from which the polynucleotide sequence is derived (e.g., a polynucleotide that is derived from a coding region of the gene, a splice variant of the gene, an exon, and the like) or to which the polynucleotide hybridizes to under stringent conditions.

The term "label" as used herein refers to a compound or composition which is conjugated or fused directly or indirectly to a reagent such as an antibody, a nucleic acid probe or a chemical agent and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The term "mimetic" as used herein refers to any entity, including natural and synthesized inorganic or organic molecules, including recombinant molecules, that mimic the properties of the molecule of which it is a mimetic. Accordingly, a mimetic of a particular antibody has the same, similar or enhanced epitope binding properties of that antibody.

The term "gene" as used herein refers to any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

The singular forms "a", "and", and "the" include plural referents unless the context clearly dictates otherwise. Thus, for example, reference to "a cell" includes a plurality of such cells and reference to "the reagent" includes reference to one or more reagents and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Detection, Prognosis and Management of Colorectal Cancer

The present invention is based on the discovery that specific proteins, including for example, KIAA0152, NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D and CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI, CISD1, FAM62B, S100A8, S100A9, MPO, MCM2, LTF, OLFM4, FERMT1, CEACAM5, SLC1A5, THBS1, NAT10, RSL1D, LMO7, LYZ and MCM3 are present at significantly higher levels in cancerous or pre-cancerous colorectal tissue as compared to normal tissue of the same cell type, even in the same individual.

This discovery serves as the basis for identification of cancerous tissue, as well as for staging and prognosing tumors, and development of therapeutic agents which target the particular cancer-associated markers. Detection of the markers disclosed herein and/or the genes encoding them, enables early diagnosis based on molecular changes leading to carcinogenesis and/or decision making in disease management. For example, a relatively increased level of a particular protein, such as FAM62B, compared to normal cells or tissues of the same type can be indicative of a poorer prognosis, and therefore warrant more aggressive therapy (e.g., chemotherapy following surgery). The correlation of tumor specific markers with response to treatment and outcome in patients can define prognostic indicators that allow the design of tailored therapy based on the molecular profile of the tumor. These therapies include antibody targeting, antagonists (e.g., small molecules), and gene therapy. Determining colon cancer-specific protein levels and comparison of a patient's profile with known levels in normal tissue and variants of the disease allows a determination of optimal treatment strategies. The marker expression pattern can also be used to better classify (i.e. stage and grade), and thus diagnose and treat different forms of cancer. Furthermore, a protein identified as being differentially or specifically expressed in, one type of cancer may also have implications for development or risk of development of other types of cancer.

Colorectal cancer is one of the most common neoplasms in humans and perhaps the most frequent form of hereditary neoplasia. Prevention and early detection are key factors in controlling and curing colorectal cancer. Colorectal cancer begins as polyps, which are small, benign growths of cells that form on the inner lining of the colon. Over a period of several years, some of these polyps accumulate additional mutations and become cancerous. Multiple familial colorectal cancer disorders have been identified, as follows: 1) Familial adenomatous polyposis (FAP); 2) Gardner's syndrome; 3) Hereditary nonpolyposis colon cancer (HNPCC); and 4) Familial colorectal cancer in Ashkenazi Jews.

Staging is a process used in the medical arts to describe how advanced the cancerous state is in a patient. While staging systems vary with the types of cancer, they generally involve the "TNM" system: "T" indicates the type of tumor, "N" indicates whether the cancer has metastasized to nearby lymph nodes; and "M" indicates whether the cancer has metastasized to other parts of the body. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or other site, are Stage IV, the most advanced stage.

The grade of a cancer describes how closely a tumor resembles normal tissue of its same type. The microscopic appearance of a tumor is used to identify tumor grade based on parameters such as cell morphology, cellular organization, and other markers of differentiation. As a general rule, the grade of a tumor corresponds to its rate of growth or aggressiveness, with undifferentiated or high-grade tumors generally being more aggressive than well differentiated or low-grade tumors. The following guidelines are generally used for grading tumors: GX, Grade cannot be assessed; G1, Well differentiated; G2, Moderately well differentiated; G3, Poorly differentiated; G4, Undifferentiated.

Methods of detection, prognosis, and characterization as disclosed herein are based on levels of at least one, and preferably a panel or multiplicity of cancer-associated proteins, in comparison to levels of the same protein(s) in suitable non-cancerous or cancerous control samples. For example, a detection of cancer may be enabled by the detection of a level of one or more proteins of interest in a sample, such as FAM62b, that is increased at least by 50% or 100% or greater or, alternatively by 2-fold, 3-fold 5-fold, 10-fold, 30-fold, or greater, relative to a normal non-cancerous sample of the same tissue type. The normal non-cancerous sample may be from the same individual as the test sample or from one or more different individuals. Preferably, the level in the normal non-cancerous sample is a statistical average of multiple determinations, such as from a group of healthy individuals or from multiple healthy tissue sites in a single individual.

Similarly, prognosis and characterization of the cancer may be established on the levels of proteins of interest relative to reference standards established for particular grades, stages and forms of cancer. For example, detection of a level of a particular protein which is 1.5-fold compared to that of the control may be taken to indicate a relatively positive prognosis and/or relatively non-aggressive type of cancer, whereas detection of a level of the same protein of 10-fold or more compared to that of the control may be taken to indicate a poorer prognosis and/or a substantially aggressive type of cancer.

Assay Systems and Methods

The methods of the invention may be carried out using various assay systems and methods for detection of the level of the protein of interest in a test biological sample. Suitable systems include those employing an immunoassay, a nucleic acid hybridization assay, a binding assay, an array, a phage display library, or a combination thereof.

Immunoassays

Immunoassays for detecting levels of specific binding between an antibody and its target antigen are known in the art and include for example, radioimmunoassay, (RIA), fluorescent immunoassay, (FIA) enzyme-linked immunosorbant assay (ELISA), immunohistochemistry (IHC) and fluorescent activated cell sorting (FACS) (see, e.g., Harlow and Lane, Using Antibodies, A Laboratory Manual, Cold Spring Harbor Laboratory, New York (1999)). In general, an immunoassay may be either direct or indirect. In a direct assay, the binding of antibody to the target antigen is determined directly using a labeled reagent, such as a fluorescent labeled or an enzyme-labeled primary antibody, which can be detected without further antibody interaction. In a typical indirect assay, unconjugated primary antibody binds to the antigen and then a labeled secondary antibody binds to the primary antibody. Signal amplification occurs because several secondary antibodies may react with different epitopes on the primary antibody. Alternately, both the primary and secondary antibodies may be unlabeled and labeled tertiary antibody is employed. Where the antibody (primary, secondary or tertiary) is conjugated to an enzymatic label, a chromagenic or fluorogenic substrate is added to provide detection of the antigen.

The primary antibody used for detection of the protein(s) of interest is stably associated with e.g., directly or indirectly bound to, the surface of a solid support, e.g. column, microtiter plate, beads, membrane, typically made of glass, plastic, polysaccharides, nylon or nitrocellulose. A multiplicity of antibody specificities for detecting a panel of tumor-associated proteins may be simultaneously bound to the same support, such as in an array.

The test sample is allowed to contact the support during a period of incubation, generally following blocking of non-specific binding sites with non-interfering proteins such as bovine serum albumin. After incubation with each reagent e.g. blocking agent, primary antibody, secondary antibody, the support is washed to remove non-bound components. Determination of suitable reagents, conditions for washing, incubation etc. is within the ability of one of average skill in the art.

Immunoassays can also be employed histologically, as in immunofluorescence or immunoelectron microscopy, for in situ detection of tumor associated antigen. In situ detection can be accomplished by removing a histological sample from a subject, and contacting the sample with a labeled antibody. The antibody is typically contacted with the sample by overlaying the labeled antibody onto the sample. Through the use of such a procedure, the presence of the tumor associated antigen can be determined and/or the distribution of the antigen in the histological sample can be examined. Those of ordinary skill in the art will readily appreciate that any of a wide variety of histological methods (such as staining procedures) can be modified in order to achieve such in situ detection.

Detectable labels suitable for conjugation to antibodies and other binding reagents include radioisotopes, fluorescent labels, enzyme-substrate labels, chromogenic labels, chemiluminescent labels and colloidal gold particles.

Radioisotopes include for example, $^{35}S$, $^{14}C$, $^{125}I$, $^{32}P$ and $^{131}I$. Fluorescent labels include for example, fluorescent molecules fluorescein isothiocyanate (FITC), rhodamine, phycoerythrin (PE), phycocyanin, allophycocyanin, ortho-phthaldehyde, fluorescamine, peridinin-chlorophyll a (PerCP), $Cy_3$ (indocarbocyanine), $Cy_5$ (indodicarbocyanine), lanthanide phosphors, and the like.

Enzymatic labels include luciferases (e.g. firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); alkaline phosphatase (AP) with para-nitrophenyl phosphate as chromogenic substrate; and β-D-galactosidase β-D-Gal) with a chromogenic substrate (e.g., p-nitrophenyl-β-D-galactosidase) or fluorogenic substrate (e.g., 4-methylumbelliferyl-β-D-galactosidase).

A label may be indirectly conjugated with an antibody or other reagent, as is known in the art. For example, an antibody can be conjugated with biotin and any of the types of labels mentioned above can be conjugated with avidin, or vice versa. Biotin binds selectively to avidin, and thus, the label can be conjugated with the antibody in an indirect manner. In some cases, detectable labels are attached by spacer arms of various lengths to reduce potential steric hindrance.

Detection of bound, labeled antibody can be carried out by standard colorimetric, radioactive, photometric and/or fluorescent detection means. For fluorescent labels, signal can be detected by, for example, a scanning confocal microscope in photon counting mode. Appropriate scanning devices are described by, for example, U.S. Pat. Nos. 5,578,832 and 5,631,734. For antibodies labeled with biotin, the reaction can be treated with the appropriate streptavidin-conjugate (e.g., streptavidin-horseradish peroxidase, streptavidin-alkaline phosphatase, streptavidin-luciferase, and the like) and then treated with the appropriate reagents for calorimetric or photometric detection. For radiolabeled antibody, signal can be detected using a scintillation counter, phosphoimager or similar device.

Arrays

Cancer associated proteins in a sample may be detected using an array-based binding assay system. Such an array-based system may incorporate an immunoassay as described above, or incorporate small molecule chemical entities which specifically interact with particular cancer associated proteins. In either case, the solid substrate used for the array comprises a plurality of binding reagents attached to the substrate, wherein each binding reagent has specificity for a different cancer associated protein. The protein panel or "set"

for which the array is predetermined to specifically bind and detect is characteristic of a particular disease, or stage of form of a disease. The binding reagents, are immobilized onto the substrate surface, preferably in a spatially addressable manner. The binding reagents may be antibodies, antibody fragments or small molecule chemical entities.

The nature and geometry of the solid substrate will depend upon a variety of factors, including, among others, the type of array (e.g., one-dimensional, two-dimensional or three-dimensional). Generally, the surface can be composed of any material which will permit immobilization of the binding reagents and which will not substantially degrade under the conditions used in the applications of the array.

The solid substrate used for the array may be in the form of beads, particles or sheets, and may be permeable or impermeable, depending on the type of array, wherein the surface is coated with a suitable material enabling binding of the binding reagents at high affinity. For example, for linear or three-dimensional arrays the surface may be in the form of beads or particles, fibers (such as glass wool or other glass or plastic fibers) or glass or plastic capillary tubes. For two-dimensional arrays, the solid surface may be in the form of plastic, micromachined chips, membranes, slides, plates or sheets in which at least one surface is substantially flat, wherein these surfaces may comprise glass, plastic, silicon, low cross-linked and high cross-linked polystyrene, silica gel, polyamide, and the like.

Fluorescence tagged beads are also an addressable (liquid) array in which each bead is tagged with a different set of fluorescent colors and bound with an antibody; specific to an array is detected with devices such as fluorescence scanners for arrays or FACS for beads.

The arrays used for the present invention may be of any desired size. The upper and lower limits on the size of the array are determined solely by the practical considerations of resolution, size of molecules expressed at each address and the like.

Either a population of discrete proteins is employed to form the array, such that each address presents a different molecule, or a single or a few addresses are employed with a similar protein. In many applications, redundancies in the spots are desirable for the purposes of acting as internal controls.

Technologies for the deposition of droplets containing protein binding reagents onto a suitable solid surface are known in the art. An ink-jet printing technology for deposition of small droplets while avoiding overlap or splatter is disclosed in U.S. Pat. No. 5,449,754.

In order to conduct array-based binding assays, the test sample is allowed to contact the array comprising a coated surface containing the anchored binding reagents. Following contact, the array is optionally washed, typically under conditions such that any complexes formed will remain immobilized on the solid surface and unbound material will be removed.

The detection of complexes anchored on the solid surface can be accomplished in a number of ways. In some embodiments, the non-immobilized sample is pre-labeled, and the detection is directed to label immobilized on the surface indicating that complexes were formed. In other embodiments, an indirect label can be used to detect complexes anchored on the surface; e.g., using a labeled antibody specific for the previously non-immobilized sample (the antibody, in turn, may be directly labeled or indirectly labeled with a labeled anti-Ig antibody). In another embodiment, the immobilized molecules of the microarray are labeled, the array can be scanned or otherwise analyzed for detectable assay signal, and the signal from each labeled spot, or alternatively from all spots, quantified.

An important consideration is the presence of an amount of a label at each position within the array that is proportional to the amount of molecule immobilized at that particular spot. Thus, it is important that the efficiencies of the coupling reactions which are used to immobilize the labeled molecules are substantially similar.

Virtually any label that produces a detectable, quantifiable signal and that is capable of being attached to an immobilized binding reagent on a substrate can be used in conjunction with the array of the invention. Suitable labels include: radioisotopes, fluorophores, chromophores, chemiluminescent moieties, as described above.

Preferably, the position of the label will not interfere with interaction between a desired sample and the immobilized molecules and with the detection in case of an interaction between the desired sample and an immobilized molecule of the array. Suitable methods of making labeled molecules are well known in the art.

In the case where each spot in the array contains an amount of a label or "tracer" proportional to the amount of molecules immobilized at the particular spot, the signals obtained from the arrays of the invention can be normalized. As a consequence, signal intensities from spots within a single array, or across multiple arrays, can be directly compared. A normalized signal of a particular spot may be defined by $(I_t-I_o)/I_o$, where $I_t$ is the intensity of the signal of the spot after contacting with a sample of interest and $I_o$ is the intensity of the background signal of the spot before contacting with a sample of interest.

Various methods and devices for detection and analysis of the array are known in the art. Practically, any imaging system that is capable of detecting with a resolution appropriate to the size of the array features can be utilized. For example, a method for screening an array of proteins for interactions with a fluid sample is disclosed in U.S. Pat. No. 6,475,809. Imaging apparatus may be selected, for example, from ScanArray 4000 (General Scanning), Biochip Imager (Hewlett Packard), GMS 418 Array Scanner (Genetic Microsystems), GeneTAC 1000 (Genomic Solutions), Chip Reader (Virtek). Phosphorimager systems are available for detecting radiolabels, e.g. Cyclone (Packard Instrument Co.) and BAS-5000 (Fujifilm).

Hybridization Assays

Hybridization assays generally comprise contacting a sample containing nucleic acids (target nucleic acids) with a nucleic acid probe capable of hybridizing to tumor associated antigen nucleic acids, under conditions such that hybridization can occur, and detecting or measuring any resulting hybridization.

Suitable hybridization assays include, for example, Northern blots, dot blots, RT-PCR, and quantitative PCR. Such procedures can be performed in situ directly for example, in tissue sections (e.g., fixed and/or frozen) of subject tissue obtained from biopsies or resections, such that no nucleic acid purification is necessary. Tumor associated antigen nucleic acids can be used as probes and/or primers for such procedures (see e.g., Nuovo, PCR In Situ Hybridization: Protocols and Applications, Raven Press, NY (1992)).

Detection of tumor associated antigen nucleic acids typically involves contacting and incubating nucleic acids from a test sample with one or more labeled nucleic acids, (i.e. "probes") under conditions favorable for the specific annealing of the nucleic acids to their complementary sequences. Typically, the lengths of the nucleic acid reagents are at least 15 to 30 nucleotides. After incubation, all non-annealed nucleic acids are removed. The presence of bound i.e. hybridized, nucleic acids from the sample, if any such molecules exist, is then detected. Using such a detection scheme, the nucleic acid from the tissue or cell type of interest can be immobilized, to a solid support such as a membrane, or a plastic surface such as that on a microtiter plate or polystyrene beads.

Nucleic acid arrays can be used to monitor the expression of tumor associated genes, such as, for example, those corresponding to KIAA0152, NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D and CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI, CISD1, FAM62B, S100A8, S100A9, MPO, MCM2, LTF, OLFM4, FERMT1, CEACAM5, SLC1A5, THBS1, NAT10, RSL1D, LMO7, LYZ and/or MCM3. For detection of a multiplicity of genes encoding distinct cancer associated proteins, an array of polynucleotide probes may be contacted with a sample of target nucleic acids to produce a hybridization pattern. The binding of the target nucleic acids to one or more probes of the array is then detected to obtain a qualitative and/or quantitative profile of expression of the tumor associated antigen gene.

A variety of different arrays can be used and are known in the art. The polymeric or probe molecules of the arrays can be polynucleotides or hybridizing derivatives or analogs thereof, including: nucleic acids in which the phosphodiester linkage has been replaced with a substitute linkage, such as phosphorothioate, methylimino, methyl-phosphonate, phosphoramidate, guanidine, and the like; nucleic acids in which the ribose subunit has been substituted, for example, hexose phosphodiester; peptide nucleic acids; and the like. The length of the probes will generally range from about 10 to about 1000 nucleotides, typically, from about 15 to about 150 nucleotides in length, but also possibly from about 150 to about 1000 nucleotides in length. The probes can be single or double stranded, usually single stranded, and can be PCR fragments amplified from cDNA. The probe molecules on the surface of the substrates will typically correspond to at least one of the tumor associated antigen genes and be positioned on the array at known locations so that positive hybridization events can be correlated to expression of a particular gene in the physiological source from which the target nucleic acid sample is derived. Because of the manner in which the target nucleic acid sample is generated, the arrays of probes will generally have sequences that are complementary to the non-template strands of the gene to which they correspond.

The substrate for the array can be fabricated from a variety of materials, including plastics, ceramics, metals, gels, membranes, glasses, and the like. The arrays can be produced according to any convenient methodology, such as pre-forming the probes and then stably associating them with the surface of the support or growing the probes directly on the support. A number of different array configurations and methods for their production are known to those of skill in the art and disclosed in, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637.

The target nucleic acid is typically contacted with the array under conditions sufficient for hybridization of target nucleic acid to probe to occur. Suitable hybridization conditions are well known to those of skill in the art (see, e.g., Sambrook et al., Molecular Cloning, A Laboratory Manual, 3rd ed., Cold Spring Harbor, Cold Spring Harbor, N.Y. (2001)).

The amount of tumor associated antigen nucleic acids in the sample can be quantitated (see, e.g., U.S. Pat. No. 6,004,755). For example, the target nucleic acids in the sample can be end-labeled in a manner such that each of the target nucleic acids in the sample produces a signal of the same specific activity. By generating the same specific activity is meant that each individual target polynucleotide in the sample being assayed is labeled in a manner such that the molecule is capable of providing the same signal (e.g., the same intensity of signal) as every other labeled target in the sample. Each of the target nucleic acids generates a signal of the same specific activity because the number of labeled nucleotide bases in each of the target molecules is either identical or substantially the same.

The label is capable of providing a detectable signal, either directly or through interaction with one or more additional members of a signal producing system. Suitable detectable labels include radioactive, fluorescent and enzymatic labels as described above.

In some applications, it is desired to analyze populations of target nucleic acids from two or more samples. Such samples can be differentially labeled. Alternatively, target nucleic acids from different samples are separately contacted to identical probe arrays under conditions of hybridization, typically stringent hybridization conditions, such that labeled nucleic acids hybridize to their complementary probes on the substrate surface, and the target nucleic acids bound to the array separately detected. A set of standard nucleic acid molecules can optionally be used. For example, the standard nucleic acids can be provided by reverse transcribing standard RNA.

Following hybridization, a washing step is usually employed to remove non-specifically bound nucleic acid from the support surface, generating a pattern of hybridized nucleic acid on the substrate surface. Various wash solutions and protocols for their use are known to those of skill in the art.

Where the label on the target nucleic acid is not directly detectable, the array can be contacted with the other member (s) of the signal producing system that is being employed. For example, where the label on the target is biotin, the array can be contacted with streptavidin-fluorophore conjugate under conditions sufficient for binding between the specific binding member pairs to occur. Following contact, any unbound members of the signal producing system will then be removed (e.g., by washing).

The resultant hybridization pattern(s) of target nucleic acids bound to the array can be visualized or detected in a variety of ways, with the particular manner of detection being chosen based on the particular label of the nucleic acid. For example, detection means can include scintillation counting, autoradiography, fluorescence measurement, colorimetric measurement, light emission measurement, and the like.

Prior to detection or visualization, the array of hybridized target/probe complexes can be optionally treated with an endonuclease, for example, mung bean nuclease, S1 nuclease, and the like. The endonuclease degrades single stranded, but not double stranded DNA.

Following detection or visualization, the hybridization pattern can be used to determine qualitative and/or quantitative information about the expression of tumor associated antigen genes. The hybridization patterns of different samples can be compared with each other, or with a control sample, to identify differences between the patterns. The hybridization arrays can also be used to identify differential gene expression, in the analysis of diseased and normal tissue.

Antibody Production

Antibodies directed against cancer associated proteins include polyclonal antibodies, monoclonal antibodies, chimeric antibodies, single chain antibodies, antibody fragments (e.g., Fab, Fab', $F(ab')_2$, Fv, or hypervariable regions), bi-specific antibodies and humanized antibodies, methods of production of which are known in the art.

For the production of polyclonal antibodies, a host animal (e.g., rabbits, mice, rats, sheep, goats, and the like) can be immunized by injection with a tumor associated antigen, fragment, derivative or analog. Various adjuvants can be used to increase the immunological response, depending on the host species. Such adjuvants include, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and other adjuvants, such as BCG (bacille Calmette-Guerin) and *Corynebacterium parvum.*

Techniques for preparation of monoclonal antibodies include the original Kohler and Milstein hybridoma technique (see, e.g., Nature 256:495 97 (1975)), the trioma technique (see, e.g., Hagiwara and Yuasa, Hum. Antibodies Hybridomas 4:15 19 (1993); Hering et al., Biomed. Biochim. Acta 47:211 16 (1988)), the human B-cell hybridoma technique (see, e.g., Kozbor et al., Immunology Today 4:72 (1983)), and the EBV-hybridoma technique (see, e.g., Cole et al., In: Monoclonal Antibodies and Cancer Therapy, Alan R. Liss, Inc., pp. 77 96 (1985)). Human antibodies can be obtained using human hybridomas (see, e.g., Cote et al., Proc. Natl. Acad. Sci. USA 80:2026 30 (1983)) or by transforming human B cells with EBV virus in vitro (see, e.g., Cole et al., supra).

Chimeric antibodies are typically prepared by splicing the genes (of one species) for an antibody molecule specific for tumor associated antigen together with genes from another species of antibody molecule of appropriate biological activity. It can be desirable to transfer the antigen binding regions (e.g., Fab', $F(ab')_2$, Fab, Fv, or hypervariable regions) of antibodies from one species into the framework of an antibody from another species by recombinant DNA techniques to produce a chimeric molecule. Methods for producing such molecules are described in, for example, U.S. Pat. Nos. 4,816,567; 4,816,397; 5,693,762, and 5,712,120. A human monoclonal antibody or portion(s) thereof can be identified by screening a human B-cell cDNA library for nucleic acid molecules that encode antibodies that specifically bind to a tumor associated antigen according to the method generally set forth by Huse et al. (Science 246:1275 81 (1989)). The nucleic acid molecule can then be cloned and amplified to obtain sequences that encode the antibody (or antigen-binding domain) of the desired specificity. Phage display technology offers another technique for selecting antibodies that bind to tumor associated antigens, fragments, derivatives or analogs thereof (see, e.g., International Patent Publications WO 91/17271 and WO 92/01047; Huse et al., supra.)

Techniques for the production of single chain antibodies are described for example in U.S. Pat. Nos. 4,946,778 and 5,969,108. A Fab expression library (see, e.g., Huse et al., supra) allows rapid and easy identification of monoclonal Fab fragments with the desired specificity for tumor associated antigens, fragments, derivatives, or analogs thereof.

$F(ab')_2$ antibody fragments can be produced by pepsin digestion of an antibody molecule. Fab' fragments can be generated by reducing the disulfide bridges of a $F(ab')_2$ fragment, Fab and Fv fragments can be generated by treating an antibody molecule with papain and a reducing agent. Recombinant Fv fragments can also be produced in eukaryotic cells using, for example, as described in U.S. Pat. No. 5,965,405.

Bi-specific antibodies can be monoclonal antibodies that have binding specificities for at least two different antigens. For example, one of the binding specificities can be for a tumor associated antigen and the other one is for any other antigen. Alternatively, one specificity is for a first tumor associated antigen, while the other specificity is for a second, different tumor associated antigen. Methods for making bi-specific antibodies may be based on the co-expression of two immunoglobulin heavy-chain/light-chain pairs, where the two heavy chains have different specificities (see, e.g., Milstein and Cuello, Nature 305:537 39 (1983)). Because of the random assortment of immunoglobulin heavy and light chains, these hybridomas produce a potential mixture of different antibody molecules, some of which have the desired bi-specific structure. The purification of the correct molecule is usually accomplished by affinity chromatography steps.

Antibody variable domains with the desired binding specificities (antibody-antigen combining sites) can be fused to immunoglobulin constant domain sequences. The fusion typically is with an immunoglobulin heavy-chain constant domain, comprising at least part of the hinge, CH2, and CH3 regions. The first heavy-chain constant region (CH1) containing the site necessary for light-chain binding is usually present in at least one of the fusions. DNAs encoding the immunoglobulin heavy-chain fusions and, if desired, the immunoglobulin light chain, are inserted into separate expression vectors, and are co-transfected into a suitable host organism. For further details of generating bi-specific antibodies see, for example, Suresh et al (Methods in Enzymology 121:210 (1986)).

To generate a phage antibody library, a cDNA library is first obtained from mRNA which is isolated from cells, e.g., the hybridoma, which expresses the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Pharmaceutical Compositions and Agents

A pharmaceutical or antigen composition according to the invention comprises at least one protein selected from the group consisting of KIAA0152, NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D, CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI, CISD1, LYZ, LOC442497; SLC3A2, DMBT1, NUCB1, GGH, AGR3, TM9SF2, SYK, GCA, HDLBP, C1QBP and CLIC1, or an immunogenic fragment thereof.

The composition may be used in a therapeutic method for preventing or treating cancer, wherein an effective amount of the composition is administered to a subject in need thereof. A subject in need thereof may be for example, an individual in which colorectal polyps have been identified, and/or has been determined to have other risk factors for development of colorectal cancer. Accordingly, a method of preventing colorectal cancer may comprise administering an effective amount of a pharmaceutical composition comprising at least one protein highly expressed in polyps, for example any of CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI and CISD1.

Further provided are pharmaceutical compositions comprising one or more reagents suitable for detecting the level of at least one protein selected from the group consisting of KIAA0152, NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D, CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI, CISD1, LYZ, LOC442497; SLC3A2, DMBT1, NUCB1, UGH, AGR3, TM9SF2, SYK, GCA, HDLBP, C1QBP and CLIC1.

As hereinbefore described, such reagents may comprise labeled antibodies, antibody mimetics or nucleic acids as the active ingredients. Advantageously such reagents are provided as a “cocktail” tailored to detect in vivo a particular panel of cancer associated proteins, or genes expressing same, Following administration, the localization of such reagents to specific body and organ regions may be detected by means of an external monitoring apparatus or system appropriate for detection and quantitation of the specific label incorporated into the reagents.

In yet other embodiments, pharmaceutical agents, in particular antibodies and an antibody mimetics, are provided, which may be used for targeted therapy of cancers expressing particular cancer associated proteins. Such, agents may advantageously incorporate a cytotoxic moiety, such as a plant toxin, a bacterial toxin, a radioactive atom or a chemotherapeutic agent. Further, the pharmaceutical agent may be in the form of a chemical conjugate or a fusion protein and provided in a suitably formulated pharmaceutical composition.

Plant toxins include for example, ricin, abrin, pokeweed antiviral protein, saporin, gelonin, and derivatives thereof. Bacterial toxins include for example, *Pseudomonas* exotoxin, diphtheria toxin and derivatives thereof, iodine-125 and radon. Radioactive atoms include for example, radium, cesium-137, iridium-192, americium-241 and gold-198.

Chemotherapeutic agents include, without limitation, alkylating agents, for example cyclophosphamide; nitrosoureas, for example carmustine and lomustine; antimetabolites, for example 5-fluorouracil, capecitabine, 6-mercaptopurine, methotrexate, gemcitabine, cytarabine, fludarabine and pemetrexed; anthracyclines, for example daunorubicin, doxorubicin respinomycin D and idarubicin; topoisomerase inhibitors, for example topotecan, irinotecan, etoposide and teniposide; mitotic inhibitors, for example paclitaxel, docetaxel, etoposide, vinblastine and vincristine; platinum based drugs, for example cisplatin, carboplatin and oxaliplatin; steroids for example hydrocortisone, dexamethasone, methylprednisolone and prednisolone; and anti-angiogenic agents, for example bevacizumab, thalidomide, dopamine and tetrathiomolybdate.

The pharmaceutical composition can be used to administer diagnostic reagents designed to detect levels of proteins disclosed herein, in particular KIAA0152 (SEQ ID NO:1), NAMPT (SEQ ID NO:2), PYCR1 (SEQ ID NO:3), GPX2 (SEQ ID NO:4), PRKDC (SEQ ID NO:5), ALDH18A1 (SEQ ID NO:6), OCIAD2 (SEQ ID NO:7), GCS1 (SEQ ID NO:8), GMDS (SEQ ID NO:9), ARF4 (SEQ ID NO:10), ARF5 (SEQ ID NO:11), LRPPRC (SEQ ID NO:12), CTNNB1 (SEQ ID NO:13), ARF3 (SEQ ID NO:14), GCN1L1 (SEQ ID NO:15), BDH1 (SEQ ID NO:16), RPL9 (SEQ ID NO:17), UGCGL1 (SEQ ID NO:18), FAM3D (SEQ ID NO:19) and CCT4 (SEQ ID NO:20), including antibodies, antibody mimetics or nucleic acids, or therapeutic reagents designed to exert a cytotoxic affect on their cancer targets. Therapeutic compositions for targeting tumors may include a reagent which specifically interacts with a protein selected from NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, KIAA0152, UGCGL1, FAM3D, CCT4, LYZ, LOC442497; SLC3A2, DMBT1, NUCB1, GGH, AGR3, TM9SF2, SYK, GCA, HDLBP, C1QBP, KIAA0152 and CLIC1.

The pharmaceutical composition may be prepared by suspending the desired reagent in any pharmaceutically acceptable carrier, for example, HEPES buffered saline at a pH of about 7.8. Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington’s Pharmaceutical Sciences (1991, Mack Publication Co., New Jersey).

The pharmaceutical compositions may be prepared in the form of a sterile injectable aqueous or oily suspension or solution. This suspension or solution may be formulated according to the known art, and may comprise, in addition to the active ingredient, additional ingredients such as the dispersing agents, wetting agents, or suspending agents. Sterile injectable formulations may be prepared using a non-toxic parenterally-acceptable diluent or solvent, such as water or 1,3-butane diol, for example. Other acceptable diluents and solvents include, but are not limited to, Ringer’s solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

As used herein, the term “physiologically acceptable” ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Controlled- or sustained-release formulations of a pharmaceutical composition of the invention may be made using conventional technology.

A formulation of a pharmaceutical composition of the invention suitable for oral administration may be prepared in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid is one which comprises a carbon-containing liquid molecule and which exhibits a less polar character than water.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art.

Kits

The invention also includes kits for detecting, diagnosing, prognosing or staging a cancer or a tumor in a mammal. The cancer or tumor can be of any of the types described herein, and is preferably colorectal cancer. The kit comprises a container or a sample tube, or the like, for storing a sample of a cell, a population of cells, a tissue or a body fluid obtained from the mammal.

The kit also comprises one or more detection reagents selected from: an antibody or antibody mimetic which specifically bind with a cancer associated protein disclosed herein; a nucleic acid such as an oligonucleotide which specifically binds a nucleic acid (such as mRNA) encoding said cancer associated protein, and a PCR primer pair specific for a nucleic acid encoding said cancer associated protein. These detection reagents are as described herein. The kit comprises the one or more detection reagents in an amount effective to permit detection of the protein(s) of interest or a corresponding nucleic acid in the sample. Detection of the proteins or the nucleic acids is accomplished using any of the methods described herein or known to a skilled artisan for detecting a specific protein or specific nucleic acid molecule within a biological sample.

Reagents in the kit may be directed to a protein selected from KIAA0152, NAMPT, PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D, CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI and CISD1. The kit may be intended for detecting pre-cancerous or early stage colorectal cancer and include reagents detecting any protein selected from the group consisting of CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A3, SLC25A11, PDCD6, UCRC, DEFA6, DYNC1H1, HK1, CYFIP2, DCI and CISD1. In particular embodiments, the kit comprises a reagent suitable for detecting KIAA0152.

The kit also comprises at least one control biological sample, such as from non-diseased tissue, for comparison to a biological sample obtained from a subject under investigation. Control biological samples which correspond to samples from a cancer of a known stage or having a known prognosis, may also be included.

The kit also comprises an instructional material which directs the use of the reagents and the samples for the determining the amount and the location of the proteins or the nucleic acids in one or more cells of the sample. The instructional material also directs the correlation of the amount and the location of the protein or the nucleic acid in the cells of the sample with the diagnosis, prognosis and/or stage of a cancer or a tumor in the mammal.

As used herein, an "instructional material" includes a publication, a recording, a diagram, or any other medium of expression which directs or dictates the use of the components of a kit for performing the function of a method of the invention described herein. The instructional material of the kit of the invention may, for example, be affixed to a container which contains the composition or be shipped together with a container which contains the composition.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

The following methods were used in the Examples.

Protein Extraction from Frozen Tissues

Surplus snap-frozen tumor and margin non-tumoral tissue were collected from patients undergoing surgery for colorectal cancer at either of two university teaching hospitals in Israel. Around 30 mg of frozen tissue were extracted from every tissue sample by mixing the tissue sample with in 0.5 ml of 8 M urea, 400 mM ammonium bicarbonate, and homogenized by high speed tissue homogenizer (Omni-TH) for 1 min, activated at full speed.

Identification of Proteins

1) Gel-slicing method. About 50 μg of the proteins extracted from the tumor tissues or the healthy tissues were resolved by 10% of SDS-PAGE. Each gel lane was subsequently stained with Coomassie blue. The stained gel lanes were cut into 12 slices. The gel pieces were de-stained by extensive washing with acetonitrile and ammonium bicarbonate. The proteins in each gel slice were proteolyzed inside the stained gel: stained slices were reduced with 10 mM DTT, incubated at 60° C. for 30 min, alkylated with 10 mM iodoacetamide, at room temperature for 30 min and digested with trypsin overnight at 37° C., using modified trypsin (Promega) at a 1:100 enzyme-to-substrate ratio. The tryptic peptides were analyzed by AC-MS/MS using the OrbitrapXL mass spectrometer (Thermo-Fisher) fitted with a capillary HPLC (Eksigent). The peptides were resolved on homemade capillary columns (75 micron ID) packed with reversed phase 3.5 micron beads Reprosil C18-Aqua, using a method described by (Ishihama, Rappsilber et al. 2002). The HPLC separations of the peptides were at flow rates of about 250 nanoliters per minute during 2 hrs and with 7-40% gradients of acetonitrile in the presence of 0.1% formic acid. The capillary columns were connected on line to the Orbitrap mass spectrometer through an electrospray interface. The mass spectrometer was operated in a data-dependent mode where the masses of the eluting peptides were measured at high accuracy in the Orbitrap part of the machine and the seven most intense masses, detected at each full MS spectra whose charge states were determined to be double and triple, were selected for fragmentation by CID in the linear trap at the subsequent seven CID fragmentations.

2) Multidimensional chromatography coupled with mass spectrometry. 50 μg of total protein extracts mixed with 100 μg in 8 M urea, 100 mM ammonium bicarbonate were treated for blocking all the sulfhydryls by first reducing disulfides by addition of 10 mM DTT, incubation at 60° C. for 30 min. The free disulfides were next blocked by carboxymethylation using 10 mM iodoacetamide and incubation at room temperature for 30 min. The denatured and carboxymethylated protein mixtures were diluted three-fold with water to reduce urea concentration to about 2M followed by digestion in solution, overnight at 37° C. using modified trypsin (Promega) at a 1:100 enzyme-to-substrate ratio. The resulting peptides from the trypsinized proteins were desalted with reversed-phase with a C18 tip disposable micro-columns (Harvard), eluted with 90% acetonitrile, dried and dissolved in 0.1% formic acid. The resulting peptides were resolved by multi-dimensional chromatography with on-line first dimension of strong cation exchange (SCX) chromatography 0.3×5 mm columns (LC Packings) using ten salt steps of 20, 40, 60, 80, 100, 120, 160, 200, 300 and 500 mM ammonium acetate in 5% acetonitrile with 0.1% acetic acid. The peptides from each increased salt elution from the SCX columns were transferred on-line to a C18 trap column (0.3×5 mm, LC-Packings), which was connected on-line to a Reprosil C18 home-made capillary columns (75 micron ID), resolved by 7-40% acetonitrile gradients, during 2 hrs, in the presence of 0.1% formic acid as described before for the gel-slicing method.

Resolving peptides by two-dimensional capillary chromatography has been described (Link, Eng et al. 1999), reviewed in (Link 2002). The mass spectrometry analysis was performed on-line as described above using data-dependent LC-MS/MS analysis with full MS in the Orbitrap and subsequent seven dependent ion-trap CID spectra of the most abundant doubly and triply charged peptides, detected in the full MS.

3) Isotope labeling peptides to enable quantitative analysis. Labeling tryptic peptides with light or heavy stable isotope reagents may rely on commercial reagents, reviewed in (Ong and Mann 2005; Regnier and Julka 2006). To facilitate the accurate comparison of the relative amounts of each of the proteins in the different samples, the mixture of peptides produced by the trypsinization of the entire in-solution protein proteolysis were covalently modified with light and heavy stable-isotope reagents. Reductive dimethylation labeling was done with heavy and light formaldehyde as described by (Hsu, Huang et al. 2003).

50 ug of proteolytic peptides were covalently modified with stable-isotope labeled (heavy and light formaldehyde) reagents (reductive dimethylation). The labeled peptides were resolved by multi-dimensional chromatography with on-line SCX column as described above.

Stable isotope labeling was also performed by iTRAQ (Ross, Huang et al. 2004) using a labeling kit that was purchased from Applied Biosystems and labeling was done according to the manufacturer's protocol. The labeled peptides were resolved by multi-dimensional chromatography with on-line SCX column as described above.

Bioinformatics

The mass spectrometry data of both the tryptic peptides obtained from proteolysis in the gel slices mentioned above and the tryptic peptides resolved by multidimensional chromatography were clustered and analyzed using the Pep-Miner software tool (Beer, Barnea et al. 2004). The search against the human part of the IPI database was done by using multiple search engines: Pep-Miner (Beer, Barnea et al. 2004), Mascot (Perkins, Pappin et al. 1999) and Sequest (Eng, McCormack et al. 1994). Both Mascot and Sequest were run together using the Protein Discoverer software tool (Thermo-Fisher).

Peptides were selected according to the following critera: 1) Mascot: ionScore>identityHigh and expValue<0.05 and deltaScore=0; 2) Sequest: ((xCorr>2 and chg</=2) or (xCorr>2.5 and chg>/=3)) and probability>15 and deltaScore=0 A peptide was used for the analysis if it was identified with the above criteria at least once for Sequest and once for Mascot, although not necessarily both in the same scan or run or patient.

Example 1

Clinical Characteristics of Patients Undergoing Surgical Gastrointestinal Re-Sectioning The entire protein repertoires of healthy and diseased gastrointestinal tissues were analyzed from samples obtained from greater than 50 patients undergoing surgery for colorectal cancer.

The clinical characteristics of the patients studied are provided in Table 2.

TABLE 2

| Patient No. | Age at Diagnosis | Gender | Appearance | Diagnosis | TNM | Stage | Grade |
|---|---|---|---|---|---|---|---|
| 201 | 78 | M | primary | Adeno-carcinoma | T3N1M0 | III | high |
| 202 | 81 | F | primary | Mucinous adeno-carcinoma | T3N1 | III | low |
| 203 | 85 | M | primary | Adeno-carcinoma | T3N0M0 | II | high |
| 205 | 71 | F | primary | Adeno-carcinoma | T3N1M0 | III | high |
| 207 | 81 | F | primary | Adeno-carcinoma | T3N2 | III | high |
| 208 | 78 | M | primary | Adeno-carcinoma | T3N2M1 | IV | high |
| 209 | 71 | M | primary | Adeno-carcinoma | T3N0M1 | II | high |
| 211 | 57 | F | primary | Adeno-carcinoma | T2N0M0 | I | intermed |
| 212 | 50 | F | primary | Adeno-carcinoma | T3N1M0 | III | high |

TABLE 2-continued

| | | | | | | | |
|---|---|---|---|---|---|---|---|
| 214 | 54 | F | primary | Adeno-carcinoma | T3N1M0 | III | high |
| 217 | 77 | F | Local recurrance | Adeno-carcinoma | T3N0M0 | II | high |
| 218 (T + P + N) | 79 | M | primary | Adeno-carcinoma | T3N2M1 | IV | low |
| 219 | 60 | M | primary | Adeno-carcinoma | T3N1M0 | III | high |
| 220 | 73 | M | primary | Adeno-carcinoma | T3N2M1 | IV | high |

| Patient No. | Age at Diagnosis | Gender | Type of surgery | Diagnosis | Tumor location | Stage | Grade |
|---|---|---|---|---|---|---|---|
| J1 (T + N) | 61 | F | Lt colectomy | Adeno-carcinoma | left colon | IV | intermed |
| J2 (T + N) | 67 | M | Lt colectomy | Adeno-carcinoma | left colon | II | intermed |
| J3 (T + N) | 70 | M | Rt colectomy | Adeno-carcinoma | right colon | II | intermed |
| J4 (T + N) | 83 | F | Sigmoidectomy | Adeno-carcinoma | left colon | II | intermed |
| J5 (T + N) | 41 | M | Lt colectomy | Adeno-carcinoma | left colon | I | intermed |
| J6 (T + N) | 67 | M | Lt colectomy | Adeno-carcinoma | left colon | IV | intermed |
| J7 (T + N) | 95 | M | Rt colectomy | Adeno-carcinoma | right colon | III (T3N1) | intermed |
| J8 (T + N) | 72 | F | Rt colectomy | Adeno-carcinoma | right + left colon | III T3N4 | high |
| J9 (T + N) | 56 | F | Rt colectomy | Adeno-carcinoma | right colon | II T4N0M0 | intermed |
| J10 (T + N) | 64 | M | Anterior Resection | Adeno-carcinoma of rectum | rectum | II T4N0Mx | low |
| J11 (T + N) | 61 | F | Rt colectomy | Adeno-carcinoma | right colon | I | low |
| J12 (T + N) | 61 | M | colectomy | Adeno-carcinoma | rectum | II | intermed |
| J13 (T + N) | 60 | M | Rt colectomy | Adeno-carcinoma | right colon | I | intermed |
| J14 (T + N) | 53 | F | colectomy | Adeno-carcinoma | left colon | II | intermed |
| J15 (P + N) | 44 | M | Lt colectomy | Colonic polyps | left colon | | |
| J16 (P + N + Pbig) | 64 | M | Rt colectomy | Tubulo-villus | right colon | | |
| J17 (T + N) | 81 | M | Rt colectomy | Adeno-carcinoma | right colon | II | intermed |
| J18 (P + N) | 58 | F | Rt colectomy | Adeno-carcinoma in TVA | right colon | I | intermed |
| J19 (T + N + P) | 72 | M | Rt colectomy | Adeno-carcinoma | right colon | II | intermed |
| J20 (T + N) | 60 | F | Rt colectomy | Adeno-carcinoma | left colon | II | intermed |
| J21 (T + N) | 29 | F | Rt colectomy | Adeno-carcinoma | right colon | IV | low |
| J22 (T + N) | 70 | M | Rt colectomy | Adeno-carcinoma | right colon | II | high |
| J23 (T + N) | 92 | F | Rt colectomy | Adeno-carcinoma | right colon | III | intermed |
| J24 (P + N) | 75 | M | Rt colectomy | Villo-tubulos adenoma | right colon | | |
| J25 (T + N) | 47 | M | Rt colectomy | Adeno-carcinoma | Rectac-toigmoid | III | intermed |
| J26 (T + N) | 77 | M | Rt colectomy | Adeno-carcinoma | right colon | III | intermed |
| J27 (T + N) | 77 | M | Lt colectomy | Adeno-carcinoma | left colon | II | intermed |
| J28 (Pbig + N + P) | 77 | M | ext Rt colectomy | Villo-tubulos adenoma | right colon | | high |
| J29 (T + N) | 78 | M | Lt colectomy | Adeno-carcinoma | left colon | II | intermed |
| J30 (T + N) | 67 | F | Lt colectomy | Adeno-carcinoma | right colon | III | intermed |
| J31 (T + N) | 83 | M | Sigmoidectomy | Adeno-carcinoma | right colon | II | low |

TABLE 2-continued

| | | | | | | | |
|---|---|---|---|---|---|---|---|
| J32 (T + N) | 65 | F | Anterior Resaction | Adeno-carcinoma | right colon | II | intermed |
| J33 (N + P1 − 5) | 83 | M | Rt colectomy | Adeno-carcinoma | right colon | II | intermed |
| J34 (T + N) | 82 | M | Rt colectomy | Adeno-carcinoma | right colon | II | intermed-high |
| J35 (T + N) | 81 | M | Gastrectomy | Adeno-carcinoma | stomach | III | high |
| J36 (T + N) | 62 | M | Resaction | Adeno-carcinoma | recto signuoid | III | intermed |
| J37 (T + N) | 55 | M | Rt colectomy | Adeno-carcinoma | | III | intermed-high |
| J38 (T + N + P1 − P2) | 80 | M | Rt colectomy | Adeno-carcinoma | right colon | III | intermed-low |
| J39 (T + P) | 62 | M | Rt colectomy | Villo-tubulos adenoma | right colon | I | high |
| J40 (T + N) | 52 | M | Anterior Resection | Adeno-carcinoma | Sigmoid | III | intermed-low |
| J41 (T + N + P1 + P2) | 87 | M | Rt colectomy | Adeno-carcinoma | right colon | III | intermed-low |
| J42 (T + N + P1 + P2) | 87 | M | Rt colectomy | Adeno-carcinoma | | I | intermed |

T, tumor;
N, normal;
P, polyp;
high grade = poorly differentiated;
low grade = well differentiated;
intermediate grade = moderately well differentiated.

Example 2

Identification of a Group of Protein Markers that are Found in Polyps and in Advanced Stages of Colorectal Cancer Table 3 lists proteins that were observed to be highly expressed in polyps, as well as in early and advanced stages of various colorectal cancers. As shown in Table 3 and in FIG. 2, in a large number of patients, the expression level of these proteins in polyps or cancerous tissue was at least 3 times greater than the expression level in healthy tissue from the same patient. Similarly, few if any, of the patients exhibited decreased expression levels of the same proteins in polyps or cancerous tissue as compared to the corresponding level in healthy tissue from the same patient. That is, a ratio of protein expression (polyps/tumor vs healthy tissue from the same patient), that was less than 1:3, was rarely observed. Accordingly, a diagnostic array of reagents directed to detection of at least some of the proteins in this group may be used as a general screening test for colorectal cancers.

TABLE 3

| IPI Acc. No. | nPeptides | Protein | nBigT | nSmallT | nBigP | nSmallP |
|---|---|---|---|---|---|---|
| IPI00022649 | 18 | SLC12A2 Isoform 1 of Solute carrier family 12 member 2 | 14 | 2 | 16 | 0 |
| IPI00017526 | 3 | S100P Protein S100-P | 27 | 0 | 15 | 0 |
| IPI00022255 | 16 | OLFM4 Olfactomedin-4 precursor | 21 | 2 | 15 | 0 |
| IPI00024095 | 16 | ANXA3 Annexin A3 | 19 | 1 | 15 | 0 |
| IPI00555902 | 6 | OCIAD2 Isoform 1 of OCIA domain-containing protein 2 | 15 | 0 | 15 | 0 |
| IPI00376503 | 7 | PYCR1 pyrroline-5-carboxylate reductase 1 isoform 2 | 20 | 0 | 14 | 0 |
| IPI00298176 | 7 | GPX2 Glutathione peroxidase 2 | 18 | 0 | 14 | 0 |
| IPI00296337 | 55 | PRKDC Isoform 1 of DNA-dependent protein kinase catalytic subunit | 16 | 2 | 14 | 0 |
| IPI00215919 | 9 | ARF5 ADP-ribosylation factor 5 | 11 | 2 | 14 | 0 |
| IPI00619903 | 21 | UGCGL1 UDP-glucose:glycoprotein glucosyltransferase 1 precursor | 9 | 2 | 14 | 0 |

TABLE 3-continued

| IPI Acc. No. | nPeptides | Protein | nBigT | nSmallT | nBigP | nSmallP |
|---|---|---|---|---|---|---|
| IPI00018873 | 18 | NAMPT Isoform 1 of Nicotinamide phosphoribosyltransferase | 17 | 2 | 13 | 0 |
| IPI00008982 | 16 | ALDH18A1 Isoform Long of Delta-1-pyrroline-5-carboxylate synthetase | 16 | 2 | 13 | 0 |
| IPI00328170 | 6 | GCS1 Mannosyl-oligosaccharide glucosidase | 15 | 0 | 13 | 0 |
| IPI00216057 | 8 | SORD Sorbitol dehydrogenase | 14 | 2 | 13 | 0 |
| IPI00030207 | 16 | GMDS GDP-mannose 4,6 dehydratase | 13 | 2 | 13 | 0 |
| IPI00215918 | 10 | ARF4 ADP-ribosylation factor 4 | 12 | 2 | 13 | 0 |
| IPI00783271 | 45 | LRPPRC Leucine-rich PPR motif-containing protein, mitochondrial precursor | 11 | 3 | 13 | 0 |
| IPI00017292 | 23 | CTNNB1 Isoform 1 of Catenin beta-1 | 11 | 2 | 13 | 0 |
| IPI00215917 | 10 | ARF3 ADP-ribosylation factor 3 | 11 | 2 | 13 | 0 |
| IPI00001159 | 18 | GCN1L1 Translational activator GCN1 | 11 | 1 | 13 | 0 |
| IPI00025341 | 10 | BDH1 D-beta-hydroxybutyrate dehydrogenase, mitochondrial precursor | 10 | 4 | 13 | 0 |
| IPI00031691 | 9 | RPL9 60S ribosomal protein L9 | 10 | 1 | 13 | 0 |
| IPI00029046 | 7 | KIAA0152 Uncharacterized protein KIAA0152 precursor | 10 | 0 | 13 | 0 |
| IPI00060143 | 5 | FAM3D Protein FAM3D precursor | 9 | 4 | 13 | 0 |
| IPI00302927 | 18 | CCT4 T-complex protein 1 subunit delta | 8 | 1 | 13 | 0 |
| IPI00643623 | 6 | LCN2 Lipocalin 2 | 23 | 0 | 12 | 0 |
| IPI00217223 | 13 | PAICS Multifunctional protein ADE2 | 17 | 2 | 12 | 0 |
| IPI00012501 | 4 | REG4 Isoform 1 of Regenerating islet-derived protein 4 precursor | 16 | 0 | 12 | 0 |
| IPI00793443 | 14 | IPO5 RAN binding protein 5 | 15 | 1 | 12 | 0 |
| IPI00025273 | 15 | GART Isoform Long of Trifunctional purine biosynthetic protein adenosine-3 | 15 | 1 | 12 | 0 |
| IPI00646687 | 19 | POF1B Isoform 2 of Protein POF1B | 14 | 2 | 12 | 0 |
| IPI00023728 | 8 | GGH Gamma-glutamyl hydrolase precursor | 14 | 1 | 12 | 0 |
| IPI00306301 | 13 | PDHA1 Mitochondrial PDHA1 | 13 | 3 | 12 | 1 |
| IPI00006379 | 12 | NOP5/NOP58 Nucleolar protein 5 | 13 | 0 | 12 | 0 |
| IPI00171692 | 7 | ABHD11 Isoform 1 of Abhydrolase domain-containing protein 11 | 13 | 2 | 12 | 0 |
| IPI00329719 | 25 | MYO1D Isoform 1 of Myosin-Id | 12 | 4 | 12 | 0 |
| IPI00216225 | 16 | ITGA6 Isoform Alpha-6X1X2A of Integrin alpha-6 precursor | 12 | 2 | 12 | 0 |
| IPI00103994 | 15 | LARS Leucyl-tRNA synthetase, cytoplasmic | 12 | 2 | 12 | 0 |
| IPI00005198 | 8 | ILF2 Interleukin enhancer-binding factor 2 | 12 | 1 | 12 | 0 |
| IPI00783625 | 5 | SERPINB5 Serpin B5 precursor | 12 | 0 | 12 | 0 |
| IPI00789324 | 22 | JUP JUP protein | 11 | 2 | 12 | 0 |
| IPI00871852 | 21 | EIF4A1 46 kDa protein | 11 | 2 | 12 | 0 |

TABLE 3-continued

| IPI Acc. No. | nPeptides | Protein | nBigT | nSmallT | nBigP | nSmallP |
|---|---|---|---|---|---|---|
| IPI00646493 | 28 | COPA coatomer protein complex, subunit alpha isoform 1 | 11 | 2 | 12 | 0 |
| IPI00783982 | 20 | COPG Coatomer subunit gamma | 11 | 2 | 12 | 0 |
| IPI00295851 | 23 | COPB1 Coatomer subunit beta | 11 | 2 | 12 | 0 |
| IPI00007928 | 17 | PRPF8 Pre-mRNA-processing-splicing factor 8 | 11 | 1 | 12 | 0 |
| IPI00008164 | 17 | PREP Prolyl endopeptidase | 11 | 1 | 12 | 0 |
| IPI00848161 | 15 | BAT1 Isoform 1 of Spliceosome RNA helicase BAT1 | 10 | 1 | 12 | 0 |
| IPI00844578 | 26 | DHX9 ATP-dependent RNA helicase A | 10 | 2 | 12 | 0 |
| IPI00383680 | 19 | RPN2 Ribophorin II | 10 | 2 | 12 | 0 |
| IPI00011253 | 14 | RPS3 40S ribosomal protein S3 | 10 | 1 | 12 | 0 |
| IPI00300371 | 13 | SF3B3 Isoform 1 of Splicing factor 3B subunit 3 | 10 | 0 | 12 | 0 |
| IPI00893013 | 11 | XPO1 123 kDa protein | 10 | 1 | 12 | 0 |
| IPI00790342 | 11 | RPL6 60S ribosomal protein L6 | 10 | 2 | 12 | 0 |
| IPI00011511 | 7 | CECR5 Isoform 2 of Cat eye syndrome critical region protein 5 precursor | 10 | 4 | 12 | 0 |
| IPI00023542 | 4 | TMED9 transmembrane emp24 protein transport domain containing 9 | 10 | 0 | 12 | 0 |
| IPI00073772 | 8 | FBP1 Fructose-1,6-bisphosphatase 1 | 9 | 4 | 12 | 0 |
| IPI00893057 | 16 | PDXDC1 87 kDa protein | 8 | 3 | 12 | 0 |
| IPI00029012 | 15 | EIF3A Eukaryotic translation initiation factor 3 subunit A | 8 | 1 | 12 | 0 |
| IPI00003833 | 10 | MTCH2 Mitochondrial carrier homolog 2 | 8 | 2 | 12 | 0 |
| IPI00792875 | 3 | SERPINB5 14 kDa protein | 8 | 2 | 12 | 0 |
| IPI00306960 | 9 | NARS Asparaginyl-tRNA synthetase, cytoplasmic | 7 | 1 | 12 | 0 |
| IPI00012912 | 12 | CPT2 Carnitine O-palmitoyltransferase 2, mitochondrial precursor | 6 | 5 | 12 | 0 |
| IPI00219518 | 4 | ARL1 ADP-ribosylation factor-like protein 1 | 6 | 1 | 12 | 0 |
| IPI00236556 | 23 | MPO Isoform H7 of Myeloperoxidase precursor | 24 | 2 | 11 | 0 |
| IPI00218993 | 20 | HSPH1 Isoform Beta of Heat shock protein 105 kDa | 21 | 3 | 11 | 0 |
| IPI00477179 | 8 | DDX21 Isoform 2 of Nucleolar RNA helicase 2 | 17 | 1 | 11 | 0 |
| IPI00215801 | 10 | RBM39 Isoform 2 of RNA-binding protein 39 | 15 | 1 | 11 | 0 |
| IPI00554788 | 32 | KRT18 Keratin, type I cytoskeletal 18 | 13 | 2 | 11 | 0 |
| IPI00893918 | 14 | VARS Valyl-tRNA synthetase | 13 | 2 | 11 | 0 |
| IPI00877938 | 11 | IARS isoleucyl-tRNA synthetase | 13 | 1 | 11 | 0 |
| IPI00641181 | 2 | MARCKSL1 MARCKS-related protein | 13 | 0 | 11 | 0 |
| IPI00401990 | 17 | ACSL5 acyl-CoA synthetase long-chain family member 5 isoform a | 12 | 2 | 11 | 0 |

TABLE 3-continued

| IPI Acc. No. | nPeptides | Protein | nBigT | nSmallT | nBigP | nSmallP |
|---|---|---|---|---|---|---|
| IPI00396435 | 16 | DHX15 Putative pre-mRNA-splicing factor ATP-dependent RNA helicase DHX15 | 12 | 2 | 11 | 0 |
| IPI00026089 | 14 | SF3B1 Splicing factor 3B subunit 1 | 12 | 1 | 11 | 0 |
| IPI00005158 | 14 | LONP1 Lon protease homolog, mitochondrial precursor | 12 | 2 | 11 | 0 |
| IPI00479262 | 12 | EIF4G1 Isoform B of Eukaryotic translation initiation factor 4 gamma 1 | 12 | 1 | 11 | 0 |
| IPI00644431 | 12 | DDX39 ATP-dependent RNA helicase DDX39 | 11 | 2 | 11 | 0 |
| IPI00028931 | 26 | DSG2 Desmoglein-2 precursor | 11 | 4 | 11 | 0 |
| IPI00013452 | 20 | EPRS Bifunctional aminoacyl-tRNA synthetase | 11 | 3 | 11 | 0 |
| IPI00418313 | 17 | ILF3 Isoform 4 of Interleukin enhancer-binding factor 3 | 11 | 3 | 11 | 0 |
| IPI00017376 | 7 | SEC23B Protein transport protein Sec23B | 11 | 2 | 11 | 0 |
| IPI00297084 | 8 | DDOST dolichyl-diphosphooligosaccharide-protein glycosyltransferase precursor | 11 | 1 | 11 | 0 |
| IPI00411937 | 5 | NOL5A Nucleolar protein 5A | 11 | 1 | 11 | 1 |
| IPI00221091 | 5 | RPS15A 40S ribosomal protein S15a | 11 | 0 | 11 | 0 |
| IPI00015872 | 3 | TSPAN8 Tetraspanin-8 | 11 | 7 | 11 | 0 |
| IPI00784044 | 11 | MCCC2 Isoform 1 of Methylcrotonoyl-CoA carboxylase beta chain, mitochondrial precursor | 10 | 3 | 11 | 0 |
| IPI00013485 | 10 | RPS2 40S ribosomal protein S2 | 10 | 2 | 11 | 0 |
| IPI00006684 | 7 | API5 58 kDa protein | 10 | 2 | 11 | 0 |
| IPI00028004 | 5 | PSMB3 Proteasome subunit beta type-3 | 10 | 2 | 11 | 0 |
| IPI00019385 | 5 | SSR4 Translocon-associated protein subunit delta precursor | 10 | 2 | 11 | 0 |
| IPI00016608 | 5 | TMED2 Transmembrane emp24 domain-containing protein 2 precursor | 10 | 1 | 11 | 0 |
| IPI00329791 | 5 | DDX46 cDNA FLJ78679, highly similar to Homo sapiens DEAD (Asp-Glu-Ala-Asp) box polypeptide 46 (DDX46), mRNA | 10 | 0 | 11 | 0 |
| IPI00215948 | 35 | CTNNA1 Isoform 1 of Catenin alpha-1 | 9 | 3 | 11 | 0 |
| IPI00217952 | 29 | GFPT1 Isoform 1 of Glucosamine--fructose-6-phosphate aminotransferase [isomerizing] 1 | 9 | 2 | 11 | 0 |
| IPI00220834 | 18 | XRCC5 ATP-dependent DNA helicase 2 subunit 2 | 9 | 1 | 11 | 0 |
| IPI00514622 | 3 | RANBP6 Ran-binding protein 6 | 9 | 0 | 11 | 0 |
| IPI00027252 | 16 | PHB2 Prohibitin-2 | 9 | 2 | 11 | 0 |
| IPI00020672 | 13 | DPP3; BBS1 Isoform 1 of Dipeptidyl-peptidase 3 | 9 | 3 | 11 | 0 |
| IPI00017895 | 13 | GPD2 Isoform 1 of Glycerol-3-phosphate dehydrogenase, mitochondrial precursor | 9 | 2 | 11 | 0 |

TABLE 3-continued

| IPI Acc. No. | nPeptides | Protein | nBigT | nSmallT | nBigP | nSmallP |
|---|---|---|---|---|---|---|
| IPI00872756 | 10 | ASL 58 kDa protein | 9 | 4 | 11 | 0 |
| IPI00329598 | 8 | HSD17B11 Estradiol 17-beta-dehydrogenase 11 precursor | 9 | 3 | 11 | 1 |
| IPI00013296 | 6 | RPS18; LOC100130553 40S ribosomal protein S18 | 9 | 1 | 11 | 0 |
| IPI00477831 | 14 | ERAP1 Isoform 1 of Endoplasmic reticulum aminopeptidase 1 | 8 | 2 | 11 | 0 |
| IPI00303207 | 7 | ABCE1 ATP-binding cassette sub-family E member 1 | 8 | 0 | 11 | 0 |
| IPI00847192 | 6 | RPS9 protein (Fragment) | 8 | 1 | 11 | 0 |
| IPI00441344 | 5 | GLB1 Isoform 1 of Beta-galactosidase precursor | 8 | 1 | 11 | 0 |
| IPI00418497 | 3 | TIMM50 Isoform 2 of Import inner membrane translocase subunit TIM50, mitochondrial precursor | 8 | 0 | 11 | 0 |
| IPI00646182 | 40 | ATP1A1 ATPase, Na+/K+ transporting, alpha 1 polypeptide | 7 | 3 | 11 | 0 |
| IPI00009634 | 20 | SQRDL Sulfide:quinone oxidoreductase, mitochondrial precursor | 7 | 3 | 11 | 0 |
| IPI00304171 | 12 | H2AFY Isoform 2 of Core histone macro-H2A.1 | 7 | 1 | 11 | 0 |
| IPI00022887 | 6 | ERGIC1 Isoform 1 of Endoplasmic reticulum-Golgi intermediate compartment protein 1 | 7 | 5 | 11 | 0 |
| IPI00171626 | 2 | LPCAT1 1-acylglycerophosphocholine O-acyltransferase 1 | 7 | 0 | 11 | 0 |
| IPI00332371 | 20 | PFKL Isoform 1 of 6-phosphofructokinase, liver type | 6 | 2 | 11 | 0 |
| IPI00018206 | 15 | GOT2 Aspartate aminotransferase, mitochondrial precursor | 6 | 3 | 11 | 0 |
| IPI00643591 | 5 | AP1G1 AP-1 complex subunit gamma-1 | 6 | 1 | 11 | 0 |
| IPI00413860 | 2 | STRBP Isoform 2 of Spermatid perinuclear RNA-binding protein | 6 | 0 | 11 | 0 |
| IPI00014625 | 42 | CLCA1 Calcium-activated chloride channel regulator 1 precursor | 4 | 13 | 11 | 1 |
| IPI00644231 | 14 | CYFIP1 Isoform 1 of Cytoplasmic FMR1-interacting protein 1 | 4 | 2 | 11 | 0 |
| IPI00470631 | 4 | COQ9 Isoform 1 of Ubiquinone biosynthesis protein COQ9, mitochondrial precursor | 4 | 3 | 11 | 0 |
| IPI00003968 | 9 | NDUFA9 NADH dehydrogenase [ubiquinone] 1 alpha subcomplex subunit 9, mitochondrial precursor | 3 | 4 | 11 | 0 |
| IPI00221234 | 14 | ALDH7A1 Similar to Antiquitin | 2 | 5 | 11 | 0 |
| IPI00007047 | 6 | S100A8 Protein S100-A8 | 29 | 0 | 10 | 0 |
| IPI00027462 | 6 | S100A9 Protein S100-A9 | 27 | 1 | 10 | 0 |
| IPI00021700 | 8 | PCNA Proliferating cell nuclear antigen | 18 | 0 | 10 | 0 |
| IPI00297579 | 7 | CBX3; LOC653972 Chromobox protein homolog 3 | 18 | 1 | 10 | 0 |

TABLE 3-continued

| IPI Acc. No. | nPeptides | Protein | nBigT | nSmallT | nBigP | nSmallP |
|---|---|---|---|---|---|---|
| IPI00642046 | 4 | RSL1D1 RSL1D1 protein | 18 | 1 | 10 | 0 |
| IPI00002520 | 14 | SHMT2 Serine hydroxymethyltransferase, mitochondrial precursor | 17 | 2 | 10 | 0 |
| IPI00219871 | 2 | LSM8 U6 snRNA-associated Sm-like protein LSm8 | 16 | 2 | 10 | 1 |
| IPI00030275 | 17 | TRAP1 Heat shock protein 75 kDa, mitochondrial precursor | 15 | 2 | 10 | 0 |
| IPI00893035 | 8 | CAD Putative uncharacterized protein CAD | 15 | 2 | 10 | 0 |
| IPI00553131 | 9 | GALE UDP-glucose 4-epimerase | 14 | 2 | 10 | 0 |
| IPI00217477 | 3 | HMGB3 High mobility group protein B3 | 14 | 3 | 10 | 0 |
| IPI00295992 | 9 | ATAD3A Isoform 2 of ATPase family AAA domain-containing protein 3A | 13 | 2 | 10 | 0 |
| IPI00646721 | 9 | USP7 Ubiquitin carboxyl-terminal hydrolase | 13 | 9 | 10 | 0 |
| IPI00465044 | 8 | RCC2 Protein RCC2 | 13 | 1 | 10 | 0 |
| IPI00420014 | 17 | ASCC3L1 Isoform 1 of U5 small nuclear ribonucleoprotein 200 kDa helicase | 12 | 0 | 10 | 0 |
| IPI00027444 | 16 | SERPINB1 Leukocyte elastase inhibitor | 12 | 2 | 10 | 0 |
| IPI00216308 | 14 | VDAC1 Voltage-dependent anion-selective channel protein 1 | 12 | 2 | 10 | 0 |
| IPI00334175 | 14 | PTBP1 Isoform 2 of Polypyrimidine tract-binding protein 1 | 12 | 2 | 10 | 0 |
| IPI00218466 | 8 | SEC61A1 Isoform 1 of Protein transport protein Sec61 subunit alpha isoform 1 | 12 | 1 | 10 | 0 |
| IPI00019912 | 24 | HSD17B4 Peroxisomal multifunctional enzyme type 2 | 11 | 1 | 10 | 0 |
| IPI00002557 | 4 | COPG2 Coatomer subunit gamma-2 | 11 | 3 | 10 | 0 |
| IPI00449049 | 16 | PARP1 Poly [ADP-ribose] polymerase 1 | 11 | 1 | 10 | 0 |
| IPI00014238 | 10 | KARS Lysyl-tRNA synthetase | 11 | 2 | 10 | 0 |
| IPI00008530 | 10 | RPLP0 60S acidic ribosomal protein P0 | 11 | 2 | 10 | 0 |
| IPI00009950 | 8 | LMAN2 Vesicular integral-membrane protein VIP36 precursor | 11 | 2 | 10 | 0 |
| IPI00026202 | 6 | RPL18A 60S ribosomal protein L18a | 11 | 2 | 10 | 0 |
| IPI00018597 | 3 | SYK Isoform Long of Tyrosine-protein kinase SYK | 11 | 0 | 10 | 0 |
| IPI00216951 | 21 | DARS Aspartyl-tRNA synthetase, cytoplasmic | 10 | 2 | 10 | 0 |
| IPI00747497 | 14 | EEF1G 50 kDa protein | 10 | 2 | 10 | 0 |
| IPI00032038 | 14 | CPT1A Isoform 1 of Carnitine O-palmitoyltransferase I, liver isoform | 10 | 7 | 10 | 0 |
| IPI00297492 | 10 | STT3A Dolichyl-diphosphooligosaccharide--protein glycosyltransferase subunit STT3A | 10 | 1 | 10 | 0 |
| IPI00549672 | 8 | PSMD13 HSPC027 | 10 | 0 | 10 | 0 |
| IPI00221089 | 7 | RPS13 40S ribosomal protein S13 | 10 | 1 | 10 | 0 |

TABLE 3-continued

| IPI Acc. No. | nPeptides | Protein | nBigT | nSmallT | nBigP | nSmallP |
|---|---|---|---|---|---|---|
| IPI00152377 | 7 | STT3B Dolichyl-diphosphooligosaccharide--protein glycosyltransferase subunit STT3B | 10 | 0 | 10 | 0 |
| IPI00028055 | 6 | TMED10 Transmembrane emp24 domain-containing protein 10 precursor | 10 | 2 | 10 | 0 |
| IPI00032139 | 3 | SERPINB9 Serpin B9 | 10 | 1 | 10 | 0 |
| IPI00290089 | 28 | CDH17 Cadherin-17 precursor | 9 | 5 | 10 | 0 |
| IPI00797038 | 21 | PCK2 mitochondrial phosphoenolpyruvate carboxykinase 2 isoform 1 precursor | 9 | 2 | 10 | 0 |
| IPI00004860 | 18 | RARS Isoform Complexed of Arginyl-tRNA synthetase, cytoplasmic | 9 | 2 | 10 | 0 |
| IPI00026665 | 13 | QARS Glutaminyl-tRNA synthetase | 9 | 1 | 10 | 0 |
| IPI00017283 | 10 | IARS2 Isoleucyl-tRNA synthetase, mitochondrial precursor | 9 | 2 | 10 | 0 |
| IPI00030847 | 7 | TM9SF3 Transmembrane 9 superfamily member 3 precursor | 9 | 1 | 10 | 0 |
| IPI00014361 | 5 | TSTA3 GDP-L-fucose synthetase | 9 | 0 | 10 | 0 |
| IPI00008298 | 1 | DEFA5 Defensin-5 precursor | 9 | 0 | 10 | 0 |
| IPI00033022 | 15 | DNM2 Isoform 1 of Dynamin-2 | 8 | 1 | 10 | 0 |
| IPI00220847 | 19 | ITGB4 Isoform Beta-4D of Integrin beta-4 precursor | 8 | 5 | 10 | 0 |
| IPI00847318 | 15 | PKP2 plakophilin 2 isoform 2a | 8 | 5 | 10 | 0 |
| IPI00215911 | 11 | APEX1 DNA-(apurinic or apyrimidinic site) lyase | 8 | 1 | 10 | 0 |
| IPI00874185 | 10 | HIBCH 46 kDa protein | 8 | 5 | 10 | 0 |
| IPI00182533 | 6 | RPL28 60S ribosomal protein L28 | 8 | 6 | 10 | 0 |
| IPI00296909 | 6 | PARP4 Poly [ADP-ribose] polymerase 4 | 8 | 2 | 10 | 0 |
| IPI00023876 | 5 | CASP6 Isoform Alpha of Caspase-6 precursor | 8 | 3 | 10 | 0 |
| IPI00744194 | 5 | Similar to Sodium/potassium-transporting ATPase alpha-1 chain precursor | 7 | 4 | 10 | 0 |
| IPI00302925 | 28 | CCT8 59 kDa protein | 7 | 2 | 10 | 0 |
| IPI00100160 | 19 | CAND1 Isoform 1 of Cullin-associated NEDD8-dissociated protein 1 | 7 | 1 | 10 | 0 |
| IPI00337494 | 13 | SLC25A24 Isoform 1 of Calcium-binding mitochondrial carrier protein SCaMC-1 | 7 | 3 | 10 | 0 |
| IPI00747849 | 6 | ATP1B1 Isoform 1 of Sodium/potassium-transporting ATPase subunit beta-1 | 7 | 3 | 10 | 0 |
| IPI00008433 | 5 | RPS5 40S ribosomal protein S5 | 7 | 2 | 10 | 0 |
| IPI00008475 | 3 | HMGCS1 Hydroxymethylglutaryl-CoA synthase, cytoplasmic | 6 | 4 | 10 | 0 |
| IPI00337541 | 18 | NNT NAD(P) transhydrogenase, mitochondrial precursor | 6 | 2 | 10 | 0 |

TABLE 3-continued

| IPI Acc. No. | nPeptides | Protein | nBigT | nSmallT | nBigP | nSmallP |
|---|---|---|---|---|---|---|
| IPI00876999 | 12 | PRDX5 Uncharacterized protein PRDX5 (Fragment) | 6 | 2 | 10 | 0 |
| IPI00007247 | 12 | PCCB Propionyl-CoA carboxylase beta chain, mitochondrial precursor | 6 | 5 | 10 | 0 |
| IPI00032851 | 5 | COPZ1 Coatomer subunit zeta-1 | 6 | 4 | 10 | 0 |
| IPI00845474 | 5 | BAX BCL2-associated X protein isoform sigma | 6 | 2 | 10 | 0 |
| IPI00152981 | 3 | ACAD9 Acyl-CoA dehydrogenase family member 9, mitochondrial precursor | 6 | 0 | 10 | 0 |
| IPI00172656 | 1 | UBXD8 UBX domain-containing protein 8 | 6 | 1 | 10 | 0 |
| IPI00008934 | 20 | HMGCS2 Hydroxymethylglutaryl-CoA synthase, mitochondrial precursor | 5 | 12 | 10 | 0 |
| IPI00790115 | 11 | SLC25A3 cDNA FLJ90278 fis, clone NT2RP1000325, highly similar to Phosphate carrier protein, mitochondrialprecursor | 5 | 1 | 10 | 0 |
| IPI00219729 | 9 | SLC25A11 Mitochondrial 2-oxoglutarate/malate carrier protein | 5 | 4 | 10 | 0 |
| IPI00025277 | 5 | PDCD6 Programmed cell death protein 6 | 5 | 0 | 10 | 0 |
| IPI00554701 | 2 | UCRC Cytochrome b-c1 complex subunit 9 | 4 | 0 | 10 | 0 |
| IPI00008301 | 2 | DEFA6 Defensin-6 precursor | 4 | 0 | 10 | 0 |
| IPI00456969 | 88 | DYNC1H1 Cytoplasmic dynein 1 heavy chain 1 | 3 | 1 | 10 | 0 |
| IPI00220663 | 17 | HK1 Isoform 2 of Hexokinase-1 | 3 | 1 | 10 | 0 |
| IPI00719600 | 7 | CYFIP2 Isoform 2 of Cytoplasmic FMR1-interacting protein 2 | 3 | 2 | 10 | 0 |
| IPI00398758 | 5 | DCI Isoform 2 of 3,2-trans-enoyl-CoA isomerase, mitochondrial precursor | 3 | 5 | 10 | 0 |
| IPI00020510 | 3 | CISD1 CDGSH iron sulfur domain-containing protein 1 | 1 | 1 | 10 | 0 |
| IPI00294443 | 2 | CLIC5 Isoform 1 of Chloride intracellular channel protein 5 | 21 | 0 | 9 | 0 |
| IPI00031564 | 7 | C7orf24 Uncharacterized protein C7orf24 | 17 | 1 | 9 | 0 |
| IPI00871140 | 10 | NP Purine nucleoside phosphorylase | 16 | 1 | 9 | 0 |
| IPI00291510 | 9 | IMPDH2 Inosine-5'-monophosphate dehydrogenase 2 | 15 | 1 | 9 | 0 |
| IPI00792186 | 5 | ABCF1 ATP-binding cassette, sub-family F (GCN20), member 1 | 15 | 0 | 9 | 0 |
| IPI00029744 | 4 | SSBP1 Single-stranded DNA-binding protein, mitochondrial precursor | 15 | 3 | 9 | 0 |
| IPI00166680 | 2 | MINK1 Isoform 3 of Misshapen-like kinase 1 | 15 | 1 | 9 | 0 |
| IPI00152441 | 3 | HM13 Isoform 1 of Minor histocompatibility antigen H13 | 14 | 0 | 9 | 0 |
| IPI00303318 | 8 | FAM49B Protein FAM49B | 13 | 2 | 9 | 0 |

TABLE 3-continued

| IPI Acc. No. | nPeptides | Protein | nBigT | nSmallT | nBigP | nSmallP |
|---|---|---|---|---|---|---|
| IPI00643166 | 4 | PGM3 Isoform 2 of Phosphoacetylglucosamine mutase | 13 | 0 | 9 | 0 |
| IPI00641950 | 14 | GNB2L1 Lung cancer oncogene 7 | 12 | 2 | 9 | 0 |
| IPI00293464 | 11 | DDB1 DNA damage-binding protein 1 | 12 | 1 | 9 | 0 |
| IPI00783097 | 10 | GARS Glycyl-tRNA synthetase | 12 | 2 | 9 | 0 |
| IPI00219617 | 4 | PRPS2 Isoform 1 of Ribose-phosphate pyrophosphokinase 2 | 12 | 1 | 9 | 0 |
| IPI00018415 | 7 | TM9SF2 Transmembrane 9 superfamily member 2 precursor | 12 | 1 | 9 | 0 |
| IPI00550032 | 4 | LOC653232; RPL15 Ribosomal protein L15 pseudogene 3 | 12 | 0 | 9 | 0 |
| IPI00013933 | 65 | DSP Isoform DPI of Desmoplakin | 11 | 2 | 9 | 0 |
| IPI00009032 | 15 | SSB Lupus La protein | 11 | 1 | 9 | 0 |
| IPI00792100 | 10 | C14orf166 CLE | 11 | 1 | 9 | 0 |
| IPI00010491 | 3 | RAB27B Ras-related protein Rab-27B | 11 | 2 | 9 | 0 |
| IPI00302850 | 3 | SNRPD1 Small nuclear ribonucleoprotein Sm D1 | 11 | 1 | 9 | 0 |
| IPI00644712 | 20 | XRCC6 ATP-dependent DNA helicase 2 subunit 1 | 10 | 1 | 9 | 0 |
| IPI00025874 | 20 | RPN1 Dolichyl-diphosphooligosaccharide--protein glycosyltransferase 67 kDa subunit precursor | 10 | 2 | 9 | 0 |
| IPI00744889 | 9 | CDH1 E-cadherin | 10 | 2 | 9 | 0 |
| IPI00002372 | 8 | ABCD3 Isoform 1 of ATP-binding cassette sub-family D member 3 | 10 | 4 | 9 | 0 |
| IPI00289601 | 4 | HDAC2 histone deacetylase 2 | 10 | 2 | 9 | 0 |
| IPI00328867 | 5 | SRC Isoform 2 of Proto-oncogene tyrosine-protein kinase Src | 10 | 0 | 9 | 0 |
| IPI00872474 | 3 | LYN LYN protein (Fragment) | 10 | 0 | 9 | 0 |
| IPI00031804 | 8 | VDAC3 Isoform 1 of Voltage-dependent anion-selective channel protein 3 | 10 | 2 | 9 | 0 |
| IPI00654777 | 7 | EIF3F Eukaryotic translation initiation factor 3 subunit 5 | 10 | 0 | 9 | 0 |
| IPI00440703 | 6 | GSTK1 GSTK1 protein | 10 | 3 | 9 | 0 |
| IPI00885106 | 3 | TM9SF4 Isoform 2 of Transmembrane 9 superfamily member 4 precursor | 10 | 0 | 9 | 0 |
| IPI00029267 | 2 | SNRPB2 U2 small nuclear ribonucleoprotein B" | 10 | 2 | 9 | 0 |
| IPI00414717 | 12 | GLG1 golgi apparatus protein 1 | 9 | 1 | 9 | 0 |
| IPI00216293 | 11 | TST Thiosulfate sulfurtransferase | 9 | 6 | 9 | 0 |
| IPI00029629 | 11 | TRIM25 Tripartite motif-containing protein 25 | 9 | 2 | 9 | 0 |
| IPI00219147 | 4 | CSDA Isoform 2 of DNA-binding protein A | 9 | 1 | 9 | 0 |
| IPI00219953 | 9 | CMPK1 cytidine monophosphate (UMP-CMP) kinase 1, cytosolic | 9 | 3 | 9 | 0 |
| IPI00827508 | 7 | RPL10A 25 kDa protein | 9 | 2 | 9 | 0 |
| IPI00014053 | 6 | TOMM40 Isoform 1 of Mitochondrial import | 9 | 0 | 9 | 0 |

TABLE 3-continued

| IPI Acc. No. | nPeptides | Protein | nBigT | nSmallT | nBigP | nSmallP |
|---|---|---|---|---|---|---|
| | | receptor subunit TOM40 homolog | | | | |
| IPI00299048 | 20 | IQGAP2 Isoform 1 of Ras GTPase-activating-like protein IQGAP2 | 8 | 2 | 9 | 0 |
| IPI00242956 | 70 | FCGBP IgGFc-binding protein precursor | 8 | 9 | 9 | 2 |
| IPI00291467 | 18 | SLC25A6 ADP/ATP translocase 3 | 8 | 2 | 9 | 0 |
| IPI00290566 | 22 | TCP1 T-complex protein 1 subunit alpha | 8 | 2 | 9 | 0 |
| IPI00470502 | 14 | PPA2 Isoform 2 of Inorganic pyrophosphatase 2, mitochondrial precursor | 8 | 1 | 9 | 0 |
| IPI00003482 | 12 | DECR1 2,4-dienoyl-CoA reductase, mitochondrial precursor | 8 | 4 | 9 | 0 |
| IPI00456750 | 10 | FAM129B Niban-like protein 1 | 8 | 3 | 9 | 0 |
| IPI00303158 | 10 | CMAS Isoform 1 of N-acylneuraminate cytidylyltransferase | 8 | 2 | 9 | 0 |
| IPI00001466 | 8 | EML4 Echinoderm microtubule-associated protein-like 4 | 8 | 2 | 9 | 0 |
| IPI00105598 | 7 | PSMD11 Proteasome 26S non-ATPase subunit 11 variant (Fragment) | 8 | 1 | 9 | 0 |
| IPI00011916 | 4 | JTV1 Multisynthetase complex auxiliary component p38 | 8 | 1 | 9 | 0 |
| IPI00100460 | 3 | DARS2 Aspartyl-tRNA synthetase, mitochondrial precursor | 8 | 1 | 9 | 0 |
| IPI00030706 | 3 | AHSA1 Activator of 90 kDa heat shock protein ATPase homolog 1 | 8 | 1 | 9 | 0 |
| IPI00874145 | 3 | DKC1 Uncharacterized protein DKC1 (Fragment) | 8 | 0 | 9 | 0 |
| IPI00177817 | 24 | ATP2A2 Isoform SERCA2A of Sarcoplasmic/endoplasmic reticulum calcium ATPase 2 | 7 | 2 | 9 | 0 |
| IPI00409717 | 13 | EIF4A2 Isoform 2 of Eukaryotic initiation factor 4A-II | 7 | 1 | 9 | 0 |
| IPI00719752 | 15 | EIF3B Isoform 2 of Eukaryotic translation initiation factor 3 subunit B | 7 | 2 | 9 | 0 |
| IPI00001091 | 12 | AFG3L2 AFG3-like protein 2 | 7 | 7 | 9 | 0 |
| IPI00026530 | 10 | LMAN1 Protein ERGIC-53 precursor | 7 | 2 | 9 | 0 |
| IPI00007676 | 9 | HSD17B12 Estradiol 17-beta-dehydrogenase 12 | 7 | 2 | 9 | 0 |
| IPI00291930 | 8 | CLINT1 Isoform 1 of Clathrin interactor 1 | 7 | 2 | 9 | 0 |
| IPI00293853 | 7 | GPA33 Cell surface A33 antigen precursor | 7 | 6 | 9 | 0 |
| IPI00797738 | 5 | COX6B1 12 kDa protein | 7 | 2 | 9 | 0 |
| IPI00885058 | 3 | MBOAT7 Isoform 2 of Membrane-bound O-acyltransferase domain-containing protein 7 | 7 | 5 | 9 | 0 |
| IPI00455383 | 68 | CLTC Isoform 2 of Clathrin heavy chain 1 | 6 | 2 | 9 | 0 |
| IPI00102864 | 12 | HK2 Hexokinase-2 | 6 | 2 | 9 | 0 |
| IPI00018931 | 16 | VPS35 Vacuolar protein sorting-associated protein 35 | 6 | 0 | 9 | 1 |

TABLE 3-continued

| IPI Acc. No. | nPeptides | Protein | nBigT | nSmallT | nBigP | nSmallP |
|---|---|---|---|---|---|---|
| IPI00010157 | 8 | MAT2A S-adenosylmethionine synthetase isoform type-2 | 6 | 1 | 9 | 1 |
| IPI00328715 | 6 | MTDH Protein LYRIC | 6 | 1 | 9 | 0 |
| IPI00171573 | 5 | CCDC109A Isoform 1 of Coiled-coil domain-containing protein 109A | 6 | 0 | 9 | 0 |
| IPI00411426 | 5 | VPS26A Vacuolar protein sorting-associated protein 26A | 6 | 1 | 9 | 0 |
| IPI00017767 | 2 | MGST2 Microsomal glutathione S-transferase 2 | 6 | 2 | 9 | 0 |
| IPI00556311 | 2 | DUOX2 Dual oxidase 2 variant (Fragment) | 6 | 0 | 9 | 0 |
| IPI00011201 | 10 | ME2 NAD-dependent malic enzyme, mitochondrial precursor | 5 | 3 | 9 | 0 |
| IPI00329672 | 5 | MYO1E Myosin-Ie | 5 | 1 | 9 | 0 |
| IPI00020928 | 4 | TFAM Transcription factor A, mitochondrial precursor | 5 | 4 | 9 | 0 |
| IPI00009104 | 12 | RUVBL2 RuvB-like 2 | 4 | 0 | 9 | 0 |
| IPI00744115 | 12 | PCCA propionyl-Coenzyme A carboxylase, alpha polypeptide precursor | 4 | 3 | 9 | 0 |
| IPI00219029 | 10 | GOT1 Aspartate aminotransferase, cytoplasmic | 4 | 3 | 9 | 0 |
| IPI00029264 | 7 | CYC1 Cytochrome c1, heme protein, mitochondrial precursor | 4 | 2 | 9 | 0 |
| IPI00027448 | 5 | ATP5L ATP synthase subunit g, mitochondrial | 4 | 2 | 9 | 0 |
| IPI00215920 | 2 | ARF6 ADP-ribosylation factor 6 | 4 | 0 | 9 | 0 |
| IPI00220244 | 1 | TRIM23 Isoform Beta of GTP-binding protein ARD-1 | 4 | 0 | 9 | 0 |
| IPI00006674 | 7 | ABCC3 Isoform 3 of Canalicular multispecific organic anion transporter 2 | 3 | 4 | 9 | 0 |
| IPI00843876 | 7 | TNPO1 Transportin-1 | 3 | 0 | 9 | 0 |
| IPI00023001 | 3 | C3orf28 E2-induced gene 5 protein | 3 | 5 | 9 | 0 |
| IPI00019038 | 4 | LYZ Lysozyme C precursor | 17 | 2 | 8 | 0 |
| IPI00022462 | 14 | TFRC Transferrin receptor protein 1 | 16 | 0 | 8 | 0 |
| IPI00554722 | 7 | LOC442497; SLC3A2 solute carrier family 3 (activators of dibasic and neutral amino acid transport), member 2 isoform e | 16 | 1 | 8 | 0 |
| IPI00010341 | 6 | PRG2 Bone marrow proteoglycan precursor | 16 | 7 | 8 | 0 |
| IPI00010320 | 2 | CBX1 Chromobox protein homolog 1 | 16 | 1 | 8 | 0 |
| IPI00006690 | 27 | EPX Eosinophil peroxidase precursor | 15 | 8 | 8 | 0 |
| IPI00099110 | 4 | DMBT1 Isoform 1 of Deleted in malignant brain tumors 1 protein precursor | 15 | 0 | 8 | 1 |
| IPI00008240 | 8 | MARS Methionyl-tRNA synthetase, cytoplasmic | 14 | 1 | 8 | 0 |
| IPI00414676 | 41 | HSP90AB1 Heat shock protein HSP 90-beta | 13 | 2 | 8 | 0 |
| IPI00140420 | 27 | SND1 Staphylococcal nuclease domain-containing protein 1 | 13 | 2 | 8 | 0 |
| IPI00807557 | 14 | PA2G4 PA2G4 protein (Fragment) | 13 | 2 | 8 | 0 |

TABLE 3-continued

| IPI Acc. No. | nPeptides | Protein | nBigT | nSmallT | nBigP | nSmallP |
|---|---|---|---|---|---|---|
| IPI00215879 | 6 | SFRS6 Isoform SRP55-3 of Splicing factor, arginine/serine-rich 6 | 13 | 1 | 8 | 0 |
| IPI00301936 | 8 | ELAVL1 ELAV-like protein 1 | 13 | 1 | 8 | 0 |
| IPI00025039 | 7 | FBL rRNA 2'-O-methyltransferase fibrillarin | 13 | 2 | 8 | 0 |
| IPI00025427 | 4 | RNASE3 Eosinophil cationic protein precursor | 13 | 6 | 8 | 1 |
| IPI00873179 | 4 | CLC Uncharacterized protein CLC (Fragment) | 13 | 6 | 8 | 0 |
| IPI00655650 | 3 | LOC728937; RPS26 40S ribosomal protein S26 | 13 | 1 | 8 | 0 |
| IPI00888987 | 2 | LOC345630 similar to hCG1641252 | 13 | 1 | 8 | 0 |
| IPI00026952 | 13 | PKP3 Plakophilin-3 | 12 | 1 | 8 | 0 |
| IPI00009328 | 12 | EIF4A3 Eukaryotic initiation factor 4A-III | 12 | 2 | 8 | 0 |
| IPI00759824 | 6 | ANP32B Isoform 2 of Acidic leucine-rich nuclear phosphoprotein 32 family member B | 12 | 2 | 8 | 1 |
| IPI00029048 | 9 | TTLL12 Tubulin--tyrosine ligase-like protein 12 | 12 | 3 | 8 | 0 |
| IPI00029764 | 6 | SF3A3 Splicing factor 3A subunit 3 | 12 | 1 | 8 | 0 |
| IPI00303954 | 4 | CYB5B cytochrome b5 outer mitochondrial membrane precursor | 12 | 2 | 8 | 0 |
| IPI00007402 | 4 | IPO7 Importin-7 | 12 | 0 | 8 | 0 |
| IPI00012382 | 2 | SNRPA U1 small nuclear ribonucleoprotein A | 12 | 2 | 8 | 0 |
| IPI00446377 | 2 | ENG cDNA FLJ41744 fis, clone HSYRA2005496, highly similar to ENDOGLIN | 12 | 0 | 8 | 0 |
| IPI00186290 | 45 | EEF2 Elongation factor 2 | 11 | 2 | 8 | 0 |
| IPI00304596 | 18 | NONO Non-POU domain-containing octamer-binding protein | 11 | 2 | 8 | 0 |
| IPI00220219 | 17 | COPB2 Coatomer subunit beta' | 11 | 2 | 8 | 0 |
| IPI00003918 | 16 | RPL4 60S ribosomal protein L4 | 11 | 2 | 8 | 0 |
| IPI00020632 | 14 | ASS1 Argininosuccinate synthase | 11 | 3 | 8 | 0 |
| IPI00396661 | 5 | CYP2S1 Isoform 1 of Cytochrome P450 2S1 | 11 | 0 | 8 | 0 |
| IPI00005589 | 5 | hCG__18290 Uncharacterized protein ENSP00000275524 | 11 | 1 | 8 | 0 |
| IPI00178440 | 4 | EEF1B2 Elongation factor 1-beta | 11 | 1 | 8 | 0 |
| IPI00894416 | 4 | BZW2 47 kDa protein | 11 | 0 | 8 | 0 |
| IPI00793862 | 3 | SHMT1 Serine hydroxymethyltransferase | 11 | 0 | 8 | 0 |
| IPI00029750 | 3 | RPS24 Isoform 1 of 40S ribosomal protein S24 | 11 | 1 | 8 | 0 |
| IPI00873680 | 3 | EIF4E Uncharacterized protein EIF4E (Fragment) | 11 | 2 | 8 | 0 |
| IPI00784154 | 45 | HSPD1 60 kDa heat shock protein, mitochondrial precursor | 10 | 3 | 8 | 0 |
| IPI00219005 | 15 | FKBP4 FK506-binding protein 4 | 10 | 2 | 8 | 0 |
| IPI00003519 | 13 | EFTUD2 116 kDa U5 small nuclear ribonucleoprotein component | 10 | 1 | 8 | 0 |
| IPI00013774 | 4 | HDAC1 Histone deacetylase 1 | 10 | 3 | 8 | 0 |

TABLE 3-continued

| IPI Acc. No. | nPeptides | Protein | nBigT | nSmallT | nBigP | nSmallP |
|---|---|---|---|---|---|---|
| IPI00428967 | 6 | TICAM2; TMED7 Toll-like receptor adapter molecule 2 | 10 | 1 | 8 | 0 |
| IPI00219445 | 5 | PSME3 Isoform 2 of Proteasome activator complex subunit 3 | 10 | 1 | 8 | 0 |
| IPI00029731 | 4 | RPL35A 60S ribosomal protein L35a | 10 | 2 | 8 | 0 |
| IPI00025329 | 3 | RPL19 60S ribosomal protein L19 | 10 | 4 | 8 | 0 |
| IPI00455757 | 3 | Similar to 60S ribosomal protein L35 | 10 | 2 | 8 | 0 |
| IPI00009407 | 2 | DAD1 Dolichyl-diphosphooligosaccharide--protein glycosyltransferase subunit DAD1 | 10 | 0 | 8 | 0 |
| IPI00010951 | 33 | EPPK1 Epiplakin | 9 | 1 | 8 | 0 |
| IPI00658109 | 16 | LOC100133623; CKMT1B; CKMT1A Creatine kinase, ubiquitous mitochondrial precursor | 9 | 9 | 8 | 0 |
| IPI00293721 | 9 | AKR7A3 Aflatoxin B1 aldehyde reductase member 3 | 9 | 4 | 8 | 0 |
| IPI00642211 | 15 | RNPEP Aminopeptidase B | 9 | 2 | 8 | 0 |
| IPI00299608 | 14 | PSMD1 Isoform 1 of 26S proteasome non-ATPase regulatory subunit 1 | 9 | 2 | 8 | 0 |
| IPI00017726 | 13 | HSD17B10 Isoform 1 of 3-hydroxyacyl-CoA dehydrogenase type-2 | 9 | 2 | 8 | 0 |
| IPI00479722 | 13 | PSME1 Proteasome activator complex subunit 1 | 9 | 1 | 8 | 0 |
| IPI00009750 | 12 | LGALS4 Galectin-4 | 9 | 6 | 8 | 0 |
| IPI00334190 | 10 | STOML2 Stomatin-like protein 2 | 9 | 2 | 8 | 0 |
| IPI00853220 | 10 | SEC31A Isoform 6 of Protein transport protein Sec31A | 9 | 2 | 8 | 0 |
| IPI00030131 | 9 | TMPO Isoform Beta of Lamina-associated polypeptide 2, isoforms beta/gamma | 9 | 2 | 8 | 0 |
| IPI00640155 | 8 | PSMB8 proteasome beta 8 subunit isoform E2 proprotein | 9 | 3 | 8 | 0 |
| IPI00221222 | 7 | SUB1 Activated RNA polymerase II transcriptional coactivator p15 | 9 | 2 | 8 | 0 |
| IPI00465361 | 6 | RPL13 60S ribosomal protein L13 | 9 | 2 | 8 | 0 |
| IPI00005537 | 6 | MRPL12 39S ribosomal protein L12, mitochondrial precursor | 9 | 4 | 8 | 1 |
| IPI00293564 | 5 | HMGCL Hydroxymethylglutaryl-CoA lyase, mitochondrial precursor | 9 | 3 | 8 | 0 |
| IPI00785096 | 4 | BZW1 Isoform 1 of Basic leucine zipper and W2 domain-containing protein 1 | 9 | 1 | 8 | 0 |
| IPI00100656 | 4 | GPSN2 Isoform 1 of Synaptic glycoprotein SC2 | 9 | 0 | 8 | 1 |
| IPI00009922 | 4 | C14orf156 SRA stem-loop-interacting RNA-binding protein, mitochondrial precursor | 9 | 1 | 8 | 0 |
| IPI00007188 | 17 | SLC25A5 ADP/ATP translocase 2 | 8 | 2 | 8 | 0 |

TABLE 3-continued

| IPI Acc. No. | nPeptides | Protein | nBigT | nSmallT | nBigP | nSmallP |
|---|---|---|---|---|---|---|
| IPI00017375 | 9 | SEC23A Protein transport protein Sec23A | 8 | 1 | 8 | 0 |
| IPI00873762 | 3 | TAF15 65 kDa protein | 8 | 0 | 8 | 0 |
| IPI00885213 | 7 | TXNRD1 Isoform 6 of Thioredoxin reductase 1, cytoplasmic | 8 | 1 | 8 | 3 |
| IPI00329352 | 6 | NOMO1; NOMO3 Nodal modulator 1 precursor | 8 | 3 | 8 | 0 |
| IPI00029628 | 3 | RCN2 Reticulocalbin-2 precursor | 8 | 0 | 8 | 0 |
| IPI00797230 | 2 | RPL8 32 kDa protein | 8 | 3 | 8 | 0 |
| IPI00220835 | 2 | SEC61B Protein transport protein Sec61 subunit beta | 8 | 2 | 8 | 0 |
| IPI00784366 | 13 | AP2B1 Isoform 2 of AP-2 complex subunit beta-1 | 7 | 0 | 8 | 0 |
| IPI00220994 | 5 | H2AFY2 Core histone macro-H2A.2 | 7 | 1 | 8 | 0 |
| IPI00012268 | 12 | PSMD2 26S proteasome non-ATPase regulatory subunit 2 | 7 | 2 | 8 | 0 |
| IPI00013068 | 12 | EIF3E Eukaryotic translation initiation factor 3 subunit E | 7 | 0 | 8 | 0 |
| IPI00472054 | 11 | FAM120A Isoform A of Constitutive coactivator of PPAR-gamma-like protein 1 | 7 | 4 | 8 | 0 |
| IPI00383046 | 6 | CMBL Carboxymethylenebutenolidase homolog | 7 | 8 | 8 | 1 |
| IPI00031820 | 5 | FARSA Phenylalanyl-tRNA synthetase alpha chain | 7 | 2 | 8 | 0 |
| IPI00004845 | 4 | NIPSNAP3A Protein NipSnap homolog 3A | 7 | 3 | 8 | 0 |
| IPI00018465 | 24 | CCT7 T-complex protein 1 subunit eta | 6 | 2 | 8 | 0 |
| IPI00027442 | 19 | AARS Alanyl-tRNA synthetase, cytoplasmic | 6 | 3 | 8 | 0 |
| IPI00017592 | 9 | LETM1 Leucine zipper-EF-hand-containing transmembrane protein 1, mitochondrial precursor | 6 | 2 | 8 | 0 |
| IPI00300050 | 8 | HSD11B2 Corticosteroid 11-beta-dehydrogenase isozyme 2 | 6 | 13 | 8 | 2 |
| IPI00306516 | 8 | TIMM44 Import inner membrane translocase subunit TIM44, mitochondrial precursor | 6 | 1 | 8 | 0 |
| IPI00293267 | 5 | LGALS9 Isoform Short of Galectin-9 | 6 | 3 | 8 | 0 |
| IPI00021258 | 7 | ARFIP1 Isoform B of Arfaptin-1 | 6 | 2 | 8 | 1 |
| IPI00303568 | 5 | PTGES2 Prostaglandin E synthase 2 | 6 | 1 | 8 | 0 |
| IPI00003870 | 5 | CLPP Putative ATP-dependent Clp protease proteolytic subunit, mitochondrial precursor | 6 | 2 | 8 | 0 |
| IPI00843910 | 4 | FUCA1 Tissue alpha-L-fucosidase precursor | 6 | 16 | 8 | 4 |
| IPI00452747 | 4 | LOC653566 Similar to Signal peptidase complex subunit 2 | 6 | 1 | 8 | 0 |
| IPI00304612 | 2 | RPL13A 60S ribosomal protein L13a | 6 | 1 | 8 | 0 |
| IPI00871366 | 9 | RAB1B Small GTP-binding protein | 5 | 1 | 8 | 0 |
| IPI00006451 | 9 | NSF Vesicle-fusing ATPase | 5 | 0 | 8 | 1 |

TABLE 3-continued

| IPI Acc. No. | nPeptides | Protein | nBigT | nSmallT | nBigP | nSmallP |
|---|---|---|---|---|---|---|
| IPI00025239 | 6 | NDUFS2 NADH dehydrogenase [ubiquinone] iron-sulfur protein 2, mitochondrial precursor | 5 | 2 | 8 | 0 |
| IPI00550644 | 5 | LL22NC03-5H6.5 UPF0530 protein | 5 | 3 | 8 | 0 |
| IPI00016077 | 3 | GBAS Protein NipSnap homolog 2 | 5 | 6 | 8 | 0 |
| IPI00031534 | 2 | ST6GALNAC1 Alpha-N-acetylgalactosaminide alpha-2,6-sialyltransferase 1 | 5 | 5 | 8 | 0 |
| IPI00025796 | 9 | NDUFS3 NADH dehydrogenase [ubiquinone] iron-sulfur protein 3, mitochondrial precursor | 4 | 1 | 8 | 0 |
| IPI00794899 | 3 | 37 kDa protein | 4 | 4 | 8 | 0 |
| IPI00029054 | 4 | NT5C2 Cytosolic purine 5'-nucleotidase | 4 | 0 | 8 | 0 |
| IPI00002255 | 4 | LRBA Lipopolysaccharide-responsive and beige-like anchor protein | 4 | 3 | 8 | 0 |
| IPI00253050 | 2 | L1TD1 LINE-1 type transposase domain-containing protein 1 | 4 | 0 | 8 | 0 |
| IPI00465179 | 8 | PFKM cDNA FLJ44241 fis, clone THYMU3008436, highly similar to 6-phosphofructokinase, muscle type | 3 | 1 | 8 | 0 |
| IPI00294187 | 9 | PADI2 Protein-arginine deiminase type-2 | 3 | 13 | 8 | 2 |
| IPI00102581 | 7 | SULT1B1 Sulfotransferase family cytosolic 1B member 1 | 3 | 9 | 8 | 0 |
| IPI00023647 | 4 | UBA6 Isoform 1 of Ubiquitin-like modifier-activating enzyme 6 | 3 | 2 | 8 | 0 |
| IPI00030320 | 5 | DDX6 Probable ATP-dependent RNA helicase DDX6 | 2 | 1 | 8 | 0 |
| IPI00220740 | 8 | NPM1 Isoform 2 of Nucleophosmin | 17 | 2 | 7 | 0 |
| IPI00386755 | 7 | ERO1L ERO1-like protein alpha precursor | 17 | 1 | 7 | 1 |
| IPI00295542 | 13 | NUCB1 Nucleobindin-1 precursor | 15 | 3 | 7 | 0 |
| IPI00293655 | 13 | DDX1 ATP-dependent RNA helicase DDX1 | 14 | 1 | 7 | 0 |
| IPI00007084 | 11 | SLC25A13 Mitochondrial aspartate-glutamate carrier protein | 14 | 2 | 7 | 0 |
| IPI00007427 | 8 | AGR2 AGR2 | 14 | 5 | 7 | 0 |
| IPI00152409 | 7 | AGR3 Anterior gradient protein 3 homolog precursor | 14 | 4 | 7 | 0 |
| IPI00004573 | 27 | PIGR Polymeric immunoglobulin receptor precursor | 13 | 5 | 7 | 1 |
| IPI00021290 | 15 | ACLY ATP-citrate synthase | 13 | 1 | 7 | 0 |
| IPI00456919 | 14 | HUWE1 Isoform 1 of E3 ubiquitin-protein ligase HUWE1 | 13 | 0 | 7 | 0 |
| IPI00015018 | 13 | PPA1 Inorganic pyrophosphatase | 13 | 2 | 7 | 0 |
| IPI00218493 | 8 | HPRT1 Hypoxanthine-guanine phosphoribosyltransferase | 13 | 1 | 7 | 0 |
| IPI00876962 | 6 | INF2 Isoform 2 of Inverted formin-2 | 13 | 2 | 7 | 0 |
| IPI00479997 | 5 | STMN1 Stathmin | 13 | 1 | 7 | 0 |
| IPI00791426 | 5 | RPL24 13 kDa protein | 13 | 1 | 7 | 0 |

TABLE 3-continued

| IPI Acc. No. | nPeptides | Protein | nBigT | nSmallT | nBigP | nSmallP |
|---|---|---|---|---|---|---|
| IPI00215719 | 4 | RPL18 60S ribosomal protein L18 | 13 | 1 | 7 | 0 |
| IPI00334713 | 9 | HNRNPAB Isoform 3 of Heterogeneous nuclear ribonucleoprotein A/B | 12 | 3 | 7 | 0 |
| IPI00012442 | 8 | G3BP1 Ras GTPase-activating protein-binding protein 1 | 12 | 0 | 7 | 0 |
| IPI00301311 | 8 | SET Isoform 2 of Protein SET | 12 | 2 | 7 | 0 |
| IPI00011913 | 6 | HNRNPA0 Heterogeneous nuclear ribonucleoprotein A0 | 12 | 2 | 7 | 0 |
| IPI00413673 | 5 | BCLAF1 Isoform 4 of Bcl-2-associated transcription factor 1 | 12 | 3 | 7 | 0 |
| IPI00059292 | 4 | MAGOHB Protein mago nashi homolog 2 | 12 | 0 | 7 | 1 |
| IPI00409635 | 3 | FAM62B Isoform 2 of Extended synaptotagmin-2 | 12 | 0 | 7 | 0 |
| IPI00555747 | 9 | PABPC4 Isoform 2 of Polyadenylate-binding protein 4 | 11 | 2 | 7 | 0 |
| IPI00604620 | 25 | NCL Isoform 1 of Nucleolin | 11 | 3 | 7 | 0 |
| IPI00000877 | 24 | HYOU1 Hypoxia up-regulated protein 1 precursor | 11 | 2 | 7 | 0 |
| IPI00141318 | 24 | CKAP4 Isoform 1 of Cytoskeleton-associated protein 4 | 11 | 2 | 7 | 0 |
| IPI00217468 | 10 | HIST1H1B Histone H1.5 | 11 | 2 | 7 | 0 |
| IPI00797148 | 15 | HNRNPA1 HNRPA1 protein | 11 | 2 | 7 | 0 |
| IPI00438229 | 15 | TRIM28 Isoform 1 of Transcription intermediary factor 1-beta | 11 | 1 | 7 | 0 |
| IPI00031812 | 6 | YBX1 Nuclease-sensitive element-binding protein 1 | 11 | 2 | 7 | 0 |
| IPI00221092 | 8 | RPS16 40S ribosomal protein S16 | 11 | 2 | 7 | 0 |
| IPI00396321 | 8 | LRRC59 Leucine-rich repeat-containing protein 59 | 11 | 3 | 7 | 0 |
| IPI00009659 | 4 | C20orf77 Uncharacterized protein C20orf77 | 11 | 1 | 7 | 0 |
| IPI00157790 | 4 | KIAA0368 KIAA0368 protein | 11 | 0 | 7 | 0 |
| IPI00794978 | 2 | MRPL47 MRPL47 protein | 11 | 1 | 7 | 0 |
| IPI00004524 | 2 | GCA Grancalcin | 11 | 0 | 7 | 0 |
| IPI00217437 | 7 | TTBK2 Tau-tubulin kinase | 10 | 5 | 7 | 0 |
| IPI00880104 | 3 | KRT74 59 kDa protein | 10 | 3 | 7 | 0 |
| IPI00550661 | 3 | KRT13 Isoform 2 of Keratin, type I cytoskeletal 13 | 10 | 5 | 7 | 0 |
| IPI00382470 | 44 | HSP90AA1 heat shock protein 90 kDa alpha (cytosolic), class A member 1 isoform 1 | 10 | 1 | 7 | 0 |
| IPI00651677 | 24 | DDX17 Isoform 2 of Probable ATP-dependent RNA helicase DDX17 | 10 | 2 | 7 | 0 |
| IPI00017617 | 20 | DDX5 Probable ATP-dependent RNA helicase DDX5 | 10 | 3 | 7 | 0 |
| IPI00010471 | 29 | LCP1 Plastin-2 | 10 | 1 | 7 | 1 |

TABLE 3-continued

| IPI Acc. No. | nPeptides | Protein | nBigT | nSmallT | nBigP | nSmallP |
|---|---|---|---|---|---|---|
| IPI00007765 | 34 | HSPA9 Stress-70 protein, mitochondrial precursor | 10 | 2 | 7 | 0 |
| IPI00298520 | 16 | ARCN1 Putative uncharacterized protein DKFZp686M09245 | 10 | 2 | 7 | 0 |
| IPI00217030 | 14 | RPS4X 40S ribosomal protein S4, X isoform | 10 | 2 | 7 | 0 |
| IPI00000494 | 13 | RPL5 60S ribosomal protein L5 | 10 | 2 | 7 | 0 |
| IPI00012585 | 10 | HEXB Beta-hexosaminidase subunit beta precursor | 10 | 3 | 7 | 0 |
| IPI00026105 | 10 | SCP2 Isoform SCPx of Non-specific lipid-transfer protein | 10 | 4 | 7 | 0 |
| IPI00008455 | 8 | MYO6 Isoform 2 of Myosin-VI | 10 | 1 | 7 | 0 |
| IPI00399183 | 7 | APOB48R Isoform 1 of Apolipoprotein B-100 receptor | 10 | 5 | 7 | 1 |
| IPI00744364 | 6 | SFRS7 Uncharacterized protein SFRS7 | 10 | 4 | 7 | 0 |
| IPI00465132 | 5 | COPE Coatomer subunit epsilon | 10 | 1 | 7 | 0 |
| IPI00607584 | 5 | MYBBP1A Isoform 2 of Myb-binding protein 1A | 10 | 0 | 7 | 0 |
| IPI00787692 | 4 | LOC650788 similar to 40S ribosomal protein S28 | 10 | 2 | 7 | 0 |
| IPI00014808 | 3 | PAFAH1B3 Platelet-activating factor acetylhydrolase IB subunit gamma | 10 | 0 | 7 | 0 |
| IPI00019449 | 3 | LOC100133484; HLA-DQB1; HLA-DRB1; hCG_1998957; HLA-DRB4; LOC100133811; LOC100133583; HLA-DRB3; HLA-DRB5; HLA-DQB2; HLA-DRB2; ZNF749; LOC100133661; RNASE2 Non-secretory ribonuclease precursor | 10 | 9 | 7 | 1 |
| IPI00217975 | 31 | LMNB1 Lamin-B1 | 9 | 3 | 7 | 1 |
| IPI00455599 | 12 | HSP90AB2P Heat shock protein 90Bb | 9 | 2 | 7 | 0 |
| IPI00853059 | 14 | FUBP1 Isoform 2 of Far upstream element-binding protein 1 | 9 | 1 | 7 | 0 |
| IPI00218852 | 30 | VIL1 Villin-1 | 9 | 3 | 7 | 0 |
| IPI00789551 | 15 | MATR3 Uncharacterized protein MATR3 | 9 | 1 | 7 | 0 |
| IPI00410693 | 11 | SERBP1 Isoform 1 of Plasminogen activator inhibitor 1 RNA-binding protein | 9 | 4 | 7 | 0 |
| IPI00646899 | 10 | RPL10 Ribosomal protein L10 | 9 | 2 | 7 | 0 |
| IPI00220362 | 9 | HSPE1 10 kDa heat shock protein, mitochondrial | 9 | 3 | 7 | 0 |
| IPI00299573 | 9 | RPL7A 60S ribosomal protein L7a | 9 | 2 | 7 | 0 |
| IPI00221354 | 5 | FUS Isoform Short of RNA-binding protein FUS | 9 | 2 | 7 | 0 |
| IPI00893715 | 7 | TACSTD1 38 kDa protein | 9 | 4 | 7 | 0 |
| IPI00872533 | 6 | CD2AP 76 kDa protein | 9 | 1 | 7 | 0 |
| IPI00006181 | 6 | EIF3D Eukaryotic translation initiation factor 3 subunit D | 9 | 3 | 7 | 0 |
| IPI00009368 | 5 | SFXN1 Sideroflexin-1 | 9 | 2 | 7 | 1 |

TABLE 3-continued

| IPI Acc. No. | nPeptides | Protein | nBigT | nSmallT | nBigP | nSmallP |
|---|---|---|---|---|---|---|
| IPI00219516 | 4 | GUSB Isoform Short of Beta-glucuronidase precursor | 9 | 2 | 7 | 0 |
| IPI00398135 | 4 | hCG_21078 hypothetical protein LOC389435 | 9 | 2 | 7 | 0 |
| IPI00082310 | 3 | KHDRBS1 Isoform 3 of KH domain-containing, RNA-binding, signal transduction-associated protein 1 | 9 | 1 | 7 | 0 |
| IPI00328268 | 2 | EIF4G3 EIF4G3 protein | 9 | 0 | 7 | 0 |
| IPI00644079 | 21 | HNRNPU heterogeneous nuclear ribonucleoprotein U isoform a | 8 | 2 | 7 | 0 |
| IPI00414980 | 9 | MYO1B Isoform 2 of Myosin-Ib | 8 | 5 | 7 | 4 |
| IPI00646304 | 13 | PPIB peptidylprolyl isomerase B precursor | 8 | 3 | 7 | 0 |
| IPI00017334 | 13 | PHB Prohibitin | 8 | 1 | 7 | 0 |
| IPI00744692 | 13 | TALDO1 Transaldolase | 8 | 1 | 7 | 0 |
| IPI00329633 | 12 | TARS Threonyl-tRNA synthetase, cytoplasmic | 8 | 1 | 7 | 0 |
| IPI00030009 | 11 | PAPSS2 Isoform A of Bifunctional 3'-phosphoadenosine 5'-phosphosulfate synthetase 2 | 8 | 10 | 7 | 1 |
| IPI00027851 | 7 | HEXA Beta-hexosaminidase subunit alpha precursor | 8 | 3 | 7 | 0 |
| IPI00013174 | 7 | RBM14 Isoform 1 of RNA-binding protein 14 | 8 | 3 | 7 | 0 |
| IPI00024933 | 7 | RPL12 60S ribosomal protein L12 | 8 | 2 | 7 | 0 |
| IPI00793375 | 6 | XPNPEP1 Xaa-Pro aminopeptidase 1 | 8 | 1 | 7 | 0 |
| IPI00219160 | 5 | RPL34 60S ribosomal protein L34 | 8 | 4 | 7 | 0 |
| IPI00010949 | 5 | SIAE Isoform 1 of Sialate O-acetylesterase precursor | 8 | 7 | 7 | 1 |
| IPI00005737 | 4 | SURF4 Isoform 1 of Surfeit locus protein 4 | 8 | 1 | 7 | 0 |
| IPI00029631 | 3 | ERH Enhancer of rudimentary homolog | 8 | 0 | 7 | 0 |
| IPI00029601 | 15 | CTTN Src substrate cortactin | 7 | 3 | 7 | 0 |
| IPI00030179 | 11 | RPL7 60S ribosomal protein L7 | 7 | 3 | 7 | 0 |
| IPI00644570 | 3 | 18 kDa protein | 7 | 4 | 7 | 0 |
| IPI00456887 | 13 | HNRNPUL2 Heterogeneous nuclear ribonucleoprotein U-like protein 2 | 7 | 0 | 7 | 0 |
| IPI00031169 | 11 | RAB2A Ras-related protein Rab-2A | 7 | 0 | 7 | 0 |
| IPI00016910 | 11 | EIF3CL; EIF3C Eukaryotic translation initiation factor 3 subunit C | 7 | 3 | 7 | 0 |
| IPI00031583 | 11 | USO1 Putative uncharacterized protein DKFZp451D234 | 7 | 4 | 7 | 4 |
| IPI00165360 | 9 | MPST 3-mercaptopyruvate sulfurtransferase | 7 | 3 | 7 | 0 |
| IPI00025019 | 7 | PSMB1 Proteasome subunit beta type-1 precursor | 7 | 2 | 7 | 0 |
| IPI00335930 | 4 | DAZAP1 Isoform 2 of DAZ-associated protein 1 | 7 | 1 | 7 | 0 |
| IPI00015029 | 4 | PTGES3 Prostaglandin E synthase 3 | 7 | 2 | 7 | 0 |

TABLE 3-continued

| IPI Acc. No. | nPeptides | Protein | nBigT | nSmallT | nBigP | nSmallP |
|---|---|---|---|---|---|---|
| IPI00029039 | 4 | REG3A Regenerating islet-derived protein 3 alpha precursor | 7 | 0 | 7 | 0 |
| IPI00061525 | 3 | GNPNAT1 Glucosamine 6-phosphate N-acetyltransferase | 7 | 0 | 7 | 0 |
| IPI00026167 | 3 | NHP2L1 NHP2-like protein 1 | 7 | 0 | 7 | 0 |
| IPI00000811 | 3 | PSMB6 Proteasome subunit beta type-6 precursor | 7 | 2 | 7 | 1 |
| IPI00790799 | 3 | SEC11A 16 kDa protein | 7 | 0 | 7 | 0 |
| IPI00413654 | 3 | SFRS5 Isoform SRP40-4 of Splicing factor, arginine/serine-rich 5 | 7 | 2 | 7 | 0 |
| IPI00006092 | 3 | PMM2 Phosphomannomutase 2 | 7 | 1 | 7 | 0 |
| IPI00328840 | 3 | THOC4 THO complex subunit 4 | 7 | 1 | 7 | 0 |
| IPI00216237 | 3 | RPL36 60S ribosomal protein L36 | 7 | 3 | 7 | 1 |
| IPI00173589 | 2 | LOC284064 similar to ribosomal protein L29 | 7 | 3 | 7 | 0 |
| IPI00009342 | 64 | IQGAP1 Ras GTPase-activating-like protein IQGAP1 | 6 | 2 | 7 | 0 |
| IPI00413947 | 10 | AP1B1 Isoform B of AP-1 complex subunit beta-1 | 6 | 0 | 7 | 0 |
| IPI00398798 | 5 | H2AFV H2A histone family, member V isoform 3 | 6 | 4 | 7 | 0 |
| IPI00303882 | 13 | M6PRBP1 Isoform B of Mannose-6-phosphate receptor-binding protein 1 | 6 | 2 | 7 | 0 |
| IPI00790743 | 5 | Protein | 6 | 5 | 7 | 0 |
| IPI00021800 | 8 | CASP1 Isoform Alpha of Caspase-1 precursor | 6 | 5 | 7 | 0 |
| IPI00060181 | 7 | EFHD2 EF-hand domain-containing protein D2 | 6 | 0 | 7 | 1 |
| IPI00017510 | 6 | MT-CO2 Cytochrome c oxidase subunit 2 | 6 | 6 | 7 | 0 |
| IPI00006443 | 6 | CRYL1 Lambda-crystallin homolog | 6 | 6 | 7 | 0 |
| IPI00020956 | 6 | HDGF Hepatoma-derived growth factor | 6 | 2 | 7 | 0 |
| IPI00060200 | 5 | GALM Aldose 1-epimerase | 6 | 6 | 7 | 0 |
| IPI00185374 | 5 | PSMD12 26S proteasome non-ATPase regulatory subunit 12 | 6 | 1 | 7 | 0 |
| IPI00012340 | 4 | SFRS9 Splicing factor, arginine/serine-rich 9 | 6 | 3 | 7 | 1 |
| IPI00016405 | 4 | OCIAD1 Isoform 1 of OCIA domain-containing protein 1 | 6 | 5 | 7 | 0 |
| IPI00019329 | 3 | DYNLL1 Dynein light chain 1, cytoplasmic | 6 | 4 | 7 | 0 |
| IPI00642816 | 3 | SRP9; hCG_1781062 Signal recognition particle 9 kDa protein | 6 | 2 | 7 | 0 |
| IPI00013968 | 3 | COX7C Cytochrome c oxidase subunit 7C, mitochondrial precursor | 6 | 2 | 7 | 0 |
| IPI00026570 | 2 | COX7A2 Cytochrome c oxidase polypeptide VIIa-liver/heart, mitochondrial precursor | 6 | 4 | 7 | 0 |
| IPI00005719 | 10 | RAB1A Isoform 1 of Ras-related protein Rab-1A | 5 | 2 | 7 | 0 |
| IPI00374686 | 6 | Uncharacterized protein ENSP00000341227 (Fragment) | 5 | 1 | 7 | 0 |

TABLE 3-continued

| IPI Acc. No. | nPeptides | Protein | nBigT | nSmallT | nBigP | nSmallP |
|---|---|---|---|---|---|---|
| IPI00219077 | 15 | LTA4H Isoform 1 of Leukotriene A-4 hydrolase | 5 | 2 | 7 | 0 |
| IPI00025366 | 13 | CS Citrate synthase, mitochondrial precursor | 5 | 1 | 7 | 1 |
| IPI00290110 | 13 | PDCD4 Programmed cell death protein 4 | 5 | 5 | 7 | 0 |
| IPI00332828 | 10 | CES2 carboxylesterase 2 isoform 1 | 5 | 7 | 7 | 5 |
| IPI00182757 | 7 | KIAA1967 Isoform 1 of Protein KIAA1967 | 5 | 3 | 7 | 0 |
| IPI00030654 | 6 | CPSF6 Isoform 2 of Cleavage and polyadenylation specificity factor subunit 6 | 5 | 1 | 7 | 0 |
| IPI00789848 | 5 | IVD Isovaleryl-CoA dehydrogenase, mitochondrial precursor | 5 | 7 | 7 | 0 |
| IPI00024934 | 4 | MUT Methylmalonyl-CoA mutase, mitochondrial precursor | 5 | 0 | 7 | 0 |
| IPI00015972 | 4 | COX6C Cytochrome c oxidase polypeptide VIc precursor | 5 | 6 | 7 | 0 |
| IPI00031772 | 3 | C15orf48 Normal mucosa of esophagus-specific gene 1 protein | 5 | 7 | 7 | 0 |
| IPI00019888 | 2 | ALDH5A1 Succinate-semialdehyde dehydrogenase, mitochondrial precursor | 5 | 0 | 7 | 0 |
| IPI00873259 | 2 | ATP5J2 10 kDa protein | 5 | 2 | 7 | 0 |
| IPI00005159 | 11 | ACTR2 Actin-related protein 2 | 4 | 1 | 7 | 0 |
| IPI00465256 | 8 | AK3 GTP:AMP phosphotransferase mitochondrial | 4 | 2 | 7 | 1 |
| IPI00513827 | 8 | ACADM Putative uncharacterized protein DKFZp686M24262 | 4 | 4 | 7 | 0 |
| IPI00554811 | 6 | ARPC4; TTLL3 Actin-related protein 2/3 complex subunit 4 | 4 | 2 | 7 | 0 |
| IPI00874156 | 6 | OTUB1 Isoform 1 of Ubiquitin thioesterase OTUB1 | 4 | 2 | 7 | 0 |
| IPI00024661 | 4 | SEC24C Protein transport protein Sec24C | 4 | 2 | 7 | 1 |
| IPI00028387 | 4 | C20orf116 Isoform 1 of Uncharacterized protein C20orf116 precursor | 4 | 1 | 7 | 0 |
| IPI00022277 | 4 | CCDC56 Coiled-coil domain-containing protein 56 | 4 | 6 | 7 | 0 |
| IPI00024742 | 2 | UQCRQ Cytochrome b-c1 complex subunit 8 | 4 | 3 | 7 | 0 |
| IPI00307547 | 2 | C9orf46 Uncharacterized protein C9orf46 | 4 | 1 | 7 | 0 |
| IPI00029133 | 10 | ATP5F1 ATP synthase subunit b, mitochondrial precursor | 3 | 3 | 7 | 0 |
| IPI00651719 | 6 | PBLD MAWD binding protein isoform b | 3 | 2 | 7 | 1 |
| IPI00219755 | 1 | SPCS1 Signal peptidase complex subunit 1 | 3 | 3 | 7 | 0 |
| IPI00880101 | 9 | CEACAM5 Protein | 29 | 0 | 6 | 0 |
| IPI00302944 | 51 | COL12A1 Isoform 4 of Collagen alpha-1(XII) chain precursor | 24 | 3 | 6 | 0 |
| IPI00027769 | 5 | ELA2 Leukocyte elastase precursor | 23 | 0 | 6 | 0 |
| IPI00026781 | 46 | FASN Fatty acid synthase | 20 | 2 | 6 | 0 |
| IPI00304754 | 5 | FERMT1 Isoform 1 of Fermitin family homolog 1 | 18 | 3 | 6 | 0 |

TABLE 3-continued

| IPI Acc. No. | nPeptides | Protein | nBigT | nSmallT | nBigP | nSmallP |
|---|---|---|---|---|---|---|
| IPI00019472 | 5 | SLC1A5 Neutral amino acid transporter B | 16 | 0 | 6 | 0 |
| IPI00026833 | 5 | ADSS Adenylosuccinate synthetase isozyme 2 | 16 | 0 | 6 | 0 |
| IPI00026328 | 3 | TXNDC12 Thioredoxin domain-containing protein 12 precursor | 14 | 2 | 6 | 0 |
| IPI00009904 | 36 | PDIA4 Protein disulfide-isomerase A4 precursor | 13 | 3 | 6 | 0 |
| IPI00216044 | 8 | RALY Isoform 1 of RNA-binding protein Raly | 13 | 0 | 6 | 0 |
| IPI00215790 | 6 | RPL38 60S ribosomal protein L38 | 13 | 2 | 6 | 0 |
| IPI00872940 | 6 | RPL30 Uncharacterized protein RPL30 (Fragment) | 13 | 1 | 6 | 0 |
| IPI00012007 | 11 | AHCY Adenosylhomocysteinase | 12 | 2 | 6 | 0 |
| IPI00012069 | 6 | NQO1 NAD | 12 | 1 | 6 | 0 |
| IPI00385267 | 5 | SRPR Signal recognition particle receptor subunit alpha | 12 | 1 | 6 | 0 |
| IPI00856058 | 4 | RPL31 ribosomal protein L31 isoform 3 | 12 | 3 | 6 | 0 |
| IPI00395865 | 3 | RBBP7 Histone-binding protein RBBP7 | 12 | 0 | 6 | 0 |
| IPI00215734 | 3 | PRMT1 Isoform 2 of Protein arginine N-methyltransferase 1 | 12 | 0 | 6 | 0 |
| IPI00554648 | 51 | KRT8 Keratin, type II cytoskeletal 8 | 11 | 3 | 6 | 0 |
| IPI00027201 | 64 | MUC2 Mucin-2 precursor | 11 | 4 | 6 | 1 |
| IPI00789401 | 22 | PLS1 PLS1 protein | 11 | 2 | 6 | 0 |
| IPI00215743 | 48 | RRBP1 Isoform 3 of Ribosome-binding protein 1 | 11 | 3 | 6 | 0 |
| IPI00003881 | 11 | HNRNPF Heterogeneous nuclear ribonucleoprotein F | 11 | 2 | 6 | 0 |
| IPI00410017 | 18 | PABPC1 Isoform 2 of Polyadenylate-binding protein 1 | 11 | 2 | 6 | 0 |
| IPI00022228 | 21 | HDLBP Vigilin | 11 | 2 | 6 | 0 |
| IPI00401264 | 11 | TXNDC4 Thioredoxin domain-containing protein 4 precursor | 11 | 2 | 6 | 0 |
| IPI00008438 | 9 | RPS10 40S ribosomal protein S10 | 11 | 2 | 6 | 0 |
| IPI00295741 | 9 | CTSB Cathepsin B precursor | 11 | 5 | 6 | 0 |
| IPI00004968 | 7 | PRPF19 Pre-mRNA-processing factor 19 | 11 | 0 | 6 | 1 |
| IPI00014230 | 6 | C1QBP Complement component 1 Q subcomponent-binding protein, mitochondrial precursor | 11 | 2 | 6 | 0 |
| IPI00646917 | 4 | NUDT21 Cleavage and polyadenylation specificity factor subunit 5 | 11 | 0 | 6 | 0 |
| IPI00219155 | 4 | RPL27 60S ribosomal protein L27 | 11 | 1 | 6 | 0 |
| IPI00218606 | 4 | RPS23 40S ribosomal protein S23 | 11 | 5 | 6 | 0 |
| IPI00101405 | 4 | FDPS Farnesyl diphosphate synthase | 11 | 2 | 6 | 0 |
| IPI00028006 | 3 | PSMB2 Proteasome subunit beta type-2 | 11 | 2 | 6 | 0 |
| IPI00386662 | 2 | FUSIP1 Isoform 4 of FUS-interacting serine-arginine-rich protein 1 | 11 | 1 | 6 | 0 |
| IPI00027230 | 43 | HSP90B1 Endoplasmin precursor | 10 | 2 | 6 | 0 |

TABLE 3-continued

| IPI Acc. No. | nPeptides | Protein | nBigT | nSmallT | nBigP | nSmallP |
|---|---|---|---|---|---|---|
| IPI00027834 | 15 | HNRNPL heterogeneous nuclear ribonucleoprotein L isoform a | 10 | 1 | 6 | 0 |
| IPI00219870 | 23 | CTNND1 Isoform 1A of Catenin delta-1 | 10 | 3 | 6 | 0 |
| IPI00383296 | 21 | HNRNPM Isoform 2 of Heterogeneous nuclear ribonucleoprotein M | 10 | 2 | 6 | 0 |
| IPI00020599 | 19 | CALR Calreticulin precursor | 10 | 2 | 6 | 0 |
| IPI00644989 | 18 | PDIA6 Isoform 1 of Protein disulfide-isomerase A6 precursor | 10 | 2 | 6 | 0 |
| IPI00646486 | 9 | HP1BP3 Heterochromatin protein 1, binding protein 3 | 10 | 2 | 6 | 0 |
| IPI00010896 | 15 | CLIC1 Chloride intracellular channel protein 1 | 10 | 2 | 6 | 0 |
| IPI00000690 | 13 | AIFM1 Isoform 1 of Apoptosis-inducing factor 1, mitochondrial precursor | 10 | 4 | 6 | 0 |

nPeptides, number of peptides that were identified in all the samples analyzed;
nBigT, number of patients in which the ratio (expression level in tumor tissue/expression level in healthy tissue) was >3;
nSmallT, number of patients in which the ratio (expression level in tumor tissue/expression level in healthy tissue) was <1/3;
nBigP, number of patients in which the ratio (expression level in polyp tissue/expression level in healthy tissue) was >3;
nSmallP, number of patients in which the ratio (expression level in polyp tissue/expression level in healthy tissue) was <1/3.

Example 3

Identification of a Group of Protein Markers that are More Highly Expressed in Polyps than in Advanced Stages of Colorectal Cancer Table 4 lists proteins that were observed to be highly expressed in polyps, whereas in more advanced stages of colorectal cancer these proteins tended to have decreased levels of expression. Accordingly, a diagnostic array of reagents directed to detection of at least some of the proteins in this group may be used as a screening test for very early detection of colorectal cancer. Such a screening test could identify susceptible at-risk individuals, even prior to the stage at which polyp visualization is possible by endoscopic techniques.

TABLE 4

| Protein (IPI Acc. No.) | nBigTumor | nSmallTumor | nBigPolyp | nSmallPolyp |
|---|---|---|---|---|
| CPT2 Carnitine O-palmitoyltransferase 2, mitochondrial precursor (IPI00012912) | 6 | 5 | 12 | 0 |
| ARL1 ADP-ribosylation factor-like protein 1 (IPI00219518) | 6 | 1 | 12 | 0 |
| PFKL Isoform 1 of 6-phosphofructokinase, liver type (IPI00332371) | 6 | 2 | 11 | 0 |
| GOT2 Aspartate aminotransferase, mitochondrial precursor (IPI00018206) | 6 | 3 | 11 | 0 |
| AP1G1 AP-1 complex subunit gamma-1 (IPI00643591) | 6 | 1 | 11 | 0 |
| STRBP Isoform 2 of Spermatid perinuclear RNA-binding protein (IPI00413860) | 6 | 0 | 11 | 0 |
| CLCA1 Calcium-activated chloride channel regulator 1 precursor (IPI00014625) | 4 | 13 | 11 | 1 |
| CYFIP1 Isoform 1 of Cytoplasmic FMR1-interacting protein 1 (IPI00644231) | 4 | 2 | 11 | 0 |

TABLE 4-continued

| Protein (IPI Acc. No.) | nBigTumor | nSmallTumor | nBigPolyp | nSmallPolyp |
|---|---|---|---|---|
| COQ9 Isoform 1 of Ubiquinone biosynthesis protein COQ9, mitochondrial precursor (IPI00470631) | 4 | 3 | 11 | 0 |
| NDUFA9 NADH dehydrogenase [ubiquinone] 1 alpha subcomplex subunit 9, mitochondrial precursor (IPI00003968) | 3 | 4 | 11 | 0 |
| ALDH7A1 Similar to Antiquitin (IPI00221234) | 2 | 5 | 11 | 0 |
| HMGCS1 Hydroxymethylglutaryl-CoA synthase, cytoplasmic (IPI00008475) | 6 | 4 | 10 | 0 |
| NNT NAD(P) transhydrogenase, mitochondrial precursor (IPI00337541) | 6 | 2 | 10 | 0 |
| PRDX5 Uncharacterized protein PRDX5 (Fragment) (IPI00876999) | 6 | 2 | 10 | 0 |
| PCCB Propionyl-CoA carboxylase beta chain, mitochondrial precursor (IPI00007247) | 6 | 5 | 10 | 0 |
| COPZ1 Coatomer subunit zeta-1 (IPI00032851) | 6 | 4 | 10 | 0 |
| BAX BCL2-associated X protein isoform sigma (IPI00845474) | 6 | 2 | 10 | 0 |
| ACAD9 Acyl-CoA dehydrogenase family member 9, mitochondrial precursor (IPI00152981) | 6 | 0 | 10 | 0 |
| UBXD8 UBX domain-containing protein 8 (IPI00172656) | 6 | 1 | 10 | 0 |
| HMGCS2 Hydroxymethylglutaryl-CoA synthase, mitochondrial precursor (IPI00008934) | 5 | 12 | 10 | 0 |
| SLC25A3 cDNA FLJ90278 fis, clone NT2RP1000325, highly similar to Phosphate carrier protein, mitochondrialprecursor (IPI00790115) | 5 | 1 | 10 | 0 |
| SLC25A11 Mitochondrial 2-oxoglutarate/malate carrier protein (IPI00219729) | 5 | 4 | 10 | 0 |
| PDCD6 Programmed cell death protein 6 (IPI00025277) | 5 | 0 | 10 | 0 |
| UCRC Cytochrome b-c1 complex subunit 9 (IPI00554701) | 4 | 0 | 10 | 0 |
| DEFA6 Defensin-6 precursor (IPI00008301) | 4 | 0 | 10 | 0 |
| DYNC1H1 Cytoplasmic dynein 1 heavy chain 1 (IPI00456969) | 3 | 1 | 10 | 0 |
| HK1 Isoform 2 of Hexokinase-1 (IPI00220663) | 3 | 1 | 10 | 0 |
| CYFIP2 Isoform 2 of Cytoplasmic FMR1-interacting protein 2 (IPI00719600) | 3 | 2 | 10 | 0 |
| DCI Isoform 2 of 3,2-trans-enoyl-CoA isomerase, mitochondrial precursor (IPI00398758) | 3 | 5 | 10 | 0 |

TABLE 4-continued

| Protein (IPI Acc. No.) | nBigTumor | nSmallTumor | nBigPolyp | nSmallPolyp |
|---|---|---|---|---|
| CISD1 CDGSH iron sulfur domain-containing protein 1 (IPI00020510) | 1 | 1 | 10 | 0 |

nBigTumor, number of patients in which the ratio (expression level in tumor tissue/expression level in healthy tissue) was >3;
nSmallTumor, number of patients in which the ratio (expression level in tumor tissue/expression level in healthy tissue) was <1/3;
nBigPolyp, number of patients in which the ratio (expression level in polyp tissue/expression level in healthy tissue) was >3;
nSmallPolyp, number of patients in which the ratio (expression level in polyp tissue/expression level in healthy tissue) was <1/3.

Example 4

Cancer Associated Proteins Identified by Isotopic Labeling

The proteins identified by isotopic labeling included those listed in Table 5. All of the listed proteins were found to be present in colon cancer tissue at levels that were at least 2.5-fold greater than the level of the same protein in healthy colon tissue from the same subject, as indicated by the median ratios of the protein levels (i.e. cancerous tissue:healthy tissue) listed in the column denoted "MED".

TABLE 5

| Protein Name | IPI Acc. No. | nPEP | MED | #>2.5 |
|---|---|---|---|---|
| DPEP1 Dipeptidase 1 precursor | IPI00059476 | 12 | 50 | 8 |
| LCN2 Lipocalin 2 | IPI00643623 | 6 | 48.75 | 13 |
| FAM62B Isoform 2 of Extended synaptotagmin-2 | IPI00409635 | 10 | 39.73 | 10 |
| MTA2 Metastasis-associated protein MTA2 | IPI00171798 | 8 | 31.45 | 8 |
| S100A8 Protein S100-A8 | IPI00007047 | 7 | 30.72 | 17 |
| S100A9 Protein S100-A9 | IPI00027462 | 7 | 28.205 | 17 |
| MPO Isoform H7 of Myeloperoxidase precursor | IPI00236556 | 26 | 25.57 | 14 |
| MCM2 DNA replication licensing factor MCM2 | IPI00184330 | 12 | 23.37 | 11 |
| FDFT1 Squalene synthetase | IPI00020944 | 5 | 23.155 | 7 |
| DMBT1 Isoform 1 of Deleted in malignant brain tumors 1 protein precursor | IPI00099110 | 7 | 22.86 | 7 |
| LTF Lactotransferrin precursor | IPI00848342 | 30 | 20.45 | 17 |
| SERPINB5 Serpin B5 precursor | IPI00783625 | 7 | 20.44 | 8 |
| OLFM4 Olfactomedin-4 precursor | IPI00022255 | 20 | 19.49 | 13 |
| FERMT1 Isoform 1 of Fermitin family homolog 1 | IPI00304754 | 9 | 16.05 | 14 |
| C1R; ACYP1; C17orf13 Complement C1r subcomponent precursor | IPI00296165 | 5 | 15.61 | 7 |
| PLOD3 Procollagen-lysine, 2-oxoglutarate 5-dioxygenase 3 precursor | IPI00030255 | 10 | 15.17 | 8 |
| CEACAM5 Carcinoembryonic antigen-related cell adhesion molecule 5 precursor | IPI00027486 | 9 | 14.12 | 17 |
| PYCR1 pyrroline-5-carboxylate reductase 1 isoform 2 | IPI00376503 | 6 | 12.505 | 12 |
| MCM6 DNA replication licensing factor MCM6 | IPI00031517 | 9 | 12.29 | 6 |
| SLC1A5 Neutral amino acid transporter B | IPI00019472 | 8 | 10.03 | 10 |
| THBS1 Thrombospondin-1 precursor | IPI00296099 | 13 | 8.55 | 14 |
| LACTB2 Beta-lactamase-like protein 2 | IPI00006952 | 5 | 8.445 | 8 |
| NAT10 N-acetyltransferase 10 | IPI00300127 | 11 | 7.85 | 10 |
| RSL1D1 RSL1D1 protein | IPI00642046 | 11 | 7.845 | 12 |
| LMO7 Isoform 3 of LIM domain only protein 7 | IPI00291802 | 11 | 7.74 | 10 |

TABLE 5-continued

| Protein Name | IPI Acc. No. | nPEP | MED | #>2.5 |
|---|---|---|---|---|
| LYZ Lysozyme C precursor | IPI00019038 | 7 | 7.64 | 15 |
| MCM7 Isoform 1 of DNA replication licensing factor MCM7 | IPI00299904 | 10 | 7.435 | 7 |
| F11R Junctional adhesion molecule A precursor | IPI00001754 | 5 | 6.775 | 7 |
| MCM3 DNA replication licensing factor MCM3 | IPI00013214 | 11 | 6.605 | 10 |
| ATP6V1E1 vacuolar H+ ATPase E1 isoform b | IPI00719806 | 5 | 6.34 | 9 |
| TNC Isoform 1 of Tenascin precursor | IPI00031008 | 58 | 6.2 | 12 |
| COL12A1 Isoform 1 of Collagen alpha-1(XII) chain precursor | IPI00329573 | 49 | 6.175 | 17 |
| SORD 11 kDa protein | IPI00791243 | 5 | 5.78 | 7 |
| PYCR2 Pyrroline-5-carboxylate reductase 2 | IPI00470610 | 5 | 5.645 | 9 |
| GTF2I Isoform 2 of General transcription factor II-I | IPI00293242 | 10 | 5.515 | 7 |
| DDX18 ATP-dependent RNA helicase DDX18 | IPI00301323 | 8 | 5.38 | 8 |
| RBM39 Isoform 2 of RNA-binding protein 39 | IPI00215801 | 11 | 5.19 | 12 |
| NQO1 NAD | IPI00012069 | 6 | 4.9 | 8 |
| DNAJA3 Isoform 2 of DnaJ homolog subfamily A member 3, mitochondrial precursor | IPI00179187 | 7 | 4.73 | 9 |
| NCBP1 Nuclear cap-binding protein subunit 1 | IPI00019380 | 8 | 4.42 | 9 |
| HSPH1 Isoform Beta of Heat shock protein 105 kDa | IPI00218993 | 33 | 4.365 | 13 |
| ADSS Adenylosuccinate synthetase isozyme 2 | IPI00026833 | 7 | 4.36 | 11 |
| PSAT1 Isoform 1 of Phosphoserine aminotransferase | IPI00001734 | 9 | 4.295 | 8 |
| ALG5 Dolichyl-phosphate beta-glucosyltransferase | IPI00002506 | 6 | 4.135 | 10 |
| PCNA Proliferating cell nuclear antigen | IPI00021700 | 12 | 4.04 | 10 |
| TCOF1 Isoform 2 of Treacle protein | IPI00298696 | 12 | 3.92 | 9 |
| SERPINH1 Serpin H1 precursor | IPI00032140 | 20 | 3.9 | 16 |
| ERO1L ERO1-like protein alpha precursor | IPI00386755 | 8 | 3.81 | 12 |
| ILVBL Isoform 1 of Acetolactate synthase-like protein | IPI00554541 | 15 | 3.8 | 11 |
| ANXA3 Annexin A3 | IPI00024095 | 17 | 3.645 | 16 |
| NAMPT Isoform 1 of Nicotinamide phosphoribosyltransferase | IPI00018873 | 25 | 3.61 | 12 |
| TFRC Transferrin receptor protein 1 | IPI00022462 | 23 | 3.56 | 9 |
| SERPINB9 Serpin B9 | IPI00032139 | 8 | 3.41 | 10 |
| EIF2S2 Eukaryotic translation initiation factor 2 subunit 2 | IPI00021728 | 8 | 3.38 | 8 |
| SRRM2 Isoform 1 of Serine/arginine repetitive matrix protein 2 | IPI00782992 | 8 | 3.365 | 8 |

TABLE 5-continued

| Protein Name | IPI Acc. No. | nPEP | MED | #>2.5 |
|---|---|---|---|---|
| ARHGEF1 Isoform 1 of Rho guanine nucleotide exchange factor 1 | IPI00647786 | 5 | 3.31 | 7 |
| COMT Isoform Soluble of Catechol O-methyltransferase | IPI00375513 | 9 | 3.31 | 10 |
| DEK 48 kDa protein | IPI00871695 | 8 | 3.285 | 10 |
| SYK Isoform Long of Tyrosine-protein kinase SYK | IPI00018597 | 6 | 3.275 | 7 |
| S100A11 Protein S100-A11 | IPI00013895 | 8 | 3.2 | 12 |
| HSDL2 Isoform 1 of Hydroxysteroid dehydrogenase-like protein 2 | IPI00414384 | 10 | 3.14 | 10 |
| C7orf24 Uncharacterized protein C7orf24 | IPI00031564 | 5 | 3.125 | 9 |
| HM13 Isoform 1 of Minor histocompatibility antigen H13 | IPI00152441 | 7 | 3.09 | 9 |
| RCN1 Reticulocalbin-1 precursor | IPI00015842 | 14 | 3.07 | 11 |
| DIAPH1 Diaphanous homolog 1 | IPI00884341 | 10 | 3.06 | 8 |
| SRM Spermidine synthase | IPI00292020 | 5 | 2.97 | 11 |
| ATAD3A Isoform 2 of ATPase family AAA domain-containing protein 3A | IPI00295992 | 20 | 2.965 | 10 |
| GPX2 Glutathione peroxidase 2 | IPI00298176 | 9 | 2.945 | 9 |
| LOC442497; SLC3A2 solute carrier family 3 (activators of dibasic and neutral amino acid transport), member 2 isoform e | IPI00554722 | 13 | 2.9 | 12 |
| SAE1 SUMO-activating enzyme subunit 1 | IPI00033130 | 8 | 2.89 | 9 |
| IPO7 Importin-7 | IPI00007402 | 11 | 2.85 | 9 |
| SET Isoform 2 of Protein SET | IPI00301311 | 9 | 2.85 | 11 |
| PAICS Multifunctional protein ADE2 | IPI00217223 | 15 | 2.84 | 11 |
| OCIAD2 Isoform 1 of OCIA domain-containing protein 2 | IPI00555902 | 6 | 2.83 | 10 |
| GLT25D1 Glycosyltransferase 25 family member 1 precursor | IPI00168262 | 5 | 2.82 | 7 |
| RCC2 Protein RCC2 | IPI00465044 | 12 | 2.79 | 10 |
| CTSG Cathepsin G precursor | IPI00028064 | 10 | 2.77 | 12 |
| CHD4 Isoform 2 of Chromodomain-helicase-DNA-binding protein 4 | IPI00455210 | 10 | 2.765 | 8 |
| SSBP1 Single-stranded DNA-binding protein, mitochondrial precursor | IPI00029744 | 6 | 2.765 | 10 |
| ACOT7 Isoform 1 of Cytosolic acyl coenzyme A thioester hydrolase | IPI00010415 | 6 | 2.76 | 8 |
| AK3 GTP:AMP phosphotransferase mitochondrial | IPI00465256 | 13 | 2.72 | 9 |
| GCA Grancalcin | IPI00004524 | 6 | 2.71 | 9 |
| ACIN1 Isoform 1 of Apoptotic chromatin condensation inducer in the nucleus | IPI00007334 | 5 | 2.69 | 9 |
| TM9SF4 Isoform 2 of Transmembrane 9 superfamily member 4 precursor | IPI00885106 | 8 | 2.69 | 8 |
| CAD Putative uncharacterized protein CAD | IPI00893035 | 17 | 2.675 | 9 |
| FASN Fatty acid synthase | IPI00026781 | 74 | 2.66 | 11 |
| TJP2 Isoform A1 of Tight junction protein ZO-2 | IPI00003843 | 16 | 2.66 | 8 |
| GLRX3 Glutaredoxin-3 | IPI00008552 | 6 | 2.595 | 7 |
| RCC1 regulator of chromosome condensation 1 isoform b | IPI00787306 | 5 | 2.59 | 7 |
| TOP1 DNA topoisomerase 1 | IPI00413611 | 10 | 2.57 | 9 |
| GGH Gamma-glutamyl hydrolase precursor | IPI00023728 | 11 | 2.565 | 10 |
| PUF60 Isoform 5 of Poly | IPI00856076 | 10 | 2.56 | 9 |
| TPR nuclear pore complex-associated protein TPR | IPI00742682 | 16 | 2.545 | 9 |
| GMPS GMP synthase | IPI00029079 | 11 | 2.525 | 10 |
| PKP3 Plakophilin-3 | IPI00026952 | 19 | 2.52 | 10 |
| LOC731605 similar to BCL2-associated transcription factor 1 isoform 2 | IPI00886854 | 7 | 2.515 | 9 |

TABLE 5-continued

| Protein Name | IPI Acc. No. | nPEP | MED | #>2.5 |
|---|---|---|---|---|
| SLC2A1 Solute carrier family 2, facilitated glucose transporter member 1 | IPI00220194 | 8 | 2.515 | 7 |
| C8orf55 Uncharacterized protein C8orf55 precursor | IPI00171421 | 7 | 2.51 | 8 |
| HCFC1 Uncharacterized protein HCFC1 | IPI00641743 | 7 | 2.51 | 10 |

IPI Acc. No, accession number in IPI database;
nPEP, number of identified peptides in all the samples,
MED, median of the ratio tumor/healthy from all the patients;
#>2.5, number of patients in which tumor/healthy >2.5.

Example 5

Cancer Associated Proteins Identified by Multidimensional Chromatography

The proteins identified on the basis of the peptides detected by the multidimensional chromatography technique include those listed in Table 6, and reflects the abundance of these proteins in cancerous tissues. None of the proteins listed in Table 6 were identified by the isotopic labeling technique. The proteins listed in Tables 3 and 6 appear to be specifically expressed in colorectal cancer tissue, as they were substantially undetectable in all healthy colorectal tissues obtained from the colorectal cancer patients.

TABLE 6

| Protein Name | IPI Acc. No. | AVG | SD | No. of tumors |
|---|---|---|---|---|
| ADAMDEC1 ADAM DEC1 precursor | 4480 | 50 | 0 | |
| AMACR Alpha-methylacyl-CoA racemase | 847727 | 50 | 0 | 7 |
| AMACR; C1QTNF3 alpha-methylacyl-CoA racemase isoform 1 | 5918 | 50 | 0 | 7 |
| ARID1A Isoform 1 of AT-rich interactive domain-containing protein 1A | 643722 | 50 | 0 | |
| CEBPZ CCAAT/enhancer-binding protein zeta | 306723 | 50 | 0 | |
| COL5A1 Collagen alpha-1(V) chain precursor | 844090 | 50 | 0 | |
| EFEMP2 Mutant p53 binding protein 1 variant (Fragment) | 556657 | 50 | 0 | |
| FAM84B Protein FAM84B | 64666 | 50 | 0 | |
| FKBP10 FK506-binding protein 10 precursor | 303300 | 50 | 0 | 8 |
| FKBP9 FK506-binding protein 9 precursor | 182126 | 50 | 0 | 9 |
| GPRC5A Retinoic acid-induced protein 3 | 22624 | 50 | 0 | 8 |
| KPNA2 Karyopherin alpha 2 | 789457 | 50 | 0 | |
| MMP1 Interstitial collagenase precursor | 8561 | 50 | 0 | |
| PNMA5 Paraneoplastic antigen-like protein 5 | 514588 | 50 | 0 | |
| POLR1C Isoform 1 of DNA-directed RNA polymerases I and III subunit RPAC1 | 5179 | 50 | 0 | 9 |
| SPARC SPARC precursor | 14572 | 50 | 0 | 5 |
| UBAP2 Ubiquitin-associated protein 2 | 171127 | 50 | 0 | 5 |
| UCK2 Isoform 1 of Uridine-cytidine kinase 2 | 65671 | 50 | 0 | |
| WDR74 Isoform 1 of WD repeat-containing protein 74 | 18192 | 50 | 0 | |

Example 6

Cancer Associated Proteins as Potential Therapeutic Targets

Table 7 lists proteins that are considered potential targets for development of cytotoxic reagents specifically directed to these proteins, for example, specific antibody or antibody fragments conjugated to toxic moieties for targeted elimination of cancer cells. As well as being highly expressed in early stage polyps and in tumors, these proteins are generally exposed, and considered vulnerable to attack by targeted cytotoxic reagents.

TABLE 7

| Protein (IPI Acc. No.) | nBigTumor | nSmallTumor | nBigPolyp | nSmallPolyp | Ontology |
|---|---|---|---|---|---|
| DEFA3 Neutrophil defensin 3 precursor (IPI00021827) | 26 | 2 | 5 | 0 | EX |
| ELA2 Leukocyte elastase precursor (IPI00027769) | 23 | 0 | 6 | 0 | EX |
| LYZ Lysozyme C precursor (IPI00019038) | 17 | 2 | 8 | 0 | EX |
| LOC442497; SLC3A2 solute carrier family 3 (activators of dibasic and neutral amino acid transport), member 2 isoform e (IPI00554722) | 16 | 1 | 8 | 0 | PM |
| SLC1A5 Neutral amino acid transporter B (IPI00019472) | 16 | 0 | 6 | 0 | PM |
| DMBT1 Isoform 1 of Deleted in malignant brain tumors 1 protein precursor (IPI00099110) | 15 | 0 | 8 | 1 | EX AM |
| NUCB1 Nucleobindin-1 precursor (IPI00295542) | 15 | 3 | 7 | 0 | EX AM |
| SLC12A2 Isoform 1 of Solute carrier family 12 member 2 (IPI00022649) | 14 | 2 | 16 | 0 | PM |
| GGH Gamma-glutamyl hydrolase precursor (IPI00023728) | 14 | 1 | 12 | 0 | EX |
| AGR3 Anterior gradient protein 3 homolog precursor (IPI00152409) | 14 | 4 | 7 | 0 | EX |
| MARCKSL1 MARCKS-related protein (IPI00641181) | 13 | 0 | 11 | 0 | PM |
| TM9SF2 Transmembrane 9 superfamily member 2 precursor (IPI00018415) | 12 | 1 | 9 | 0 | PM |
| SYK Isoform Long of Tyrosine-protein kinase SYK (IPI00018597) | 11 | 0 | 10 | 0 | PM |
| GCA Grancalcin (IPI00004524) | 11 | 0 | 7 | 0 | PM |
| HDLBP Vigilin (IPI00022228) | 11 | 2 | 6 | 0 | PM |
| C1QBP Complement component 1 Q subcomponent-binding protein, mitochondrial precursor (IPI00014230) | 11 | 2 | 6 | 0 | PM |
| KIAA0152 Uncharacterized protein KIAA0152 precursor (IPI00029046) | 10 | 0 | 13 | 0 | PM |

TABLE 7-continued

| Protein (IPI Acc. No.) | nBigTumor | nSmallTumor | nBigPolyp | nSmallPolyp | Ontology |
|---|---|---|---|---|---|
| CLIC1 Chloride intracellular channel protein 1 (IPI00010896) | 10 | 2 | 6 | 0 | PM |

nBigTumor, number of patients in which the ratio (expression level in tumor tissue/expression level in healthy tissue) was >3;
nSmallTumor, number of patients in which the ratio (expression level in tumor tissue/expression level in healthy tissue) was <1/3;
nBigPolyp, number of patients in which the ratio (expression level in polyp tissue/expression level in healthy tissue) was >3;
nSmallPolyp, number of patients in which the ratio (expression level in polyp tissue/expression level in healthy tissue) was <1/3;
EX, extracellular region;
PM, plasma membrane;
AM, additional membrane.

REFERENCES CITED

Aebersold, R. and M. Mann (2003). "Mass spectrometry-based proteomics." Nature 422(6928): 198-207.

Beer, I., E. et al. (2004). "Improving large-scale proteomics by clustering of mass spectrometry data." Proteomics 4(4): 950-60.

Eng, J., et al. (1994). "An approach to correlate tandem mass spectral data of peptides with amino acid sequences in a protein database." J. Amer. Soc. Mass. Spect. 5: 976-989.

Hsu, J. L., et al. (2003). "Stable-isotope dimethyl labeling for quantitative proteomics." Anal Chem 75(24): 6843-52.

Ishihama, Y., et al. (2002). "Microcolumns with self-assembled particle frits for proteomics." J Chromatogr A 979(1-2): 233-9.

Link, A. J. (2002). "Multidimensional peptide separations in proteomics." Trends Biotechnol 20(12 Suppl): S8-13.

Link, A. J. et al. (1999). "Direct analysis of protein complexes using mass spectrometry." Nat. Biotechnol. 17(7): 676-82.

Ong, S. E. and M. Mann (2005). "Mass spectrometry-based proteomics turns quantitative." Nat Chem Biol 1(5): 252-62.

Perkins, D. N. et al. (1999). "Probability-based protein identification by searching sequence databases using mass spectrometry data." Electrophoresis 20(18): 3551-67.

Regnier, F. E. and S. Julka (2006). "Primary amine coding as a path to comparative proteomics." Proteomics 6(14): 3968-79.

Ross, P. L. et al. (2004). "Multiplexed protein quantitation in *Saccharomyces cerevisiae* using amine-reactive isobaric tagging reagents." Mol Cell Proteomics 3(12): 1154-69.

The foregoing description of the specific embodiments will so fully reveal the general nature of the invention that others can, by applying current knowledge, readily modify and/or adapt for various applications such specific embodiments without undue experimentation and without departing from the brand concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for detecting a colorectal pre-cancerous tissue in a subject, comprising the steps of:

(i) contacting in vivo a colorectal tissue with a pharmaceutical composition comprising a reagent suitable for detecting a combination of polypeptide markers; and (ii) detecting in said colorectal tissue the presence of said combination, wherein said combination comprises: NAMPT and OLFM4, thereby detecting a colorectal pre-cancerous tissue in a subject.

2. The method according to claim 1, wherein said detecting step is detecting in said colorectal tissue an expression level above the expression level of a reference colorectal tissue.

3. The method according to claim 2, wherein said reference colorectal tissue is a non-diseased tissue.

4. The method according to claim 1, wherein said detecting in-vivo is detecting in an intact colorectal tissue.

5. The method according to claim 1, wherein said reagent comprises an antibody, or an antibody mimetic.

6. The method according to claim 1, wherein said reagent comprises a bi-specific antibody.

7. The method according to claim 1, wherein said pharmaceutical composition further comprises a chemotherapeutic agent.

8. The method according to claim 2, wherein said expression level detected is at least 3-fold above the expression level of the reference colorectal tissue.

9. The method according to claim 1, wherein said subject is at risk for developing colorectal cancer.

10. The method according to claim 1, wherein said pre-cancerous tissue is a pre-cancerous polyp.

11. The method according to claim 2, wherein said reference colorectal tissue is from said subject.

12. The method according to claim 1, wherein said detecting step is detecting a fluorescent dye.

13. The method according to claim 1, wherein said combination of markers further comprises at least one additional marker selected from the group consisting of PYCR1, GPX2, PRKDC, ALDH18A1, OCIAD2, GCS1, GMDS, ARF4, ARF5, LRPPRC, CTNNB1, ARF3, GCN1L1, BDH1, RPL9, UGCGL1, FAM3D, CCT4, CPT2, ARL1, PFKL, GOT2, AP1G1, STRBP, CLCA1, CYFIP1, COQ9, NDUFA9, ALDH7A1, HMGCS1, NNT, PRDX5, PCCB, COPZ1, BAX, ACAD9, UBXD8, HMGCS2, SLC25A, PDCD6, UCRC, DEFA6, DYNC1H1, HK1, CYFIP2, DC1, S100A8, S100A9, CEACAM5, LTF, COL12A1, MPO, DEFA3, GGH, CISD1, ELA2, SLC12A2, VDAC1, AGR2, PIGR, CTSG, CTNNB1, AGR3, TNC, APOB48R, CDH17, FCGBP, CDH1, GPA33, ANXA3, LCN2, SERPINB5, DSG2, COPA, HSD17B11, ATP2A2, CDH1, and any combination thereof.

* * * * *

```
                    SEQUENCE LISTING

<160> NUMBER OF SEQ ID NOS: 93

<210> SEQ ID NO 1
<211> LENGTH: 292
<212> TYPE: PRT
<213> ORGANISM: Artificial Sequence
<220> FEATURE:
<223> OTHER INFORMATION: Synthetic

<400> SEQUENCE: 1

Met Leu Gly Ala Trp Ala Val Glu Gly Thr Ala Val Ala Leu Leu Arg
1               5                   10                  15

Leu Leu Leu Leu Leu Leu Pro Pro Ala Ile Arg Gly Pro Gly Leu Gly
            20                  25                  30

Val Ala Gly Val Ala Gly Ala Ala Gly Ala Gly Leu Pro Glu Ser Val
        35                  40                  45

Ile Trp Ala Val Asn Ala Gly Gly Glu Ala His Val Asp Val His Gly
    50                  55                  60

Ile His Phe Arg Lys Asp Pro Leu Glu Gly Arg Val Gly Arg Ala Ser
65                  70                  75                  80

Asp Tyr Gly Met Lys Leu Pro Ile Leu Arg Ser Asn Pro Glu Asp Gln
```

```
                85                  90                  95

Ile Leu Tyr Gln Thr Glu Arg Tyr Asn Glu Glu Thr Phe Gly Tyr Glu
            100                 105                 110

Val Pro Ile Lys Glu Glu Gly Asp Tyr Val Leu Val Leu Lys Phe Ala
        115                 120                 125

Glu Val Tyr Phe Ala Gln Ser Gln Gln Lys Val Phe Asp Val Arg Leu
    130                 135                 140

Asn Gly His Val Val Val Lys Asp Leu Asp Ile Phe Asp Arg Val Gly
145                 150                 155                 160

His Ser Thr Ala His Asp Glu Ile Ile Pro Met Ser Ile Arg Lys Gly
                165                 170                 175

Lys Leu Ser Val Gln Gly Glu Val Ser Thr Phe Thr Gly Lys Leu Tyr
            180                 185                 190

Ile Glu Phe Val Lys Gly Tyr Tyr Asp Asn Pro Lys Val Cys Ala Leu
        195                 200                 205

Tyr Ile Met Ala Gly Thr Val Asp Asp Val Pro Lys Leu Gln Pro His
    210                 215                 220

Pro Gly Leu Glu Lys Lys Glu Glu Glu Glu Glu Glu Glu Glu Tyr Asp
225                 230                 235                 240

Glu Gly Ser Asn Leu Lys Lys Gln Thr Asn Lys Asn Arg Val Gln Ser
                245                 250                 255

Gly Pro Arg Thr Pro Asn Pro Tyr Ala Ser Asp Asn Ser Ser Leu Met
            260                 265                 270

Phe Pro Ile Leu Val Ala Phe Gly Val Phe Ile Pro Thr Leu Phe Cys
        275                 280                 285

Leu Cys Arg Leu
    290
```

<210> SEQ ID NO 2
<211> LENGTH: 491
<212> TYPE: PRT
<213> ORGANISM: Artificial Sequence
<220> FEATURE:
<223> OTHER INFORMATION: Synthetic

<400> SEQUENCE: 2

```
Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160
```

Val Ala Thr Asn Ser Arg Glu Gln Lys Lys Ile Leu Ala Lys Tyr Leu
165 170 175

Leu Glu Thr Ser Gly Asn Leu Asp Gly Leu Glu Tyr Lys Leu His Asp
180 185 190

Phe Gly Tyr Arg Gly Val Ser Ser Gln Glu Thr Ala Gly Ile Gly Ala
195 200 205

Ser Ala His Leu Val Asn Phe Lys Gly Thr Asp Thr Val Ala Gly Leu
210 215 220

Ala Leu Ile Lys Lys Tyr Tyr Gly Thr Lys Asp Pro Val Pro Gly Tyr
225 230 235 240

Ser Val Pro Ala Ala Glu His Ser Thr Ile Thr Ala Trp Gly Lys Asp
245 250 255

His Glu Lys Asp Ala Phe Glu His Ile Val Thr Gln Phe Ser Ser Val
260 265 270

Pro Val Ser Val Val Ser Asp Ser Tyr Asp Ile Tyr Asn Ala Cys Glu
275 280 285

Lys Ile Trp Gly Glu Asp Leu Arg His Leu Ile Val Ser Arg Ser Thr
290 295 300

Gln Ala Pro Leu Ile Ile Arg Pro Asp Ser Gly Asn Pro Leu Asp Thr
305 310 315 320

Val Leu Lys Val Leu Glu Ile Leu Gly Lys Lys Phe Pro Val Thr Glu
325 330 335

Asn Ser Lys Gly Tyr Lys Leu Leu Pro Pro Tyr Leu Arg Val Ile Gln
340 345 350

Gly Asp Gly Val Asp Ile Asn Thr Leu Gln Glu Ile Val Glu Gly Met
355 360 365

Lys Gln Lys Met Trp Ser Ile Glu Asn Ile Ala Phe Gly Ser Gly Gly
370 375 380

Gly Leu Leu Gln Lys Leu Thr Arg Asp Leu Leu Asn Cys Ser Phe Lys
385 390 395 400

Cys Ser Tyr Val Val Thr Asn Gly Leu Gly Ile Asn Val Phe Lys Asp
405 410 415

Pro Val Ala Asp Pro Asn Lys Arg Ser Lys Lys Gly Arg Leu Ser Leu
420 425 430

His Arg Thr Pro Ala Gly Asn Phe Val Thr Leu Glu Glu Gly Lys Gly
435 440 445

Asp Leu Glu Glu Tyr Gly Gln Asp Leu Leu His Thr Val Phe Lys Asn
450 455 460

Gly Lys Val Thr Lys Ser Tyr Ser Phe Asp Glu Ile Arg Lys Asn Ala
465 470 475 480

Gln Leu Asn Ile Glu Leu Glu Ala Ala His His
485 490

<210> SEQ ID NO 3
<211> LENGTH: 316
<212> TYPE: PRT
<213> ORGANISM: Artificial Sequence
<220> FEATURE:
<223> OTHER INFORMATION: Synthetic

<400> SEQUENCE: 3

Met Ser Val Gly Phe Ile Gly Ala Gly Gln Leu Ala Phe Ala Leu Ala
1 5 10 15

Lys Gly Phe Thr Ala Ala Gly Val Leu Ala Ala His Lys Ile Met Ala
20 25 30

Ser Ser Pro Asp Met Asp Leu Ala Thr Val Ser Ala Leu Arg Lys Met
35 40 45

Gly Val Lys Leu Thr Pro His Asn Lys Glu Thr Val Gln His Ser Asp
50 55 60

Val Leu Phe Leu Ala Val Lys Pro His Ile Ile Pro Phe Ile Leu Asp
65 70 75 80

Glu Ile Gly Ala Asp Ile Glu Asp Arg His Ile Val Val Ser Cys Ala
85 90 95

Ala Gly Val Thr Ile Ser Ser Ile Glu Lys Lys Leu Ser Ala Phe Arg
100 105 110

Pro Ala Pro Arg Val Ile Arg Cys Met Thr Asn Thr Pro Val Val Val
115 120 125

Arg Glu Gly Ala Thr Val Tyr Ala Thr Gly Thr His Ala Gln Val Glu
130 135 140

Asp Gly Arg Leu Met Glu Gln Leu Leu Ser Ser Val Gly Phe Cys Thr
145 150 155 160

Glu Val Glu Glu Asp Leu Ile Asp Ala Val Thr Gly Leu Ser Gly Ser
165 170 175

Gly Pro Ala Tyr Ala Phe Thr Ala Leu Asp Ala Leu Ala Asp Gly Gly
180 185 190

Val Lys Met Gly Leu Pro Arg Arg Leu Ala Val Arg Leu Gly Ala Gln
195 200 205

Ala Leu Leu Gly Ala Ala Lys Met Leu Leu His Ser Glu Gln His Pro
210 215 220

Gly Gln Leu Lys Asp Asn Val Ser Ser Pro Gly Gly Ala Thr Ile His
225 230 235 240

Ala Leu His Val Leu Glu Ser Gly Gly Phe Arg Ser Leu Leu Ile Asn
245 250 255

Ala Val Glu Ala Ser Cys Ile Arg Thr Arg Glu Leu Gln Ser Met Ala
260 265 270

Asp Gln Glu Gln Val Ser Pro Ala Ala Ile Lys Lys Thr Ile Leu Asp
275 280 285

Lys Asp His Leu Pro Leu Glu Leu Gly Ser Pro Glu Gly Leu His Pro
290 295 300

Leu Leu Leu Gln Tyr Gln Leu Ala Arg Ala Pro Ser
305 310 315

<210> SEQ ID NO 4
<211> LENGTH: 190
<212> TYPE: PRT
<213> ORGANISM: Artificial Sequence
<220> FEATURE:
<223> OTHER INFORMATION: Synthetic

<400> SEQUENCE: 4

Met Ala Phe Ile Ala Lys Ser Phe Tyr Asp Leu Ser Ala Ile Ser Leu
1 5 10 15

Asp Gly Glu Lys Val Asp Phe Asn Thr Phe Arg Gly Arg Ala Val Leu
20 25 30

Ile Glu Asn Val Ala Ser Leu Cys Gly Thr Thr Thr Arg Asp Phe Thr
35 40 45

Gln Leu Asn Glu Leu Gln Cys Arg Phe Pro Arg Arg Leu Val Val Leu
50 55 60

Gly Phe Pro Cys Asn Gln Phe Gly His Gln Glu Asn Cys Gln Asn Glu
65 70 75 80

Glu Ile Leu Asn Ser Leu Lys Tyr Val Arg Pro Gly Gly Gly Tyr Gln 85 90 95

Pro Thr Phe Thr Leu Val Gln Lys Cys Glu Val Asn Gly Gln Asn Glu
100 105 110

His Pro Val Phe Ala Tyr Leu Lys Asp Lys Leu Pro Tyr Pro Tyr Asp
115 120 125

Asp Pro Phe Ser Leu Met Thr Asp Pro Lys Leu Ile Ile Trp Ser Pro
130 135 140

Val Arg Arg Ser Asp Val Ala Trp Asn Phe Glu Lys Phe Leu Ile Gly
145 150 155 160

Pro Glu Gly Glu Pro Phe Arg Arg Tyr Ser Arg Thr Phe Pro Thr Ile
165 170 175

Asn Ile Glu Pro Asp Ile Lys Arg Leu Leu Lys Val Ala Ile
180 185 190

<210> SEQ ID NO 5
<211> LENGTH: 4128
<212> TYPE: PRT
<213> ORGANISM: Artificial Sequence
<220> FEATURE:
<223> OTHER INFORMATION: Synthetic

<400> SEQUENCE: 5

Met Ala Gly Ser Gly Ala Gly Val Arg Cys Ser Leu Leu Arg Leu Gln
1 5 10 15

Glu Thr Leu Ser Ala Ala Asp Arg Cys Gly Ala Ala Leu Ala Gly His
20 25 30

Gln Leu Ile Arg Gly Leu Gly Gln Glu Cys Val Leu Ser Ser Ser Pro
35 40 45

Ala Val Leu Ala Leu Gln Thr Ser Leu Val Phe Ser Arg Asp Phe Gly
50 55 60

Leu Leu Val Phe Val Arg Lys Ser Leu Asn Ser Ile Glu Phe Arg Glu
65 70 75 80

Cys Arg Glu Glu Ile Leu Lys Phe Leu Cys Ile Phe Leu Glu Lys Met
85 90 95

Gly Gln Lys Ile Ala Pro Tyr Ser Val Glu Ile Lys Asn Thr Cys Thr
100 105 110

Ser Val Tyr Thr Lys Asp Arg Ala Ala Lys Cys Lys Ile Pro Ala Leu
115 120 125

Asp Leu Leu Ile Lys Leu Leu Gln Thr Phe Arg Ser Ser Arg Leu Met
130 135 140

Asp Glu Phe Lys Ile Gly Glu Leu Phe Ser Lys Phe Tyr Gly Glu Leu
145 150 155 160

Ala Leu Lys Lys Lys Ile Pro Asp Thr Val Leu Glu Lys Val Tyr Glu
165 170 175

Leu Leu Gly Leu Leu Gly Glu Val His Pro Ser Glu Met Ile Asn Asn
180 185 190

Ala Glu Asn Leu Phe Arg Ala Phe Leu Gly Glu Leu Lys Thr Gln Met
195 200 205

Thr Ser Ala Val Arg Glu Pro Lys Leu Pro Val Leu Ala Gly Cys Leu
210 215 220

Lys Gly Leu Ser Ser Leu Leu Cys Asn Phe Thr Lys Ser Met Glu Glu
225 230 235 240

Asp Pro Gln Thr Ser Arg Glu Ile Phe Asn Phe Val Leu Lys Ala Ile
245 250 255

Arg Pro Gln Ile Asp Leu Lys Arg Tyr Ala Val Pro Ser Ala Gly Leu
260 265 270

```
Arg Leu Phe Ala Leu His Ala Ser Gln Phe Ser Thr Cys Leu Leu Asp
        275                 280                 285

Asn Tyr Val Ser Leu Phe Glu Val Leu Leu Lys Trp Cys Ala His Thr
    290                 295                 300

Asn Val Glu Leu Lys Lys Ala Ala Leu Ser Ala Leu Glu Ser Phe Leu
305                 310                 315                 320

Lys Gln Val Ser Asn Met Val Ala Lys Asn Ala Glu Met His Lys Asn
                325                 330                 335

Lys Leu Gln Tyr Phe Met Glu Gln Phe Tyr Gly Ile Ile Arg Asn Val
            340                 345                 350

Asp Ser Asn Asn Lys Glu Leu Ser Ile Ala Ile Arg Gly Tyr Gly Leu
        355                 360                 365

Phe Ala Gly Pro Cys Lys Val Ile Asn Ala Lys Asp Val Asp Phe Met
    370                 375                 380

Tyr Val Glu Leu Ile Gln Arg Cys Lys Gln Met Phe Leu Thr Gln Thr
385                 390                 395                 400

Asp Thr Gly Asp Asp Arg Val Tyr Gln Met Pro Ser Phe Leu Gln Ser
                405                 410                 415

Val Ala Ser Val Leu Leu Tyr Leu Asp Thr Val Pro Glu Val Tyr Thr
            420                 425                 430

Pro Val Leu Glu His Leu Val Val Met Gln Ile Asp Ser Phe Pro Gln
        435                 440                 445

Tyr Ser Pro Lys Met Gln Leu Val Cys Cys Arg Ala Ile Val Lys Val
    450                 455                 460

Phe Leu Ala Leu Ala Ala Lys Gly Pro Val Leu Arg Asn Cys Ile Ser
465                 470                 475                 480

Thr Val Val His Gln Gly Leu Ile Arg Ile Cys Ser Lys Pro Val Val
                485                 490                 495

Leu Pro Lys Gly Pro Glu Ser Glu Ser Glu Asp His Arg Ala Ser Gly
            500                 505                 510

Glu Val Arg Thr Gly Lys Trp Lys Val Pro Thr Tyr Lys Asp Tyr Val
        515                 520                 525

Asp Leu Phe Arg His Leu Leu Ser Ser Asp Gln Met Met Asp Ser Ile
    530                 535                 540

Leu Ala Asp Glu Ala Phe Phe Ser Val Asn Ser Ser Ser Glu Ser Leu
545                 550                 555                 560

Asn His Leu Leu Tyr Asp Glu Phe Val Lys Ser Val Leu Lys Ile Val
                565                 570                 575

Glu Lys Leu Asp Leu Thr Leu Glu Ile Gln Thr Val Gly Glu Gln Glu
            580                 585                 590

Asn Gly Asp Glu Ala Pro Gly Val Trp Met Ile Pro Thr Ser Asp Pro
        595                 600                 605

Ala Ala Asn Leu His Pro Ala Lys Pro Lys Asp Phe Ser Ala Phe Ile
    610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Val Ser Pro
        675                 680                 685

Lys Ser Leu Lys His Ser Pro Glu Asp Pro Glu Lys Tyr Ser Cys Phe
```

-continued

```
    690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
            740                 745                 750

Gln Met Ala Phe Lys Leu Gly Leu Ser Tyr Thr Pro Leu Ala Glu Val
        755                 760                 765

Gly Leu Asn Ala Leu Glu Glu Trp Ser Ile Tyr Ile Asp Arg His Val
    770                 775                 780

Met Gln Pro Tyr Tyr Lys Asp Ile Leu Pro Cys Leu Asp Gly Tyr Leu
785                 790                 795                 800

Lys Thr Ser Ala Leu Ser Asp Glu Thr Lys Asn Asn Trp Glu Val Ser
                805                 810                 815

Ala Leu Ser Arg Ala Ala Gln Lys Gly Phe Asn Lys Val Val Leu Lys
            820                 825                 830

His Leu Lys Lys Thr Lys Asn Leu Ser Ser Asn Glu Ala Ile Ser Leu
        835                 840                 845

Glu Glu Ile Arg Ile Arg Val Val Gln Met Leu Gly Ser Leu Gly Gly
    850                 855                 860

Gln Ile Asn Lys Asn Leu Leu Thr Val Thr Ser Ser Asp Glu Met Met
865                 870                 875                 880

Lys Ser Tyr Val Ala Trp Asp Arg Glu Lys Arg Leu Ser Phe Ala Val
                885                 890                 895

Pro Phe Arg Glu Met Lys Pro Val Ile Phe Leu Asp Val Phe Leu Pro
            900                 905                 910

Arg Val Thr Glu Leu Ala Leu Thr Ala Ser Asp Arg Gln Thr Lys Val
        915                 920                 925

Ala Ala Cys Glu Leu Leu His Ser Met Val Met Phe Met Leu Gly Lys
    930                 935                 940

Ala Thr Gln Met Pro Glu Gly Gly Gln Gly Ala Pro Pro Met Tyr Gln
945                 950                 955                 960

Leu Tyr Lys Arg Thr Phe Pro Val Leu Leu Arg Leu Ala Cys Asp Val
                965                 970                 975

Asp Gln Val Thr Arg Gln Leu Tyr Glu Pro Leu Val Met Gln Leu Ile
            980                 985                 990

His Trp Phe Thr Asn Asn Lys Lys  Phe Glu Ser Gln Asp  Thr Val Ala
        995                 1000                1005

Leu Leu  Glu Ala Ile Leu Asp  Gly Ile Val Asp Pro  Val Asp Ser
    1010                1015                1020

Thr Leu  Arg Asp Phe Cys Gly  Arg Cys Ile Arg Glu  Phe Leu Lys
    1025                1030                1035

Trp Ser  Ile Lys Gln Ile Thr  Pro Gln Gln Gln Glu  Lys Ser Pro
    1040                1045                1050

Val Asn  Thr Lys Ser Leu Phe  Lys Arg Leu Tyr Ser  Leu Ala Leu
    1055                1060                1065

His Pro  Asn Ala Phe Lys Arg  Leu Gly Ala Ser Leu  Ala Phe Asn
    1070                1075                1080

Asn Ile  Tyr Arg Glu Phe Arg  Glu Glu Glu Ser Leu  Val Glu Gln
    1085                1090                1095

Phe Val  Phe Glu Ala Leu Val  Ile Tyr Met Glu Ser  Leu Ala Leu
    1100                1105                1110
```

-continued

```
Ala His  Ala Asp Glu Lys Ser  Leu Gly Thr Ile Gln  Gln Cys Cys
    1115                 1120                 1125

Asp Ala  Ile Asp His Leu Cys  Arg Ile Ile Glu Lys  Lys His Val
    1130                 1135                 1140

Ser Leu  Asn Lys Ala Lys Lys  Arg Arg Leu Pro Arg  Gly Phe Pro
    1145                 1150                 1155

Pro Ser  Ala Ser Leu Cys Leu  Leu Asp Leu Val Lys  Trp Leu Leu
    1160                 1165                 1170

Ala His  Cys Gly Arg Pro Gln  Thr Glu Cys Arg His  Lys Ser Ile
    1175                 1180                 1185

Glu Leu  Phe Tyr Lys Phe Val  Pro Leu Leu Pro Gly  Asn Arg Ser
    1190                 1195                 1200

Pro Asn  Leu Trp Leu Lys Asp  Val Leu Lys Glu Glu  Gly Val Ser
    1205                 1210                 1215

Phe Leu  Ile Asn Thr Phe Glu  Gly Gly Gly Cys Gly  Gln Pro Ser
    1220                 1225                 1230

Gly Ile  Leu Ala Gln Pro Thr  Leu Leu Tyr Leu Arg  Gly Pro Phe
    1235                 1240                 1245

Ser Leu  Gln Ala Thr Leu Cys  Trp Leu Asp Leu Leu  Leu Ala Ala
    1250                 1255                 1260

Leu Glu  Cys Tyr Asn Thr Phe  Ile Gly Glu Arg Thr  Val Gly Ala
    1265                 1270                 1275

Leu Gln  Val Leu Gly Thr Glu  Ala Gln Ser Ser Leu  Leu Lys Ala
    1280                 1285                 1290

Val Ala  Phe Phe Leu Glu Ser  Ile Ala Met His Asp  Ile Ile Ala
    1295                 1300                 1305

Ala Glu  Lys Cys Phe Gly Thr  Gly Ala Ala Gly Asn  Arg Thr Ser
    1310                 1315                 1320

Pro Gln  Glu Gly Glu Arg Tyr  Asn Tyr Ser Lys Cys  Thr Val Val
    1325                 1330                 1335

Val Arg  Ile Met Glu Phe Thr  Thr Thr Leu Leu Asn  Thr Ser Pro
    1340                 1345                 1350

Glu Gly  Trp Lys Leu Leu Lys  Lys Asp Leu Cys Asn  Thr His Leu
    1355                 1360                 1365

Met Arg  Val Leu Val Gln Thr  Leu Cys Glu Pro Ala  Ser Ile Gly
    1370                 1375                 1380

Phe Asn  Ile Gly Asp Val Gln  Val Met Ala His Leu  Pro Asp Val
    1385                 1390                 1395

Cys Val  Asn Leu Met Lys Ala  Leu Lys Met Ser Pro  Tyr Lys Asp
    1400                 1405                 1410

Ile Leu  Glu Thr His Leu Arg  Glu Lys Ile Thr Ala  Gln Ser Ile
    1415                 1420                 1425

Glu Glu  Leu Cys Ala Val Asn  Leu Tyr Gly Pro Asp  Ala Gln Val
    1430                 1435                 1440

Asp Arg  Ser Arg Leu Ala Ala  Val Val Ser Ala Cys  Lys Gln Leu
    1445                 1450                 1455

His Arg  Ala Gly Leu Leu His  Asn Ile Leu Pro Ser  Gln Ser Thr
    1460                 1465                 1470

Asp Leu  His His Ser Val Gly  Thr Glu Leu Leu Ser  Leu Val Tyr
    1475                 1480                 1485

Lys Gly  Ile Ala Pro Gly Asp  Glu Arg Gln Cys Leu  Pro Ser Leu
    1490                 1495                 1500

Asp Leu  Ser Cys Lys Gln Leu  Ala Ser Gly Leu Leu  Glu Leu Ala
    1505                 1510                 1515
```

```
Phe Ala  Phe Gly Gly Leu Cys  Glu Arg Leu Val Ser  Leu Leu Leu
    1520                 1525                 1530

Asn Pro  Ala Val Leu Ser Thr  Ala Ser Leu Gly Ser  Ser Gln Gly
    1535                 1540                 1545

Ser Val  Ile His Phe Ser His  Gly Glu Tyr Phe Tyr  Ser Leu Phe
    1550                 1555                 1560

Ser Glu  Thr Ile Asn Thr Glu  Leu Leu Lys Asn Leu  Asp Leu Ala
    1565                 1570                 1575

Val Leu  Glu Leu Met Gln Ser  Ser Val Asp Asn Thr  Lys Met Val
    1580                 1585                 1590

Ser Ala  Val Leu Asn Gly Met  Leu Asp Gln Ser Phe  Arg Glu Arg
    1595                 1600                 1605

Ala Asn  Gln Lys His Gln Gly  Leu Lys Leu Ala Thr  Thr Ile Leu
    1610                 1615                 1620

Gln His  Trp Lys Lys Cys Asp  Ser Trp Trp Ala Lys  Asp Ser Pro
    1625                 1630                 1635

Leu Glu  Thr Lys Met Ala Val  Leu Ala Leu Leu Ala  Lys Ile Leu
    1640                 1645                 1650

Gln Ile  Asp Ser Ser Val Ser  Phe Asn Thr Ser His  Gly Ser Phe
    1655                 1660                 1665

Pro Glu  Val Phe Thr Thr Tyr  Ile Ser Leu Leu Ala  Asp Thr Lys
    1670                 1675                 1680

Leu Asp  Leu His Leu Lys Gly  Gln Ala Val Thr Leu  Leu Pro Phe
    1685                 1690                 1695

Phe Thr  Ser Leu Thr Gly Gly  Ser Leu Glu Glu Leu  Arg Arg Val
    1700                 1705                 1710

Leu Glu  Gln Leu Ile Val Ala  His Phe Pro Met Gln  Ser Arg Glu
    1715                 1720                 1725

Phe Pro  Pro Gly Thr Pro Arg  Phe Asn Asn Tyr Val  Asp Cys Met
    1730                 1735                 1740

Lys Lys  Phe Leu Asp Ala Leu  Glu Leu Ser Gln Ser  Pro Met Leu
    1745                 1750                 1755

Leu Glu  Leu Met Thr Glu Val  Leu Cys Arg Glu Gln  Gln His Val
    1760                 1765                 1770

Met Glu  Glu Leu Phe Gln Ser  Ser Phe Arg Arg Ile  Ala Arg Arg
    1775                 1780                 1785

Gly Ser  Cys Val Thr Gln Val  Gly Leu Leu Glu Ser  Val Tyr Glu
    1790                 1795                 1800

Met Phe  Arg Lys Asp Asp Pro  Arg Leu Ser Phe Thr  Arg Gln Ser
    1805                 1810                 1815

Phe Val  Asp Arg Ser Leu Leu  Thr Leu Leu Trp His  Cys Ser Leu
    1820                 1825                 1830

Asp Ala  Leu Arg Glu Phe Phe  Ser Thr Ile Val Val  Asp Ala Ile
    1835                 1840                 1845

Asp Val  Leu Lys Ser Arg Phe  Thr Lys Leu Asn Glu  Ser Thr Phe
    1850                 1855                 1860

Asp Thr  Gln Ile Thr Lys Lys  Met Gly Tyr Tyr Lys  Ile Leu Asp
    1865                 1870                 1875

Val Met  Tyr Ser Arg Leu Pro  Lys Asp Asp Val His  Ala Lys Glu
    1880                 1885                 1890

Ser Lys  Ile Asn Gln Val Phe  His Gly Ser Cys Ile  Thr Glu Gly
    1895                 1900                 1905

Asn Glu  Leu Thr Lys Thr Leu  Ile Lys Leu Cys Tyr  Asp Ala Phe
```

```
    1910                1915                1920

Thr Glu  Asn Met Ala Gly Glu  Asn Gln Leu Leu Glu  Arg Arg Arg
    1925                1930                1935

Leu Tyr  His Cys Ala Ala Tyr  Asn Cys Ala Ile Ser  Val Ile Cys
    1940                1945                1950

Cys Val  Phe Asn Glu Leu Lys  Phe Tyr Gln Gly Phe  Leu Phe Ser
    1955                1960                1965

Glu Lys  Pro Glu Lys Asn Leu  Leu Ile Phe Glu Asn  Leu Ile Asp
    1970                1975                1980

Leu Lys  Arg Arg Tyr Asn Phe  Pro Val Glu Val Glu  Val Pro Met
    1985                1990                1995

Glu Arg  Lys Lys Lys Tyr Ile  Glu Ile Arg Lys Glu  Ala Arg Glu
    2000                2005                2010

Ala Ala  Asn Gly Asp Ser Asp  Gly Pro Ser Tyr Met  Ser Ser Leu
    2015                2020                2025

Ser Tyr  Leu Ala Asp Ser Thr  Leu Ser Glu Glu Met  Ser Gln Phe
    2030                2035                2040

Asp Phe  Ser Thr Gly Val Gln  Ser Tyr Ser Tyr Ser  Ser Gln Asp
    2045                2050                2055

Pro Arg  Pro Ala Thr Gly Arg  Phe Arg Arg Arg Glu  Gln Arg Asp
    2060                2065                2070

Pro Thr  Val His Asp Asp Val  Leu Glu Leu Glu Met  Asp Glu Leu
    2075                2080                2085

Asn Arg  His Glu Cys Met Ala  Pro Leu Thr Ala Leu  Val Lys His
    2090                2095                2100

Met His  Arg Ser Leu Gly Pro  Pro Gln Gly Glu Glu  Asp Ser Val
    2105                2110                2115

Pro Arg  Asp Leu Pro Ser Trp  Met Lys Phe Leu His  Gly Lys Leu
    2120                2125                2130

Gly Asn  Pro Ile Val Pro Leu  Asn Ile Arg Leu Phe  Leu Ala Lys
    2135                2140                2145

Leu Val  Ile Asn Thr Glu Glu  Val Phe Arg Pro Tyr  Ala Lys His
    2150                2155                2160

Trp Leu  Ser Pro Leu Leu Gln  Leu Ala Ala Ser Glu  Asn Asn Gly
    2165                2170                2175

Gly Glu  Gly Ile His Tyr Met  Val Val Glu Ile Val  Ala Thr Ile
    2180                2185                2190

Leu Ser  Trp Thr Gly Leu Ala  Thr Pro Thr Gly Val  Pro Lys Asp
    2195                2200                2205

Glu Val  Leu Ala Asn Arg Leu  Leu Asn Phe Leu Met  Lys His Val
    2210                2215                2220

Phe His  Pro Lys Arg Ala Val  Phe Arg His Asn Leu  Glu Ile Ile
    2225                2230                2235

Lys Thr  Leu Val Glu Cys Trp  Lys Asp Cys Leu Ser  Ile Pro Tyr
    2240                2245                2250

Arg Leu  Ile Phe Glu Lys Phe  Ser Gly Lys Asp Pro  Asn Ser Lys
    2255                2260                2265

Asp Asn  Ser Val Gly Ile Gln  Leu Leu Gly Ile Val  Met Ala Asn
    2270                2275                2280

Asp Leu  Pro Pro Tyr Asp Pro  Gln Cys Gly Ile Gln  Ser Ser Glu
    2285                2290                2295

Tyr Phe  Gln Ala Leu Val Asn  Asn Met Ser Phe Val  Arg Tyr Lys
    2300                2305                2310
```

-continued

Glu Val Tyr Ala Ala Ala Ala Glu Val Leu Gly Leu Ile Leu Arg
2315 2320 2325

Tyr Val Met Glu Arg Lys Asn Ile Leu Glu Glu Ser Leu Cys Glu
2330 2335 2340

Leu Val Ala Lys Gln Leu Lys Gln His Gln Asn Thr Met Glu Asp
2345 2350 2355

Lys Phe Ile Val Cys Leu Asn Lys Val Thr Lys Ser Phe Pro Pro
2360 2365 2370

Leu Ala Asp Arg Phe Met Asn Ala Val Phe Phe Leu Leu Pro Lys
2375 2380 2385

Phe His Gly Val Leu Lys Thr Leu Cys Leu Glu Val Val Leu Cys
2390 2395 2400

Arg Val Glu Gly Met Thr Glu Leu Tyr Phe Gln Leu Lys Ser Lys
2405 2410 2415

Asp Phe Val Gln Val Met Arg His Arg Asp Asp Glu Arg Gln Lys
2420 2425 2430

Val Cys Leu Asp Ile Ile Tyr Lys Met Met Pro Lys Leu Lys Pro
2435 2440 2445

Val Glu Leu Arg Glu Leu Leu Asn Pro Val Val Glu Phe Val Ser
2450 2455 2460

His Pro Ser Thr Thr Cys Arg Glu Gln Met Tyr Asn Ile Leu Met
2465 2470 2475

Trp Ile His Asp Asn Tyr Arg Asp Pro Glu Ser Glu Thr Asp Asn
2480 2485 2490

Asp Ser Gln Glu Ile Phe Lys Leu Ala Lys Asp Val Leu Ile Gln
2495 2500 2505

Gly Leu Ile Asp Glu Asn Pro Gly Leu Gln Leu Ile Ile Arg Asn
2510 2515 2520

Phe Trp Ser His Glu Thr Arg Leu Pro Ser Asn Thr Leu Asp Arg
2525 2530 2535

Leu Leu Ala Leu Asn Ser Leu Tyr Ser Pro Lys Ile Glu Val His
2540 2545 2550

Phe Leu Ser Leu Ala Thr Asn Phe Leu Leu Glu Met Thr Ser Met
2555 2560 2565

Ser Pro Asp Tyr Pro Asn Pro Met Phe Glu His Pro Leu Ser Glu
2570 2575 2580

Cys Glu Phe Gln Glu Tyr Thr Ile Asp Ser Asp Trp Arg Phe Arg
2585 2590 2595

Ser Thr Val Leu Thr Pro Met Phe Val Glu Thr Gln Ala Ser Gln
2600 2605 2610

Gly Thr Leu Gln Thr Arg Thr Gln Glu Gly Ser Leu Ser Ala Arg
2615 2620 2625

Trp Pro Val Ala Gly Gln Ile Arg Ala Thr Gln Gln Gln His Asp
2630 2635 2640

Phe Thr Leu Thr Gln Thr Ala Asp Gly Arg Ser Ser Phe Asp Trp
2645 2650 2655

Leu Thr Gly Ser Ser Thr Asp Pro Leu Val Asp His Thr Ser Pro
2660 2665 2670

Ser Ser Asp Ser Leu Leu Phe Ala His Lys Arg Ser Glu Arg Leu
2675 2680 2685

Gln Arg Ala Pro Leu Lys Ser Val Gly Pro Asp Phe Gly Lys Lys
2690 2695 2700

Arg Leu Gly Leu Pro Gly Asp Glu Val Asp Asn Lys Val Lys Gly
2705 2710 2715

```
Ala Ala  Gly Arg Thr Asp Leu  Leu Arg Leu Arg Arg  Arg Phe Met
    2720                 2725                 2730

Arg Asp  Gln Glu Lys Leu Ser  Leu Met Tyr Ala Arg  Lys Gly Val
    2735                 2740                 2745

Ala Glu  Gln Lys Arg Glu Lys  Glu Ile Lys Ser Glu  Leu Lys Met
    2750                 2755                 2760

Lys Gln  Asp Ala Gln Val Val  Leu Tyr Arg Ser Tyr  Arg His Gly
    2765                 2770                 2775

Asp Leu  Pro Asp Ile Gln Ile  Lys His Ser Ser Leu  Ile Thr Pro
    2780                 2785                 2790

Leu Gln  Ala Val Ala Gln Arg  Asp Pro Ile Ile Ala  Lys Gln Leu
    2795                 2800                 2805

Phe Ser  Ser Leu Phe Ser Gly  Ile Leu Lys Glu Met  Asp Lys Phe
    2810                 2815                 2820

Lys Thr  Leu Ser Glu Lys Asn  Asn Ile Thr Gln Lys  Leu Leu Gln
    2825                 2830                 2835

Asp Phe  Asn Arg Phe Leu Asn  Thr Thr Phe Ser Phe  Phe Pro Pro
    2840                 2845                 2850

Phe Val  Ser Cys Ile Gln Asp  Ile Ser Cys Gln His  Ala Ala Leu
    2855                 2860                 2865

Leu Ser  Leu Asp Pro Ala Ala  Val Ser Ala Gly Cys  Leu Ala Ser
    2870                 2875                 2880

Leu Gln  Gln Pro Val Gly Ile  Arg Leu Leu Glu Glu  Ala Leu Leu
    2885                 2890                 2895

Arg Leu  Leu Pro Ala Glu Leu  Pro Ala Lys Arg Val  Arg Gly Lys
    2900                 2905                 2910

Ala Arg  Leu Pro Pro Asp Val  Leu Arg Trp Val Glu  Leu Ala Lys
    2915                 2920                 2925

Leu Tyr  Arg Ser Ile Gly Glu  Tyr Asp Val Leu Arg  Gly Ile Phe
    2930                 2935                 2940

Thr Ser  Glu Ile Gly Thr Lys  Gln Ile Thr Gln Ser  Ala Leu Leu
    2945                 2950                 2955

Ala Glu  Ala Arg Ser Asp Tyr  Ser Glu Ala Ala Lys  Gln Tyr Asp
    2960                 2965                 2970

Glu Ala  Leu Asn Lys Gln Asp  Trp Val Asp Gly Glu  Pro Thr Glu
    2975                 2980                 2985

Ala Glu  Lys Asp Phe Trp Glu  Leu Ala Ser Leu Asp  Cys Tyr Asn
    2990                 2995                 3000

His Leu  Ala Glu Trp Lys Ser  Leu Glu Tyr Cys Ser  Thr Ala Ser
    3005                 3010                 3015

Ile Asp  Ser Glu Asn Pro Pro  Asp Leu Asn Lys Ile  Trp Ser Glu
    3020                 3025                 3030

Pro Phe  Tyr Gln Glu Thr Tyr  Leu Pro Tyr Met Ile  Arg Ser Lys
    3035                 3040                 3045

Leu Lys  Leu Leu Leu Gln Gly  Glu Ala Asp Gln Ser  Leu Leu Thr
    3050                 3055                 3060

Phe Ile  Asp Lys Ala Met His  Gly Glu Leu Gln Lys  Ala Ile Leu
    3065                 3070                 3075

Glu Leu  His Tyr Ser Gln Glu  Leu Ser Leu Leu Tyr  Leu Leu Gln
    3080                 3085                 3090

Asp Asp  Val Asp Arg Ala Lys  Tyr Tyr Ile Gln Asn  Gly Ile Gln
    3095                 3100                 3105

Ser Phe  Met Gln Asn Tyr Ser  Ser Ile Asp Val Leu  Leu His Gln
```

-continued

```
    3110                3115                3120

Ser Arg  Leu Thr Lys Leu Gln  Ser Val Gln Ala Leu  Thr Glu Ile
    3125                3130                3135

Gln Glu  Phe Ile Ser Phe Ile  Ser Lys Gln Gly Asn  Leu Ser Ser
    3140                3145                3150

Gln Val  Pro Leu Lys Arg Leu  Leu Asn Thr Trp Thr  Asn Arg Tyr
    3155                3160                3165

Pro Asp  Ala Lys Met Asp Pro  Met Asn Ile Trp Asp  Asp Ile Ile
    3170                3175                3180

Thr Asn  Arg Cys Phe Phe Leu  Ser Lys Ile Glu Glu  Lys Leu Thr
    3185                3190                3195

Pro Leu  Pro Glu Asp Asn Ser  Met Asn Val Asp Gln  Asp Gly Asp
    3200                3205                3210

Pro Ser  Asp Arg Met Glu Val  Gln Glu Gln Glu Glu  Asp Ile Ser
    3215                3220                3225

Ser Leu  Ile Arg Ser Cys Lys  Phe Ser Met Lys Met  Lys Met Ile
    3230                3235                3240

Asp Ser  Ala Arg Lys Gln Asn  Asn Phe Ser Leu Ala  Met Lys Leu
    3245                3250                3255

Leu Lys  Glu Leu His Lys Glu  Ser Lys Thr Arg Asp  Asp Trp Leu
    3260                3265                3270

Val Ser  Trp Val Gln Ser Tyr  Cys Arg Leu Ser His  Cys Arg Ser
    3275                3280                3285

Arg Ser  Gln Gly Cys Ser Glu  Gln Val Leu Thr Val  Leu Lys Thr
    3290                3295                3300

Val Ser  Leu Leu Asp Glu Asn  Asn Val Ser Ser Tyr  Leu Ser Lys
    3305                3310                3315

Asn Ile  Leu Ala Phe Arg Asp  Gln Asn Ile Leu Leu  Gly Thr Thr
    3320                3325                3330

Tyr Arg  Ile Ile Ala Asn Ala  Leu Ser Ser Glu Pro  Ala Cys Leu
    3335                3340                3345

Ala Glu  Ile Glu Glu Asp Lys  Ala Arg Arg Ile Leu  Glu Leu Ser
    3350                3355                3360

Gly Ser  Ser Ser Glu Asp Ser  Glu Lys Val Ile Ala  Gly Leu Tyr
    3365                3370                3375

Gln Arg  Ala Phe Gln His Leu  Ser Glu Ala Val Gln  Ala Ala Glu
    3380                3385                3390

Glu Glu  Ala Gln Pro Pro Ser  Trp Ser Cys Gly Pro  Ala Ala Gly
    3395                3400                3405

Val Ile  Asp Ala Tyr Met Thr  Leu Ala Asp Phe Cys  Asp Gln Gln
    3410                3415                3420

Leu Arg  Lys Glu Glu Glu Asn  Ala Ser Val Ile Asp  Ser Ala Glu
    3425                3430                3435

Leu Gln  Ala Tyr Pro Ala Leu  Val Val Glu Lys Met  Leu Lys Ala
    3440                3445                3450

Leu Lys  Leu Asn Ser Asn Glu  Ala Arg Leu Lys Phe  Pro Arg Leu
    3455                3460                3465

Leu Gln  Ile Ile Glu Arg Tyr  Pro Glu Glu Thr Leu  Ser Leu Met
    3470                3475                3480

Thr Lys  Glu Ile Ser Ser Val  Pro Cys Trp Gln Phe  Ile Ser Trp
    3485                3490                3495

Ile Ser  His Met Val Ala Leu  Leu Asp Lys Asp Gln  Ala Val Ala
    3500                3505                3510
```

-continued

```
Val Gln His Ser Val Glu Glu Ile Thr Asp Asn Tyr Pro Gln Ala
    3515                3520                3525

Ile Val Tyr Pro Phe Ile Ile Ser Ser Glu Ser Tyr Ser Phe Lys
    3530                3535                3540

Asp Thr Ser Thr Gly His Lys Asn Lys Glu Phe Val Ala Arg Ile
    3545                3550                3555

Lys Ser Lys Leu Asp Gln Gly Gly Val Ile Gln Asp Phe Ile Asn
    3560                3565                3570

Ala Leu Asp Gln Leu Ser Asn Pro Glu Leu Leu Phe Lys Asp Trp
    3575                3580                3585

Ser Asn Asp Val Arg Ala Glu Leu Ala Lys Thr Pro Val Asn Lys
    3590                3595                3600

Lys Asn Ile Glu Lys Met Tyr Glu Arg Met Tyr Ala Ala Leu Gly
    3605                3610                3615

Asp Pro Lys Ala Pro Gly Leu Gly Ala Phe Arg Arg Lys Phe Ile
    3620                3625                3630

Gln Thr Phe Gly Lys Glu Phe Asp Lys His Phe Gly Lys Gly Gly
    3635                3640                3645

Ser Lys Leu Leu Arg Met Lys Leu Ser Asp Phe Asn Asp Ile Thr
    3650                3655                3660

Asn Met Leu Leu Leu Lys Met Asn Lys Asp Ser Lys Pro Pro Gly
    3665                3670                3675

Asn Leu Lys Glu Cys Ser Pro Trp Met Ser Asp Phe Lys Val Glu
    3680                3685                3690

Phe Leu Arg Asn Glu Leu Glu Ile Pro Gly Gln Tyr Asp Gly Arg
    3695                3700                3705

Gly Lys Pro Leu Pro Glu Tyr His Val Arg Ile Ala Gly Phe Asp
    3710                3715                3720

Glu Arg Val Thr Val Met Ala Ser Leu Arg Arg Pro Lys Arg Ile
    3725                3730                3735

Ile Ile Arg Gly His Asp Glu Arg Glu His Pro Phe Leu Val Lys
    3740                3745                3750

Gly Gly Glu Asp Leu Arg Gln Asp Gln Arg Val Glu Gln Leu Phe
    3755                3760                3765

Gln Val Met Asn Gly Ile Leu Ala Gln Asp Ser Ala Cys Ser Gln
    3770                3775                3780

Arg Ala Leu Gln Leu Arg Thr Tyr Ser Val Val Pro Met Thr Ser
    3785                3790                3795

Arg Leu Gly Leu Ile Glu Trp Leu Glu Asn Thr Val Thr Leu Lys
    3800                3805                3810

Asp Leu Leu Leu Asn Thr Met Ser Gln Glu Glu Lys Ala Ala Tyr
    3815                3820                3825

Leu Ser Asp Pro Arg Ala Pro Pro Cys Glu Tyr Lys Asp Trp Leu
    3830                3835                3840

Thr Lys Met Ser Gly Lys His Asp Val Gly Ala Tyr Met Leu Met
    3845                3850                3855

Tyr Lys Gly Ala Asn Arg Thr Glu Thr Val Thr Ser Phe Arg Lys
    3860                3865                3870

Arg Glu Ser Lys Val Pro Ala Asp Leu Leu Lys Arg Ala Phe Val
    3875                3880                3885

Arg Met Ser Thr Ser Pro Glu Ala Phe Leu Ala Leu Arg Ser His
    3890                3895                3900

Phe Ala Ser Ser His Ala Leu Ile Cys Ile Ser His Trp Ile Leu
    3905                3910                3915
```

Gly Ile Gly Asp Arg His Leu Asn Asn Phe Met Val Ala Met Glu
3920 3925 3930

Thr Gly Gly Val Ile Gly Ile Asp Phe Gly His Ala Phe Gly Ser
3935 3940 3945

Ala Thr Gln Phe Leu Pro Val Pro Glu Leu Met Pro Phe Arg Leu
3950 3955 3960

Thr Arg Gln Phe Ile Asn Leu Met Leu Pro Met Lys Glu Thr Gly
3965 3970 3975

Leu Met Tyr Ser Ile Met Val His Ala Leu Arg Ala Phe Arg Ser
3980 3985 3990

Asp Pro Gly Leu Leu Thr Asn Thr Met Asp Val Phe Val Lys Glu
3995 4000 4005

Pro Ser Phe Asp Trp Lys Asn Phe Glu Gln Lys Met Leu Lys Lys
4010 4015 4020

Gly Gly Ser Trp Ile Gln Glu Ile Asn Val Ala Glu Lys Asn Trp
4025 4030 4035

Tyr Pro Arg Gln Lys Ile Cys Tyr Ala Lys Arg Lys Leu Ala Gly
4040 4045 4050

Ala Asn Pro Ala Val Ile Thr Cys Asp Glu Leu Leu Leu Gly His
4055 4060 4065

Glu Lys Ala Pro Ala Phe Arg Asp Tyr Val Ala Val Ala Arg Gly
4070 4075 4080

Ser Lys Asp His Asn Ile Arg Ala Gln Glu Pro Glu Ser Gly Leu
4085 4090 4095

Ser Glu Glu Thr Gln Val Lys Cys Leu Met Asp Gln Ala Thr Asp
4100 4105 4110

Pro Asn Ile Leu Gly Arg Thr Trp Glu Gly Trp Glu Pro Trp Met
4115 4120 4125

<210> SEQ ID NO 6
<211> LENGTH: 795
<212> TYPE: PRT
<213> ORGANISM: Artificial Sequence
<220> FEATURE:
<223> OTHER INFORMATION: Synthetic

<400> SEQUENCE: 6

Met Leu Ser Gln Val Tyr Arg Cys Gly Phe Gln Pro Phe Asn Gln His
1 5 10 15

Leu Leu Pro Trp Val Lys Cys Thr Thr Val Phe Arg Ser His Cys Ile
20 25 30

Gln Pro Ser Val Ile Arg His Val Arg Ser Trp Ser Asn Ile Pro Phe
35 40 45

Ile Thr Val Pro Leu Ser Arg Thr His Gly Lys Ser Phe Ala His Arg
50 55 60

Ser Glu Leu Lys His Ala Lys Arg Ile Val Val Lys Leu Gly Ser Ala
65 70 75 80

Val Val Thr Arg Gly Asp Glu Cys Gly Leu Ala Leu Gly Arg Leu Ala
85 90 95

Ser Ile Val Glu Gln Val Ser Val Leu Gln Asn Gln Gly Arg Glu Met
100 105 110

Met Leu Val Thr Ser Gly Ala Val Ala Phe Gly Lys Gln Arg Leu Arg
115 120 125

His Glu Ile Leu Leu Ser Gln Ser Val Arg Gln Ala Leu His Ser Gly
130 135 140

```
Gln Asn Gln Leu Lys Glu Met Ala Ile Pro Val Leu Glu Ala Arg Ala
145                 150                 155                 160

Cys Ala Ala Ala Gly Gln Ser Gly Leu Met Ala Leu Tyr Glu Ala Met
                165                 170                 175

Phe Thr Gln Tyr Ser Ile Cys Ala Ala Gln Ile Leu Val Thr Asn Leu
            180                 185                 190

Asp Phe His Asp Glu Gln Lys Arg Arg Asn Leu Asn Gly Thr Leu His
        195                 200                 205

Glu Leu Leu Arg Met Asn Ile Val Pro Ile Val Asn Thr Asn Asp Ala
    210                 215                 220

Val Val Pro Pro Ala Glu Pro Asn Ser Asp Leu Gln Gly Val Asn Val
225                 230                 235                 240

Ile Ser Val Lys Asp Asn Asp Ser Leu Ala Ala Arg Leu Ala Val Glu
                245                 250                 255

Met Lys Thr Asp Leu Leu Ile Val Leu Ser Asp Val Glu Gly Leu Phe
            260                 265                 270

Asp Ser Pro Pro Gly Ser Asp Asp Ala Lys Leu Ile Asp Ile Phe Tyr
        275                 280                 285

Pro Gly Asp Gln Gln Ser Val Thr Phe Gly Thr Lys Ser Arg Val Gly
    290                 295                 300

Met Gly Gly Met Glu Ala Lys Val Lys Ala Ala Leu Trp Ala Leu Gln
305                 310                 315                 320

Gly Gly Thr Ser Val Val Ile Ala Asn Gly Thr His Pro Lys Val Ser
                325                 330                 335

Gly His Val Ile Thr Asp Ile Val Glu Gly Lys Lys Val Gly Thr Phe
            340                 345                 350

Phe Ser Glu Val Lys Pro Ala Gly Pro Thr Val Glu Gln Gln Gly Glu
        355                 360                 365

Met Ala Arg Ser Gly Gly Arg Met Leu Ala Thr Leu Glu Pro Glu Gln
    370                 375                 380

Arg Ala Glu Ile Ile His His Leu Ala Asp Leu Leu Thr Asp Gln Arg
385                 390                 395                 400

Asp Glu Ile Leu Leu Ala Asn Lys Lys Asp Leu Glu Glu Ala Glu Gly
                405                 410                 415

Arg Leu Ala Ala Pro Leu Leu Lys Arg Leu Ser Leu Ser Thr Ser Lys
            420                 425                 430

Leu Asn Ser Leu Ala Ile Gly Leu Arg Gln Ile Ala Ala Ser Ser Gln
        435                 440                 445

Asp Ser Val Gly Arg Val Leu Arg Arg Thr Arg Ile Ala Lys Asn Leu
    450                 455                 460

Glu Leu Glu Gln Val Thr Val Pro Ile Gly Val Leu Leu Val Ile Phe
465                 470                 475                 480

Glu Ser Arg Pro Asp Cys Leu Pro Gln Val Ala Ala Leu Ala Ile Ala
                485                 490                 495

Ser Gly Asn Gly Leu Leu Leu Lys Gly Gly Lys Glu Ala Ala His Ser
            500                 505                 510

Asn Arg Ile Leu His Leu Leu Thr Gln Glu Ala Leu Ser Ile His Gly
        515                 520                 525

Val Lys Glu Ala Val Gln Leu Val Asn Thr Arg Glu Glu Val Glu Asp
    530                 535                 540

Leu Cys Arg Leu Asp Lys Met Ile Asp Leu Ile Ile Pro Arg Gly Ser
545                 550                 555                 560

Ser Gln Leu Val Arg Asp Ile Gln Lys Ala Ala Lys Gly Ile Pro Val
                565                 570                 575
```

```
Met Gly His Ser Glu Gly Ile Cys His Met Tyr Val Asp Ser Glu Ala
            580                 585                 590

Ser Val Asp Lys Val Thr Arg Leu Val Arg Asp Ser Lys Cys Glu Tyr
        595                 600                 605

Pro Ala Ala Cys Asn Ala Leu Glu Thr Leu Leu Ile His Arg Asp Leu
    610                 615                 620

Leu Arg Thr Pro Leu Phe Asp Gln Ile Ile Asp Met Leu Arg Val Glu
625                 630                 635                 640

Gln Val Lys Ile His Ala Gly Pro Lys Phe Ala Ser Tyr Leu Thr Phe
                645                 650                 655

Ser Pro Ser Glu Val Lys Ser Leu Arg Thr Glu Tyr Gly Asp Leu Glu
            660                 665                 670

Leu Cys Ile Glu Val Val Asp Asn Val Gln Asp Ala Ile Asp His Ile
        675                 680                 685

His Lys Tyr Gly Ser Ser His Thr Asp Val Ile Val Thr Glu Asp Glu
    690                 695                 700

Asn Thr Ala Glu Phe Phe Leu Gln His Val Asp Ser Ala Cys Val Phe
705                 710                 715                 720

Trp Asn Ala Ser Thr Arg Phe Ser Asp Gly Tyr Arg Phe Gly Leu Gly
                725                 730                 735

Ala Glu Val Gly Ile Ser Thr Ser Arg Ile His Ala Arg Gly Pro Val
            740                 745                 750

Gly Leu Glu Gly Leu Leu Thr Thr Lys Trp Leu Leu Arg Gly Lys Asp
        755                 760                 765

His Val Val Ser Asp Phe Ser Glu His Gly Ser Leu Lys Tyr Leu His
    770                 775                 780

Glu Asn Leu Pro Ile Pro Gln Arg Asn Thr Asn
785                 790                 795
```

<210> SEQ ID NO 7
<211> LENGTH: 154
<212> TYPE: PRT
<213> ORGANISM: Artificial Sequence
<220> FEATURE:
<223> OTHER INFORMATION: Synthetic

<400> SEQUENCE: 7

```
Met Ala Ser Ala Ser Ala Arg Gly Asn Gln Asp Lys Asp Ala His Phe
1               5                   10                  15

Pro Pro Pro Ser Lys Gln Ser Leu Leu Phe Cys Pro Lys Ser Lys Leu
            20                  25                  30

His Ile His Arg Ala Glu Ile Ser Lys Ile Met Arg Glu Cys Gln Glu
        35                  40                  45

Glu Ser Phe Trp Lys Arg Ala Leu Pro Phe Ser Leu Val Ser Met Leu
    50                  55                  60

Val Thr Gln Gly Leu Val Tyr Gln Gly Tyr Leu Ala Ala Asn Ser Arg
65                  70                  75                  80

Phe Gly Ser Leu Pro Lys Val Ala Leu Ala Gly Leu Leu Gly Phe Gly
                85                  90                  95

Leu Gly Lys Val Ser Tyr Ile Gly Val Cys Gln Ser Lys Phe His Phe
            100                 105                 110

Phe Glu Asp Gln Leu Arg Gly Ala Gly Phe Gly Pro Gln His Asn Arg
        115                 120                 125

His Cys Leu Leu Thr Cys Glu Glu Cys Lys Ile Lys His Gly Leu Ser
    130                 135                 140
```

Glu Lys Gly Asp Ser Gln Pro Ser Ala Ser
145 150

<210> SEQ ID NO 8
<211> LENGTH: 837
<212> TYPE: PRT
<213> ORGANISM: Artificial Sequence
<220> FEATURE:
<223> OTHER INFORMATION: Synthetic

<400> SEQUENCE: 8

Met Ala Arg Gly Glu Arg Arg Arg Arg Ala Val Pro Ala Glu Gly Val
1 5 10 15

Arg Thr Ala Glu Arg Ala Ala Arg Gly Gly Pro Gly Arg Arg Asp Gly
20 25 30

Arg Gly Gly Gly Pro Arg Ser Thr Ala Gly Gly Val Ala Leu Ala Val
35 40 45

Val Val Leu Ser Leu Ala Leu Gly Met Ser Gly Arg Trp Val Leu Ala
50 55 60

Trp Tyr Arg Ala Arg Arg Ala Val Thr Leu His Ser Ala Pro Pro Val
65 70 75 80

Leu Pro Ala Asp Ser Ser Ser Pro Ala Val Ala Pro Asp Leu Phe Trp
85 90 95

Gly Thr Tyr Arg Pro His Val Tyr Phe Gly Met Lys Thr Arg Ser Pro
100 105 110

Lys Pro Leu Leu Thr Gly Leu Met Trp Ala Gln Gln Gly Thr Thr Pro
115 120 125

Gly Thr Pro Lys Leu Arg His Thr Cys Glu Gln Gly Asp Gly Val Gly
130 135 140

Pro Tyr Gly Trp Glu Phe His Asp Gly Leu Ser Phe Gly Arg Gln His
145 150 155 160

Ile Gln Asp Gly Ala Leu Arg Leu Thr Thr Glu Phe Val Lys Arg Pro
165 170 175

Gly Gly Gln His Gly Gly Asp Trp Ser Trp Arg Val Thr Val Glu Pro
180 185 190

Gln Asp Ser Gly Thr Ser Ala Leu Pro Leu Val Ser Leu Phe Phe Tyr
195 200 205

Val Val Thr Asp Gly Lys Glu Val Leu Leu Pro Glu Val Gly Ala Lys
210 215 220

Gly Gln Leu Lys Phe Ile Ser Gly His Thr Ser Glu Leu Gly Asp Phe
225 230 235 240

Arg Phe Thr Leu Leu Pro Pro Thr Ser Pro Gly Asp Thr Ala Pro Lys
245 250 255

Tyr Gly Ser Tyr Asn Val Phe Trp Thr Ser Asn Pro Gly Leu Pro Leu
260 265 270

Leu Thr Glu Met Val Lys Ser Arg Leu Asn Ser Trp Phe Gln His Arg
275 280 285

Pro Pro Gly Ala Pro Pro Glu Arg Tyr Leu Gly Leu Pro Gly Ser Leu
290 295 300

Lys Trp Glu Asp Arg Gly Pro Ser Gly Gln Gly Gln Gly Gln Phe Leu
305 310 315 320

Ile Gln Gln Val Thr Leu Lys Ile Pro Ile Ser Ile Glu Phe Val Phe
325 330 335

Glu Ser Gly Ser Ala Gln Ala Gly Gly Asn Gln Ala Leu Pro Arg Leu
340 345 350

Ala Gly Ser Leu Leu Thr Gln Ala Leu Glu Ser His Ala Glu Gly Phe

-continued

```
        355                 360                 365

Arg Glu Arg Phe Glu Lys Thr Phe Gln Leu Lys Glu Lys Gly Leu Ser
    370                 375                 380

Ser Gly Glu Gln Val Leu Gly Gln Ala Ala Leu Ser Gly Leu Leu Gly
385                 390                 395                 400

Gly Ile Gly Tyr Phe Tyr Gly Gln Gly Leu Val Leu Pro Asp Ile Gly
                405                 410                 415

Val Glu Gly Ser Glu Gln Lys Val Asp Pro Ala Leu Phe Pro Pro Val
            420                 425                 430

Pro Leu Phe Thr Ala Val Pro Ser Arg Ser Phe Phe Pro Arg Gly Phe
        435                 440                 445

Leu Trp Asp Glu Gly Phe His Gln Leu Val Val Gln Arg Trp Asp Pro
    450                 455                 460

Ser Leu Thr Arg Glu Ala Leu Gly His Trp Leu Gly Leu Leu Asn Ala
465                 470                 475                 480

Asp Gly Trp Ile Gly Arg Glu Gln Ile Leu Gly Asp Glu Ala Arg Ala
                485                 490                 495

Arg Val Pro Pro Glu Phe Leu Val Gln Arg Ala Val His Ala Asn Pro
            500                 505                 510

Pro Thr Leu Leu Leu Pro Val Ala His Met Leu Glu Val Gly Asp Pro
        515                 520                 525

Asp Asp Leu Ala Phe Leu Arg Lys Ala Leu Pro Arg Leu His Ala Trp
    530                 535                 540

Phe Ser Trp Leu His Gln Ser Gln Ala Gly Pro Leu Pro Leu Ser Tyr
545                 550                 555                 560

Arg Trp Arg Gly Arg Asp Pro Ala Leu Pro Thr Leu Leu Asn Pro Lys
                565                 570                 575

Thr Leu Pro Ser Gly Leu Asp Asp Tyr Pro Arg Ala Ser His Pro Ser
            580                 585                 590

Val Thr Glu Arg His Leu Asp Leu Arg Cys Trp Val Ala Leu Gly Ala
        595                 600                 605

Arg Val Leu Thr Arg Leu Ala Glu His Leu Gly Glu Ala Glu Val Ala
    610                 615                 620

Ala Glu Leu Gly Pro Leu Ala Ala Ser Leu Glu Ala Ala Glu Ser Leu
625                 630                 635                 640

Asp Glu Leu His Trp Ala Pro Glu Leu Gly Val Phe Ala Asp Phe Gly
                645                 650                 655

Asn His Thr Lys Ala Val Gln Leu Lys Pro Arg Pro Pro Gln Gly Leu
            660                 665                 670

Val Arg Val Val Gly Arg Pro Gln Pro Gln Leu Gln Tyr Val Asp Ala
        675                 680                 685

Leu Gly Tyr Val Ser Leu Phe Pro Leu Leu Leu Arg Leu Leu Asp Pro
    690                 695                 700

Thr Ser Ser Arg Leu Gly Pro Leu Leu Asp Ile Leu Ala Asp Ser Arg
705                 710                 715                 720

His Leu Trp Ser Pro Phe Gly Leu Arg Ser Leu Ala Ala Ser Ser Ser
                725                 730                 735

Phe Tyr Gly Gln Arg Asn Ser Glu His Asp Pro Pro Tyr Trp Arg Gly
            740                 745                 750

Ala Val Trp Leu Asn Val Asn Tyr Leu Ala Leu Gly Ala Leu His His
        755                 760                 765

Tyr Gly His Leu Glu Gly Pro His Gln Ala Arg Ala Ala Lys Leu His
    770                 775                 780
```

Gly Glu Leu Arg Ala Asn Val Val Gly Asn Val Trp Arg Gln Tyr Gln
785 790 795 800

Ala Thr Gly Phe Leu Trp Glu Gln Tyr Ser Asp Arg Asp Gly Arg Gly
805 810 815

Met Gly Cys Arg Pro Phe His Gly Trp Thr Ser Leu Val Leu Leu Ala
820 825 830

Met Ala Glu Asp Tyr
835

<210> SEQ ID NO 9
<211> LENGTH: 372
<212> TYPE: PRT
<213> ORGANISM: Artificial Sequence
<220> FEATURE:
<223> OTHER INFORMATION: Synthetic

<400> SEQUENCE: 9

Met Ala His Ala Pro Ala Arg Cys Pro Ser Ala Arg Gly Ser Gly Asp
1 5 10 15

Gly Glu Met Gly Lys Pro Arg Asn Val Ala Leu Ile Thr Gly Ile Thr
20 25 30

Gly Gln Asp Gly Ser Tyr Leu Ala Glu Phe Leu Leu Glu Lys Gly Tyr
35 40 45

Glu Val His Gly Ile Val Arg Arg Ser Ser Ser Phe Asn Thr Gly Arg
50 55 60

Ile Glu His Leu Tyr Lys Asn Pro Gln Ala His Ile Glu Gly Asn Met
65 70 75 80

Lys Leu His Tyr Gly Asp Leu Thr Asp Ser Thr Cys Leu Val Lys Ile
85 90 95

Ile Asn Glu Val Lys Pro Thr Glu Ile Tyr Asn Leu Gly Ala Gln Ser
100 105 110

His Val Lys Ile Ser Phe Asp Leu Ala Glu Tyr Thr Ala Asp Val Asp
115 120 125

Gly Val Gly Thr Leu Arg Leu Leu Asp Ala Val Lys Thr Cys Gly Leu
130 135 140

Ile Asn Ser Val Lys Phe Tyr Gln Ala Ser Thr Ser Glu Leu Tyr Gly
145 150 155 160

Lys Val Gln Glu Ile Pro Gln Lys Glu Thr Thr Pro Phe Tyr Pro Arg
165 170 175

Ser Pro Tyr Gly Ala Ala Lys Leu Tyr Ala Tyr Trp Ile Val Val Asn
180 185 190

Phe Arg Glu Ala Tyr Asn Leu Phe Ala Val Asn Gly Ile Leu Phe Asn
195 200 205

His Glu Ser Pro Arg Arg Gly Ala Asn Phe Val Thr Arg Lys Ile Ser
210 215 220

Arg Ser Val Ala Lys Ile Tyr Leu Gly Gln Leu Glu Cys Phe Ser Leu
225 230 235 240

Gly Asn Leu Asp Ala Lys Arg Asp Trp Gly His Ala Lys Asp Tyr Val
245 250 255

Glu Ala Met Trp Leu Met Leu Gln Asn Asp Glu Pro Glu Asp Phe Val
260 265 270

Ile Ala Thr Gly Glu Val His Ser Val Arg Glu Phe Val Glu Lys Ser
275 280 285

Phe Leu His Ile Gly Lys Thr Ile Val Trp Glu Gly Lys Asn Glu Asn
290 295 300

Glu Val Gly Arg Cys Lys Glu Thr Gly Lys Val His Val Thr Val Asp

```
305                 310                 315                 320

Leu Lys Tyr Tyr Arg Pro Thr Glu Val Asp Phe Leu Gln Gly Asp Cys
                325                 330                 335

Thr Lys Ala Lys Gln Lys Leu Asn Trp Lys Pro Arg Val Ala Phe Asp
            340                 345                 350

Glu Leu Val Arg Glu Met Val His Ala Asp Val Glu Leu Met Arg Thr
        355                 360                 365

Asn Pro Asn Ala
    370


<210> SEQ ID NO 10
<211> LENGTH: 180
<212> TYPE: PRT
<213> ORGANISM: Artificial Sequence
<220> FEATURE:
<223> OTHER INFORMATION: Synthetic

<400> SEQUENCE: 10

Met Gly Leu Thr Ile Ser Ser Leu Phe Ser Arg Leu Phe Gly Lys Lys
1               5                   10                  15

Gln Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Cys Phe Thr
    50                  55                  60

Val Trp Asp Val Gly Gly Gln Asp Arg Ile Arg Pro Leu Trp Lys His
65                  70                  75                  80

Tyr Phe Gln Asn Thr Gln Gly Leu Ile Phe Val Val Asp Ser Asn Asp
                85                  90                  95

Arg Glu Arg Ile Gln Glu Val Ala Asp Glu Leu Gln Lys Met Leu Leu
            100                 105                 110

Val Asp Glu Leu Arg Asp Ala Val Leu Leu Leu Phe Ala Asn Lys Gln
        115                 120                 125

Asp Leu Pro Asn Ala Met Ala Ile Ser Glu Met Thr Asp Lys Leu Gly
    130                 135                 140

Leu Gln Ser Leu Arg Asn Arg Thr Trp Tyr Val Gln Ala Thr Cys Ala
145                 150                 155                 160

Thr Gln Gly Thr Gly Leu Tyr Glu Gly Leu Asp Trp Leu Ser Asn Glu
                165                 170                 175

Leu Ser Lys Arg
            180


<210> SEQ ID NO 11
<211> LENGTH: 180
<212> TYPE: PRT
<213> ORGANISM: Artificial Sequence
<220> FEATURE:
<223> OTHER INFORMATION: Synthetic

<400> SEQUENCE: 11

Met Gly Leu Thr Val Ser Ala Leu Phe Ser Arg Ile Phe Gly Lys Lys
1               5                   10                  15

Gln Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Cys Phe Thr
```

50 55 60

Val Trp Asp Val Gly Gly Gln Asp Lys Ile Arg Pro Leu Trp Arg His
65 70 75 80

Tyr Phe Gln Asn Thr Gln Gly Leu Ile Phe Val Val Asp Ser Asn Asp
85 90 95

Arg Glu Arg Val Gln Glu Ser Ala Asp Glu Leu Gln Lys Met Leu Gln
100 105 110

Glu Asp Glu Leu Arg Asp Ala Val Leu Leu Val Phe Ala Asn Lys Gln
115 120 125

Asp Met Pro Asn Ala Met Pro Val Ser Glu Leu Thr Asp Lys Leu Gly
130 135 140

Leu Gln His Leu Arg Ser Arg Thr Trp Tyr Val Gln Ala Thr Cys Ala
145 150 155 160

Thr Gln Gly Thr Gly Leu Tyr Asp Gly Leu Asp Trp Leu Ser His Glu
165 170 175

Leu Ser Lys Arg
180

<210> SEQ ID NO 12
<211> LENGTH: 1394
<212> TYPE: PRT
<213> ORGANISM: Artificial Sequence
<220> FEATURE:
<223> OTHER INFORMATION: Synthetic

<400> SEQUENCE: 12

Met Ala Ala Leu Leu Arg Ser Ala Arg Trp Leu Leu Arg Ala Gly Ala
1 5 10 15

Ala Pro Arg Leu Pro Leu Ser Leu Arg Leu Leu Pro Gly Gly Pro Gly
20 25 30

Arg Leu His Ala Ala Ser Tyr Leu Pro Ala Ala Arg Ala Gly Pro Val
35 40 45

Ala Gly Gly Leu Leu Ser Pro Ala Arg Leu Tyr Ala Ile Ala Ala Lys
50 55 60

Glu Lys Asp Ile Gln Glu Glu Ser Thr Phe Ser Ser Arg Lys Ile Ser
65 70 75 80

Asn Gln Phe Asp Trp Ala Leu Met Arg Leu Asp Leu Ser Val Arg Arg
85 90 95

Thr Gly Arg Ile Pro Lys Lys Leu Leu Gln Lys Val Phe Asn Asp Thr
100 105 110

Cys Arg Ser Gly Gly Leu Gly Gly Ser His Ala Leu Leu Leu Leu Arg
115 120 125

Ser Cys Gly Ser Leu Leu Pro Glu Leu Lys Leu Glu Glu Arg Thr Glu
130 135 140

Phe Ala His Arg Ile Trp Asp Thr Leu Gln Lys Leu Gly Ala Val Tyr
145 150 155 160

Asp Val Ser His Tyr Asn Ala Leu Leu Lys Val Tyr Leu Gln Asn Glu
165 170 175

Tyr Lys Phe Ser Pro Thr Asp Phe Leu Ala Lys Met Glu Glu Ala Asn
180 185 190

Ile Gln Pro Asn Arg Val Thr Tyr Gln Arg Leu Ile Ala Ser Tyr Cys
195 200 205

Asn Val Gly Asp Ile Glu Gly Ala Ser Lys Ile Leu Gly Phe Met Lys
210 215 220

Thr Lys Asp Leu Pro Val Thr Glu Ala Val Phe Ser Ala Leu Val Thr
225 230 235 240

```
Gly His Ala Arg Ala Gly Asp Met Glu Asn Ala Glu Asn Ile Leu Thr
                245                 250                 255

Val Met Arg Asp Ala Gly Ile Glu Pro Gly Pro Asp Thr Tyr Leu Ala
            260                 265                 270

Leu Leu Asn Ala Tyr Ala Glu Lys Gly Asp Ile Asp His Val Lys Gln
        275                 280                 285

Thr Leu Glu Lys Val Glu Lys Ser Glu Leu His Leu Met Asp Arg Asp
    290                 295                 300

Leu Leu Gln Ile Ile Phe Ser Phe Ser Lys Ala Gly Tyr Pro Gln Tyr
305                 310                 315                 320

Val Ser Glu Ile Leu Glu Lys Val Thr Cys Glu Arg Arg Tyr Ile Pro
                325                 330                 335

Asp Ala Met Asn Leu Ile Leu Leu Leu Val Thr Glu Lys Leu Glu Asp
            340                 345                 350

Val Ala Leu Gln Ile Leu Leu Ala Cys Pro Val Ser Lys Glu Asp Gly
        355                 360                 365

Pro Ser Val Phe Gly Ser Phe Phe Leu Gln His Cys Val Thr Met Asn
    370                 375                 380

Thr Pro Val Glu Lys Leu Thr Asp Tyr Cys Lys Lys Leu Lys Glu Val
385                 390                 395                 400

Gln Met His Ser Phe Pro Leu Gln Phe Thr Leu His Cys Ala Leu Leu
                405                 410                 415

Ala Asn Lys Thr Asp Leu Ala Lys Ala Leu Met Lys Ala Val Lys Glu
            420                 425                 430

Glu Gly Phe Pro Ile Arg Pro His Tyr Phe Trp Pro Leu Leu Val Gly
        435                 440                 445

Arg Arg Lys Glu Lys Asn Val Gln Gly Ile Ile Glu Ile Leu Lys Gly
    450                 455                 460

Met Gln Glu Leu Gly Val His Pro Asp Gln Glu Thr Tyr Thr Asp Tyr
465                 470                 475                 480

Val Ile Pro Cys Phe Asp Ser Val Asn Ser Ala Arg Ala Ile Leu Gln
                485                 490                 495

Glu Asn Gly Cys Leu Ser Asp Ser Asp Met Phe Ser Gln Ala Gly Leu
            500                 505                 510

Arg Ser Glu Ala Ala Asn Gly Asn Leu Asp Phe Val Leu Ser Phe Leu
        515                 520                 525

Lys Ser Asn Thr Leu Pro Ile Ser Leu Gln Ser Ile Arg Ser Ser Leu
    530                 535                 540

Leu Leu Gly Phe Arg Arg Ser Met Asn Ile Asn Leu Trp Ser Glu Ile
545                 550                 555                 560

Thr Glu Leu Leu Tyr Lys Asp Gly Arg Tyr Cys Gln Glu Pro Arg Gly
                565                 570                 575

Pro Thr Glu Ala Val Gly Tyr Phe Leu Tyr Asn Leu Ile Asp Ser Met
            580                 585                 590

Ser Asp Ser Glu Val Gln Ala Lys Glu Glu His Leu Arg Gln Tyr Phe
        595                 600                 605

His Gln Leu Glu Lys Met Asn Val Lys Ile Pro Glu Asn Ile Tyr Arg
    610                 615                 620

Gly Ile Arg Asn Leu Leu Glu Ser Tyr His Val Pro Glu Leu Ile Lys
625                 630                 635                 640

Asp Ala His Leu Leu Val Glu Ser Lys Asn Leu Asp Phe Gln Lys Thr
                645                 650                 655

Val Gln Leu Thr Ser Ser Glu Leu Glu Ser Thr Leu Glu Thr Leu Lys
```

-continued

```
            660                 665                 670

Ala Glu Asn Gln Pro Ile Arg Asp Val Leu Lys Gln Leu Ile Leu Val
        675                 680                 685

Leu Cys Ser Glu Glu Asn Met Gln Lys Ala Leu Glu Leu Lys Ala Lys
    690                 695                 700

Tyr Glu Ser Asp Met Val Thr Gly Gly Tyr Ala Ala Leu Ile Asn Leu
705                 710                 715                 720

Cys Cys Arg His Asp Lys Val Glu Asp Ala Leu Asn Leu Lys Glu Glu
                725                 730                 735

Phe Asp Arg Leu Asp Ser Ser Ala Val Leu Asp Thr Gly Lys Tyr Val
            740                 745                 750

Gly Leu Val Arg Val Leu Ala Lys His Gly Lys Leu Gln Asp Ala Ile
        755                 760                 765

Asn Ile Leu Lys Glu Met Lys Glu Lys Asp Val Leu Ile Lys Asp Thr
    770                 775                 780

Thr Ala Leu Ser Phe Phe His Met Leu Asn Gly Ala Ala Leu Arg Gly
785                 790                 795                 800

Glu Ile Glu Thr Val Lys Gln Leu His Glu Ala Ile Val Thr Leu Gly
                805                 810                 815

Leu Ala Glu Pro Ser Thr Asn Ile Ser Phe Pro Leu Val Thr Val His
            820                 825                 830

Leu Glu Lys Gly Asp Leu Ser Thr Ala Leu Glu Val Ala Ile Asp Cys
        835                 840                 845

Tyr Glu Lys Tyr Lys Val Leu Pro Arg Ile His Asp Val Leu Cys Lys
    850                 855                 860

Leu Val Glu Lys Gly Glu Thr Asp Leu Ile Gln Lys Ala Met Asp Phe
865                 870                 875                 880

Val Ser Gln Glu Gln Gly Glu Met Val Met Leu Tyr Asp Leu Phe Phe
                885                 890                 895

Ala Phe Leu Gln Thr Gly Asn Tyr Lys Glu Ala Lys Lys Ile Ile Glu
            900                 905                 910

Thr Pro Gly Ile Arg Ala Arg Ser Ala Arg Leu Gln Trp Phe Cys Asp
        915                 920                 925

Arg Cys Val Ala Asn Asn Gln Val Glu Thr Leu Glu Lys Leu Val Glu
    930                 935                 940

Leu Thr Gln Lys Leu Phe Glu Cys Asp Arg Asp Gln Met Tyr Tyr Asn
945                 950                 955                 960

Leu Leu Lys Leu Tyr Lys Ile Asn Gly Asp Trp Gln Arg Ala Asp Ala
                965                 970                 975

Val Trp Asn Lys Ile Gln Glu Glu Asn Val Ile Pro Arg Glu Lys Thr
            980                 985                 990

Leu Arg Leu Leu Ala Glu Ile Leu  Arg Glu Gly Asn Gln  Glu Val Pro
        995                 1000                 1005

Phe Asp  Val Pro Glu Leu Trp  Tyr Glu Asp Glu Lys  His Ser Leu
    1010                 1015                 1020

Asn Ser  Ser Ser Ala Ser Thr  Thr Glu Pro Asp Phe  Gln Lys Asp
    1025                 1030                 1035

Ile Leu  Ile Ala Cys Arg Leu  Asn Gln Lys Lys Gly  Ala Tyr Asp
    1040                 1045                 1050

Ile Phe  Leu Asn Ala Lys Glu  Gln Asn Ile Val Phe  Asn Ala Glu
    1055                 1060                 1065

Thr Tyr  Ser Asn Leu Ile Lys  Leu Leu Met Ser Glu  Asp Tyr Phe
    1070                 1075                 1080
```

Thr Gln Ala Met Glu Val Lys Ala Phe Ala Glu Thr His Ile Lys
1085 1090 1095

Gly Phe Thr Leu Asn Asp Ala Ala Asn Ser Arg Leu Ile Ile Thr
1100 1105 1110

Gln Val Arg Arg Asp Tyr Leu Lys Glu Ala Val Thr Thr Leu Lys
1115 1120 1125

Thr Val Leu Asp Gln Gln Gln Thr Pro Ser Arg Leu Ala Val Thr
1130 1135 1140

Arg Val Ile Gln Ala Leu Ala Met Lys Gly Asp Val Glu Asn Ile
1145 1150 1155

Glu Val Val Gln Lys Met Leu Asn Gly Leu Glu Asp Ser Ile Gly
1160 1165 1170

Leu Ser Lys Met Val Phe Ile Asn Asn Ile Ala Leu Ala Gln Ile
1175 1180 1185

Lys Asn Asn Asn Ile Asp Ala Ala Ile Glu Asn Ile Glu Asn Met
1190 1195 1200

Leu Thr Ser Glu Asn Lys Val Ile Glu Pro Gln Tyr Phe Gly Leu
1205 1210 1215

Ala Tyr Leu Phe Arg Lys Val Ile Glu Glu Gln Leu Glu Pro Ala
1220 1225 1230

Val Glu Lys Ile Ser Ile Met Ala Glu Arg Leu Ala Asn Gln Phe
1235 1240 1245

Ala Ile Tyr Lys Pro Val Thr Asp Phe Phe Leu Gln Leu Val Asp
1250 1255 1260

Ala Gly Lys Val Asp Asp Ala Arg Ala Leu Leu Gln Arg Cys Gly
1265 1270 1275

Ala Ile Ala Glu Gln Thr Pro Ile Leu Leu Leu Phe Leu Leu Arg
1280 1285 1290

Asn Ser Arg Lys Gln Gly Lys Ala Ser Thr Val Lys Ser Val Leu
1295 1300 1305

Glu Leu Ile Pro Glu Leu Asn Glu Lys Glu Glu Ala Tyr Asn Ser
1310 1315 1320

Leu Met Lys Ser Tyr Val Ser Glu Lys Asp Val Thr Ser Ala Lys
1325 1330 1335

Ala Leu Tyr Glu His Leu Thr Ala Lys Asn Thr Lys Leu Asp Asp
1340 1345 1350

Leu Phe Leu Lys Arg Tyr Ala Ser Leu Leu Lys Tyr Ala Gly Glu
1355 1360 1365

Pro Val Pro Phe Ile Glu Pro Pro Glu Ser Phe Glu Phe Tyr Ala
1370 1375 1380

Gln Gln Leu Arg Lys Leu Arg Glu Asn Ser Ser
1385 1390

<210> SEQ ID NO 13
<211> LENGTH: 781
<212> TYPE: PRT
<213> ORGANISM: Artificial Sequence
<220> FEATURE:
<223> OTHER INFORMATION: Synthetic

<400> SEQUENCE: 13

Met Ala Thr Gln Ala Asp Leu Met Glu Leu Asp Met Ala Met Glu Pro
1 5 10 15

Asp Arg Lys Ala Ala Val Ser His Trp Gln Gln Gln Ser Tyr Leu Asp
20 25 30

Ser Gly Ile His Ser Gly Ala Thr Thr Thr Ala Pro Ser Leu Ser Gly

-continued

```
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460
```

Ile Cys Ala Leu Arg His Leu Thr Ser Arg His Gln Glu Ala Glu Met
465 470 475 480

Ala Gln Asn Ala Val Arg Leu His Tyr Gly Leu Pro Val Val Val Lys
485 490 495

Leu Leu His Pro Pro Ser His Trp Pro Leu Ile Lys Ala Thr Val Gly
500 505 510

Leu Ile Arg Asn Leu Ala Leu Cys Pro Ala Asn His Ala Pro Leu Arg
515 520 525

Glu Gln Gly Ala Ile Pro Arg Leu Val Gln Leu Leu Val Arg Ala His
530 535 540

Gln Asp Thr Gln Arg Arg Thr Ser Met Gly Gly Thr Gln Gln Gln Phe
545 550 555 560

Val Glu Gly Val Arg Met Glu Glu Ile Val Glu Gly Cys Thr Gly Ala
565 570 575

Leu His Ile Leu Ala Arg Asp Val His Asn Arg Ile Val Ile Arg Gly
580 585 590

Leu Asn Thr Ile Pro Leu Phe Val Gln Leu Leu Tyr Ser Pro Ile Glu
595 600 605

Asn Ile Gln Arg Val Ala Ala Gly Val Leu Cys Glu Leu Ala Gln Asp
610 615 620

Lys Glu Ala Ala Glu Ala Ile Glu Ala Glu Gly Ala Thr Ala Pro Leu
625 630 635 640

Thr Glu Leu Leu His Ser Arg Asn Glu Gly Val Ala Thr Tyr Ala Ala
645 650 655

Ala Val Leu Phe Arg Met Ser Glu Asp Lys Pro Gln Asp Tyr Lys Lys
660 665 670

Arg Leu Ser Val Glu Leu Thr Ser Ser Leu Phe Arg Thr Glu Pro Met
675 680 685

Ala Trp Asn Glu Thr Ala Asp Leu Gly Leu Asp Ile Gly Ala Gln Gly
690 695 700

Glu Pro Leu Gly Tyr Arg Gln Asp Asp Pro Ser Tyr Arg Ser Phe His
705 710 715 720

Ser Gly Gly Tyr Gly Gln Asp Ala Leu Gly Met Asp Pro Met Met Glu
725 730 735

His Glu Met Gly Gly His His Pro Gly Ala Asp Tyr Pro Val Asp Gly
740 745 750

Leu Pro Asp Leu Gly His Ala Gln Asp Leu Met Asp Gly Leu Pro Pro
755 760 765

Gly Asp Ser Asn Gln Leu Ala Trp Phe Asp Thr Asp Leu
770 775 780

<210> SEQ ID NO 14
<211> LENGTH: 181
<212> TYPE: PRT
<213> ORGANISM: Artificial Sequence
<220> FEATURE:
<223> OTHER INFORMATION: Synthetic

<400> SEQUENCE: 14

Met Gly Asn Ile Phe Gly Asn Leu Leu Lys Ser Leu Ile Gly Lys Lys
1 5 10 15

Glu Met Arg Ile Leu Met Val Gly Leu Asp Ala Ala Gly Lys Thr Thr
20 25 30

Ile Leu Tyr Lys Leu Lys Leu Gly Glu Ile Val Thr Thr Ile Pro Thr
35 40 45

Ile Gly Phe Asn Val Glu Thr Val Glu Tyr Lys Asn Ile Ser Phe Thr

```
    50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                85                  90                  95

Arg Glu Arg Val Asn Glu Ala Arg Glu Glu Leu Met Arg Met Leu Ala
            100                 105                 110

Glu Asp Glu Leu Arg Asp Ala Val Leu Leu Val Phe Ala Asn Lys Gln
        115                 120                 125

Asp Leu Pro Asn Ala Met Asn Ala Ala Glu Ile Thr Asp Lys Leu Gly
    130                 135                 140

Leu His Ser Leu Arg His Arg Asn Trp Tyr Ile Gln Ala Thr Cys Ala
145                 150                 155                 160

Thr Ser Gly Asp Gly Leu Tyr Glu Gly Leu Asp Trp Leu Ala Asn Gln
                165                 170                 175

Leu Lys Asn Lys Lys
            180


<210> SEQ ID NO 15
<211> LENGTH: 2671
<212> TYPE: PRT
<213> ORGANISM: Artificial Sequence
<220> FEATURE:
<223> OTHER INFORMATION: Synthetic

<400> SEQUENCE: 15

Met Ala Ala Asp Thr Gln Val Ser Glu Thr Leu Lys Arg Phe Ala Gly
1               5                   10                  15

Lys Val Thr Thr Ala Ser Val Lys Glu Arg Arg Glu Ile Leu Ser Glu
            20                  25                  30

Leu Gly Lys Cys Val Ala Gly Lys Asp Leu Pro Glu Gly Ala Val Lys
        35                  40                  45

Gly Leu Cys Lys Leu Phe Cys Leu Thr Leu His Arg Tyr Arg Asp Ala
    50                  55                  60

Ala Ser Arg Arg Ala Leu Gln Ala Ala Ile Gln Gln Leu Ala Glu Ala
65                  70                  75                  80

Gln Pro Glu Ala Thr Ala Lys Asn Leu Leu His Ser Leu Gln Ser Ser
                85                  90                  95

Gly Ile Gly Ser Lys Ala Gly Val Pro Ser Lys Ser Ser Gly Ser Ala
            100                 105                 110

Ala Leu Leu Ala Leu Thr Trp Thr Cys Leu Leu Val Arg Ile Val Phe
        115                 120                 125

Pro Ser Arg Ala Lys Arg Gln Gly Asp Ile Trp Asn Lys Leu Val Glu
    130                 135                 140

Val Gln Cys Leu Leu Leu Leu Glu Val Leu Gly Gly Ser His Lys His
145                 150                 155                 160

Ala Val Asp Gly Ala Val Lys Lys Leu Thr Lys Leu Trp Lys Glu Asn
                165                 170                 175

Pro Gly Leu Val Glu Gln Tyr Leu Ser Ala Ile Leu Ser Leu Glu Pro
            180                 185                 190

Asn Gln Asn Tyr Ala Gly Met Leu Gly Leu Leu Val Gln Phe Cys Thr
        195                 200                 205

Ser His Lys Glu Met Asp Val Val Ser Gln His Lys Ser Ala Leu Leu
    210                 215                 220

Asp Phe Tyr Met Lys Asn Ile Leu Met Ser Lys Val Lys Pro Pro Lys
225                 230                 235                 240
```

-continued

```
Tyr Leu Leu Asp Ser Cys Ala Pro Leu Leu Arg Tyr Leu Ser His Ser
                245                 250                 255

Glu Phe Lys Asp Leu Ile Leu Pro Thr Ile Gln Lys Ser Leu Leu Arg
            260                 265                 270

Ser Pro Glu Asn Val Ile Glu Thr Ile Ser Ser Leu Leu Ala Ser Val
        275                 280                 285

Thr Leu Asp Phe Ser Gln Tyr Ala Met Asp Ile Val Lys Gly Leu Ala
    290                 295                 300

Gly His Leu Lys Ser Asn Ser Pro Arg Leu Met Asp Glu Ala Val Leu
305                 310                 315                 320

Ala Leu Arg Asn Leu Ala Arg Gln Cys Ser Asp Ser Ser Ala Met Glu
                325                 330                 335

Ser Leu Thr Lys His Leu Phe Ala Ile Leu Gly Gly Ser Glu Gly Lys
            340                 345                 350

Leu Thr Val Val Ala Gln Lys Met Ser Val Leu Ser Gly Ile Gly Ser
        355                 360                 365

Val Ser His His Val Val Ser Gly Pro Ser Ser Gln Val Leu Asn Gly
    370                 375                 380

Ile Val Ala Glu Leu Phe Ile Pro Phe Leu Gln Gln Glu Val His Glu
385                 390                 395                 400

Gly Thr Leu Val His Ala Val Ser Val Leu Ala Leu Trp Cys Asn Arg
                405                 410                 415

Phe Thr Met Glu Val Pro Lys Lys Leu Thr Glu Trp Phe Lys Lys Ala
            420                 425                 430

Phe Ser Leu Lys Thr Ser Thr Ser Ala Val Arg His Ala Tyr Leu Gln
        435                 440                 445

Cys Met Leu Ala Ser Tyr Arg Gly Asp Thr Leu Leu Gln Ala Leu Asp
    450                 455                 460

Leu Leu Pro Leu Leu Ile Gln Thr Val Glu Lys Ala Ala Ser Gln Ser
465                 470                 475                 480

Thr Gln Val Pro Thr Ile Thr Glu Gly Val Ala Ala Ala Leu Leu Leu
                485                 490                 495

Leu Lys Leu Ser Val Ala Asp Ser Gln Ala Glu Ala Lys Leu Ser Ser
            500                 505                 510

Phe Trp Gln Leu Ile Val Asp Glu Lys Lys Gln Val Phe Thr Ser Glu
        515                 520                 525

Lys Phe Leu Val Met Ala Ser Glu Asp Ala Leu Cys Thr Val Leu His
    530                 535                 540

Leu Thr Glu Arg Leu Phe Leu Asp His Pro His Arg Leu Thr Gly Asn
545                 550                 555                 560

Lys Val Gln Gln Tyr His Arg Ala Leu Val Ala Val Leu Leu Ser Arg
                565                 570                 575

Thr Trp His Val Arg Arg Gln Ala Gln Gln Thr Val Arg Lys Leu Leu
            580                 585                 590

Ser Ser Leu Gly Gly Phe Lys Leu Ala His Gly Leu Leu Glu Glu Leu
        595                 600                 605

Lys Thr Val Leu Ser Ser His Lys Val Leu Pro Leu Glu Ala Leu Val
    610                 615                 620

Thr Asp Ala Gly Glu Val Thr Glu Ala Gly Lys Ala Tyr Val Pro Pro
625                 630                 635                 640

Arg Val Leu Gln Glu Ala Leu Cys Val Ile Ser Gly Val Pro Gly Leu
                645                 650                 655

Lys Gly Asp Val Thr Asp Thr Glu Gln Leu Ala Gln Glu Met Leu Ile
```

-continued

```
            660                 665                 670

Ile Ser His His Pro Ser Leu Val Ala Val Gln Ser Gly Leu Trp Pro
        675                 680                 685

Ala Leu Leu Ala Arg Met Lys Ile Asp Pro Glu Ala Phe Ile Thr Arg
    690                 695                 700

His Leu Asp Gln Ile Ile Pro Arg Met Thr Thr Gln Ser Pro Leu Asn
705                 710                 715                 720

Gln Ser Ser Met Asn Ala Met Gly Ser Leu Ser Val Leu Ser Pro Asp
                725                 730                 735

Arg Val Leu Pro Gln Leu Ile Ser Thr Ile Thr Ala Ser Val Gln Asn
            740                 745                 750

Pro Ala Leu Arg Leu Val Thr Arg Glu Glu Phe Ala Ile Met Gln Thr
        755                 760                 765

Pro Ala Gly Glu Leu Tyr Asp Lys Ser Ile Ile Gln Ser Ala Gln Gln
    770                 775                 780

Asp Ser Ile Lys Lys Ala Asn Met Lys Arg Glu Asn Lys Ala Tyr Ser
785                 790                 795                 800

Phe Lys Glu Gln Ile Ile Glu Leu Glu Leu Lys Glu Glu Ile Lys Lys
                805                 810                 815

Lys Lys Gly Ile Lys Glu Glu Val Gln Leu Thr Ser Lys Gln Lys Glu
            820                 825                 830

Met Leu Gln Ala Gln Leu Asp Arg Glu Ala Gln Val Arg Arg Arg Leu
        835                 840                 845

Gln Glu Leu Asp Gly Glu Leu Glu Ala Ala Leu Gly Leu Leu Asp Ile
    850                 855                 860

Ile Leu Ala Lys Asn Pro Ser Gly Leu Thr Gln Tyr Ile Pro Val Leu
865                 870                 875                 880

Val Asp Ser Phe Leu Pro Leu Leu Lys Ser Pro Leu Ala Ala Pro Arg
                885                 890                 895

Ile Lys Asn Pro Phe Leu Ser Leu Ala Ala Cys Val Met Pro Ser Arg
            900                 905                 910

Leu Lys Ala Leu Gly Thr Leu Val Ser His Val Thr Leu Arg Leu Leu
        915                 920                 925

Lys Pro Glu Cys Val Leu Asp Lys Ser Trp Cys Gln Glu Glu Leu Ser
    930                 935                 940

Val Ala Val Lys Arg Ala Val Met Leu Leu His Thr His Thr Ile Thr
945                 950                 955                 960

Ser Arg Val Gly Lys Gly Glu Pro Gly Ala Ala Pro Leu Ser Ala Pro
                965                 970                 975

Ala Phe Ser Leu Val Phe Pro Phe Leu Lys Met Val Leu Thr Glu Met
            980                 985                 990

Pro His His Ser Glu Glu Glu Glu  Glu Trp Met Ala Gln  Ile Leu Gln
        995                 1000                1005

Ile Leu  Thr Val Gln Ala Gln  Leu Arg Ala Ser Pro  Asn Thr Pro
    1010                1015                1020

Pro Gly  Arg Val Asp Glu Asn  Gly Pro Glu Leu Leu  Pro Arg Val
    1025                1030                1035

Ala Met  Leu Arg Leu Leu Thr  Trp Val Ile Gly Thr  Gly Ser Pro
    1040                1045                1050

Arg Leu  Gln Val Leu Ala Ser  Asp Thr Leu Thr Thr  Leu Cys Ala
    1055                1060                1065

Ser Ser  Ser Gly Asp Asp Gly  Cys Ala Phe Ala Glu  Gln Glu Glu
    1070                1075                1080
```

-continued

Val Asp Val Leu Leu Cys Ala Leu Gln Ser Pro Cys Ala Ser Val
1085 1090 1095

Arg Glu Thr Val Leu Arg Gly Leu Met Glu Leu His Met Val Leu
1100 1105 1110

Pro Ala Pro Asp Thr Asp Glu Lys Asn Gly Leu Asn Leu Leu Arg
1115 1120 1125

Arg Leu Trp Val Val Lys Phe Asp Lys Glu Glu Glu Ile Arg Lys
1130 1135 1140

Leu Ala Glu Arg Leu Trp Ser Met Met Gly Leu Asp Leu Gln Pro
1145 1150 1155

Asp Leu Cys Ser Leu Leu Ile Asp Asp Val Ile Tyr His Glu Ala
1160 1165 1170

Ala Val Arg Gln Ala Gly Ala Glu Ala Leu Ser Gln Ala Val Ala
1175 1180 1185

Arg Tyr Gln Arg Gln Ala Ala Glu Val Met Gly Arg Leu Met Glu
1190 1195 1200

Ile Tyr Gln Glu Lys Leu Tyr Arg Pro Pro Pro Val Leu Asp Ala
1205 1210 1215

Leu Gly Arg Val Ile Ser Glu Ser Pro Pro Asp Gln Trp Glu Ala
1220 1225 1230

Arg Cys Gly Leu Ala Leu Ala Leu Asn Lys Leu Ser Gln Tyr Leu
1235 1240 1245

Asp Ser Ser Gln Val Lys Pro Leu Phe Gln Phe Phe Val Pro Asp
1250 1255 1260

Ala Leu Asn Asp Arg His Pro Asp Val Arg Lys Cys Met Leu Asp
1265 1270 1275

Ala Ala Leu Ala Thr Leu Asn Thr His Gly Lys Glu Asn Val Asn
1280 1285 1290

Ser Leu Leu Pro Val Phe Glu Glu Phe Leu Lys Asn Ala Pro Asn
1295 1300 1305

Asp Ala Ser Tyr Asp Ala Val Arg Gln Ser Val Val Val Leu Met
1310 1315 1320

Gly Ser Leu Ala Lys His Leu Asp Lys Ser Asp Pro Lys Val Lys
1325 1330 1335

Pro Ile Val Ala Lys Leu Ile Ala Ala Leu Ser Thr Pro Ser Gln
1340 1345 1350

Gln Val Gln Glu Ser Val Ala Ser Cys Leu Pro Pro Leu Val Pro
1355 1360 1365

Ala Ile Lys Glu Asp Ala Gly Gly Met Ile Gln Arg Leu Met Gln
1370 1375 1380

Gln Leu Leu Glu Ser Asp Lys Tyr Ala Glu Arg Lys Gly Ala Ala
1385 1390 1395

Tyr Gly Leu Ala Gly Leu Val Lys Gly Leu Gly Ile Leu Ser Leu
1400 1405 1410

Lys Gln Gln Glu Met Met Ala Ala Leu Thr Asp Ala Ile Gln Asp
1415 1420 1425

Lys Lys Asn Phe Arg Arg Arg Glu Gly Ala Leu Phe Ala Phe Glu
1430 1435 1440

Met Leu Cys Thr Met Leu Gly Lys Leu Phe Glu Pro Tyr Val Val
1445 1450 1455

His Val Leu Pro His Leu Leu Leu Cys Phe Gly Asp Gly Asn Gln
1460 1465 1470

Tyr Val Arg Glu Ala Ala Asp Asp Cys Ala Lys Ala Val Met Ser
1475 1480 1485

```
Asn Leu  Ser Ala His Gly Val  Lys Leu Val Leu Pro  Ser Leu Leu
    1490                 1495                 1500

Ala Ala  Leu Glu Glu Glu Ser  Trp Arg Thr Lys Ala  Gly Ser Val
    1505                 1510                 1515

Glu Leu  Leu Gly Ala Met Ala  Tyr Cys Ala Pro Lys  Gln Leu Ser
    1520                 1525                 1530

Ser Cys  Leu Pro Asn Ile Val  Pro Lys Leu Thr Glu  Val Leu Thr
    1535                 1540                 1545

Asp Ser  His Val Lys Val Gln  Lys Ala Gly Gln Gln  Ala Leu Arg
    1550                 1555                 1560

Gln Ile  Gly Ser Val Ile Arg  Asn Pro Glu Ile Leu  Ala Ile Ala
    1565                 1570                 1575

Pro Val  Leu Leu Asp Ala Leu  Thr Asp Pro Ser Arg  Lys Thr Gln
    1580                 1585                 1590

Lys Cys  Leu Gln Thr Leu Leu  Asp Thr Lys Phe Val  His Phe Ile
    1595                 1600                 1605

Asp Ala  Pro Ser Leu Ala Leu  Ile Met Pro Ile Val  Gln Arg Ala
    1610                 1615                 1620

Phe Gln  Asp Arg Ser Thr Asp  Thr Arg Lys Met Ala  Ala Gln Ile
    1625                 1630                 1635

Ile Gly  Asn Met Tyr Ser Leu  Thr Asp Gln Lys Asp  Leu Ala Pro
    1640                 1645                 1650

Tyr Leu  Pro Ser Val Thr Pro  Gly Leu Lys Ala Ser  Leu Leu Asp
    1655                 1660                 1665

Pro Val  Pro Glu Val Arg Thr  Val Ser Ala Lys Ala  Leu Gly Ala
    1670                 1675                 1680

Met Val  Lys Gly Met Gly Glu  Ser Cys Phe Glu Asp  Leu Leu Pro
    1685                 1690                 1695

Trp Leu  Met Glu Thr Leu Thr  Tyr Glu Gln Ser Ser  Val Asp Arg
    1700                 1705                 1710

Ser Gly  Ala Ala Gln Gly Leu  Ala Glu Val Met Ala  Gly Leu Gly
    1715                 1720                 1725

Val Glu  Lys Leu Glu Lys Leu  Met Pro Glu Ile Val  Ala Thr Ala
    1730                 1735                 1740

Ser Lys  Val Asp Ile Ala Pro  His Val Arg Asp Gly  Tyr Ile Met
    1745                 1750                 1755

Met Phe  Asn Tyr Leu Pro Ile  Thr Phe Gly Asp Lys  Phe Thr Pro
    1760                 1765                 1770

Tyr Val  Gly Pro Ile Ile Pro  Cys Ile Leu Lys Ala  Leu Ala Asp
    1775                 1780                 1785

Glu Asn  Glu Phe Val Arg Asp  Thr Ala Leu Arg Ala  Gly Gln Arg
    1790                 1795                 1800

Val Ile  Ser Met Tyr Ala Glu  Thr Ala Ile Ala Leu  Leu Leu Pro
    1805                 1810                 1815

Gln Leu  Glu Gln Gly Leu Phe  Asp Asp Leu Trp Arg  Ile Arg Phe
    1820                 1825                 1830

Ser Ser  Val Gln Leu Leu Gly  Asp Leu Leu Phe His  Ile Ser Gly
    1835                 1840                 1845

Val Thr  Gly Lys Met Thr Thr  Glu Thr Ala Ser Glu  Asp Asp Asn
    1850                 1855                 1860

Phe Gly  Thr Ala Gln Ser Asn  Lys Ala Ile Ile Thr  Ala Leu Gly
    1865                 1870                 1875

Val Glu  Arg Arg Asn Arg Val  Leu Ala Gly Leu Tyr  Met Gly Arg
```

1880 1885 1890

Ser Asp Thr Gln Leu Val Val Arg Gln Ala Ser Leu His Val Trp
1895 1900 1905

Lys Ile Val Val Ser Asn Thr Pro Arg Thr Leu Arg Glu Ile Leu
1910 1915 1920

Pro Thr Leu Phe Gly Leu Leu Leu Gly Phe Leu Ala Ser Thr Cys
1925 1930 1935

Ala Asp Lys Arg Thr Ile Ala Ala Arg Thr Leu Gly Asp Leu Val
1940 1945 1950

Arg Lys Leu Gly Glu Lys Ile Leu Pro Glu Ile Ile Pro Ile Leu
1955 1960 1965

Glu Glu Gly Leu Arg Ser Gln Lys Ser Asp Glu Arg Gln Gly Val
1970 1975 1980

Cys Ile Gly Leu Ser Glu Ile Met Lys Ser Thr Ser Arg Asp Ala
1985 1990 1995

Val Leu Tyr Phe Ser Glu Ser Leu Val Pro Thr Ala Arg Lys Ala
2000 2005 2010

Leu Cys Asp Pro Leu Glu Glu Val Arg Glu Ala Ala Ala Lys Thr
2015 2020 2025

Phe Glu Gln Leu His Ser Thr Ile Gly His Gln Ala Leu Glu Asp
2030 2035 2040

Ile Leu Pro Phe Leu Leu Lys Gln Leu Asp Asp Glu Glu Val Ser
2045 2050 2055

Glu Phe Ala Leu Asp Gly Leu Lys Gln Val Met Ala Ile Lys Ser
2060 2065 2070

Arg Val Val Leu Pro Tyr Leu Val Pro Lys Leu Thr Thr Pro Pro
2075 2080 2085

Val Asn Thr Arg Val Leu Ala Phe Leu Ser Ser Val Ala Gly Asp
2090 2095 2100

Ala Leu Thr Arg His Leu Gly Val Ile Leu Pro Ala Val Met Leu
2105 2110 2115

Ala Leu Lys Glu Lys Leu Gly Thr Pro Asp Glu Gln Leu Glu Met
2120 2125 2130

Ala Asn Cys Gln Ala Val Ile Leu Ser Val Glu Asp Asp Thr Gly
2135 2140 2145

His Arg Ile Ile Ile Glu Asp Leu Leu Glu Ala Thr Arg Ser Pro
2150 2155 2160

Glu Val Gly Met Arg Gln Ala Ala Ala Ile Ile Leu Asn Ile Tyr
2165 2170 2175

Cys Ser Arg Ser Lys Ala Asp Tyr Thr Ser His Leu Arg Ser Leu
2180 2185 2190

Val Ser Gly Leu Ile Arg Leu Phe Asn Asp Ser Ser Pro Val Val
2195 2200 2205

Leu Glu Glu Ser Trp Asp Ala Leu Asn Ala Ile Thr Lys Lys Leu
2210 2215 2220

Asp Ala Gly Asn Gln Leu Ala Leu Ile Glu Glu Leu His Lys Glu
2225 2230 2235

Ile Arg Leu Ile Gly Asn Glu Ser Lys Gly Glu His Val Pro Gly
2240 2245 2250

Phe Cys Leu Pro Lys Lys Gly Val Thr Ser Ile Leu Pro Val Leu
2255 2260 2265

Arg Glu Gly Val Leu Thr Gly Ser Pro Glu Gln Lys Glu Glu Ala
2270 2275 2280

-continued

Ala Lys Ala Leu Gly Leu Val Ile Arg Leu Thr Ser Ala Asp Ala
2285 2290 2295

Leu Arg Pro Ser Val Val Ser Ile Thr Gly Pro Leu Ile Arg Ile
2300 2305 2310

Leu Gly Asp Arg Phe Ser Trp Asn Val Lys Ala Ala Leu Leu Glu
2315 2320 2325

Thr Leu Ser Leu Leu Leu Ala Lys Val Gly Ile Ala Leu Lys Pro
2330 2335 2340

Phe Leu Pro Gln Leu Gln Thr Thr Phe Thr Lys Ala Leu Gln Asp
2345 2350 2355

Ser Asn Arg Gly Val Arg Leu Lys Ala Ala Asp Ala Leu Gly Lys
2360 2365 2370

Leu Ile Ser Ile His Ile Lys Val Asp Pro Leu Phe Thr Glu Leu
2375 2380 2385

Leu Asn Gly Ile Arg Ala Met Glu Asp Pro Gly Val Arg Asp Thr
2390 2395 2400

Met Leu Gln Ala Leu Arg Phe Val Ile Gln Gly Ala Gly Ala Lys
2405 2410 2415

Val Asp Ala Val Ile Arg Lys Asn Ile Val Ser Leu Leu Leu Ser
2420 2425 2430

Met Leu Gly His Asp Glu Asp Asn Thr Arg Ile Ser Ser Ala Gly
2435 2440 2445

Cys Leu Gly Glu Leu Cys Ala Phe Leu Thr Glu Glu Glu Leu Ser
2450 2455 2460

Ala Val Leu Gln Gln Cys Leu Leu Ala Asp Val Ser Gly Ile Asp
2465 2470 2475

Trp Met Val Arg His Gly Arg Ser Leu Ala Leu Ser Val Ala Val
2480 2485 2490

Asn Val Ala Pro Gly Arg Leu Cys Ala Gly Arg Tyr Ser Ser Asp
2495 2500 2505

Val Gln Glu Met Ile Leu Ser Ser Ala Thr Ala Asp Arg Ile Pro
2510 2515 2520

Ile Ala Val Ser Gly Val Arg Gly Met Gly Phe Leu Met Arg His
2525 2530 2535

His Ile Glu Thr Gly Gly Gly Gln Leu Pro Ala Lys Leu Ser Ser
2540 2545 2550

Leu Phe Val Lys Cys Leu Gln Asn Pro Ser Ser Asp Ile Arg Leu
2555 2560 2565

Val Ala Glu Lys Met Ile Trp Trp Ala Asn Lys Asp Pro Leu Pro
2570 2575 2580

Pro Leu Asp Pro Gln Ala Ile Lys Pro Ile Leu Lys Ala Leu Leu
2585 2590 2595

Asp Asn Thr Lys Asp Lys Asn Thr Val Val Arg Ala Tyr Ser Asp
2600 2605 2610

Gln Ala Ile Val Asn Leu Leu Lys Met Arg Gln Gly Glu Glu Val
2615 2620 2625

Phe Gln Ser Leu Ser Lys Ile Leu Asp Val Ala Ser Leu Glu Val
2630 2635 2640

Leu Asn Glu Val Asn Arg Arg Ser Leu Lys Lys Leu Ala Ser Gln
2645 2650 2655

Ala Asp Ser Thr Glu Gln Val Asp Asp Thr Ile Leu Thr
2660 2665 2670

<210> SEQ ID NO 16

<211> LENGTH: 343
<212> TYPE: PRT
<213> ORGANISM: Artificial Sequence
<220> FEATURE:
<223> OTHER INFORMATION: Synthetic

<400> SEQUENCE: 16

```
Met Leu Ala Thr Arg Leu Ser Arg Pro Leu Ser Arg Leu Pro Gly Lys
1               5                   10                  15

Thr Leu Ser Ala Cys Asp Arg Glu Asn Gly Ala Arg Arg Pro Leu Leu
            20                  25                  30

Leu Gly Ser Thr Ser Phe Ile Pro Ile Gly Arg Arg Thr Tyr Ala Ser
        35                  40                  45

Ala Ala Glu Pro Val Gly Ser Lys Ala Val Leu Val Thr Gly Cys Asp
    50                  55                  60

Ser Gly Phe Gly Phe Ser Leu Ala Lys His Leu His Ser Lys Gly Phe
65                  70                  75                  80

Leu Val Phe Ala Gly Cys Leu Met Lys Asp Lys Gly His Asp Gly Val
                85                  90                  95

Lys Glu Leu Asp Ser Leu Asn Ser Asp Arg Leu Arg Thr Val Gln Leu
            100                 105                 110

Asn Val Cys Ser Ser Glu Glu Val Glu Lys Val Val Glu Ile Val Arg
        115                 120                 125

Ser Ser Leu Lys Asp Pro Glu Lys Gly Met Trp Gly Leu Val Asn Asn
    130                 135                 140

Ala Gly Ile Ser Thr Phe Gly Glu Val Glu Phe Thr Ser Leu Glu Thr
145                 150                 155                 160

Tyr Lys Gln Val Ala Glu Val Asn Leu Trp Gly Thr Val Arg Met Thr
                165                 170                 175

Lys Ser Phe Leu Pro Leu Ile Arg Arg Ala Lys Gly Arg Val Val Asn
            180                 185                 190

Ile Ser Ser Met Leu Gly Arg Met Ala Asn Pro Ala Arg Ser Pro Tyr
        195                 200                 205

Cys Ile Thr Lys Phe Gly Val Glu Ala Phe Ser Asp Cys Leu Arg Tyr
    210                 215                 220

Glu Met Tyr Pro Leu Gly Val Lys Val Ser Val Val Glu Pro Gly Asn
225                 230                 235                 240

Phe Ile Ala Ala Thr Ser Leu Tyr Ser Pro Glu Ser Ile Gln Ala Ile
                245                 250                 255

Ala Lys Lys Met Trp Glu Glu Leu Pro Glu Val Val Arg Lys Asp Tyr
            260                 265                 270

Gly Lys Lys Tyr Phe Asp Glu Lys Ile Ala Lys Met Glu Thr Tyr Cys
        275                 280                 285

Ser Ser Gly Ser Thr Asp Thr Ser Pro Val Ile Asp Ala Val Thr His
    290                 295                 300

Ala Leu Thr Ala Thr Thr Pro Tyr Thr Arg Tyr His Pro Met Asp Tyr
305                 310                 315                 320

Tyr Trp Trp Leu Arg Met Gln Ile Met Thr His Leu Pro Gly Ala Ile
                325                 330                 335

Ser Asp Met Ile Tyr Ile Arg
            340
```

<210> SEQ ID NO 17
<211> LENGTH: 192
<212> TYPE: PRT
<213> ORGANISM: Artificial Sequence
<220> FEATURE:

-continued

<223> OTHER INFORMATION: Synthetic

<400> SEQUENCE: 17

Met Lys Thr Ile Leu Ser Asn Gln Thr Val Asp Ile Pro Glu Asn Val
1 5 10 15

Asp Ile Thr Leu Lys Gly Arg Thr Val Ile Val Lys Gly Pro Arg Gly
20 25 30

Thr Leu Arg Arg Asp Phe Asn His Ile Asn Val Glu Leu Ser Leu Leu
35 40 45

Gly Lys Lys Lys Lys Arg Leu Arg Val Asp Lys Trp Trp Gly Asn Arg
50 55 60

Lys Glu Leu Ala Thr Val Arg Thr Ile Cys Ser His Val Gln Asn Met
65 70 75 80

Ile Lys Gly Val Thr Leu Gly Phe Arg Tyr Lys Met Arg Ser Val Tyr
85 90 95

Ala His Phe Pro Ile Asn Val Val Ile Gln Glu Asn Gly Ser Leu Val
100 105 110

Glu Ile Arg Asn Phe Leu Gly Glu Lys Tyr Ile Arg Arg Val Arg Met
115 120 125

Arg Pro Gly Val Ala Cys Ser Val Ser Gln Ala Gln Lys Asp Glu Leu
130 135 140

Ile Leu Glu Gly Asn Asp Ile Glu Leu Val Ser Asn Ser Ala Ala Leu
145 150 155 160

Ile Gln Gln Ala Thr Thr Val Lys Asn Lys Asp Ile Arg Lys Phe Leu
165 170 175

Asp Gly Ile Tyr Val Ser Glu Lys Gly Thr Val Gln Gln Ala Asp Glu
180 185 190

<210> SEQ ID NO 18
<211> LENGTH: 1531
<212> TYPE: PRT
<213> ORGANISM: Artificial Sequence
<220> FEATURE:
<223> OTHER INFORMATION: Synthetic

<400> SEQUENCE: 18

Met Gly Val Leu Val Val Leu Thr Val Leu Trp Leu Phe Ser Ser Val
1 5 10 15

Lys Ala Asp Ser Lys Ala Ile Thr Thr Ser Leu Thr Thr Lys Trp Phe
20 25 30

Ser Thr Pro Leu Leu Leu Glu Ala Ser Glu Phe Leu Ala Glu Asp Ser
35 40 45

Gln Glu Lys Phe Trp Asn Phe Val Glu Ala Ser Gln Asn Ile Gly Ser
50 55 60

Ser Asp His Asp Gly Thr Asp Tyr Ser Tyr Tyr His Ala Ile Leu Glu
65 70 75 80

Ala Ala Phe Gln Phe Leu Ser Pro Leu Gln Gln Asn Leu Phe Lys Phe
85 90 95

Cys Leu Ser Leu Arg Ser Tyr Ser Ala Thr Ile Gln Ala Phe Gln Gln
100 105 110

Ile Ala Ala Asp Glu Pro Pro Pro Glu Gly Cys Asn Ser Phe Phe Ser
115 120 125

Val His Gly Lys Lys Thr Cys Glu Ser Asp Thr Leu Glu Ala Leu Leu
130 135 140

Leu Thr Ala Ser Glu Arg Pro Lys Pro Leu Leu Phe Lys Gly Asp His
145 150 155 160

```
Arg Tyr Pro Ser Ser Asn Pro Glu Ser Pro Val Val Ile Phe Tyr Ser
                165                 170                 175

Glu Ile Gly Ser Glu Glu Phe Ser Asn Phe His Arg Gln Leu Ile Ser
            180                 185                 190

Lys Ser Asn Ala Gly Lys Ile Asn Tyr Val Phe Arg His Tyr Ile Phe
        195                 200                 205

Asn Pro Arg Lys Glu Pro Val Tyr Leu Ser Gly Tyr Gly Val Glu Leu
    210                 215                 220

Ala Ile Lys Ser Thr Glu Tyr Lys Ala Lys Asp Asp Thr Gln Val Lys
225                 230                 235                 240

Gly Thr Glu Val Asn Thr Thr Val Ile Gly Glu Asn Asp Pro Ile Asp
                245                 250                 255

Glu Val Gln Gly Phe Leu Phe Gly Lys Leu Arg Asp Leu His Pro Asp
            260                 265                 270

Leu Glu Gly Gln Leu Lys Glu Leu Arg Lys His Leu Val Glu Ser Thr
        275                 280                 285

Asn Glu Met Ala Pro Leu Lys Val Trp Gln Leu Gln Asp Leu Ser Phe
    290                 295                 300

Gln Thr Ala Ala Arg Ile Leu Ala Ser Pro Val Glu Leu Ala Leu Val
305                 310                 315                 320

Val Met Lys Asp Leu Ser Gln Asn Phe Pro Thr Lys Ala Arg Ala Ile
                325                 330                 335

Thr Lys Thr Ala Val Ser Ser Glu Leu Arg Thr Glu Val Glu Glu Asn
            340                 345                 350

Gln Lys Tyr Phe Lys Gly Thr Leu Gly Leu Gln Pro Gly Asp Ser Ala
        355                 360                 365

Leu Phe Ile Asn Gly Leu His Met Asp Leu Asp Thr Gln Asp Ile Phe
    370                 375                 380

Ser Leu Phe Asp Val Leu Arg Asn Glu Ala Arg Val Met Glu Gly Leu
385                 390                 395                 400

His Arg Leu Gly Ile Glu Gly Leu Ser Leu His Asn Val Leu Lys Leu
                405                 410                 415

Asn Ile Gln Pro Ser Glu Ala Asp Tyr Ala Val Asp Ile Arg Ser Pro
            420                 425                 430

Ala Ile Ser Trp Val Asn Asn Leu Glu Val Asp Ser Arg Tyr Asn Ser
        435                 440                 445

Trp Pro Ser Ser Leu Gln Glu Leu Leu Arg Pro Thr Phe Pro Gly Val
    450                 455                 460

Ile Arg Gln Ile Arg Lys Asn Leu His Asn Met Val Phe Ile Val Asp
465                 470                 475                 480

Pro Ala His Glu Thr Thr Ala Glu Leu Met Asn Thr Ala Glu Met Phe
                485                 490                 495

Leu Ser Asn His Ile Pro Leu Arg Ile Gly Phe Ile Phe Val Val Asn
            500                 505                 510

Asp Ser Glu Asp Val Asp Gly Met Gln Asp Ala Gly Val Ala Val Leu
        515                 520                 525

Arg Ala Tyr Asn Tyr Val Ala Gln Glu Val Asp Asp Tyr His Ala Phe
    530                 535                 540

Gln Thr Leu Thr His Ile Tyr Asn Lys Val Arg Thr Gly Glu Lys Val
545                 550                 555                 560

Lys Val Glu His Val Val Ser Val Leu Glu Lys Lys Tyr Pro Tyr Val
                565                 570                 575

Glu Val Asn Ser Ile Leu Gly Ile Asp Ser Ala Tyr Asp Arg Asn Arg
            580                 585                 590
```

```
Lys Glu Ala Arg Gly Tyr Tyr Glu Gln Thr Gly Val Gly Pro Leu Pro
        595                 600                 605

Val Val Leu Phe Asn Gly Met Pro Phe Glu Arg Glu Gln Leu Asp Pro
    610                 615                 620

Asp Glu Leu Glu Thr Ile Thr Met His Lys Ile Leu Glu Thr Thr Thr
625                 630                 635                 640

Phe Phe Gln Arg Ala Val Tyr Leu Gly Glu Leu Pro His Asp Gln Asp
                645                 650                 655

Val Val Glu Tyr Ile Met Asn Gln Pro Asn Val Val Pro Arg Ile Asn
            660                 665                 670

Ser Arg Ile Leu Thr Ala Glu Arg Asp Tyr Leu Asp Leu Thr Ala Ser
        675                 680                 685

Asn Asn Phe Phe Val Asp Asp Tyr Ala Arg Phe Thr Ile Leu Asp Ser
    690                 695                 700

Gln Gly Lys Thr Ala Ala Val Ala Asn Ser Met Asn Tyr Leu Thr Lys
705                 710                 715                 720

Lys Gly Met Ser Ser Lys Glu Ile Tyr Asp Asp Ser Phe Ile Arg Pro
                725                 730                 735

Val Thr Phe Trp Ile Val Gly Asp Phe Asp Ser Pro Ser Gly Arg Gln
            740                 745                 750

Leu Leu Tyr Asp Ala Ile Lys His Gln Lys Ser Ser Asn Asn Val Arg
        755                 760                 765

Ile Ser Met Ile Asn Asn Pro Ala Lys Glu Ile Ser Tyr Glu Asn Thr
    770                 775                 780

Gln Ile Ser Arg Ala Ile Trp Ala Ala Leu Gln Thr Gln Thr Ser Asn
785                 790                 795                 800

Ala Ala Lys Asn Phe Ile Thr Lys Met Ala Lys Glu Gly Ala Ala Glu
                805                 810                 815

Ala Leu Ala Ala Gly Ala Asp Ile Ala Glu Phe Ser Val Gly Gly Met
            820                 825                 830

Asp Phe Ser Leu Phe Lys Glu Val Phe Glu Ser Ser Lys Met Asp Phe
        835                 840                 845

Ile Leu Ser His Ala Val Tyr Cys Arg Asp Val Leu Lys Leu Lys Lys
    850                 855                 860

Gly Gln Arg Ala Val Ile Ser Asn Gly Arg Ile Ile Gly Pro Leu Glu
865                 870                 875                 880

Asp Ser Glu Leu Phe Asn Gln Asp Asp Phe His Leu Leu Glu Asn Ile
                885                 890                 895

Ile Leu Lys Thr Ser Gly Gln Lys Ile Lys Ser His Ile Gln Gln Leu
            900                 905                 910

Arg Val Glu Glu Asp Val Ala Ser Asp Leu Val Met Lys Val Asp Ala
        915                 920                 925

Leu Leu Ser Ala Gln Pro Lys Gly Asp Pro Arg Ile Glu Tyr Gln Phe
    930                 935                 940

Phe Glu Asp Arg His Ser Ala Ile Lys Leu Arg Pro Lys Glu Gly Glu
945                 950                 955                 960

Thr Tyr Phe Asp Val Val Ala Val Val Asp Pro Val Thr Arg Glu Ala
                965                 970                 975

Gln Arg Leu Ala Pro Leu Leu Leu Val Leu Ala Gln Leu Ile Asn Met
            980                 985                 990

Asn Leu Arg Val Phe Met Asn Cys  Gln Ser Lys Leu Ser  Asp Met Pro
        995                 1000                 1005

Leu Lys  Ser Phe Tyr Arg Tyr  Val Leu Glu Pro Glu  Ile Ser Phe
```

```
    1010                1015                1020

Thr Ser  Asp Asn Ser Phe Ala  Lys Gly Pro Ile Ala  Lys Phe Leu
    1025                1030                1035

Asp Met  Pro Gln Ser Pro Leu  Phe Thr Leu Asn Leu  Asn Thr Pro
    1040                1045                1050

Glu Ser  Trp Met Val Glu Ser  Val Arg Thr Pro Tyr  Asp Leu Asp
    1055                1060                1065

Asn Ile  Tyr Leu Glu Glu Val  Asp Ser Val Val Ala  Ala Glu Tyr
    1070                1075                1080

Glu Leu  Glu Tyr Leu Leu Leu  Glu Gly His Cys Tyr  Asp Ile Thr
    1085                1090                1095

Thr Gly  Gln Pro Pro Arg Gly  Leu Gln Phe Thr Leu  Gly Thr Ser
    1100                1105                1110

Ala Asn  Pro Val Ile Val Asp  Thr Ile Val Met Ala  Asn Leu Gly
    1115                1120                1125

Tyr Phe  Gln Leu Lys Ala Asn  Pro Gly Ala Trp Ile  Leu Arg Leu
    1130                1135                1140

Arg Lys  Gly Arg Ser Glu Asp  Ile Tyr Arg Ile Tyr  Ser His Asp
    1145                1150                1155

Gly Thr  Asp Ser Pro Pro Asp  Ala Asp Glu Val Val  Ile Val Leu
    1160                1165                1170

Asn Asn  Phe Lys Ser Lys Ile  Ile Lys Val Lys Val  Gln Lys Lys
    1175                1180                1185

Ala Asp  Met Val Asn Glu Asp  Leu Leu Ser Asp Gly  Thr Ser Glu
    1190                1195                1200

Asn Glu  Ser Gly Phe Trp Asp  Ser Phe Lys Trp Gly  Phe Thr Gly
    1205                1210                1215

Gln Lys  Thr Glu Glu Val Lys  Gln Asp Lys Asp Asp  Ile Ile Asn
    1220                1225                1230

Ile Phe  Ser Val Ala Ser Gly  His Leu Tyr Glu Arg  Phe Leu Arg
    1235                1240                1245

Ile Met  Met Leu Ser Val Leu  Lys Asn Thr Lys Thr  Pro Val Lys
    1250                1255                1260

Phe Trp  Phe Leu Lys Asn Tyr  Leu Ser Pro Thr Phe  Lys Glu Phe
    1265                1270                1275

Ile Pro  Tyr Met Ala Asn Glu  Tyr Asn Phe Gln Tyr  Glu Leu Val
    1280                1285                1290

Gln Tyr  Lys Trp Pro Arg Trp  Leu His Gln Gln Thr  Glu Lys Gln
    1295                1300                1305

Arg Ile  Ile Trp Gly Tyr Lys  Ile Leu Phe Leu Asp  Val Leu Phe
    1310                1315                1320

Pro Leu  Val Val Asp Lys Phe  Leu Phe Val Asp Ala  Asp Gln Ile
    1325                1330                1335

Val Arg  Thr Asp Leu Lys Glu  Leu Arg Asp Phe Asn  Leu Asp Gly
    1340                1345                1350

Ala Pro  Tyr Gly Tyr Thr Pro  Phe Cys Asp Ser Arg  Arg Glu Met
    1355                1360                1365

Asp Gly  Tyr Arg Phe Trp Lys  Ser Gly Tyr Trp Ala  Ser His Leu
    1370                1375                1380

Ala Gly  Arg Lys Tyr His Ile  Ser Ala Leu Tyr Val  Val Asp Leu
    1385                1390                1395

Lys Lys  Phe Arg Lys Ile Ala  Ala Gly Asp Arg Leu  Arg Gly Gln
    1400                1405                1410
```

```
Tyr Gln  Gly Leu Ser Gln Asp  Pro Asn Ser Leu Ser  Asn Leu Asp
    1415                 1420                 1425

Gln Asp  Leu Pro Asn Asn Met  Ile His Gln Val Pro  Ile Lys Ser
    1430                 1435                 1440

Leu Pro  Gln Glu Trp Leu Trp  Cys Glu Thr Trp Cys  Asp Asp Ala
    1445                 1450                 1455

Ser Lys  Lys Arg Ala Lys Thr  Ile Asp Leu Cys Asn  Asn Pro Met
    1460                 1465                 1470

Thr Lys  Glu Pro Lys Leu Glu  Ala Ala Val Arg Ile  Val Pro Glu
    1475                 1480                 1485

Trp Gln  Asp Tyr Asp Gln Glu  Ile Lys Gln Leu Gln  Ile Arg Phe
    1490                 1495                 1500

Gln Lys  Glu Lys Glu Thr Gly  Ala Leu Tyr Lys Glu  Lys Thr Lys
    1505                 1510                 1515

Glu Pro  Ser Arg Glu Gly Pro  Gln Lys Arg Glu Glu  Leu
    1520                 1525                 1530
```

<210> SEQ ID NO 19
<211> LENGTH: 224
<212> TYPE: PRT
<213> ORGANISM: Artificial Sequence
<220> FEATURE:
<223> OTHER INFORMATION: Synthetic

<400> SEQUENCE: 19

```
Met Arg Val Ser Gly Val Leu Arg Leu Leu Ala Leu Ile Phe Ala Ile
1               5                   10                  15

Val Thr Thr Trp Met Phe Ile Arg Ser Tyr Met Ser Phe Ser Met Lys
            20                  25                  30

Thr Ile Arg Leu Pro Arg Trp Leu Ala Ala Ser Pro Thr Lys Glu Ile
        35                  40                  45

Gln Val Lys Lys Tyr Lys Cys Gly Leu Ile Lys Pro Cys Pro Ala Asn
    50                  55                  60

Tyr Phe Ala Phe Lys Ile Cys Ser Gly Ala Ala Asn Val Val Gly Pro
65                  70                  75                  80

Thr Met Cys Phe Glu Asp Arg Met Ile Met Ser Pro Val Lys Asn Asn
                85                  90                  95

Val Gly Arg Gly Leu Asn Ile Ala Leu Val Asn Gly Thr Thr Gly Ala
            100                 105                 110

Val Leu Gly Gln Lys Ala Phe Asp Met Tyr Ser Gly Asp Val Met His
        115                 120                 125

Leu Val Lys Phe Leu Lys Glu Ile Pro Gly Gly Ala Leu Val Leu Val
    130                 135                 140

Ala Ser Tyr Asp Asp Pro Gly Thr Lys Met Asn Asp Glu Ser Arg Lys
145                 150                 155                 160

Leu Phe Ser Asp Leu Gly Ser Ser Tyr Ala Lys Gln Leu Gly Phe Arg
                165                 170                 175

Asp Ser Trp Val Phe Ile Gly Ala Lys Asp Leu Arg Gly Lys Ser Pro
            180                 185                 190

Phe Glu Gln Phe Leu Lys Asn Ser Pro Asp Thr Asn Lys Tyr Glu Gly
        195                 200                 205

Trp Pro Glu Leu Leu Glu Met Glu Gly Cys Met Pro Pro Lys Pro Phe
    210                 215                 220
```

<210> SEQ ID NO 20
<211> LENGTH: 539
<212> TYPE: PRT

<213> ORGANISM: Artificial Sequence
<220> FEATURE:
<223> OTHER INFORMATION: Synthetic

<400> SEQUENCE: 20

```
Met Pro Glu Asn Val Ala Pro Arg Ser Gly Ala Thr Ala Gly Ala Ala
1               5                   10                  15

Gly Gly Arg Gly Lys Gly Ala Tyr Gln Asp Arg Asp Lys Pro Ala Gln
            20                  25                  30

Ile Arg Phe Ser Asn Ile Ser Ala Ala Lys Ala Val Ala Asp Ala Ile
        35                  40                  45

Arg Thr Ser Leu Gly Pro Lys Gly Met Asp Lys Met Ile Gln Asp Gly
    50                  55                  60

Lys Gly Asp Val Thr Ile Thr Asn Asp Gly Ala Thr Ile Leu Lys Gln
65                  70                  75                  80

Met Gln Val Leu His Pro Ala Ala Arg Met Leu Val Glu Leu Ser Lys
                85                  90                  95

Ala Gln Asp Ile Glu Ala Gly Asp Gly Thr Thr Ser Val Val Ile Ile
            100                 105                 110

Ala Gly Ser Leu Leu Asp Ser Cys Thr Lys Leu Leu Gln Lys Gly Ile
        115                 120                 125

His Pro Thr Ile Ile Ser Glu Ser Phe Gln Lys Ala Leu Glu Lys Gly
    130                 135                 140

Ile Glu Ile Leu Thr Asp Met Ser Arg Pro Val Glu Leu Ser Asp Arg
145                 150                 155                 160

Glu Thr Leu Leu Asn Ser Ala Thr Thr Ser Leu Asn Ser Lys Val Val
                165                 170                 175

Ser Gln Tyr Ser Ser Leu Leu Ser Pro Met Ser Val Asn Ala Val Met
            180                 185                 190

Lys Val Ile Asp Pro Ala Thr Ala Thr Ser Val Asp Leu Arg Asp Ile
        195                 200                 205

Lys Ile Val Lys Lys Leu Gly Gly Thr Ile Asp Asp Cys Glu Leu Val
    210                 215                 220

Glu Gly Leu Val Leu Thr Gln Lys Val Ser Asn Ser Gly Ile Thr Arg
225                 230                 235                 240

Val Glu Lys Ala Lys Ile Gly Leu Ile Gln Phe Cys Leu Ser Ala Pro
                245                 250                 255

Lys Thr Asp Met Asp Asn Gln Ile Val Val Ser Asp Tyr Ala Gln Met
            260                 265                 270

Asp Arg Val Leu Arg Glu Glu Arg Ala Tyr Ile Leu Asn Leu Val Lys
        275                 280                 285

Gln Ile Lys Lys Thr Gly Cys Asn Val Leu Leu Ile Gln Lys Ser Ile
    290                 295                 300

Leu Arg Asp Ala Leu Ser Asp Leu Ala Leu His Phe Leu Asn Lys Met
305                 310                 315                 320

Lys Ile Met Val Ile Lys Asp Ile Glu Arg Glu Asp Ile Glu Phe Ile
                325                 330                 335

Cys Lys Thr Ile Gly Thr Lys Pro Val Ala His Ile Asp Gln Phe Thr
            340                 345                 350

Ala Asp Met Leu Gly Ser Ala Glu Leu Ala Glu Glu Val Asn Leu Asn
        355                 360                 365

Gly Ser Gly Lys Leu Leu Lys Ile Thr Gly Cys Ala Ser Pro Gly Lys
    370                 375                 380

Thr Val Thr Ile Val Val Arg Gly Ser Asn Lys Leu Val Ile Glu Glu
385                 390                 395                 400
```

Ala Glu Arg Ser Ile His Asp Ala Leu Cys Val Ile Arg Cys Leu Val
405 410 415

Lys Lys Arg Ala Leu Ile Ala Gly Gly Gly Ala Pro Glu Ile Glu Leu
420 425 430

Ala Leu Arg Leu Thr Glu Tyr Ser Arg Thr Leu Ser Gly Met Glu Ser
435 440 445

Tyr Cys Val Arg Ala Phe Ala Asp Ala Met Glu Val Ile Pro Ser Thr
450 455 460

Leu Ala Glu Asn Ala Gly Leu Asn Pro Ile Ser Thr Val Thr Glu Leu
465 470 475 480

Arg Asn Arg His Ala Gln Gly Glu Lys Thr Ala Gly Ile Asn Val Arg
485 490 495

Lys Gly Gly Ile Ser Asn Ile Leu Glu Glu Leu Val Val Gln Pro Leu
500 505 510

Leu Val Ser Val Ser Ala Leu Thr Leu Ala Thr Glu Thr Val Arg Ser
515 520 525

Ile Leu Lys Ile Asp Asp Val Val Asn Thr Arg
530 535

<210> SEQ ID NO 21
<211> LENGTH: 658
<212> TYPE: PRT
<213> ORGANISM: Artificial Sequence
<220> FEATURE:
<223> OTHER INFORMATION: SYNTHETIC

<400> SEQUENCE: 21

Met Val Pro Arg Leu Leu Leu Arg Ala Trp Pro Arg Gly Pro Ala Val
1 5 10 15

Gly Pro Gly Ala Pro Ser Arg Pro Leu Ser Ala Gly Ser Gly Pro Gly
20 25 30

Gln Tyr Leu Gln Arg Ser Ile Val Pro Thr Met His Tyr Gln Asp Ser
35 40 45

Leu Pro Arg Leu Pro Ile Pro Lys Leu Glu Asp Thr Ile Arg Arg Tyr
50 55 60

Leu Ser Ala Gln Lys Pro Leu Leu Asn Asp Gly Gln Phe Arg Lys Thr
65 70 75 80

Glu Gln Phe Cys Lys Ser Phe Glu Asn Gly Ile Gly Lys Glu Leu His
85 90 95

Glu Gln Leu Val Ala Leu Asp Lys Gln Asn Lys His Thr Ser Tyr Ile
100 105 110

Ser Gly Pro Trp Phe Asp Met Tyr Leu Ser Ala Arg Asp Ser Val Val
115 120 125

Leu Asn Phe Asn Pro Phe Met Ala Phe Asn Pro Asp Pro Lys Ser Glu
130 135 140

Tyr Asn Asp Gln Leu Thr Arg Ala Thr Asn Met Thr Val Ser Ala Ile
145 150 155 160

Arg Phe Leu Lys Thr Leu Arg Ala Gly Leu Leu Glu Pro Glu Val Phe
165 170 175

His Leu Asn Pro Ala Lys Ser Asp Thr Ile Thr Phe Lys Arg Leu Ile
180 185 190

Arg Phe Val Pro Ser Ser Leu Ser Trp Tyr Gly Ala Tyr Leu Val Asn
195 200 205

Ala Tyr Pro Leu Asp Met Ser Gln Tyr Phe Arg Leu Phe Asn Ser Thr
210 215 220

-continued

```
Arg Leu Pro Lys Pro Ser Arg Asp Glu Leu Phe Thr Asp Asp Lys Ala
225                 230                 235                 240

Arg His Leu Leu Val Leu Arg Lys Gly Asn Phe Tyr Ile Phe Asp Val
                245                 250                 255

Leu Asp Gln Asp Gly Asn Ile Val Ser Pro Ser Glu Ile Gln Ala His
            260                 265                 270

Leu Lys Tyr Ile Leu Ser Asp Ser Ser Pro Ala Pro Glu Phe Pro Leu
        275                 280                 285

Ala Tyr Leu Thr Ser Glu Asn Arg Asp Ile Trp Ala Glu Leu Arg Gln
    290                 295                 300

Lys Leu Met Ser Ser Gly Asn Glu Glu Ser Leu Arg Lys Val Asp Ser
305                 310                 315                 320

Ala Val Phe Cys Leu Cys Leu Asp Asp Phe Pro Ile Lys Asp Leu Val
                325                 330                 335

His Leu Ser His Asn Met Leu His Gly Asp Gly Thr Asn Arg Trp Phe
            340                 345                 350

Asp Lys Ser Phe Asn Leu Ile Ile Ala Lys Asp Gly Ser Thr Ala Val
        355                 360                 365

His Phe Glu His Ser Trp Gly Asp Gly Val Ala Val Leu Arg Phe Phe
    370                 375                 380

Asn Glu Val Phe Lys Asp Ser Thr Gln Thr Pro Ala Val Thr Pro Gln
385                 390                 395                 400

Ser Gln Pro Ala Thr Thr Asp Ser Thr Val Thr Val Gln Lys Leu Asn
                405                 410                 415

Phe Glu Leu Thr Asp Ala Leu Lys Thr Gly Ile Thr Ala Ala Lys Glu
            420                 425                 430

Lys Phe Asp Ala Thr Met Lys Thr Leu Thr Ile Asp Cys Val Gln Phe
        435                 440                 445

Gln Arg Gly Gly Lys Glu Phe Leu Lys Lys Gln Lys Leu Ser Pro Asp
    450                 455                 460

Ala Val Ala Gln Leu Ala Phe Gln Met Ala Phe Leu Arg Gln Tyr Gly
465                 470                 475                 480

Gln Thr Val Ala Thr Tyr Glu Ser Cys Ser Thr Ala Ala Phe Lys His
                485                 490                 495

Gly Arg Thr Glu Thr Ile Arg Pro Ala Ser Val Tyr Thr Lys Arg Cys
            500                 505                 510

Ser Glu Ala Phe Val Arg Glu Pro Ser Arg His Ser Ala Gly Glu Leu
        515                 520                 525

Gln Gln Met Met Val Glu Cys Ser Lys Tyr His Gly Gln Leu Thr Lys
    530                 535                 540

Glu Ala Ala Met Gly Gln Gly Phe Asp Arg His Leu Phe Ala Leu Arg
545                 550                 555                 560

His Leu Ala Ala Ala Lys Gly Ile Ile Leu Pro Glu Leu Tyr Leu Asp
                565                 570                 575

Pro Ala Tyr Gly Gln Ile Asn His Asn Val Leu Ser Thr Ser Thr Leu
            580                 585                 590

Ser Ser Pro Ala Val Asn Leu Gly Gly Phe Ala Pro Val Val Ser Asp
        595                 600                 605

Gly Phe Gly Val Gly Tyr Ala Val His Asp Asn Trp Ile Gly Cys Asn
    610                 615                 620

Val Ser Ser Tyr Pro Gly Arg Asn Ala Arg Glu Phe Leu Gln Cys Val
625                 630                 635                 640

Glu Lys Ala Leu Glu Asp Met Phe Asp Ala Leu Glu Gly Lys Ser Ile
                645                 650                 655
```

Lys Ser

<210> SEQ ID NO 22
<211> LENGTH: 181
<212> TYPE: PRT
<213> ORGANISM: Artificial Sequence
<220> FEATURE:
<223> OTHER INFORMATION: Synthetic

<400> SEQUENCE: 22

```
Met Gly Gly Phe Phe Ser Ser Ile Phe Ser Ser Leu Phe Gly Thr Arg
1               5                   10                  15

Glu Met Arg Ile Leu Ile Leu Gly Leu Asp Gly Ala Gly Lys Thr Thr
            20                  25                  30

Ile Leu Tyr Arg Leu Gln Val Gly Glu Val Val Thr Thr Ile Pro Thr
        35                  40                  45

Ile Gly Phe Asn Val Glu Thr Val Thr Tyr Lys Asn Leu Lys Phe Gln
    50                  55                  60

Val Trp Asp Leu Gly Gly Gln Thr Ser Ile Arg Pro Tyr Trp Arg Cys
65                  70                  75                  80

Tyr Tyr Ser Asn Thr Asp Ala Val Ile Tyr Val Val Asp Ser Cys Asp
                85                  90                  95

Arg Asp Arg Ile Gly Ile Ser Lys Ser Glu Leu Val Ala Met Leu Glu
            100                 105                 110

Glu Glu Glu Leu Arg Lys Ala Ile Leu Val Val Phe Ala Asn Lys Gln
        115                 120                 125

Asp Met Glu Gln Ala Met Thr Ser Ser Glu Met Ala Asn Ser Leu Gly
    130                 135                 140

Leu Pro Ala Leu Lys Asp Arg Lys Trp Gln Ile Phe Lys Thr Ser Ala
145                 150                 155                 160

Thr Lys Gly Thr Gly Leu Asp Glu Ala Met Glu Trp Leu Val Glu Thr
                165                 170                 175

Leu Lys Ser Arg Gln
            180
```

<210> SEQ ID NO 23
<211> LENGTH: 780
<212> TYPE: PRT
<213> ORGANISM: Artificial Sequence
<220> FEATURE:
<223> OTHER INFORMATION: Synthetic

<400> SEQUENCE: 23

```
Met Ala Ala Val Asp Leu Glu Lys Leu Arg Ala Ser Gly Ala Gly Lys
1               5                   10                  15

Ala Ile Gly Val Leu Thr Ser Gly Gly Asp Ala Gln Gly Met Asn Ala
            20                  25                  30

Ala Val Arg Ala Val Thr Arg Met Gly Ile Tyr Val Gly Ala Lys Val
        35                  40                  45

Phe Leu Ile Tyr Glu Gly Tyr Glu Gly Leu Val Glu Gly Gly Glu Asn
    50                  55                  60

Ile Lys Gln Ala Asn Trp Leu Ser Val Ser Asn Ile Ile Gln Leu Gly
65                  70                  75                  80

Gly Thr Ile Ile Gly Ser Ala Arg Cys Lys Ala Phe Thr Thr Arg Glu
                85                  90                  95

Gly Arg Arg Ala Ala Ala Tyr Asn Leu Val Gln His Gly Ile Thr Asn
            100                 105                 110
```

-continued

```
Leu Cys Val Ile Gly Gly Asp Gly Ser Leu Thr Gly Ala Asn Ile Phe
        115                 120                 125

Arg Ser Glu Trp Gly Ser Leu Leu Glu Glu Leu Val Ala Glu Gly Lys
    130                 135                 140

Ile Ser Glu Thr Thr Ala Arg Thr Tyr Ser His Leu Asn Ile Ala Gly
145                 150                 155                 160

Leu Val Gly Ser Ile Asp Asn Asp Phe Cys Gly Thr Asp Met Thr Ile
                165                 170                 175

Gly Thr Asp Ser Ala Leu His Arg Ile Met Glu Val Ile Asp Ala Ile
            180                 185                 190

Thr Thr Thr Ala Gln Ser His Gln Arg Thr Phe Val Leu Glu Val Met
        195                 200                 205

Gly Arg His Cys Gly Tyr Leu Ala Leu Val Ser Ala Leu Ala Ser Gly
    210                 215                 220

Ala Asp Trp Leu Phe Ile Pro Glu Ala Pro Pro Glu Asp Gly Trp Glu
225                 230                 235                 240

Asn Phe Met Cys Glu Arg Leu Gly Glu Thr Arg Ser Arg Gly Ser Arg
                245                 250                 255

Leu Asn Ile Ile Ile Ile Ala Glu Gly Ala Ile Asp Arg Asn Gly Lys
            260                 265                 270

Pro Ile Ser Ser Ser Tyr Val Lys Asp Leu Val Val Gln Arg Leu Gly
        275                 280                 285

Phe Asp Thr Arg Val Thr Val Leu Gly His Val Gln Arg Gly Gly Thr
    290                 295                 300

Pro Ser Ala Phe Asp Arg Ile Leu Ser Ser Lys Met Gly Met Glu Ala
305                 310                 315                 320

Val Met Ala Leu Leu Glu Ala Thr Pro Asp Thr Pro Ala Cys Val Val
                325                 330                 335

Thr Leu Ser Gly Asn Gln Ser Val Arg Leu Pro Leu Met Glu Cys Val
            340                 345                 350

Gln Met Thr Lys Glu Val Gln Lys Ala Met Asp Asp Lys Arg Phe Asp
        355                 360                 365

Glu Ala Thr Gln Leu Arg Gly Gly Ser Phe Glu Asn Asn Trp Asn Ile
    370                 375                 380

Tyr Lys Leu Leu Ala His Gln Lys Pro Pro Lys Glu Lys Ser Asn Phe
385                 390                 395                 400

Ser Leu Ala Ile Leu Asn Val Gly Ala Pro Ala Ala Gly Met Asn Ala
                405                 410                 415

Ala Val Arg Ser Ala Val Arg Thr Gly Ile Ser His Gly His Thr Val
            420                 425                 430

Tyr Val Val His Asp Gly Phe Glu Gly Leu Ala Lys Gly Gln Val Gln
        435                 440                 445

Glu Val Gly Trp His Asp Val Ala Gly Trp Leu Gly Arg Gly Gly Ser
    450                 455                 460

Met Leu Gly Thr Lys Arg Thr Leu Pro Lys Gly Gln Leu Glu Ser Ile
465                 470                 475                 480

Val Glu Asn Ile Arg Ile Tyr Gly Ile His Ala Leu Leu Val Val Gly
                485                 490                 495

Gly Phe Glu Ala Tyr Glu Gly Val Leu Gln Leu Val Glu Ala Arg Gly
            500                 505                 510

Arg Tyr Glu Glu Leu Cys Ile Val Met Cys Val Ile Pro Ala Thr Ile
        515                 520                 525

Ser Asn Asn Val Pro Gly Thr Asp Phe Ser Leu Gly Ser Asp Thr Ala
    530                 535                 540
```

Val Asn Ala Ala Met Glu Ser Cys Asp Arg Ile Lys Gln Ser Ala Ser
545 550 555 560

Gly Thr Lys Arg Arg Val Phe Ile Val Glu Thr Met Gly Gly Tyr Cys
565 570 575

Gly Tyr Leu Ala Thr Val Thr Gly Ile Ala Val Gly Ala Asp Ala Ala
580 585 590

Tyr Val Phe Glu Asp Pro Phe Asn Ile His Asp Leu Lys Val Asn Val
595 600 605

Glu His Met Thr Glu Lys Met Lys Thr Asp Ile Gln Arg Gly Leu Val
610 615 620

Leu Arg Asn Glu Lys Cys His Asp Tyr Tyr Thr Thr Glu Phe Leu Tyr
625 630 635 640

Asn Leu Tyr Ser Ser Glu Gly Lys Gly Val Phe Asp Cys Arg Thr Asn
645 650 655

Val Leu Gly His Leu Gln Gln Gly Gly Ala Pro Thr Pro Phe Asp Arg
660 665 670

Asn Tyr Gly Thr Lys Leu Gly Val Lys Ala Met Leu Trp Leu Ser Glu
675 680 685

Lys Leu Arg Glu Val Tyr Arg Lys Gly Arg Val Phe Ala Asn Ala Pro
690 695 700

Asp Ser Ala Cys Val Ile Gly Leu Lys Lys Lys Ala Val Ala Phe Ser
705 710 715 720

Pro Val Thr Glu Leu Lys Lys Asp Thr Asp Phe Glu His Arg Met Pro
725 730 735

Arg Glu Gln Trp Trp Leu Ser Leu Arg Leu Met Leu Lys Met Leu Ala
740 745 750

Gln Tyr Arg Ile Ser Met Ala Ala Tyr Val Ser Gly Glu Leu Glu His
755 760 765

Val Thr Arg Arg Thr Leu Ser Met Asp Lys Gly Phe
770 775 780

<210> SEQ ID NO 24
<211> LENGTH: 430
<212> TYPE: PRT
<213> ORGANISM: Artificial Sequence
<220> FEATURE:
<223> OTHER INFORMATION: Synthetic

<400> SEQUENCE: 24

Met Ala Leu Leu His Ser Gly Arg Val Leu Pro Gly Ile Ala Ala Ala
1 5 10 15

Phe His Pro Gly Leu Ala Ala Ala Ala Ser Ala Arg Ala Ser Ser Trp
20 25 30

Trp Thr His Val Glu Met Gly Pro Pro Asp Pro Ile Leu Gly Val Thr
35 40 45

Glu Ala Phe Lys Arg Asp Thr Asn Ser Lys Lys Met Asn Leu Gly Val
50 55 60

Gly Ala Tyr Arg Asp Asp Asn Gly Lys Pro Tyr Val Leu Pro Ser Val
65 70 75 80

Arg Lys Ala Glu Ala Gln Ile Ala Ala Lys Asn Leu Asp Lys Glu Tyr
85 90 95

Leu Pro Ile Gly Gly Leu Ala Glu Phe Cys Lys Ala Ser Ala Glu Leu
100 105 110

Ala Leu Gly Glu Asn Ser Glu Val Leu Lys Ser Gly Arg Phe Val Thr
115 120 125

Val Gln Thr Ile Ser Gly Thr Gly Ala Leu Arg Ile Gly Ala Ser Phe
130 135 140

Leu Gln Arg Phe Phe Lys Phe Ser Arg Asp Val Phe Leu Pro Lys Pro
145 150 155 160

Thr Trp Gly Asn His Thr Pro Ile Phe Arg Asp Ala Gly Met Gln Leu
165 170 175

Gln Gly Tyr Arg Tyr Tyr Asp Pro Lys Thr Cys Gly Phe Asp Phe Thr
180 185 190

Gly Ala Val Glu Asp Ile Ser Lys Ile Pro Glu Gln Ser Val Leu Leu
195 200 205

Leu His Ala Cys Ala His Asn Pro Thr Gly Val Asp Pro Arg Pro Glu
210 215 220

Gln Trp Lys Glu Ile Ala Thr Val Val Lys Lys Arg Asn Leu Phe Ala
225 230 235 240

Phe Phe Asp Met Ala Tyr Gln Gly Phe Ala Ser Gly Asp Gly Asp Lys
245 250 255

Asp Ala Trp Ala Val Arg His Phe Ile Glu Gln Gly Ile Asn Val Cys
260 265 270

Leu Cys Gln Ser Tyr Ala Lys Asn Met Gly Leu Tyr Gly Glu Arg Val
275 280 285

Gly Ala Phe Thr Met Val Cys Lys Asp Ala Asp Glu Ala Lys Arg Val
290 295 300

Glu Ser Gln Leu Lys Ile Leu Ile Arg Pro Met Tyr Ser Asn Pro Pro
305 310 315 320

Leu Asn Gly Ala Arg Ile Ala Ala Ala Ile Leu Asn Thr Pro Asp Leu
325 330 335

Arg Lys Gln Trp Leu Gln Glu Val Lys Gly Met Ala Asp Arg Ile Ile
340 345 350

Gly Met Arg Thr Gln Leu Val Ser Asn Leu Lys Lys Glu Gly Ser Thr
355 360 365

His Asn Trp Gln His Ile Thr Asp Gln Ile Gly Met Phe Cys Phe Thr
370 375 380

Gly Leu Lys Pro Glu Gln Val Glu Arg Leu Ile Lys Glu Phe Ser Ile
385 390 395 400

Tyr Met Thr Lys Asp Gly Arg Ile Ser Val Ala Gly Val Thr Ser Ser
405 410 415

Asn Val Gly Tyr Leu Ala His Ala Ile His Gln Val Thr Lys
420 425 430

<210> SEQ ID NO 25
<211> LENGTH: 845
<212> TYPE: PRT
<213> ORGANISM: Artificial Sequence
<220> FEATURE:
<223> OTHER INFORMATION: Synthetic

<400> SEQUENCE: 25

Met Glu Lys Asn Ile Asn Leu Arg Asn Cys Gln Thr Leu Asn Thr Tyr
1 5 10 15

Val Met Leu Thr His Leu Arg Met Pro Ala Pro Ile Arg Leu Arg Glu
20 25 30

Leu Ile Arg Thr Ile Arg Thr Ala Arg Thr Gln Ala Glu Glu Arg Glu
35 40 45

Met Ile Gln Lys Glu Cys Ala Ala Ile Arg Ser Ser Phe Arg Glu Glu
50 55 60

Asp Asn Thr Tyr Arg Cys Arg Asn Val Ala Lys Leu Leu Tyr Met His

```
65                  70                  75                  80

Met Leu Gly Tyr Pro Ala His Phe Gly Gln Leu Glu Cys Leu Lys Leu
                85                  90                  95

Ile Ala Ser Gln Lys Phe Thr Asp Lys Arg Ile Gly Tyr Leu Gly Ala
            100                 105                 110

Met Leu Leu Leu Asp Glu Arg Gln Asp Val His Leu Leu Met Thr Asn
        115                 120                 125

Cys Ile Lys Asn Asp Leu Asn His Ser Thr Gln Phe Val Gln Gly Leu
    130                 135                 140

Ala Leu Cys Thr Leu Gly Cys Met Gly Ser Ser Glu Met Cys Arg Asp
145                 150                 155                 160

Leu Ala Gly Glu Val Glu Lys Leu Leu Lys Thr Ser Asn Ser Tyr Leu
                165                 170                 175

Arg Lys Lys Ala Ala Leu Cys Ala Val His Val Ile Arg Lys Val Pro
            180                 185                 190

Glu Leu Met Glu Met Phe Leu Pro Ala Thr Lys Asn Leu Leu Asn Glu
        195                 200                 205

Lys Asn His Gly Val Leu His Thr Ser Val Val Leu Leu Thr Glu Met
    210                 215                 220

Cys Glu Arg Ser Pro Asp Met Leu Ala His Phe Arg Lys Leu Val Pro
225                 230                 235                 240

Gln Leu Val Arg Ile Leu Lys Asn Leu Ile Met Ser Gly Tyr Ser Pro
                245                 250                 255

Glu His Asp Val Ser Gly Ile Ser Asp Pro Phe Leu Gln Val Arg Ile
            260                 265                 270

Leu Arg Leu Leu Arg Ile Leu Gly Arg Asn Asp Asp Asp Ser Ser Glu
        275                 280                 285

Ala Met Asn Asp Ile Leu Ala Gln Val Ala Thr Asn Thr Glu Thr Ser
    290                 295                 300

Lys Asn Val Gly Asn Ala Ile Leu Tyr Glu Thr Val Leu Thr Ile Met
305                 310                 315                 320

Asp Ile Lys Ser Glu Ser Gly Leu Arg Val Leu Ala Ile Asn Ile Leu
                325                 330                 335

Gly Arg Phe Leu Leu Asn Asn Asp Lys Asn Ile Arg Tyr Val Ala Leu
            340                 345                 350

Thr Ser Leu Leu Lys Thr Val Gln Thr Asp His Asn Ala Val Gln Arg
        355                 360                 365

His Arg Ser Thr Ile Val Asp Cys Leu Lys Asp Leu Asp Val Ser Ile
    370                 375                 380

Lys Arg Arg Ala Met Glu Leu Ser Phe Ala Leu Val Asn Gly Asn Asn
385                 390                 395                 400

Ile Arg Gly Met Met Lys Glu Leu Leu Tyr Phe Leu Asp Ser Cys Glu
                405                 410                 415

Pro Glu Phe Lys Ala Asp Cys Ala Ser Gly Ile Phe Leu Ala Ala Glu
            420                 425                 430

Lys Tyr Ala Pro Ser Lys Arg Trp His Ile Asp Thr Ile Met Arg Val
        435                 440                 445

Leu Thr Thr Ala Gly Ser Tyr Val Arg Asp Asp Ala Val Pro Asn Leu
    450                 455                 460

Ile Gln Leu Ile Thr Asn Ser Val Glu Met His Ala Tyr Thr Val Gln
465                 470                 475                 480

Arg Leu Tyr Lys Ala Ile Leu Gly Asp Tyr Ser Gln Gln Pro Leu Val
                485                 490                 495
```

```
Gln Val Ala Ala Trp Cys Ile Gly Glu Tyr Gly Asp Leu Leu Val Ser
            500                 505                 510

Gly Gln Cys Glu Glu Glu Glu Pro Ile Gln Val Thr Glu Asp Glu Val
        515                 520                 525

Leu Asp Ile Leu Glu Ser Val Leu Ile Ser Asn Met Ser Thr Ser Val
    530                 535                 540

Thr Arg Gly Tyr Ala Leu Thr Ala Ile Met Lys Leu Ser Thr Arg Phe
545                 550                 555                 560

Thr Cys Thr Val Asn Arg Ile Lys Lys Val Val Ser Ile Tyr Gly Ser
                565                 570                 575

Ser Ile Asp Val Glu Leu Gln Gln Arg Ala Val Glu Tyr Asn Ala Leu
            580                 585                 590

Phe Lys Lys Tyr Asp His Met Arg Ser Ala Leu Leu Glu Arg Met Pro
        595                 600                 605

Val Met Glu Lys Val Thr Thr Asn Gly Pro Thr Glu Ile Val Gln Thr
    610                 615                 620

Asn Gly Glu Thr Glu Pro Ala Pro Leu Glu Thr Lys Pro Pro Pro Ser
625                 630                 635                 640

Gly Pro Gln Pro Thr Ser Gln Ala Asn Asp Leu Leu Asp Leu Leu Gly
                645                 650                 655

Gly Asn Asp Ile Thr Pro Val Ile Pro Thr Ala Pro Thr Ser Lys Pro
            660                 665                 670

Ser Ser Ala Gly Gly Glu Leu Leu Asp Leu Leu Gly Asp Ile Asn Leu
        675                 680                 685

Thr Gly Ala Pro Ala Ala Ala Pro Ala Pro Ala Ser Val Pro Gln Ile
    690                 695                 700

Ser Gln Pro Pro Phe Leu Leu Asp Gly Leu Ser Ser Gln Pro Leu Phe
705                 710                 715                 720

Asn Asp Ile Ala Ala Gly Ile Pro Ser Ile Thr Ala Tyr Ser Lys Asn
                725                 730                 735

Gly Leu Lys Ile Glu Phe Thr Phe Glu Arg Ser Asn Thr Asn Pro Ser
            740                 745                 750

Val Thr Val Ile Thr Ile Gln Ala Ser Asn Ser Thr Glu Leu Asp Met
        755                 760                 765

Thr Asp Phe Val Phe Gln Ala Ala Val Pro Lys Thr Phe Gln Leu Gln
    770                 775                 780

Leu Leu Ser Pro Ser Ser Ser Ile Val Pro Ala Phe Asn Thr Gly Thr
785                 790                 795                 800

Ile Thr Gln Val Ile Lys Val Leu Asn Pro Gln Lys Gln Gln Leu Arg
                805                 810                 815

Met Arg Ile Lys Leu Thr Tyr Asn His Lys Gly Ser Ala Met Gln Asp
            820                 825                 830

Leu Ala Glu Val Asn Asn Phe Pro Pro Gln Ser Trp Gln
        835                 840                 845


<210> SEQ ID NO 26
<211> LENGTH: 658
<212> TYPE: PRT
<213> ORGANISM: Artificial Sequence
<220> FEATURE:
<223> OTHER INFORMATION: Synthetic

<400> SEQUENCE: 26

Met Val Lys His Ser Thr Ile Tyr Pro Ser Pro Glu Glu Leu Glu Ala
1               5                   10                  15

Val Gln Asn Met Val Ser Thr Val Glu Cys Ala Leu Lys His Val Ser
```

-continued

```
            20                  25                  30

Asp Trp Leu Asp Glu Thr Asn Lys Gly Thr Lys Thr Glu Gly Glu Thr
        35                  40                  45

Glu Val Lys Lys Asp Glu Ala Gly Glu Asn Tyr Ser Lys Asp Gln Gly
    50                  55                  60

Gly Arg Thr Leu Cys Gly Val Met Arg Ile Gly Leu Val Ala Lys Gly
65                  70                  75                  80

Leu Leu Ile Lys Asp Asp Met Asp Leu Glu Leu Val Leu Met Cys Lys
                85                  90                  95

Asp Lys Pro Thr Glu Thr Leu Leu Asn Thr Val Lys Asp Asn Leu Pro
            100                 105                 110

Ile Gln Ile Gln Lys Leu Thr Glu Glu Lys Tyr Gln Val Glu Gln Cys
        115                 120                 125

Val Asn Glu Ala Ser Ile Ile Ile Arg Asn Thr Lys Glu Pro Thr Leu
    130                 135                 140

Thr Leu Lys Val Ile Leu Thr Ser Pro Leu Ile Arg Asp Glu Leu Glu
145                 150                 155                 160

Lys Lys Asp Gly Glu Asn Val Ser Met Lys Asp Pro Pro Asp Leu Leu
                165                 170                 175

Asp Arg Gln Lys Cys Leu Asn Ala Leu Ala Ser Leu Arg His Ala Lys
            180                 185                 190

Trp Phe Gln Ala Arg Ala Asn Gly Leu Lys Ser Cys Val Ile Val Leu
        195                 200                 205

Arg Ile Leu Arg Asp Leu Cys Asn Arg Val Pro Thr Trp Ala Pro Leu
    210                 215                 220

Lys Gly Trp Pro Leu Glu Leu Ile Cys Glu Lys Ser Ile Gly Thr Cys
225                 230                 235                 240

Asn Arg Pro Leu Gly Ala Gly Glu Ala Leu Arg Arg Val Met Glu Cys
                245                 250                 255

Leu Ala Ser Gly Ile Leu Leu Pro Gly Gly Pro Gly Leu His Asp Pro
            260                 265                 270

Cys Glu Arg Asp Pro Thr Asp Ala Leu Ser Tyr Met Thr Ile Gln Gln
        275                 280                 285

Lys Glu Asp Ile Thr His Ser Ala Gln His Ala Leu Arg Leu Ser Ala
    290                 295                 300

Phe Gly Gln Ile Tyr Lys Val Leu Glu Met Asp Pro Leu Pro Ser Ser
305                 310                 315                 320

Lys Pro Phe Gln Lys Tyr Ser Trp Ser Val Thr Asp Lys Glu Gly Ala
                325                 330                 335

Gly Ser Ser Ala Leu Lys Arg Pro Phe Glu Asp Gly Leu Gly Asp Asp
            340                 345                 350

Lys Asp Pro Asn Lys Lys Met Lys Arg Asn Leu Arg Lys Ile Leu Asp
        355                 360                 365

Ser Lys Ala Ile Asp Leu Met Asn Ala Leu Met Arg Leu Asn Gln Ile
    370                 375                 380

Arg Pro Gly Leu Gln Tyr Lys Leu Leu Ser Gln Ser Gly Pro Val His
385                 390                 395                 400

Ala Pro Val Phe Thr Met Ser Val Asp Val Asp Gly Thr Thr Tyr Glu
                405                 410                 415

Ala Ser Gly Pro Ser Lys Lys Thr Ala Lys Leu His Val Ala Val Lys
            420                 425                 430

Val Leu Gln Ala Met Gly Tyr Pro Thr Gly Phe Asp Ala Asp Ile Glu
        435                 440                 445
```

Cys Met Ser Ser Asp Glu Lys Ser Asp Asn Glu Ser Lys Asn Glu Thr
450 455 460

Val Ser Ser Asn Ser Ser Asn Asn Thr Gly Asn Ser Thr Thr Glu Thr
465 470 475 480

Ser Ser Thr Leu Glu Val Arg Thr Gln Gly Pro Ile Leu Thr Ala Ser
485 490 495

Gly Lys Asn Pro Val Met Glu Leu Asn Glu Lys Arg Arg Gly Leu Lys
500 505 510

Tyr Glu Leu Ile Ser Glu Thr Gly Gly Ser His Asp Lys Arg Phe Val
515 520 525

Met Glu Val Glu Val Asp Gly Gln Lys Phe Arg Gly Ala Gly Pro Asn
530 535 540

Lys Lys Val Ala Lys Ala Ser Ala Ala Leu Ala Ala Leu Glu Lys Leu
545 550 555 560

Phe Ser Gly Pro Asn Ala Ala Asn Asn Lys Lys Lys Lys Ile Ile Pro
565 570 575

Gln Ala Lys Gly Val Val Asn Thr Ala Val Ser Ala Ala Val Gln Ala
580 585 590

Val Arg Gly Arg Gly Arg Gly Thr Leu Thr Arg Gly Ala Phe Val Gly
595 600 605

Ala Thr Ala Ala Pro Gly Tyr Ile Ala Pro Gly Tyr Gly Thr Pro Tyr
610 615 620

Gly Tyr Ser Thr Ala Ala Pro Ala Tyr Gly Leu Pro Lys Arg Met Val
625 630 635 640

Leu Leu Pro Val Met Lys Phe Pro Thr Tyr Pro Val Pro His Tyr Ser
645 650 655

Phe Phe

<210> SEQ ID NO 27
<211> LENGTH: 914
<212> TYPE: PRT
<213> ORGANISM: Artificial Sequence
<220> FEATURE:
<223> OTHER INFORMATION: Synthetic

<400> SEQUENCE: 27

Met Gly Pro Phe Lys Ser Ser Val Phe Ile Leu Ile Leu His Leu Leu
1 5 10 15

Glu Gly Ala Leu Ser Asn Ser Leu Ile Gln Leu Asn Asn Asn Gly Tyr
20 25 30

Glu Gly Ile Val Val Ala Ile Asp Pro Asn Val Pro Glu Asp Glu Thr
35 40 45

Leu Ile Gln Gln Ile Lys Asp Met Val Thr Gln Ala Ser Leu Tyr Leu
50 55 60

Leu Glu Ala Thr Gly Lys Arg Phe Tyr Phe Lys Asn Val Ala Ile Leu
65 70 75 80

Ile Pro Glu Thr Trp Lys Thr Lys Ala Asp Tyr Val Arg Pro Lys Leu
85 90 95

Glu Thr Tyr Lys Asn Ala Asp Val Leu Val Ala Glu Ser Thr Pro Pro
100 105 110

Gly Asn Asp Glu Pro Tyr Thr Glu Gln Met Gly Asn Cys Gly Glu Lys
115 120 125

Gly Glu Arg Ile His Leu Thr Pro Asp Phe Ile Ala Gly Lys Lys Leu
130 135 140

Ala Glu Tyr Gly Pro Gln Gly Arg Ala Phe Val His Glu Trp Ala His
145 150 155 160

```
Leu Arg Trp Gly Val Phe Asp Glu Tyr Asn Asn Asp Glu Lys Phe Tyr
                165                 170                 175

Leu Ser Asn Gly Arg Ile Gln Ala Val Arg Cys Ser Ala Gly Ile Thr
            180                 185                 190

Gly Thr Asn Val Val Lys Lys Cys Gln Gly Gly Ser Cys Tyr Thr Lys
        195                 200                 205

Arg Cys Thr Phe Asn Lys Val Thr Gly Leu Tyr Glu Lys Gly Cys Glu
    210                 215                 220

Phe Val Leu Gln Ser Arg Gln Thr Glu Lys Ala Ser Ile Met Phe Ala
225                 230                 235                 240

Gln His Val Asp Ser Ile Val Glu Phe Cys Thr Glu Gln Asn His Asn
                245                 250                 255

Lys Glu Ala Pro Asn Lys Gln Asn Gln Lys Cys Asn Leu Arg Ser Thr
            260                 265                 270

Trp Glu Val Ile Arg Asp Ser Glu Asp Phe Lys Lys Thr Thr Pro Met
        275                 280                 285

Thr Thr Gln Pro Pro Asn Pro Thr Phe Ser Leu Leu Gln Ile Gly Gln
    290                 295                 300

Arg Ile Val Cys Leu Val Leu Asp Lys Ser Gly Ser Met Ala Thr Gly
305                 310                 315                 320

Asn Arg Leu Asn Arg Leu Asn Gln Ala Gly Gln Leu Phe Leu Leu Gln
                325                 330                 335

Thr Val Glu Leu Gly Ser Trp Val Gly Met Val Thr Phe Asp Ser Ala
            340                 345                 350

Ala His Val Gln Ser Glu Leu Ile Gln Ile Asn Ser Gly Ser Asp Arg
        355                 360                 365

Asp Thr Leu Ala Lys Arg Leu Pro Ala Ala Ala Ser Gly Gly Thr Ser
    370                 375                 380

Ile Cys Ser Gly Leu Arg Ser Ala Phe Thr Val Ile Arg Lys Lys Tyr
385                 390                 395                 400

Pro Thr Asp Gly Ser Glu Ile Val Leu Leu Thr Asp Gly Glu Asp Asn
                405                 410                 415

Thr Ile Ser Gly Cys Phe Asn Glu Val Lys Gln Ser Gly Ala Ile Ile
            420                 425                 430

His Thr Val Ala Leu Gly Pro Ser Ala Ala Gln Glu Leu Glu Glu Leu
        435                 440                 445

Ser Lys Met Thr Gly Gly Leu Gln Thr Tyr Ala Ser Asp Gln Val Gln
    450                 455                 460

Asn Asn Gly Leu Ile Asp Ala Phe Gly Ala Leu Ser Ser Gly Asn Gly
465                 470                 475                 480

Ala Val Ser Gln Arg Ser Ile Gln Leu Glu Ser Lys Gly Leu Thr Leu
                485                 490                 495

Gln Asn Ser Gln Trp Met Asn Gly Thr Val Ile Val Asp Ser Thr Val
            500                 505                 510

Gly Lys Asp Thr Leu Phe Leu Ile Thr Trp Thr Thr Gln Pro Pro Gln
        515                 520                 525

Ile Leu Leu Trp Asp Pro Ser Gly Gln Lys Gln Gly Gly Phe Val Val
    530                 535                 540

Asp Lys Asn Thr Lys Met Ala Tyr Leu Gln Ile Pro Gly Ile Ala Lys
545                 550                 555                 560

Val Gly Thr Trp Lys Tyr Ser Leu Gln Ala Ser Ser Gln Thr Leu Thr
                565                 570                 575

Leu Thr Val Thr Ser Arg Ala Ser Asn Ala Thr Leu Pro Pro Ile Thr
```

```
            580                 585                 590

Val Thr Ser Lys Thr Asn Lys Asp Thr Ser Lys Phe Pro Ser Pro Leu
        595                 600                 605

Val Val Tyr Ala Asn Ile Arg Gln Gly Ala Ser Pro Ile Leu Arg Ala
    610                 615                 620

Ser Val Thr Ala Leu Ile Glu Ser Val Asn Gly Lys Thr Val Thr Leu
625                 630                 635                 640

Glu Leu Leu Asp Asn Gly Ala Gly Ala Asp Ala Thr Lys Asp Asp Gly
                645                 650                 655

Val Tyr Ser Arg Tyr Phe Thr Thr Tyr Asp Thr Asn Gly Arg Tyr Ser
            660                 665                 670

Val Lys Val Arg Ala Leu Gly Gly Val Asn Ala Ala Arg Arg Arg Val
        675                 680                 685

Ile Pro Gln Gln Ser Gly Ala Leu Tyr Ile Pro Gly Trp Ile Glu Asn
    690                 695                 700

Asp Glu Ile Gln Trp Asn Pro Pro Arg Pro Glu Ile Asn Lys Asp Asp
705                 710                 715                 720

Val Gln His Lys Gln Val Cys Phe Ser Arg Thr Ser Ser Gly Gly Ser
                725                 730                 735

Phe Val Ala Ser Asp Val Pro Asn Ala Pro Ile Pro Asp Leu Phe Pro
            740                 745                 750

Pro Gly Gln Ile Thr Asp Leu Lys Ala Glu Ile His Gly Gly Ser Leu
        755                 760                 765

Ile Asn Leu Thr Trp Thr Ala Pro Gly Asp Asp Tyr Asp His Gly Thr
    770                 775                 780

Ala His Lys Tyr Ile Ile Arg Ile Ser Thr Ser Ile Leu Asp Leu Arg
785                 790                 795                 800

Asp Lys Phe Asn Glu Ser Leu Gln Val Asn Thr Thr Ala Leu Ile Pro
                805                 810                 815

Lys Glu Ala Asn Ser Glu Glu Val Phe Leu Phe Lys Pro Glu Asn Ile
            820                 825                 830

Thr Phe Glu Asn Gly Thr Asp Leu Phe Ile Ala Ile Gln Ala Val Asp
        835                 840                 845

Lys Val Asp Leu Lys Ser Glu Ile Ser Asn Ile Ala Arg Val Ser Leu
    850                 855                 860

Phe Ile Pro Pro Gln Thr Pro Pro Glu Thr Pro Ser Pro Asp Glu Thr
865                 870                 875                 880

Ser Ala Pro Cys Pro Asn Ile His Ile Asn Ser Thr Ile Pro Gly Ile
                885                 890                 895

His Ile Leu Lys Ile Met Trp Lys Trp Ile Gly Glu Leu Gln Leu Ser
            900                 905                 910

Ile Ala


<210> SEQ ID NO 28
<211> LENGTH: 1253
<212> TYPE: PRT
<213> ORGANISM: Artificial Sequence
<220> FEATURE:
<223> OTHER INFORMATION: Synthetic

<400> SEQUENCE: 28

Met Ala Ala Gln Val Thr Leu Glu Asp Ala Leu Ser Asn Val Asp Leu
1               5                   10                  15

Leu Glu Glu Leu Pro Leu Pro Asp Gln Gln Pro Cys Ile Glu Pro Pro
            20                  25                  30
```

```
Pro Ser Ser Leu Leu Tyr Gln Pro Asn Phe Asn Thr Asn Phe Glu Asp
        35                  40                  45

Arg Asn Ala Phe Val Thr Gly Ile Ala Arg Tyr Ile Glu Gln Ala Thr
    50                  55                  60

Val His Ser Ser Met Asn Glu Met Leu Glu Glu Gly Gln Glu Tyr Ala
65                  70                  75                  80

Val Met Leu Tyr Thr Trp Arg Ser Cys Ser Arg Ala Ile Pro Gln Val
                85                  90                  95

Lys Cys Asn Glu Gln Pro Asn Arg Val Glu Ile Tyr Glu Lys Thr Val
            100                 105                 110

Glu Val Leu Glu Pro Glu Val Thr Lys Leu Met Asn Phe Met Tyr Phe
        115                 120                 125

Gln Arg Asn Ala Ile Glu Arg Phe Cys Gly Glu Val Arg Arg Leu Cys
    130                 135                 140

His Ala Glu Arg Arg Lys Asp Phe Val Ser Glu Ala Tyr Leu Ile Thr
145                 150                 155                 160

Leu Gly Lys Phe Ile Asn Met Phe Ala Val Leu Asp Glu Leu Lys Asn
                165                 170                 175

Met Lys Cys Ser Val Lys Asn Asp His Ser Ala Tyr Lys Arg Ala Ala
            180                 185                 190

Gln Phe Leu Arg Lys Met Ala Asp Pro Gln Ser Ile Gln Glu Ser Gln
        195                 200                 205

Asn Leu Ser Met Phe Leu Ala Asn His Asn Lys Ile Thr Gln Ser Leu
    210                 215                 220

Gln Gln Gln Leu Glu Val Ile Ser Gly Tyr Glu Glu Leu Leu Ala Asp
225                 230                 235                 240

Ile Val Asn Leu Cys Val Asp Tyr Tyr Glu Asn Arg Met Tyr Leu Thr
                245                 250                 255

Pro Ser Glu Lys His Met Leu Leu Lys Val Met Gly Phe Gly Leu Tyr
            260                 265                 270

Leu Met Asp Gly Ser Val Ser Asn Ile Tyr Lys Leu Asp Ala Lys Lys
        275                 280                 285

Arg Ile Asn Leu Ser Lys Ile Asp Lys Tyr Phe Lys Gln Leu Gln Val
    290                 295                 300

Val Pro Leu Phe Gly Asp Met Gln Ile Glu Leu Ala Arg Tyr Ile Lys
305                 310                 315                 320

Thr Ser Ala His Tyr Glu Glu Asn Lys Ser Arg Trp Thr Cys Thr Ser
                325                 330                 335

Ser Gly Ser Ser Pro Gln Tyr Asn Ile Cys Glu Gln Met Ile Gln Ile
            340                 345                 350

Arg Glu Asp His Met Arg Phe Ile Ser Glu Leu Ala Arg Tyr Ser Asn
        355                 360                 365

Ser Glu Val Val Thr Gly Ser Gly Arg Gln Glu Ala Gln Lys Thr Asp
    370                 375                 380

Ala Glu Tyr Arg Lys Leu Phe Asp Leu Ala Leu Gln Gly Leu Gln Leu
385                 390                 395                 400

Leu Ser Gln Trp Ser Ala His Val Met Glu Val Tyr Ser Trp Lys Leu
                405                 410                 415

Val His Pro Thr Asp Lys Tyr Ser Asn Lys Asp Cys Pro Asp Ser Ala
            420                 425                 430

Glu Glu Tyr Glu Arg Ala Thr Arg Tyr Asn Tyr Thr Ser Glu Glu Lys
        435                 440                 445

Phe Ala Leu Val Glu Val Ile Ala Met Ile Lys Gly Leu Gln Val Leu
    450                 455                 460
```

-continued

Met Gly Arg Met Glu Ser Val Phe Asn His Ala Ile Arg His Thr Val
465 470 475 480

Tyr Ala Ala Leu Gln Asp Phe Ser Gln Val Thr Leu Arg Glu Pro Leu
485 490 495

Arg Gln Ala Ile Lys Lys Lys Lys Asn Val Ile Gln Ser Val Leu Gln
500 505 510

Ala Ile Arg Lys Thr Val Cys Asp Trp Glu Thr Gly His Glu Pro Phe
515 520 525

Asn Asp Pro Ala Leu Arg Gly Glu Lys Asp Pro Lys Ser Gly Phe Asp
530 535 540

Ile Lys Val Pro Arg Arg Ala Val Gly Pro Ser Ser Thr Gln Leu Tyr
545 550 555 560

Met Val Arg Thr Met Leu Glu Ser Leu Ile Ala Asp Lys Ser Gly Ser
565 570 575

Lys Lys Thr Leu Arg Ser Ser Leu Glu Gly Pro Thr Ile Leu Asp Ile
580 585 590

Glu Lys Phe His Arg Glu Ser Phe Phe Tyr Thr His Leu Ile Asn Phe
595 600 605

Ser Glu Thr Leu Gln Gln Cys Cys Asp Leu Ser Gln Leu Trp Phe Arg
610 615 620

Glu Phe Phe Leu Glu Leu Thr Met Gly Arg Arg Ile Gln Phe Pro Ile
625 630 635 640

Glu Met Ser Met Pro Trp Ile Leu Thr Asp His Ile Leu Glu Thr Lys
645 650 655

Glu Ala Ser Met Met Glu Tyr Val Leu Tyr Ser Leu Asp Leu Tyr Asn
660 665 670

Asp Ser Ala His Tyr Ala Leu Thr Arg Phe Asn Lys Gln Phe Leu Tyr
675 680 685

Asp Glu Ile Glu Ala Glu Val Asn Leu Cys Phe Asp Gln Phe Val Tyr
690 695 700

Lys Leu Ala Asp Gln Ile Phe Ala Tyr Tyr Lys Val Met Ala Gly Ser
705 710 715 720

Leu Leu Leu Asp Lys Arg Leu Arg Ser Glu Cys Lys Asn Gln Gly Ala
725 730 735

Thr Ile His Leu Pro Pro Ser Asn Arg Tyr Glu Thr Leu Leu Lys Gln
740 745 750

Arg His Val Gln Leu Leu Gly Arg Ser Ile Asp Leu Asn Arg Leu Ile
755 760 765

Thr Gln Arg Val Ser Ala Ala Met Tyr Lys Ser Leu Glu Leu Ala Ile
770 775 780

Gly Arg Phe Glu Ser Glu Asp Leu Thr Ser Ile Val Glu Leu Asp Gly
785 790 795 800

Leu Leu Glu Ile Asn Arg Met Thr His Lys Leu Leu Ser Arg Tyr Leu
805 810 815

Thr Leu Asp Gly Phe Asp Ala Met Phe Arg Glu Ala Asn His Asn Val
820 825 830

Ser Ala Pro Tyr Gly Arg Ile Thr Leu His Val Phe Trp Glu Leu Asn
835 840 845

Tyr Asp Phe Leu Pro Asn Tyr Cys Tyr Asn Gly Ser Thr Asn Arg Phe
850 855 860

Val Arg Thr Val Leu Pro Phe Ser Gln Glu Phe Gln Arg Asp Lys Gln
865 870 875 880

Pro Asn Ala Gln Pro Gln Tyr Leu His Gly Ser Lys Ala Leu Asn Leu

```
                885                 890                 895

Ala Tyr Ser Ser Ile Tyr Gly Ser Tyr Arg Asn Phe Val Gly Pro Pro
            900                 905                 910

His Phe Gln Val Ile Cys Arg Leu Leu Gly Tyr Gln Gly Ile Ala Val
        915                 920                 925

Val Met Glu Glu Leu Leu Lys Val Val Lys Ser Leu Leu Gln Gly Thr
    930                 935                 940

Ile Leu Gln Tyr Val Lys Thr Leu Met Glu Val Met Pro Lys Ile Cys
945                 950                 955                 960

Arg Leu Pro Arg His Glu Tyr Gly Ser Pro Gly Ile Leu Glu Phe Phe
                965                 970                 975

His His Gln Leu Lys Asp Ile Val Glu Tyr Ala Glu Leu Lys Thr Val
            980                 985                 990

Cys Phe Gln Asn Leu Arg Glu Val  Gly Asn Ala Ile Leu  Phe Cys Leu
        995                 1000                1005

Leu Ile  Glu Gln Ser Leu Ser  Leu Glu Glu Val Cys  Asp Leu Leu
    1010                1015                1020

His Ala  Ala Pro Phe Gln Asn  Ile Leu Pro Arg Val  His Val Lys
    1025                1030                1035

Glu Gly  Glu Arg Leu Asp Ala  Lys Met Lys Arg Leu  Glu Ser Lys
    1040                1045                1050

Tyr Ala  Pro Leu His Leu Val  Pro Leu Ile Glu Arg  Leu Gly Thr
    1055                1060                1065

Pro Gln  Gln Ile Ala Ile Ala  Arg Glu Gly Asp Leu  Leu Thr Lys
    1070                1075                1080

Glu Arg  Leu Cys Cys Gly Leu  Ser Met Phe Glu Val  Ile Leu Thr
    1085                1090                1095

Arg Ile  Arg Ser Phe Leu Asp  Asp Pro Ile Trp Arg  Gly Pro Leu
    1100                1105                1110

Pro Ser  Asn Gly Val Met His  Val Asp Glu Cys Val  Glu Phe His
    1115                1120                1125

Arg Leu  Trp Ser Ala Met Gln  Phe Val Tyr Cys Ile  Pro Val Gly
    1130                1135                1140

Thr His  Glu Phe Thr Val Glu  Gln Cys Phe Gly Asp  Gly Leu His
    1145                1150                1155

Trp Ala  Gly Cys Met Ile Ile  Val Leu Leu Gly Gln  Gln Arg Arg
    1160                1165                1170

Phe Ala  Val Leu Asp Phe Cys  Tyr His Leu Leu Lys  Val Gln Lys
    1175                1180                1185

His Asp  Gly Lys Asp Glu Ile  Ile Lys Asn Val Pro  Leu Lys Lys
    1190                1195                1200

Met Val  Glu Arg Ile Arg Lys  Phe Gln Ile Leu Asn  Asp Glu Ile
    1205                1210                1215

Ile Thr  Ile Leu Asp Lys Tyr  Leu Lys Ser Gly Asp  Gly Glu Gly
    1220                1225                1230

Thr Pro  Val Glu His Val Arg  Cys Phe Gln Pro Pro  Ile His Gln
    1235                1240                1245

Ser Leu  Ala Ser Ser
    1250
```

<210> SEQ ID NO 29
<211> LENGTH: 318
<212> TYPE: PRT
<213> ORGANISM: Artificial Sequence
<220> FEATURE:

<223> OTHER INFORMATION: Synthetic

<400> SEQUENCE: 29

```
Met Ala Ala Ala Ala Val Ser Gly Ala Leu Gly Arg Ala Gly Trp Arg
1               5                   10                  15

Leu Leu Gln Leu Arg Cys Leu Pro Val Ala Arg Cys Arg Gln Ala Leu
            20                  25                  30

Val Pro Arg Ala Phe His Ala Ser Ala Val Gly Leu Arg Ser Ser Asp
        35                  40                  45

Glu Gln Lys Gln Gln Pro Pro Asn Ser Phe Ser Gln Gln His Ser Glu
    50                  55                  60

Thr Gln Gly Ala Glu Lys Pro Asp Pro Glu Ser Ser His Ser Pro Pro
65                  70                  75                  80

Arg Tyr Thr Asp Gln Gly Gly Glu Glu Glu Glu Asp Tyr Glu Ser Glu
                85                  90                  95

Glu Gln Leu Gln His Arg Ile Leu Thr Ala Ala Leu Glu Phe Val Pro
            100                 105                 110

Ala His Gly Trp Thr Ala Glu Ala Ile Ala Glu Gly Ala Gln Ser Leu
        115                 120                 125

Gly Leu Ser Ser Ala Ala Ala Ser Met Phe Gly Lys Asp Gly Ser Glu
    130                 135                 140

Leu Ile Leu His Phe Val Thr Gln Cys Asn Thr Arg Leu Thr Arg Val
145                 150                 155                 160

Leu Glu Glu Glu Gln Lys Leu Val Gln Leu Gly Gln Ala Glu Lys Arg
                165                 170                 175

Lys Thr Asp Gln Phe Leu Arg Asp Ala Val Glu Thr Arg Leu Arg Met
            180                 185                 190

Leu Ile Pro Tyr Ile Glu His Trp Pro Arg Ala Leu Ser Ile Leu Met
        195                 200                 205

Leu Pro His Asn Ile Pro Ser Ser Leu Ser Leu Leu Thr Ser Met Val
    210                 215                 220

Asp Asp Met Trp His Tyr Ala Gly Asp Gln Ser Thr Asp Phe Asn Trp
225                 230                 235                 240

Tyr Thr Arg Arg Ala Met Leu Ala Ala Ile Tyr Asn Thr Thr Glu Leu
                245                 250                 255

Val Met Met Gln Asp Ser Ser Pro Asp Phe Glu Asp Thr Trp Arg Phe
            260                 265                 270

Leu Glu Asn Arg Val Asn Asp Ala Met Asn Met Gly His Thr Ala Lys
        275                 280                 285

Gln Val Lys Ser Thr Gly Glu Ala Leu Val Gln Gly Leu Met Gly Ala
    290                 295                 300

Ala Val Thr Leu Lys Asn Leu Thr Gly Leu Asn Gln Arg Arg
305                 310                 315
```

<210> SEQ ID NO 30
<211> LENGTH: 377
<212> TYPE: PRT
<213> ORGANISM: Artificial Sequence
<220> FEATURE:
<223> OTHER INFORMATION: Synthetic

<400> SEQUENCE: 30

```
Met Ala Ala Ala Ala Gln Ser Arg Val Val Arg Val Leu Ser Met Ser
1               5                   10                  15

Arg Ser Ala Ile Thr Ala Ile Ala Thr Ser Val Cys His Gly Pro Pro
            20                  25                  30
```

```
Cys Arg Gln Leu His His Ala Leu Met Pro His Gly Lys Gly Gly Arg
        35                  40                  45

Ser Ser Val Ser Gly Ile Val Ala Thr Val Phe Gly Ala Thr Gly Phe
    50                  55                  60

Leu Gly Arg Tyr Val Val Asn His Leu Gly Arg Met Gly Ser Gln Val
65                  70                  75                  80

Ile Ile Pro Tyr Arg Cys Asp Lys Tyr Asp Ile Met His Leu Arg Pro
                85                  90                  95

Met Gly Asp Leu Gly Gln Leu Leu Phe Leu Glu Trp Asp Ala Arg Asp
            100                 105                 110

Lys Asp Ser Ile Arg Arg Val Val Gln His Ser Asn Val Val Ile Asn
        115                 120                 125

Leu Ile Gly Arg Asp Trp Glu Thr Lys Asn Phe Asp Phe Glu Asp Val
    130                 135                 140

Phe Val Lys Ile Pro Gln Ala Ile Ala Gln Leu Ser Lys Glu Ala Gly
145                 150                 155                 160

Val Glu Lys Phe Ile His Val Ser His Leu Asn Ala Asn Ile Lys Ser
                165                 170                 175

Ser Ser Arg Tyr Leu Arg Asn Lys Ala Val Gly Glu Lys Val Val Arg
            180                 185                 190

Asp Ala Phe Pro Glu Ala Ile Ile Val Lys Pro Ser Asp Ile Phe Gly
        195                 200                 205

Arg Glu Asp Arg Phe Leu Asn Ser Phe Ala Ser Met His Arg Phe Gly
    210                 215                 220

Pro Ile Pro Leu Gly Ser Leu Gly Trp Lys Thr Val Lys Gln Pro Val
225                 230                 235                 240

Tyr Val Val Asp Val Ser Lys Gly Ile Val Asn Ala Val Lys Asp Pro
                245                 250                 255

Asp Ala Asn Gly Lys Ser Phe Ala Phe Val Gly Pro Ser Arg Tyr Leu
            260                 265                 270

Leu Phe His Leu Val Lys Tyr Ile Phe Ala Val Ala His Arg Leu Phe
        275                 280                 285

Leu Pro Phe Pro Leu Pro Leu Phe Ala Tyr Arg Trp Val Ala Arg Val
    290                 295                 300

Phe Glu Ile Ser Pro Phe Glu Pro Trp Ile Thr Arg Asp Lys Val Glu
305                 310                 315                 320

Arg Met His Ile Thr Asp Met Lys Leu Pro His Leu Pro Gly Leu Glu
                325                 330                 335

Asp Leu Gly Ile Gln Ala Thr Pro Leu Glu Leu Lys Ala Ile Glu Val
            340                 345                 350

Leu Arg Arg His Arg Thr Tyr Arg Trp Leu Ser Ala Glu Ile Glu Asp
        355                 360                 365

Val Lys Pro Ala Lys Thr Val Asn Ile
    370                 375
```

<210> SEQ ID NO 31
<211> LENGTH: 539
<212> TYPE: PRT
<213> ORGANISM: Artificial Sequence
<220> FEATURE:
<223> OTHER INFORMATION: Synthetic

<400> SEQUENCE: 31

```
Met Trp Arg Leu Pro Arg Ala Leu Cys Val His Ala Ala Lys Thr Ser
1               5                   10                  15

Lys Leu Ser Gly Pro Trp Ser Arg Pro Ala Ala Phe Met Ser Thr Leu
```

-continued

```
            20                  25                  30

Leu Ile Asn Gln Pro Gln Tyr Ala Trp Leu Lys Glu Leu Gly Leu Arg
        35                  40                  45

Glu Glu Asn Glu Gly Val Tyr Asn Gly Ser Trp Gly Gly Arg Gly Glu
    50                  55                  60

Val Ile Thr Thr Tyr Cys Pro Ala Asn Asn Glu Pro Ile Ala Arg Val
65                  70                  75                  80

Arg Gln Ala Ser Val Ala Asp Tyr Glu Glu Thr Val Lys Lys Ala Arg
                85                  90                  95

Glu Ala Trp Lys Ile Trp Ala Asp Ile Pro Ala Pro Lys Arg Gly Glu
            100                 105                 110

Ile Val Arg Gln Ile Gly Asp Ala Leu Arg Glu Lys Ile Gln Val Leu
        115                 120                 125

Gly Ser Leu Val Ser Leu Glu Met Gly Lys Ile Leu Val Glu Gly Val
    130                 135                 140

Gly Glu Val Gln Glu Tyr Val Asp Ile Cys Asp Tyr Ala Val Gly Leu
145                 150                 155                 160

Ser Arg Met Ile Gly Gly Pro Ile Leu Pro Ser Glu Arg Ser Gly His
                165                 170                 175

Ala Leu Ile Glu Gln Trp Asn Pro Val Gly Leu Val Gly Ile Ile Thr
            180                 185                 190

Ala Phe Asn Phe Pro Val Ala Val Tyr Gly Trp Asn Asn Ala Ile Ala
        195                 200                 205

Met Ile Cys Gly Asn Val Cys Leu Trp Lys Gly Ala Pro Thr Thr Ser
    210                 215                 220

Leu Ile Ser Val Ala Val Thr Lys Ile Ile Ala Lys Val Leu Glu Asp
225                 230                 235                 240

Asn Lys Leu Pro Gly Ala Ile Cys Ser Leu Thr Cys Gly Gly Ala Asp
                245                 250                 255

Ile Gly Thr Ala Met Ala Lys Asp Glu Arg Val Asn Leu Leu Ser Phe
            260                 265                 270

Thr Gly Ser Thr Gln Val Gly Lys Gln Val Gly Leu Met Val Gln Glu
        275                 280                 285

Arg Phe Gly Arg Ser Leu Leu Glu Leu Gly Gly Asn Asn Ala Ile Ile
    290                 295                 300

Ala Phe Glu Asp Ala Asp Leu Ser Leu Val Val Pro Ser Ala Leu Phe
305                 310                 315                 320

Ala Ala Val Gly Thr Ala Gly Gln Arg Cys Thr Thr Ala Arg Arg Leu
                325                 330                 335

Phe Ile His Glu Ser Ile His Asp Glu Val Val Asn Arg Leu Lys Lys
            340                 345                 350

Ala Tyr Ala Gln Ile Arg Val Gly Asn Pro Trp Asp Pro Asn Val Leu
        355                 360                 365

Tyr Gly Pro Leu His Thr Lys Gln Ala Val Ser Met Phe Leu Gly Ala
    370                 375                 380

Val Glu Glu Ala Lys Lys Glu Gly Gly Thr Val Val Tyr Gly Gly Lys
385                 390                 395                 400

Val Met Asp Arg Pro Gly Asn Tyr Val Glu Pro Thr Ile Val Thr Gly
                405                 410                 415

Leu Gly His Asp Ala Ser Ile Ala His Thr Glu Thr Phe Ala Pro Ile
            420                 425                 430

Leu Tyr Val Phe Lys Phe Lys Asn Glu Glu Glu Val Phe Ala Trp Asn
        435                 440                 445
```

```
Asn Glu Val Lys Gln Gly Leu Ser Ser Ser Ile Phe Thr Lys Asp Leu
    450                 455                 460

Gly Arg Ile Phe Arg Trp Leu Gly Pro Lys Gly Ser Asp Cys Gly Ile
465                 470                 475                 480

Val Asn Val Asn Ile Pro Thr Ser Gly Ala Glu Ile Gly Gly Ala Phe
                485                 490                 495

Gly Gly Glu Lys His Thr Gly Gly Gly Arg Glu Ser Gly Ser Asp Ala
            500                 505                 510

Trp Lys Gln Tyr Met Arg Arg Ser Thr Cys Thr Ile Asn Tyr Ser Lys
        515                 520                 525

Asp Leu Pro Leu Ala Gln Gly Ile Lys Phe Gln
    530                 535


<210> SEQ ID NO 32
<211> LENGTH: 520
<212> TYPE: PRT
<213> ORGANISM: Artificial Sequence
<220> FEATURE:
<223> OTHER INFORMATION: Synthetic

<400> SEQUENCE: 32

Met Pro Gly Ser Leu Pro Leu Asn Ala Glu Ala Cys Trp Pro Lys Asp
1               5                   10                  15

Val Gly Ile Val Ala Leu Glu Ile Tyr Phe Pro Ser Gln Tyr Val Asp
            20                  25                  30

Gln Ala Glu Leu Glu Lys Tyr Asp Gly Val Asp Ala Gly Lys Tyr Thr
        35                  40                  45

Ile Gly Leu Gly Gln Ala Lys Met Gly Phe Cys Thr Asp Arg Glu Asp
    50                  55                  60

Ile Asn Ser Leu Cys Met Thr Val Val Gln Asn Leu Met Glu Arg Asn
65                  70                  75                  80

Asn Leu Ser Tyr Asp Cys Ile Gly Arg Leu Glu Val Gly Thr Glu Thr
                85                  90                  95

Ile Ile Asp Lys Ser Lys Ser Val Lys Thr Asn Leu Met Gln Leu Phe
            100                 105                 110

Glu Glu Ser Gly Asn Thr Asp Ile Glu Gly Ile Asp Thr Thr Asn Ala
        115                 120                 125

Cys Tyr Gly Gly Thr Ala Ala Val Phe Asn Ala Val Asn Trp Ile Glu
    130                 135                 140

Ser Ser Ser Trp Asp Gly Arg Tyr Ala Leu Val Val Ala Gly Asp Ile
145                 150                 155                 160

Ala Val Tyr Ala Thr Gly Asn Ala Arg Pro Thr Gly Gly Val Gly Ala
                165                 170                 175

Val Ala Leu Leu Ile Gly Pro Asn Ala Pro Leu Ile Phe Glu Arg Gly
            180                 185                 190

Leu Arg Gly Thr His Met Gln His Ala Tyr Asp Phe Tyr Lys Pro Asp
        195                 200                 205

Met Leu Ser Glu Tyr Pro Ile Val Asp Gly Lys Leu Ser Ile Gln Cys
    210                 215                 220

Tyr Leu Ser Ala Leu Asp Arg Cys Tyr Ser Val Tyr Cys Lys Lys Ile
225                 230                 235                 240

His Ala Gln Trp Gln Lys Glu Gly Asn Asp Lys Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Leu Leu Asn Asp Phe Leu Asn Asp Gln Asn
```

```
        275                 280                 285

Arg Asp Lys Asn Ser Ile Tyr Ser Gly Leu Glu Ala Phe Gly Asp Val
    290                 295                 300

Lys Leu Glu Asp Thr Tyr Phe Asp Arg Asp Val Glu Lys Ala Phe Met
305                 310                 315                 320

Lys Ala Ser Ser Glu Leu Phe Ser Gln Lys Thr Lys Ala Ser Leu Leu
                325                 330                 335

Val Ser Asn Gln Asn Gly Asn Met Tyr Thr Ser Ser Val Tyr Gly Ser
            340                 345                 350

Leu Ala Ser Val Leu Ala Gln Tyr Ser Pro Gln Gln Leu Ala Gly Lys
        355                 360                 365

Arg Ile Gly Val Phe Ser Tyr Gly Ser Gly Leu Ala Ala Thr Leu Tyr
    370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Gly Val Ala Pro Asp Val Phe Ala Glu Asn Met Lys Leu Arg Glu Asp
            420                 425                 430

Thr His His Leu Val Asn Tyr Ile Pro Gln Gly Ser Ile Asp Ser Leu
        435                 440                 445

Phe Glu Gly Thr Trp Tyr Leu Val Arg Val Asp Glu Lys His Arg Arg
    450                 455                 460

Thr Tyr Ala Arg Arg Pro Thr Pro Asn Asp Asp Thr Leu Asp Glu Gly
465                 470                 475                 480

Val Gly Leu Val His Ser Asn Ile Ala Thr Glu His Ile Pro Ser Pro
                485                 490                 495

Ala Lys Lys Val Pro Arg Leu Pro Ala Thr Ala Ala Glu Pro Glu Ala
            500                 505                 510

Ala Val Ile Ser Asn Gly Glu His
        515                 520


<210> SEQ ID NO 33
<211> LENGTH: 1086
<212> TYPE: PRT
<213> ORGANISM: Artificial Sequence
<220> FEATURE:
<223> OTHER INFORMATION: Synthetic

<400> SEQUENCE: 33

Met Ala Asn Leu Leu Lys Thr Val Val Thr Gly Cys Ser Cys Pro Leu
1               5                   10                  15

Leu Ser Asn Leu Gly Ser Cys Lys Gly Leu Arg Val Lys Lys Asp Phe
            20                  25                  30

Leu Arg Thr Phe Tyr Thr His Gln Glu Leu Trp Cys Lys Ala Pro Val
        35                  40                  45

Lys Pro Gly Ile Pro Tyr Lys Gln Leu Thr Val Gly Val Pro Lys Glu
    50                  55                  60

Ile Phe Gln Asn Glu Lys Arg Val Ala Leu Ser Pro Ala Gly Val Gln
65                  70                  75                  80

Asn Leu Val Lys Gln Gly Phe Asn Val Val Val Glu Ser Gly Ala Gly
                85                  90                  95

Glu Ala Ser Lys Phe Ser Asp Asp His Tyr Arg Val Ala Gly Ala Gln
            100                 105                 110

Ile Gln Gly Ala Lys Glu Val Leu Ala Ser Asp Leu Val Val Lys Val
        115                 120                 125
```

```
Arg Ala Pro Met Val Asn Pro Thr Leu Gly Val His Glu Ala Asp Leu
    130                 135                 140

Leu Lys Thr Ser Gly Thr Leu Ile Ser Phe Ile Tyr Pro Ala Gln Asn
145                 150                 155                 160

Pro Glu Leu Leu Asn Lys Leu Ser Gln Arg Lys Thr Thr Val Leu Ala
                165                 170                 175

Met Asp Gln Val Pro Arg Val Thr Ile Ala Gln Gly Tyr Asp Ala Leu
            180                 185                 190

Ser Ser Met Ala Asn Ile Ala Gly Tyr Lys Ala Val Val Leu Ala Ala
        195                 200                 205

Asn His Phe Gly Arg Phe Phe Thr Gly Gln Ile Thr Ala Ala Gly Lys
    210                 215                 220

Val Pro Pro Ala Lys Ile Leu Ile Val Gly Gly Gly Val Ala Gly Leu
225                 230                 235                 240

Ala Ser Ala Gly Ala Ala Lys Ser Met Gly Ala Ile Val Arg Gly Phe
                245                 250                 255

Asp Thr Arg Ala Ala Ala Leu Glu Gln Phe Lys Ser Leu Gly Ala Glu
            260                 265                 270

Pro Leu Glu Val Asp Leu Lys Glu Ser Gly Glu Gly Gln Gly Gly Tyr
        275                 280                 285

Ala Lys Glu Met Ser Lys Glu Phe Ile Glu Ala Glu Met Lys Leu Phe
    290                 295                 300

Ala Gln Gln Cys Lys Glu Val Asp Ile Leu Ile Ser Thr Ala Leu Ile
305                 310                 315                 320

Pro Gly Lys Lys Ala Pro Val Leu Phe Asn Lys Glu Met Ile Glu Ser
                325                 330                 335

Met Lys Glu Gly Ser Val Val Val Asp Leu Ala Ala Glu Ala Gly Gly
            340                 345                 350

Asn Phe Glu Thr Thr Lys Pro Gly Glu Leu Tyr Ile His Lys Gly Ile
        355                 360                 365

Thr His Ile Gly Tyr Thr Asp Leu Pro Ser Arg Met Ala Thr Gln Ala
    370                 375                 380

Ser Thr Leu Tyr Ser Asn Asn Ile Thr Lys Leu Leu Lys Ala Ile Ser
385                 390                 395                 400

Pro Asp Lys Asp Asn Phe Tyr Phe Asp Val Lys Asp Asp Phe Asp Phe
                405                 410                 415

Gly Thr Met Gly His Val Ile Arg Gly Thr Val Val Met Lys Asp Gly
            420                 425                 430

Lys Val Ile Phe Pro Ala Pro Thr Pro Lys Asn Ile Pro Gln Gly Ala
        435                 440                 445

Pro Val Lys Gln Lys Thr Val Ala Glu Leu Glu Ala Glu Lys Ala Ala
    450                 455                 460

Thr Ile Thr Pro Phe Arg Lys Thr Met Ser Thr Ala Ser Ala Tyr Thr
465                 470                 475                 480

Ala Gly Leu Thr Gly Ile Leu Gly Leu Gly Ile Ala Ala Pro Asn Leu
                485                 490                 495

Ala Phe Ser Gln Met Val Thr Thr Phe Gly Leu Ala Gly Ile Val Gly
            500                 505                 510

Tyr His Thr Val Trp Gly Val Thr Pro Ala Leu His Ser Pro Leu Met
        515                 520                 525

Ser Val Thr Asn Ala Ile Ser Gly Leu Thr Ala Val Gly Gly Leu Ala
    530                 535                 540

Leu Met Gly Gly His Leu Tyr Pro Ser Thr Thr Ser Gln Gly Leu Ala
```

-continued 545 550 555 560

Ala Leu Ala Ala Phe Ile Ser Ser Val Asn Ile Ala Gly Gly Phe Leu
565 570 575

Val Thr Gln Arg Met Leu Asp Met Phe Lys Arg Pro Thr Asp Pro Pro
580 585 590

Glu Tyr Asn Tyr Leu Tyr Leu Leu Pro Ala Gly Thr Phe Val Gly Gly
595 600 605

Tyr Leu Ala Ala Leu Tyr Ser Gly Tyr Asn Ile Glu Gln Ile Met Tyr
610 615 620

Leu Gly Ser Gly Leu Cys Cys Val Gly Ala Leu Ala Gly Leu Ser Thr
625 630 635 640

Gln Gly Thr Ala Arg Leu Gly Asn Ala Leu Gly Met Ile Gly Val Ala
645 650 655

Gly Gly Leu Ala Ala Thr Leu Gly Val Leu Lys Pro Gly Pro Glu Leu
660 665 670

Leu Ala Gln Met Ser Gly Ala Met Ala Leu Gly Gly Thr Ile Gly Leu
675 680 685

Thr Ile Ala Lys Arg Ile Gln Ile Ser Asp Leu Pro Gln Leu Val Ala
690 695 700

Ala Phe His Ser Leu Val Gly Leu Ala Ala Val Leu Thr Cys Ile Ala
705 710 715 720

Glu Tyr Ile Ile Glu Tyr Pro His Phe Ala Thr Asp Ala Ala Ala Asn
725 730 735

Leu Thr Lys Ile Val Ala Tyr Leu Gly Thr Tyr Ile Gly Gly Val Thr
740 745 750

Phe Ser Gly Ser Leu Ile Ala Tyr Gly Lys Leu Gln Gly Leu Leu Lys
755 760 765

Ser Ala Pro Leu Leu Leu Pro Gly Arg His Leu Leu Asn Ala Gly Leu
770 775 780

Leu Ala Ala Ser Val Gly Gly Ile Ile Pro Phe Met Val Asp Pro Ser
785 790 795 800

Phe Thr Thr Gly Ile Thr Cys Leu Gly Ser Val Ser Ala Leu Ser Ala
805 810 815

Val Met Gly Val Thr Leu Thr Ala Ala Ile Gly Gly Ala Asp Met Pro
820 825 830

Val Val Ile Thr Val Leu Asn Ser Tyr Ser Gly Trp Ala Leu Cys Ala
835 840 845

Glu Gly Phe Leu Leu Asn Asn Asn Leu Leu Thr Ile Val Gly Ala Leu
850 855 860

Ile Gly Ser Ser Gly Ala Ile Leu Ser Tyr Ile Met Cys Val Ala Met
865 870 875 880

Asn Arg Ser Leu Ala Asn Val Ile Leu Gly Gly Tyr Gly Thr Thr Ser
885 890 895

Thr Ala Gly Gly Lys Pro Met Glu Ile Ser Gly Thr His Thr Glu Ile
900 905 910

Asn Leu Asp Asn Ala Ile Asp Met Ile Arg Glu Ala Asn Ser Ile Ile
915 920 925

Ile Thr Pro Gly Tyr Gly Leu Cys Ala Ala Lys Ala Gln Tyr Pro Ile
930 935 940

Ala Asp Leu Val Lys Met Leu Thr Glu Gln Gly Lys Lys Val Arg Phe
945 950 955 960

Gly Ile His Pro Val Ala Gly Arg Met Pro Gly Gln Leu Asn Val Leu
965 970 975

```
Leu Ala Glu Ala Gly Val Pro Tyr Asp Ile Val Leu Glu Met Asp Glu
            980                 985                 990

Ile Asn His Asp Phe Pro Asp Thr  Asp Leu Val Leu Val  Ile Gly Ala
        995                 1000                 1005

Asn Asp  Thr Val Asn Ser Ala  Ala Gln Glu Asp Pro  Asn Ser Ile
    1010                 1015                 1020

Ile Ala  Gly Met Pro Val Leu  Glu Val Trp Lys Ser  Lys Gln Val
    1025                 1030                 1035

Ile Val  Met Lys Arg Ser Leu  Gly Val Gly Tyr Ala  Ala Val Asp
    1040                 1045                 1050

Asn Pro  Ile Phe Tyr Lys Pro  Asn Thr Ala Met Leu  Leu Gly Asp
    1055                 1060                 1065

Ala Lys  Lys Thr Cys Asp Ala  Leu Gln Ala Lys Val  Arg Glu Ser
    1070                 1075                 1080

Tyr Gln  Lys
    1085


<210> SEQ ID NO 34
<211> LENGTH: 214
<212> TYPE: PRT
<213> ORGANISM: Artificial Sequence
<220> FEATURE:
<223> OTHER INFORMATION: Synthetic

<400> SEQUENCE: 34

Met Gly Leu Ala Gly Val Cys Ala Leu Arg Arg Ser Ala Gly Tyr Ile
1               5                   10                  15

Leu Val Gly Gly Ala Gly Gly Gln Ser Ala Ala Ala Ala Ala Arg Arg
            20                  25                  30

Cys Ser Glu Gly Glu Trp Ala Ser Gly Gly Val Arg Ser Phe Ser Arg
        35                  40                  45

Ala Ala Ala Ala Met Ala Pro Ile Lys Val Gly Asp Ala Ile Pro Ala
    50                  55                  60

Val Glu Val Phe Glu Gly Glu Pro Gly Asn Lys Val Asn Leu Ala Glu
65                  70                  75                  80

Leu Phe Lys Gly Lys Lys Gly Val Leu Phe Gly Val Pro Gly Ala Phe
                85                  90                  95

Thr Pro Gly Cys Ser Lys Thr His Leu Pro Gly Phe Val Glu Gln Ala
            100                 105                 110

Glu Ala Leu Lys Ala Lys Gly Val Gln Val Val Ala Cys Leu Ser Val
        115                 120                 125

Asn Asp Ala Phe Val Thr Gly Glu Trp Gly Arg Ala His Lys Ala Glu
    130                 135                 140

Gly Lys Val Arg Leu Leu Ala Asp Pro Thr Gly Ala Phe Gly Lys Glu
145                 150                 155                 160

Thr Asp Leu Leu Leu Asp Asp Ser Leu Val Ser Ile Phe Gly Asn Arg
                165                 170                 175

Arg Leu Lys Arg Phe Ser Met Val Val Gln Asp Gly Ile Val Lys Ala
            180                 185                 190

Leu Asn Val Glu Pro Asp Gly Thr Gly Leu Thr Cys Ser Leu Ala Pro
        195                 200                 205

Asn Ile Ile Ser Gln Leu
    210


<210> SEQ ID NO 35
<211> LENGTH: 539
<212> TYPE: PRT
```

<213> ORGANISM: Artificial Sequence
<220> FEATURE:
<223> OTHER INFORMATION: Synthetic

<400> SEQUENCE: 35

```
Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
    130                 135                 140

Met Asp Gln Ala Ile Thr Val Gly Ala Pro Val Ile Gly Leu Asn Asp
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
            180                 185                 190

Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
    210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                245                 250                 255

Ala His Arg Ala Phe Glu Asn Asp Val Asp Ala Leu Cys Asn Leu Arg
            260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
    290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335

Ala Lys Asn Ile Ile Val Gly Phe Ala Arg Met Asn Gly Arg Thr Val
            340                 345                 350

Gly Ile Val Gly Asn Gln Pro Lys Val Ala Ser Gly Cys Leu Asp Ile
        355                 360                 365

Asn Ser Ser Val Lys Gly Ala Arg Phe Val Arg Phe Cys Asp Ala Phe
    370                 375                 380

Asn Ile Pro Leu Ile Thr Phe Val Asp Val Pro Gly Phe Leu Pro Gly
385                 390                 395                 400
```

```
Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
        435                 440                 445

Gly Asp Thr Asn Tyr Ala Trp Pro Thr Ala Glu Ile Ala Val Met Gly
    450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
        515                 520                 525

Arg Pro Trp Arg Lys His Ala Asn Ile Pro Leu
    530                 535
```

<210> SEQ ID NO 36
<211> LENGTH: 177
<212> TYPE: PRT
<213> ORGANISM: Artificial Sequence
<220> FEATURE:
<223> OTHER INFORMATION: Synthetic

<400> SEQUENCE: 36

```
Met Glu Ala Leu Ile Leu Glu Pro Ser Leu Tyr Thr Val Lys Ala Ile
1               5                   10                  15

Leu Ile Leu Asp Asn Asp Gly Asp Arg Leu Phe Ala Lys Tyr Tyr Asp
            20                  25                  30

Asp Thr Tyr Pro Ser Val Lys Glu Gln Lys Ala Phe Glu Lys Asn Ile
        35                  40                  45

Phe Asn Lys Thr His Arg Thr Asp Ser Glu Ile Ala Leu Leu Glu Gly
    50                  55                  60

Leu Thr Val Val Tyr Lys Ser Ser Ile Asp Leu Tyr Phe Tyr Val Ile
65                  70                  75                  80

Gly Ser Ser Tyr Glu Asn Glu Leu Met Leu Met Ala Val Leu Asn Cys
                85                  90                  95

Leu Phe Asp Ser Leu Ser Gln Met Leu Arg Lys Asn Val Glu Lys Arg
            100                 105                 110

Ala Leu Leu Glu Asn Met Glu Gly Leu Phe Leu Ala Val Asp Glu Ile
        115                 120                 125

Val Asp Gly Gly Val Ile Leu Glu Ser Asp Pro Gln Gln Val Val His
    130                 135                 140

Arg Val Ala Leu Arg Gly Glu Asp Val Pro Leu Thr Glu Gln Thr Val
145                 150                 155                 160

Ser Gln Val Leu Gln Ser Ala Lys Glu Gln Ile Lys Trp Ser Leu Leu
                165                 170                 175

Arg
```

<210> SEQ ID NO 37
<211> LENGTH: 179
<212> TYPE: PRT
<213> ORGANISM: Artificial Sequence
<220> FEATURE:
<223> OTHER INFORMATION: Synthetic

<400> SEQUENCE: 37

Met Asp Gly Ser Gly Glu Gln Pro Arg Gly Gly Gly Pro Thr Ser Ser
1 5 10 15

Glu Gln Ile Met Lys Thr Gly Ala Leu Leu Leu Gln Gly Phe Ile Gln
20 25 30

Asp Arg Ala Gly Arg Met Gly Gly Glu Ala Pro Glu Leu Ala Leu Asp
35 40 45

Pro Val Pro Gln Asp Ala Ser Thr Lys Lys Leu Ser Glu Cys Leu Lys
50 55 60

Arg Ile Gly Asp Glu Leu Asp Ser Asn Met Glu Leu Gln Arg Met Ile
65 70 75 80

Ala Ala Val Asp Thr Asp Ser Pro Arg Glu Val Phe Phe Arg Val Ala
85 90 95

Ala Asp Met Phe Ser Asp Gly Asn Phe Asn Trp Gly Arg Val Val Ala
100 105 110

Leu Phe Tyr Phe Ala Ser Lys Leu Val Leu Lys Ala Leu Cys Thr Lys
115 120 125

Val Pro Glu Leu Ile Arg Thr Ile Met Gly Trp Thr Leu Asp Phe Leu
130 135 140

Arg Glu Arg Leu Leu Gly Trp Ile Gln Asp Gln Gly Gly Trp Thr Val
145 150 155 160

Thr Ile Phe Val Ala Gly Val Leu Thr Ala Ser Leu Thr Ile Trp Lys
165 170 175

Lys Met Gly

<210> SEQ ID NO 38
<211> LENGTH: 621
<212> TYPE: PRT
<213> ORGANISM: Artificial Sequence
<220> FEATURE:
<223> OTHER INFORMATION: Synthetic

<400> SEQUENCE: 38

Met Ser Gly Cys Gly Leu Phe Leu Arg Thr Thr Ala Ala Ala Arg Ala
1 5 10 15

Cys Arg Gly Leu Val Val Ser Thr Ala Asn Arg Arg Leu Leu Arg Thr
20 25 30

Ser Pro Pro Val Arg Ala Phe Ala Lys Glu Leu Phe Leu Gly Lys Ile
35 40 45

Lys Lys Lys Glu Val Phe Pro Phe Pro Glu Val Ser Gln Asp Glu Leu
50 55 60

Asn Glu Ile Asn Gln Phe Leu Gly Pro Val Glu Lys Phe Phe Thr Glu
65 70 75 80

Glu Val Asp Ser Arg Lys Ile Asp Gln Glu Gly Lys Ile Pro Asp Glu
85 90 95

Thr Leu Glu Lys Leu Lys Ser Leu Gly Leu Phe Gly Leu Gln Val Pro
100 105 110

Glu Glu Tyr Gly Gly Leu Gly Phe Ser Asn Thr Met Tyr Ser Arg Leu
115 120 125

Gly Glu Ile Ile Ser Met Asp Gly Ser Ile Thr Val Thr Leu Ala Ala
130 135 140

His Gln Ala Ile Gly Leu Lys Gly Ile Ile Leu Ala Gly Thr Glu Glu
145 150 155 160

Gln Lys Ala Lys Tyr Leu Pro Lys Leu Ala Ser Gly Glu His Ile Ala
165 170 175

```
Ala Phe Cys Leu Thr Glu Pro Ala Ser Gly Ser Asp Ala Ala Ser Ile
            180                 185                 190

Arg Ser Arg Ala Thr Leu Ser Glu Asp Lys Lys His Tyr Ile Leu Asn
        195                 200                 205

Gly Ser Lys Val Trp Ile Thr Asn Gly Gly Leu Ala Asn Ile Phe Thr
    210                 215                 220

Val Phe Ala Lys Thr Glu Val Val Asp Ser Asp Gly Ser Val Lys Asp
225                 230                 235                 240

Lys Ile Thr Ala Phe Ile Val Glu Arg Asp Phe Gly Gly Val Thr Asn
                245                 250                 255

Gly Lys Pro Glu Asp Lys Leu Gly Ile Arg Gly Ser Asn Thr Cys Glu
            260                 265                 270

Val His Phe Glu Asn Thr Lys Ile Pro Val Glu Asn Ile Leu Gly Glu
        275                 280                 285

Val Gly Asp Gly Phe Lys Val Ala Met Asn Ile Leu Asn Ser Gly Arg
    290                 295                 300

Phe Ser Met Gly Ser Val Val Ala Gly Leu Leu Lys Arg Leu Ile Glu
305                 310                 315                 320

Met Thr Ala Glu Tyr Ala Cys Thr Arg Lys Gln Phe Asn Lys Arg Leu
                325                 330                 335

Ser Glu Phe Gly Leu Ile Gln Glu Lys Phe Ala Leu Met Ala Gln Lys
            340                 345                 350

Ala Tyr Val Met Glu Ser Met Thr Tyr Leu Thr Ala Gly Met Leu Asp
        355                 360                 365

Gln Pro Gly Phe Pro Asp Cys Ser Ile Glu Ala Ala Met Val Lys Val
    370                 375                 380

Phe Ser Ser Glu Ala Ala Trp Gln Cys Val Ser Glu Ala Leu Gln Ile
385                 390                 395                 400

Leu Gly Gly Leu Gly Tyr Thr Arg Asp Tyr Pro Tyr Glu Arg Ile Leu
                405                 410                 415

Arg Asp Thr Arg Ile Leu Leu Ile Phe Glu Gly Thr Asn Glu Ile Leu
            420                 425                 430

Arg Met Tyr Ile Ala Leu Thr Gly Leu Gln His Ala Gly Arg Ile Leu
        435                 440                 445

Thr Thr Arg Ile His Glu Leu Lys Gln Ala Lys Val Ser Thr Val Met
    450                 455                 460

Asp Thr Val Gly Arg Arg Leu Arg Asp Ser Leu Gly Arg Thr Val Asp
465                 470                 475                 480

Leu Gly Leu Thr Gly Asn His Gly Val Val His Pro Ser Leu Ala Asp
                485                 490                 495

Ser Ala Asn Lys Phe Glu Glu Asn Thr Tyr Cys Phe Gly Arg Thr Val
            500                 505                 510

Glu Thr Leu Leu Leu Arg Phe Gly Lys Thr Ile Met Glu Glu Gln Leu
        515                 520                 525

Val Leu Lys Arg Val Ala Asn Ile Leu Ile Asn Leu Tyr Gly Met Thr
    530                 535                 540

Ala Val Leu Ser Arg Ala Ser Arg Ser Ile Arg Ile Gly Leu Arg Asn
545                 550                 555                 560

His Asp His Glu Val Leu Leu Ala Asn Thr Phe Cys Val Glu Ala Tyr
                565                 570                 575

Leu Gln Asn Leu Phe Ser Leu Ser Gln Leu Asp Lys Tyr Ala Pro Glu
            580                 585                 590

Asn Leu Asp Glu Gln Ile Lys Lys Val Ser Gln Gln Ile Leu Glu Lys
```

```
        595                 600                 605

Arg Ala Tyr Ile Cys Ala His Pro Leu Asp Arg Thr Cys
    610                 615                 620


<210> SEQ ID NO 39
<211> LENGTH: 445
<212> TYPE: PRT
<213> ORGANISM: Artificial Sequence
<220> FEATURE:
<223> OTHER INFORMATION: Synthetic

<400> SEQUENCE: 39

Met Ala Ala Pro Glu Glu Arg Asp Leu Thr Gln Glu Gln Thr Glu Lys
1               5                   10                  15

Leu Leu Gln Phe Gln Asp Leu Thr Gly Ile Glu Ser Met Asp Gln Cys
            20                  25                  30

Arg His Thr Leu Glu Gln His Asn Trp Asn Ile Glu Ala Ala Val Gln
        35                  40                  45

Asp Arg Leu Asn Glu Gln Glu Gly Val Pro Ser Val Phe Asn Pro Pro
    50                  55                  60

Pro Ser Arg Pro Leu Gln Val Asn Thr Ala Asp His Arg Ile Tyr Ser
65                  70                  75                  80

Tyr Val Val Ser Arg Pro Gln Pro Arg Gly Leu Leu Gly Trp Gly Tyr
                85                  90                  95

Tyr Leu Ile Met Leu Pro Phe Arg Phe Thr Tyr Tyr Thr Ile Leu Asp
            100                 105                 110

Ile Phe Arg Phe Ala Leu Arg Phe Ile Arg Pro Asp Pro Arg Ser Arg
        115                 120                 125

Val Thr Asp Pro Val Gly Asp Ile Val Ser Phe Met His Ser Phe Glu
    130                 135                 140

Glu Lys Tyr Gly Arg Ala His Pro Val Phe Tyr Gln Gly Thr Tyr Ser
145                 150                 155                 160

Gln Ala Leu Asn Asp Ala Lys Arg Glu Leu Arg Phe Leu Leu Val Tyr
                165                 170                 175

Leu His Gly Asp Asp His Gln Asp Ser Asp Glu Phe Cys Arg Asn Thr
            180                 185                 190

Leu Cys Ala Pro Glu Val Ile Ser Leu Ile Asn Thr Arg Met Leu Phe
        195                 200                 205

Trp Ala Cys Ser Thr Asn Lys Pro Glu Gly Tyr Arg Val Ser Gln Ala
    210                 215                 220

Leu Arg Glu Asn Thr Tyr Pro Phe Leu Ala Met Ile Met Leu Lys Asp
225                 230                 235                 240

Arg Arg Met Thr Val Val Gly Arg Leu Glu Gly Leu Ile Gln Pro Asp
                245                 250                 255

Asp Leu Ile Asn Gln Leu Thr Phe Ile Met Asp Ala Asn Gln Thr Tyr
            260                 265                 270

Leu Val Ser Glu Arg Leu Glu Arg Glu Glu Arg Asn Gln Thr Gln Val
        275                 280                 285

Leu Arg Gln Gln Gln Asp Glu Ala Tyr Leu Ala Ser Leu Arg Ala Asp
    290                 295                 300

Gln Glu Lys Glu Arg Lys Lys Arg Glu Glu Arg Glu Arg Lys Arg Arg
305                 310                 315                 320

Lys Glu Glu Glu Val Gln Gln Gln Lys Leu Ala Glu Glu Arg Arg Arg
                325                 330                 335

Gln Asn Leu Gln Glu Glu Lys Glu Arg Lys Leu Glu Cys Leu Pro Pro
            340                 345                 350
```

Glu Pro Ser Pro Asp Asp Pro Glu Ser Val Lys Ile Ile Phe Lys Leu
355 360 365

Pro Asn Asp Ser Arg Val Glu Arg Arg Phe His Phe Ser Gln Ser Leu
370 375 380

Thr Val Ile His Asp Phe Leu Phe Ser Leu Lys Glu Ser Pro Glu Lys
385 390 395 400

Phe Gln Ile Glu Ala Asn Phe Pro Arg Arg Val Leu Pro Cys Ile Pro
405 410 415

Ser Glu Glu Trp Pro Asn Pro Pro Thr Leu Gln Glu Ala Gly Leu Ser
420 425 430

His Thr Glu Val Leu Phe Val Gln Asp Leu Thr Asp Glu
435 440 445

<210> SEQ ID NO 40
<211> LENGTH: 508
<212> TYPE: PRT
<213> ORGANISM: Artificial Sequence
<220> FEATURE:
<223> OTHER INFORMATION: Synthetic

<400> SEQUENCE: 40

Met Gln Arg Leu Leu Thr Pro Val Lys Arg Ile Leu Gln Leu Thr Arg
1 5 10 15

Ala Val Gln Glu Thr Ser Leu Thr Pro Ala Arg Leu Leu Pro Val Ala
20 25 30

His Gln Arg Phe Ser Thr Ala Ser Ala Val Pro Leu Ala Lys Thr Asp
35 40 45

Thr Trp Pro Lys Asp Val Gly Ile Leu Ala Leu Glu Val Tyr Phe Pro
50 55 60

Ala Gln Tyr Val Asp Gln Thr Asp Leu Glu Lys Tyr Asn Asn Val Glu
65 70 75 80

Ala Gly Lys Tyr Thr Val Gly Leu Gly Gln Thr Arg Met Gly Phe Cys
85 90 95

Ser Val Gln Glu Asp Ile Asn Ser Leu Cys Leu Thr Val Val Gln Arg
100 105 110

Leu Met Glu Arg Ile Gln Leu Pro Trp Asp Ser Val Gly Arg Leu Glu
115 120 125

Val Gly Thr Glu Thr Ile Ile Asp Lys Ser Lys Ala Val Lys Thr Val
130 135 140

Leu Met Glu Leu Phe Gln Asp Ser Gly Asn Thr Asp Ile Glu Gly Ile
145 150 155 160

Asp Thr Thr Asn Ala Cys Tyr Gly Gly Thr Ala Ser Leu Phe Asn Ala
165 170 175

Ala Asn Trp Met Glu Ser Ser Ser Trp Asp Gly Arg Tyr Ala Met Val
180 185 190

Val Cys Gly Asp Ile Ala Val Tyr Pro Ser Gly Asn Ala Arg Pro Thr
195 200 205

Gly Gly Ala Gly Ala Val Ala Met Leu Ile Gly Pro Lys Ala Pro Leu
210 215 220

Ala Leu Glu Arg Gly Leu Arg Gly Thr His Met Glu Asn Val Tyr Asp
225 230 235 240

Phe Tyr Lys Pro Asn Leu Ala Ser Glu Tyr Pro Ile Val Asp Gly Lys
245 250 255

Leu Ser Ile Gln Cys Tyr Leu Arg Ala Leu Asp Arg Cys Tyr Thr Ser
260 265 270

```
Tyr Arg Lys Lys Ile Gln Asn Gln Trp Lys Gln Ala Gly Ser Asp Arg
        275                 280                 285

Pro Phe Thr Leu Asp Asp Leu Gln Tyr Met Ile Phe His Thr Pro Phe
    290                 295                 300

Cys Lys Met Val Gln Lys Ser Leu Ala Arg Leu Met Phe Asn Asp Phe
305                 310                 315                 320

Leu Ser Ala Ser Ser Asp Thr Gln Thr Ser Leu Tyr Lys Gly Leu Glu
                325                 330                 335

Ala Phe Gly Gly Leu Lys Leu Glu Asp Thr Tyr Thr Asn Lys Asp Leu
            340                 345                 350

Asp Lys Ala Leu Leu Lys Ala Ser Gln Asp Met Phe Asp Lys Lys Thr
        355                 360                 365

Lys Ala Ser Leu Tyr Leu Ser Thr His Asn Gly Asn Met Tyr Thr Ser
    370                 375                 380

Ser Leu Tyr Gly Cys Leu Ala Ser Leu Leu Ser His His Ser Ala Gln
385                 390                 395                 400

Glu Leu Ala Gly Ser Arg Ile Gly Ala Phe Ser Tyr Gly Ser Gly Leu
                405                 410                 415

Ala Ala Ser Phe Phe Ser Phe Arg Val Ser Gln Asp Ala Ala Pro Gly
            420                 425                 430

Ser Pro Leu Asp Lys Leu Val Ser Ser Thr Ser Asp Leu Pro Lys Arg
        435                 440                 445

Leu Ala Ser Arg Lys Cys Val Ser Pro Glu Glu Phe Thr Glu Ile Met
    450                 455                 460

Asn Gln Arg Glu Gln Phe Tyr His Lys Val Asn Phe Ser Pro Pro Gly
465                 470                 475                 480

Asp Thr Asn Ser Leu Phe Pro Gly Thr Trp Tyr Leu Glu Arg Val Asp
                485                 490                 495

Glu Gln His Arg Arg Lys Tyr Ala Arg Arg Pro Val
            500                 505
```

<210> SEQ ID NO 41
<211> LENGTH: 361
<212> TYPE: PRT
<213> ORGANISM: Artificial Sequence
<220> FEATURE:
<223> OTHER INFORMATION: Synthetic

<400> SEQUENCE: 41

```
Met Phe Ser Ser Val Ala His Leu Ala Arg Ala Asn Pro Phe Asn Thr
1               5                   10                  15

Pro His Leu Gln Leu Val His Asp Gly Leu Gly Asp Leu Arg Ser Ser
            20                  25                  30

Ser Pro Gly Pro Thr Gly Gln Pro Arg Arg Pro Arg Asn Leu Ala Ala
        35                  40                  45

Ala Ala Val Glu Glu Tyr Ser Cys Glu Phe Gly Ser Ala Lys Tyr Tyr
    50                  55                  60

Ala Leu Cys Gly Phe Gly Gly Val Leu Ser Cys Gly Leu Thr His Thr
65                  70                  75                  80

Ala Val Val Pro Leu Asp Leu Val Lys Cys Arg Met Gln Val Asp Pro
                85                  90                  95

Gln Lys Tyr Lys Gly Ile Phe Asn Gly Phe Ser Val Thr Leu Lys Glu
            100                 105                 110

Asp Gly Val Arg Gly Leu Ala Lys Gly Trp Ala Pro Thr Phe Leu Gly
        115                 120                 125

Tyr Ser Met Gln Gly Leu Cys Lys Phe Gly Phe Tyr Glu Val Phe Lys
```

130 135 140

Val Leu Tyr Ser Asn Met Leu Gly Glu Glu Asn Thr Tyr Leu Trp Arg
145 150 155 160

Thr Ser Leu Tyr Leu Ala Ala Ser Ala Ser Ala Glu Phe Phe Ala Asp
165 170 175

Ile Ala Leu Ala Pro Met Glu Ala Ala Lys Val Arg Ile Gln Thr Gln
180 185 190

Pro Gly Tyr Ala Asn Thr Leu Arg Asp Ala Ala Pro Lys Met Tyr Lys
195 200 205

Glu Glu Gly Leu Lys Ala Phe Tyr Lys Gly Val Ala Pro Leu Trp Met
210 215 220

Arg Gln Ile Pro Tyr Thr Met Met Lys Phe Ala Cys Phe Glu Arg Thr
225 230 235 240

Val Glu Ala Leu Tyr Lys Phe Val Val Pro Lys Pro Arg Ser Glu Cys
245 250 255

Ser Lys Pro Glu Gln Leu Val Val Thr Phe Val Ala Gly Tyr Ile Ala
260 265 270

Gly Val Phe Cys Ala Ile Val Ser His Pro Ala Asp Ser Val Val Ser
275 280 285

Val Leu Asn Lys Glu Lys Gly Ser Ser Ala Ser Leu Val Leu Lys Arg
290 295 300

Leu Gly Phe Lys Gly Val Trp Lys Gly Leu Phe Ala Arg Ser Ile Met
305 310 315 320

Ile Gly Thr Leu Thr Ala Leu Gln Trp Phe Ile Tyr Asp Ser Val Lys
325 330 335

Val Tyr Phe Arg Leu Pro Arg Pro Pro Pro Pro Glu Met Pro Glu Ser
340 345 350

Leu Lys Lys Lys Leu Gly Leu Thr Gln
355 360

<210> SEQ ID NO 42
<211> LENGTH: 314
<212> TYPE: PRT
<213> ORGANISM: Artificial Sequence
<220> FEATURE:
<223> OTHER INFORMATION: Synthetic

<400> SEQUENCE: 42

Met Ala Ala Thr Ala Ser Ala Gly Ala Gly Gly Ile Asp Gly Lys Pro
1 5 10 15

Arg Thr Ser Pro Lys Ser Val Lys Phe Leu Phe Gly Gly Leu Ala Gly
20 25 30

Met Gly Ala Thr Val Phe Val Gln Pro Leu Asp Leu Val Lys Asn Arg
35 40 45

Met Gln Leu Ser Gly Glu Gly Ala Lys Thr Arg Glu Tyr Lys Thr Ser
50 55 60

Phe His Ala Leu Thr Ser Ile Leu Lys Ala Glu Gly Leu Arg Gly Ile
65 70 75 80

Tyr Thr Gly Leu Ser Ala Gly Leu Leu Arg Gln Ala Thr Tyr Thr Thr
85 90 95

Thr Arg Leu Gly Ile Tyr Thr Val Leu Phe Glu Arg Leu Thr Gly Ala
100 105 110

Asp Gly Thr Pro Pro Gly Phe Leu Leu Lys Ala Val Ile Gly Met Thr
115 120 125

Ala Gly Ala Thr Gly Ala Phe Val Gly Thr Pro Ala Glu Val Ala Leu
130 135 140

```
Ile Arg Met Thr Ala Asp Gly Arg Leu Pro Ala Asp Gln Arg Arg Gly
145                 150                 155                 160

Tyr Lys Asn Val Phe Asn Ala Leu Ile Arg Ile Thr Arg Glu Glu Gly
                165                 170                 175

Val Leu Thr Leu Trp Arg Gly Cys Ile Pro Thr Met Ala Arg Ala Val
            180                 185                 190

Val Val Asn Ala Ala Gln Leu Ala Ser Tyr Ser Gln Ser Lys Gln Phe
        195                 200                 205

Leu Leu Asp Ser Gly Tyr Phe Ser Asp Asn Ile Leu Cys His Phe Cys
    210                 215                 220

Ala Ser Met Ile Ser Gly Leu Val Thr Thr Ala Ala Ser Met Pro Val
225                 230                 235                 240

Asp Ile Ala Lys Thr Arg Ile Gln Asn Met Arg Met Ile Asp Gly Lys
                245                 250                 255

Pro Glu Tyr Lys Asn Gly Leu Asp Val Leu Phe Lys Val Val Arg Tyr
            260                 265                 270

Glu Gly Phe Phe Ser Leu Trp Lys Gly Phe Thr Pro Tyr Tyr Ala Arg
        275                 280                 285

Leu Gly Pro His Thr Val Leu Thr Phe Ile Phe Leu Glu Gln Met Asn
    290                 295                 300

Lys Ala Tyr Lys Arg Leu Phe Leu Ser Gly
305                 310
```

<210> SEQ ID NO 43
<211> LENGTH: 191
<212> TYPE: PRT
<213> ORGANISM: Artificial Sequence
<220> FEATURE:
<223> OTHER INFORMATION: Synthetic

<400> SEQUENCE: 43

```
Met Ala Ala Tyr Ser Tyr Arg Pro Gly Pro Gly Ala Gly Pro Gly Pro
1               5                   10                  15

Ala Ala Gly Ala Ala Leu Pro Asp Gln Ser Phe Leu Trp Asn Val Phe
            20                  25                  30

Gln Arg Val Asp Lys Asp Arg Ser Gly Val Ile Ser Asp Thr Glu Leu
        35                  40                  45

Gln Gln Ala Leu Ser Asn Gly Thr Trp Thr Pro Phe Asn Pro Val Thr
    50                  55                  60

Val Arg Ser Ile Ile Ser Met Phe Asp Arg Glu Asn Lys Ala Gly Val
65                  70                  75                  80

Asn Phe Ser Glu Phe Thr Gly Val Trp Lys Tyr Ile Thr Asp Trp Gln
                85                  90                  95

Asn Val Phe Arg Thr Tyr Asp Arg Asp Asn Ser Gly Met Ile Asp Lys
            100                 105                 110

Asn Glu Leu Lys Gln Ala Leu Ser Gly Phe Gly Tyr Arg Leu Ser Asp
        115                 120                 125

Gln Phe His Asp Ile Leu Ile Arg Lys Phe Asp Arg Gln Gly Arg Gly
    130                 135                 140

Gln Ile Ala Phe Asp Asp Phe Ile Gln Gly Cys Ile Val Leu Gln Arg
145                 150                 155                 160

Leu Thr Asp Ile Phe Arg Arg Tyr Asp Thr Asp Gln Asp Gly Trp Ile
                165                 170                 175

Gln Val Ser Tyr Glu Gln Tyr Leu Ser Met Val Phe Ser Ile Val
            180                 185                 190
```

<210> SEQ ID NO 44
<211> LENGTH: 63
<212> TYPE: PRT
<213> ORGANISM: Artificial Sequence
<220> FEATURE:
<223> OTHER INFORMATION: Synthetic

<400> SEQUENCE: 44

```
Met Ala Ala Ala Thr Leu Thr Ser Lys Leu Tyr Ser Leu Leu Phe Arg
1               5                   10                  15

Arg Thr Ser Thr Phe Ala Leu Thr Ile Ile Val Gly Val Met Phe Phe
            20                  25                  30

Glu Arg Ala Phe Asp Gln Gly Ala Asp Ala Ile Tyr Asp His Ile Asn
        35                  40                  45

Glu Gly Lys Leu Trp Lys His Ile Lys His Lys Tyr Glu Asn Lys
    50                  55                  60
```

<210> SEQ ID NO 45
<211> LENGTH: 100
<212> TYPE: PRT
<213> ORGANISM: Artificial Sequence
<220> FEATURE:
<223> OTHER INFORMATION: Synthetic

<400> SEQUENCE: 45

```
Met Arg Thr Leu Thr Ile Leu Thr Ala Val Leu Leu Val Ala Leu Gln
1               5                   10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
        35                  40                  45

Phe Ala Val Ser Phe Ala Glu Asp Ala Ser Ser Ser Leu Arg Ala Leu
    50                  55                  60

Gly Ser Thr Arg Ala Phe Thr Cys His Cys Arg Arg Ser Cys Tyr Ser
65                  70                  75                  80

Thr Glu Tyr Ser Tyr Gly Thr Cys Thr Val Met Gly Ile Asn His Arg
                85                  90                  95

Phe Cys Cys Leu
            100
```

<210> SEQ ID NO 46
<211> LENGTH: 4646
<212> TYPE: PRT
<213> ORGANISM: Artificial Sequence
<220> FEATURE:
<223> OTHER INFORMATION: Synthetic

<400> SEQUENCE: 46

```
Met Ser Glu Pro Gly Gly Gly Gly Gly Glu Asp Gly Ser Ala Gly Leu
1               5                   10                  15

Glu Val Ser Ala Val Gln Asn Val Ala Asp Val Ser Val Leu Gln Lys
            20                  25                  30

His Leu Arg Lys Leu Val Pro Leu Leu Leu Glu Asp Gly Gly Glu Ala
        35                  40                  45

Pro Ala Ala Leu Glu Ala Ala Leu Glu Glu Lys Ser Ala Leu Glu Gln
    50                  55                  60

Met Arg Lys Phe Leu Ser Asp Pro Gln Val His Thr Val Leu Val Glu
65                  70                  75                  80

Arg Ser Thr Leu Lys Glu Asp Val Gly Asp Glu Gly Glu Glu Glu Lys
                85                  90                  95
```

```
Glu Phe Ile Ser Tyr Asn Ile Asn Ile Asp Ile His Tyr Gly Val Lys
            100                 105                 110

Ser Asn Ser Leu Ala Phe Ile Lys Arg Thr Pro Val Ile Asp Ala Asp
        115                 120                 125

Lys Pro Val Ser Ser Gln Leu Arg Val Leu Thr Leu Ser Glu Asp Ser
    130                 135                 140

Pro Tyr Glu Thr Leu His Ser Phe Ile Ser Asn Ala Val Ala Pro Phe
145                 150                 155                 160

Phe Lys Ser Tyr Ile Arg Glu Ser Gly Lys Ala Asp Arg Asp Gly Asp
                165                 170                 175

Lys Met Ala Pro Ser Val Glu Lys Lys Ile Ala Glu Leu Glu Met Gly
            180                 185                 190

Leu Leu His Leu Gln Gln Asn Ile Glu Ile Pro Glu Ile Ser Leu Pro
        195                 200                 205

Ile His Pro Met Ile Thr Asn Val Ala Lys Gln Cys Tyr Glu Arg Gly
    210                 215                 220

Glu Lys Pro Lys Val Thr Asp Phe Gly Asp Lys Val Glu Asp Pro Thr
225                 230                 235                 240

Phe Leu Asn Gln Leu Gln Ser Gly Val Asn Arg Trp Ile Arg Glu Ile
                245                 250                 255

Gln Lys Val Thr Lys Leu Asp Arg Asp Pro Ala Ser Gly Thr Ala Leu
            260                 265                 270

Gln Glu Ile Ser Phe Trp Leu Asn Leu Glu Arg Ala Leu Tyr Arg Ile
        275                 280                 285

Gln Glu Lys Arg Glu Ser Pro Glu Val Leu Leu Thr Leu Asp Ile Leu
    290                 295                 300

Lys His Gly Lys Arg Phe His Ala Thr Val Ser Phe Asp Thr Asp Thr
305                 310                 315                 320

Gly Leu Lys Gln Ala Leu Glu Thr Val Asn Asp Tyr Asn Pro Leu Met
                325                 330                 335

Lys Asp Phe Pro Leu Asn Asp Leu Leu Ser Ala Thr Glu Leu Asp Lys
            340                 345                 350

Ile Arg Gln Ala Leu Val Ala Ile Phe Thr His Leu Arg Lys Ile Arg
        355                 360                 365

Asn Thr Lys Tyr Pro Ile Gln Arg Ala Leu Arg Leu Val Glu Ala Ile
    370                 375                 380

Ser Arg Asp Leu Ser Ser Gln Leu Leu Lys Val Leu Gly Thr Arg Lys
385                 390                 395                 400

Leu Met His Val Ala Tyr Glu Glu Phe Glu Lys Val Met Val Ala Cys
                405                 410                 415

Phe Glu Val Phe Gln Thr Trp Asp Asp Glu Tyr Glu Lys Leu Gln Val
            420                 425                 430

Leu Leu Arg Asp Ile Val Lys Arg Lys Arg Glu Glu Asn Leu Lys Met
        435                 440                 445

Val Trp Arg Ile Asn Pro Ala His Arg Lys Leu Gln Ala Arg Leu Asp
    450                 455                 460

Gln Met Arg Lys Phe Arg Arg Gln His Glu Gln Leu Arg Ala Val Ile
465                 470                 475                 480

Val Arg Val Leu Arg Pro Gln Val Thr Ala Val Ala Gln Gln Asn Gln
                485                 490                 495

Gly Glu Val Pro Glu Pro Gln Asp Met Lys Val Ala Glu Val Leu Phe
            500                 505                 510

Asp Ala Ala Asp Ala Asn Ala Ile Glu Glu Val Asn Leu Ala Tyr Glu
```

```
        515                 520                 525

Asn Val Lys Glu Val Asp Gly Leu Asp Val Ser Lys Glu Gly Thr Glu
    530                 535                 540

Ala Trp Glu Ala Ala Met Lys Arg Tyr Asp Glu Arg Ile Asp Arg Val
545                 550                 555                 560

Glu Thr Arg Ile Thr Ala Arg Leu Arg Asp Gln Leu Gly Thr Ala Lys
                565                 570                 575

Asn Ala Asn Glu Met Phe Arg Ile Phe Ser Arg Phe Asn Ala Leu Phe
            580                 585                 590

Val Arg Pro His Ile Arg Gly Ala Ile Arg Glu Tyr Gln Thr Gln Leu
        595                 600                 605

Ile Gln Arg Val Lys Asp Asp Ile Glu Ser Leu His Asp Lys Phe Lys
    610                 615                 620

Val Gln Tyr Pro Gln Ser Gln Ala Cys Lys Met Ser His Val Arg Asp
625                 630                 635                 640

Leu Pro Pro Val Ser Gly Ser Ile Ile Trp Ala Lys Gln Ile Asp Arg
                645                 650                 655

Gln Leu Thr Ala Tyr Met Lys Arg Val Glu Asp Val Leu Gly Lys Gly
            660                 665                 670

Trp Glu Asn His Val Glu Gly Gln Lys Leu Lys Gln Asp Gly Asp Ser
        675                 680                 685

Phe Arg Met Lys Leu Asn Thr Gln Glu Ile Phe Asp Asp Trp Ala Arg
    690                 695                 700

Lys Val Gln Gln Arg Asn Leu Gly Val Ser Gly Arg Ile Phe Thr Ile
705                 710                 715                 720

Glu Ser Thr Arg Val Arg Gly Arg Thr Gly Asn Val Leu Lys Leu Lys
                725                 730                 735

Val Asn Phe Leu Pro Glu Ile Ile Thr Leu Ser Lys Glu Val Arg Asn
            740                 745                 750

Leu Lys Trp Leu Gly Phe Arg Val Pro Leu Ala Ile Val Asn Lys Ala
        755                 760                 765

His Gln Ala Asn Gln Leu Tyr Pro Phe Ala Ile Ser Leu Ile Glu Ser
    770                 775                 780

Val Arg Thr Tyr Glu Arg Thr Cys Glu Lys Val Glu Glu Arg Asn Thr
785                 790                 795                 800

Ile Ser Leu Leu Val Ala Gly Leu Lys Lys Glu Val Gln Ala Leu Ile
                805                 810                 815

Ala Glu Gly Ile Ala Leu Val Trp Glu Ser Tyr Lys Leu Asp Pro Tyr
            820                 825                 830

Val Gln Arg Leu Ala Glu Thr Val Phe Asn Phe Gln Glu Lys Val Asp
        835                 840                 845

Asp Leu Leu Ile Ile Glu Glu Lys Ile Asp Leu Glu Val Arg Ser Leu
    850                 855                 860

Glu Thr Cys Met Tyr Asp His Lys Thr Phe Ser Glu Ile Leu Asn Arg
865                 870                 875                 880

Val Gln Lys Ala Val Asp Asp Leu Asn Leu His Ser Tyr Ser Asn Leu
                885                 890                 895

Pro Ile Trp Val Asn Lys Leu Asp Met Glu Ile Glu Arg Ile Leu Gly
            900                 905                 910

Val Arg Leu Gln Ala Gly Leu Arg Ala Trp Thr Gln Val Leu Leu Gly
        915                 920                 925

Gln Ala Glu Asp Lys Ala Glu Val Asp Met Asp Thr Asp Ala Pro Gln
    930                 935                 940
```

-continued

```
Val Ser His Lys Pro Gly Gly Glu Pro Lys Ile Lys Asn Val Val His
945                 950                 955                 960

Glu Leu Arg Ile Thr Asn Gln Val Ile Tyr Leu Asn Pro Pro Ile Glu
                965                 970                 975

Glu Cys Arg Tyr Lys Leu Tyr Gln Glu Met Phe Ala Trp Lys Met Val
            980                 985                 990

Val Leu Ser Leu Pro Arg Ile Gln  Ser Gln Arg Tyr Gln  Val Gly Val
        995                 1000                 1005

His Tyr  Glu Leu Thr Glu Glu  Glu Lys Phe Tyr Arg  Asn Ala Leu
    1010                 1015                 1020

Thr Arg  Met Pro Asp Gly Pro  Val Ala Leu Glu Glu  Ser Tyr Ser
    1025                 1030                 1035

Ala Val  Met Gly Ile Val Ser  Glu Val Glu Gln Tyr  Val Lys Val
    1040                 1045                 1050

Trp Leu  Gln Tyr Gln Cys Leu  Trp Asp Met Gln Ala  Glu Asn Ile
    1055                 1060                 1065

Tyr Asn  Arg Leu Gly Glu Asp  Leu Asn Lys Trp Gln  Ala Leu Leu
    1070                 1075                 1080

Val Gln  Ile Arg Lys Ala Arg  Gly Thr Phe Asp Asn  Ala Glu Thr
    1085                 1090                 1095

Lys Lys  Glu Phe Gly Pro Val  Val Ile Asp Tyr Gly  Lys Val Gln
    1100                 1105                 1110

Ser Lys  Val Asn Leu Lys Tyr  Asp Ser Trp His Lys  Glu Val Leu
    1115                 1120                 1125

Ser Lys  Phe Gly Gln Met Leu  Gly Ser Asn Met Thr  Glu Phe His
    1130                 1135                 1140

Ser Gln  Ile Ser Lys Ser Arg  Gln Glu Leu Glu Gln  His Ser Val
    1145                 1150                 1155

Asp Thr  Ala Ser Thr Ser Asp  Ala Val Thr Phe Ile  Thr Tyr Val
    1160                 1165                 1170

Gln Ser  Leu Lys Arg Lys Ile  Lys Gln Phe Glu Lys  Gln Val Glu
    1175                 1180                 1185

Leu Tyr  Arg Asn Gly Gln Arg  Leu Leu Glu Lys Gln  Arg Phe Gln
    1190                 1195                 1200

Phe Pro  Pro Ser Trp Leu Tyr  Ile Asp Asn Ile Glu  Gly Glu Trp
    1205                 1210                 1215

Gly Ala  Phe Asn Asp Ile Met  Arg Arg Lys Asp Ser  Ala Ile Gln
    1220                 1225                 1230

Gln Gln  Val Ala Asn Leu Gln  Met Lys Ile Val Gln  Glu Asp Arg
    1235                 1240                 1245

Ala Val  Glu Ser Arg Thr Thr  Asp Leu Leu Thr Asp  Trp Glu Lys
    1250                 1255                 1260

Thr Lys  Pro Val Thr Gly Asn  Leu Arg Pro Glu Glu  Ala Leu Gln
    1265                 1270                 1275

Ala Leu  Thr Ile Tyr Glu Gly  Lys Phe Gly Arg Leu  Lys Asp Asp
    1280                 1285                 1290

Arg Glu  Lys Cys Ala Lys Ala  Lys Glu Ala Leu Glu  Leu Thr Asp
    1295                 1300                 1305

Thr Gly  Leu Leu Ser Gly Ser  Glu Glu Arg Val Gln  Val Ala Leu
    1310                 1315                 1320

Glu Glu  Leu Gln Asp Leu Lys  Gly Val Trp Ser Glu  Leu Ser Lys
    1325                 1330                 1335

Val Trp  Glu Gln Ile Asp Gln  Met Lys Glu Gln Pro  Trp Val Ser
    1340                 1345                 1350
```

```
Val Gln Pro Arg Lys Leu Arg Gln Asn Leu Asp Ala Leu Leu Asn
    1355                1360                1365

Gln Leu Lys Ser Phe Pro Ala Arg Leu Arg Gln Tyr Ala Ser Tyr
    1370                1375                1380

Glu Phe Val Gln Arg Leu Leu Lys Gly Tyr Met Lys Ile Asn Met
    1385                1390                1395

Leu Val Ile Glu Leu Lys Ser Glu Ala Leu Lys Asp Arg His Trp
    1400                1405                1410

Lys Gln Leu Met Lys Arg Leu His Val Asn Trp Val Val Ser Glu
    1415                1420                1425

Leu Thr Leu Gly Gln Ile Trp Asp Val Asp Leu Gln Lys Asn Glu
    1430                1435                1440

Ala Ile Val Lys Asp Val Leu Leu Val Ala Gln Gly Glu Met Ala
    1445                1450                1455

Leu Glu Glu Phe Leu Lys Gln Ile Arg Glu Val Trp Asn Thr Tyr
    1460                1465                1470

Glu Leu Asp Leu Val Asn Tyr Gln Asn Lys Cys Arg Leu Ile Arg
    1475                1480                1485

Gly Trp Asp Asp Leu Phe Asn Lys Val Lys Glu His Ile Asn Ser
    1490                1495                1500

Val Ser Ala Met Lys Leu Ser Pro Tyr Tyr Lys Val Phe Glu Glu
    1505                1510                1515

Asp Ala Leu Ser Trp Glu Asp Lys Leu Asn Arg Ile Met Ala Leu
    1520                1525                1530

Phe Asp Val Trp Ile Asp Val Gln Arg Arg Trp Val Tyr Leu Glu
    1535                1540                1545

Gly Ile Phe Thr Gly Ser Ala Asp Ile Lys His Leu Leu Pro Val
    1550                1555                1560

Glu Thr Gln Arg Phe Gln Ser Ile Ser Thr Glu Phe Leu Ala Leu
    1565                1570                1575

Met Lys Lys Val Ser Lys Ser Pro Leu Val Met Asp Val Leu Asn
    1580                1585                1590

Ile Gln Gly Val Gln Arg Ser Leu Glu Arg Leu Ala Asp Leu Leu
    1595                1600                1605

Gly Lys Ile Gln Lys Ala Leu Gly Glu Tyr Leu Glu Arg Glu Arg
    1610                1615                1620

Ser Ser Phe Pro Arg Phe Tyr Phe Val Gly Asp Glu Asp Leu Leu
    1625                1630                1635

Glu Ile Ile Gly Asn Ser Lys Asn Val Ala Lys Leu Gln Lys His
    1640                1645                1650

Phe Lys Lys Met Phe Ala Gly Val Ser Ser Ile Ile Leu Asn Glu
    1655                1660                1665

Asp Asn Ser Val Val Leu Gly Ile Ser Ser Arg Glu Gly Glu Glu
    1670                1675                1680

Val Met Phe Lys Thr Pro Val Ser Ile Thr Glu His Pro Lys Ile
    1685                1690                1695

Asn Glu Trp Leu Thr Leu Val Glu Lys Glu Met Arg Val Thr Leu
    1700                1705                1710

Ala Lys Leu Leu Ala Glu Ser Val Thr Glu Val Glu Ile Phe Gly
    1715                1720                1725

Lys Ala Thr Ser Ile Asp Pro Asn Thr Tyr Ile Thr Trp Ile Asp
    1730                1735                1740

Lys Tyr Gln Ala Gln Leu Val Val Leu Ser Ala Gln Ile Ala Trp
```

-continued

```
    1745                1750                1755

Ser Glu  Asn Val Glu Thr Ala  Leu Ser Ser Met Gly  Gly Gly Gly
    1760                1765                1770

Asp Ala  Ala Pro Leu His Ser  Val Leu Ser Asn Val  Glu Val Thr
    1775                1780                1785

Leu Asn  Val Leu Ala Asp Ser  Val Leu Met Glu Gln  Pro Pro Leu
    1790                1795                1800

Arg Arg  Arg Lys Leu Glu His  Leu Ile Thr Glu Leu  Val His Gln
    1805                1810                1815

Arg Asp  Val Thr Arg Ser Leu  Ile Lys Ser Lys Ile  Asp Asn Ala
    1820                1825                1830

Lys Ser  Phe Glu Trp Leu Ser  Gln Met Arg Phe Tyr  Phe Asp Pro
    1835                1840                1845

Lys Gln  Thr Asp Val Leu Gln  Gln Leu Ser Ile Gln  Met Ala Asn
    1850                1855                1860

Ala Lys  Phe Asn Tyr Gly Phe  Glu Tyr Leu Gly Val  Gln Asp Lys
    1865                1870                1875

Leu Val  Gln Thr Pro Leu Thr  Asp Arg Cys Tyr Leu  Thr Met Thr
    1880                1885                1890

Gln Ala  Leu Glu Ala Arg Leu  Gly Gly Ser Pro Phe  Gly Pro Ala
    1895                1900                1905

Gly Thr  Gly Lys Thr Glu Ser  Val Lys Ala Leu Gly  His Gln Leu
    1910                1915                1920

Gly Arg  Phe Val Leu Val Phe  Asn Cys Asp Glu Thr  Phe Asp Phe
    1925                1930                1935

Gln Ala  Met Gly Arg Ile Phe  Val Gly Leu Cys Gln  Val Gly Ala
    1940                1945                1950

Trp Gly  Cys Phe Asp Glu Phe  Asn Arg Leu Glu Glu  Arg Met Leu
    1955                1960                1965

Ser Ala  Val Ser Gln Gln Val  Gln Cys Ile Gln Glu  Ala Leu Arg
    1970                1975                1980

Glu His  Ser Asn Pro Asn Tyr  Asp Lys Thr Ser Ala  Pro Ile Thr
    1985                1990                1995

Cys Glu  Leu Leu Asn Lys Gln  Val Lys Val Ser Pro  Asp Met Ala
    2000                2005                2010

Ile Phe  Ile Thr Met Asn Pro  Gly Tyr Ala Gly Arg  Ser Asn Leu
    2015                2020                2025

Pro Asp  Asn Leu Lys Lys Leu  Phe Arg Ser Leu Ala  Met Thr Lys
    2030                2035                2040

Pro Asp  Arg Gln Leu Ile Ala  Gln Val Met Leu Tyr  Ser Gln Gly
    2045                2050                2055

Phe Arg  Thr Ala Glu Val Leu  Ala Asn Lys Ile Val  Pro Phe Phe
    2060                2065                2070

Lys Leu  Cys Asp Glu Gln Leu  Ser Ser Gln Ser His  Tyr Asp Phe
    2075                2080                2085

Gly Leu  Arg Ala Leu Lys Ser  Val Leu Val Ser Ala  Gly Asn Val
    2090                2095                2100

Lys Arg  Glu Arg Ile Gln Lys  Ile Lys Arg Glu Lys  Glu Glu Arg
    2105                2110                2115

Gly Glu  Ala Val Asp Glu Gly  Glu Ile Ala Glu Asn  Leu Pro Glu
    2120                2125                2130

Gln Glu  Ile Leu Ile Gln Ser  Val Cys Glu Thr Met  Val Pro Lys
    2135                2140                2145
```

Leu Val Ala Glu Asp Ile Pro Leu Leu Phe Ser Leu Leu Ser Asp
2150 2155 2160

Val Phe Pro Gly Val Gln Tyr His Arg Gly Glu Met Thr Ala Leu
2165 2170 2175

Arg Glu Glu Leu Lys Lys Val Cys Gln Glu Met Tyr Leu Thr Tyr
2180 2185 2190

Gly Asp Gly Glu Glu Val Gly Gly Met Trp Val Glu Lys Val Leu
2195 2200 2205

Gln Leu Tyr Gln Ile Thr Gln Ile Asn His Gly Leu Met Met Val
2210 2215 2220

Gly Pro Ser Gly Ser Gly Lys Ser Met Ala Trp Arg Val Leu Leu
2225 2230 2235

Lys Ala Leu Glu Arg Leu Glu Gly Val Glu Gly Val Ala His Ile
2240 2245 2250

Ile Asp Pro Lys Ala Ile Ser Lys Asp His Leu Tyr Gly Thr Leu
2255 2260 2265

Asp Pro Asn Thr Arg Glu Trp Thr Asp Gly Leu Phe Thr His Val
2270 2275 2280

Leu Arg Lys Ile Ile Asp Ser Val Arg Gly Glu Leu Gln Lys Arg
2285 2290 2295

Gln Trp Ile Val Phe Asp Gly Asp Val Asp Pro Glu Trp Val Glu
2300 2305 2310

Asn Leu Asn Ser Val Leu Asp Asp Asn Lys Leu Leu Thr Leu Pro
2315 2320 2325

Asn Gly Glu Arg Leu Ser Leu Pro Pro Asn Val Arg Ile Met Phe
2330 2335 2340

Glu Val Gln Asp Leu Lys Tyr Ala Thr Leu Ala Thr Val Ser Arg
2345 2350 2355

Cys Gly Met Val Trp Phe Ser Glu Asp Val Leu Ser Thr Asp Met
2360 2365 2370

Ile Phe Asn Asn Phe Leu Ala Arg Leu Arg Ser Ile Pro Leu Asp
2375 2380 2385

Glu Gly Glu Asp Glu Ala Gln Arg Arg Arg Lys Gly Lys Glu Asp
2390 2395 2400

Glu Gly Glu Glu Ala Ala Ser Pro Met Leu Gln Ile Gln Arg Asp
2405 2410 2415

Ala Ala Thr Ile Met Gln Pro Tyr Phe Thr Ser Asn Gly Leu Val
2420 2425 2430

Thr Lys Ala Leu Glu His Ala Phe Gln Leu Glu His Ile Met Asp
2435 2440 2445

Leu Thr Arg Leu Arg Cys Leu Gly Ser Leu Phe Ser Met Leu His
2450 2455 2460

Gln Ala Cys Arg Asn Val Ala Gln Tyr Asn Ala Asn His Pro Asp
2465 2470 2475

Phe Pro Met Gln Ile Glu Gln Leu Glu Arg Tyr Ile Gln Arg Tyr
2480 2485 2490

Leu Val Tyr Ala Ile Leu Trp Ser Leu Ser Gly Asp Ser Arg Leu
2495 2500 2505

Lys Met Arg Ala Glu Leu Gly Glu Tyr Ile Arg Arg Ile Thr Thr
2510 2515 2520

Val Pro Leu Pro Thr Ala Pro Asn Ile Pro Ile Ile Asp Tyr Glu
2525 2530 2535

Val Ser Ile Ser Gly Glu Trp Ser Pro Trp Gln Ala Lys Val Pro
2540 2545 2550

```
Gln Ile  Glu Val Glu Thr His  Lys Val Ala Ala Pro  Asp Val Val
    2555                 2560                 2565

Val Pro  Thr Leu Asp Thr Val  Arg His Glu Ala Leu  Leu Tyr Thr
    2570                 2575                 2580

Trp Leu  Ala Glu His Lys Pro  Leu Val Leu Cys Gly  Pro Pro Gly
    2585                 2590                 2595

Ser Gly  Lys Thr Met Thr Leu  Phe Ser Ala Leu Arg  Ala Leu Pro
    2600                 2605                 2610

Asp Met  Glu Val Val Gly Leu  Asn Phe Ser Ser Ala  Thr Thr Pro
    2615                 2620                 2625

Glu Leu  Leu Leu Lys Thr Phe  Asp His Tyr Cys Glu  Tyr Arg Arg
    2630                 2635                 2640

Thr Pro  Asn Gly Val Val Leu  Ala Pro Val Gln Leu  Gly Lys Trp
    2645                 2650                 2655

Leu Val  Leu Phe Cys Asp Glu  Ile Asn Leu Pro Asp  Met Asp Lys
    2660                 2665                 2670

Tyr Gly  Thr Gln Arg Val Ile  Ser Phe Ile Arg Gln  Met Val Glu
    2675                 2680                 2685

His Gly  Gly Phe Tyr Arg Thr  Ser Asp Gln Thr Trp  Val Lys Leu
    2690                 2695                 2700

Glu Arg  Ile Gln Phe Val Gly  Ala Cys Asn Pro Pro  Thr Asp Pro
    2705                 2710                 2715

Gly Arg  Lys Pro Leu Ser His  Arg Phe Leu Arg His  Val Pro Val
    2720                 2725                 2730

Val Tyr  Val Asp Tyr Pro Gly  Pro Ala Ser Leu Thr  Gln Ile Tyr
    2735                 2740                 2745

Gly Thr  Phe Asn Arg Ala Met  Leu Arg Leu Ile Pro  Ser Leu Arg
    2750                 2755                 2760

Thr Tyr  Ala Glu Pro Leu Thr  Ala Ala Met Val Glu  Phe Tyr Thr
    2765                 2770                 2775

Met Ser  Gln Glu Arg Phe Thr  Gln Asp Thr Gln Pro  His Tyr Ile
    2780                 2785                 2790

Tyr Ser  Pro Arg Glu Met Thr  Arg Trp Val Arg Gly  Ile Phe Glu
    2795                 2800                 2805

Ala Leu  Arg Pro Leu Glu Thr  Leu Pro Val Glu Gly  Leu Ile Arg
    2810                 2815                 2820

Ile Trp  Ala His Glu Ala Leu  Arg Leu Phe Gln Asp  Arg Leu Val
    2825                 2830                 2835

Glu Asp  Glu Glu Arg Arg Trp  Thr Asp Glu Asn Ile  Asp Thr Val
    2840                 2845                 2850

Ala Leu  Lys His Phe Pro Asn  Ile Asp Arg Glu Lys  Ala Met Ser
    2855                 2860                 2865

Arg Pro  Ile Leu Tyr Ser Asn  Trp Leu Ser Lys Asp  Tyr Ile Pro
    2870                 2875                 2880

Val Asp  Gln Glu Glu Leu Arg  Asp Tyr Val Lys Ala  Arg Leu Lys
    2885                 2890                 2895

Val Phe  Tyr Glu Glu Glu Leu  Asp Val Pro Leu Val  Leu Phe Asn
    2900                 2905                 2910

Glu Val  Leu Asp His Val Leu  Arg Ile Asp Arg Ile  Phe Arg Gln
    2915                 2920                 2925

Pro Gln  Gly His Leu Leu Leu  Ile Gly Val Ser Gly  Ala Gly Lys
    2930                 2935                 2940

Thr Thr  Leu Ser Arg Phe Val  Ala Trp Met Asn Gly  Leu Ser Val
```

-continued

```
    2945                2950                2955

Tyr Gln  Ile Lys Val His Arg  Lys Tyr Thr Gly Glu  Asp Phe Asp
    2960                2965                2970

Glu Asp  Leu Arg Thr Val Leu  Arg Arg Ser Gly Cys  Lys Asn Glu
    2975                2980                2985

Lys Ile  Ala Phe Ile Met Asp  Glu Ser Asn Val Leu  Asp Ser Gly
    2990                2995                3000

Phe Leu  Glu Arg Met Asn Thr  Leu Leu Ala Asn Gly  Glu Val Pro
    3005                3010                3015

Gly Leu  Phe Glu Gly Asp Glu  Tyr Ala Thr Leu Met  Thr Gln Cys
    3020                3025                3030

Lys Glu  Gly Ala Gln Lys Glu  Gly Leu Met Leu Asp  Ser His Glu
    3035                3040                3045

Glu Leu  Tyr Lys Trp Phe Thr  Ser Gln Val Ile Arg  Asn Leu His
    3050                3055                3060

Val Val  Phe Thr Met Asn Pro  Ser Ser Glu Gly Leu  Lys Asp Arg
    3065                3070                3075

Ala Ala  Thr Ser Pro Ala Leu  Phe Asn Arg Cys Val  Leu Asn Trp
    3080                3085                3090

Phe Gly  Asp Trp Ser Thr Glu  Ala Leu Tyr Gln Val  Gly Lys Glu
    3095                3100                3105

Phe Thr  Ser Lys Met Asp Leu  Glu Lys Pro Asn Tyr  Ile Val Pro
    3110                3115                3120

Asp Tyr  Met Pro Val Val Tyr  Asp Lys Leu Pro Gln  Pro Pro Ser
    3125                3130                3135

His Arg  Glu Ala Ile Val Asn  Ser Cys Val Phe Val  His Gln Thr
    3140                3145                3150

Leu His  Gln Ala Asn Ala Arg  Leu Ala Lys Arg Gly  Gly Arg Thr
    3155                3160                3165

Met Ala  Ile Thr Pro Arg His  Tyr Leu Asp Phe Ile  Asn His Tyr
    3170                3175                3180

Ala Asn  Leu Phe His Glu Lys  Arg Ser Glu Leu Glu  Glu Gln Gln
    3185                3190                3195

Met His  Leu Asn Val Gly Leu  Arg Lys Ile Lys Glu  Thr Val Asp
    3200                3205                3210

Gln Val  Glu Glu Leu Arg Arg  Asp Leu Arg Ile Lys  Ser Gln Glu
    3215                3220                3225

Leu Glu  Val Lys Asn Ala Ala  Ala Asn Asp Lys Leu  Lys Lys Met
    3230                3235                3240

Val Lys  Asp Gln Gln Glu Ala  Glu Lys Lys Lys Val  Met Ser Gln
    3245                3250                3255

Glu Ile  Gln Glu Gln Leu His  Lys Gln Gln Glu Val  Ile Ala Asp
    3260                3265                3270

Lys Gln  Met Ser Val Lys Glu  Asp Leu Asp Lys Val  Glu Pro Ala
    3275                3280                3285

Val Ile  Glu Ala Gln Asn Ala  Val Lys Ser Ile Lys  Lys Gln His
    3290                3295                3300

Leu Val  Glu Val Arg Ser Met  Ala Asn Pro Pro Ala  Ala Val Lys
    3305                3310                3315

Leu Ala  Leu Glu Ser Ile Cys  Leu Leu Leu Gly Glu  Ser Thr Thr
    3320                3325                3330

Asp Trp  Lys Gln Ile Arg Ser  Ile Ile Met Arg Glu  Asn Phe Ile
    3335                3340                3345
```

```
Pro Thr Ile Val Asn Phe Ser Ala Glu Glu Ile Ser Asp Ala Ile
    3350                 3355                3360

Arg Glu Lys Met Lys Lys Asn Tyr Met Ser Asn Pro Ser Tyr Asn
    3365                 3370                3375

Tyr Glu Ile Val Asn Arg Ala Ser Leu Ala Cys Gly Pro Met Val
    3380                 3385                3390

Lys Trp Ala Ile Ala Gln Leu Asn Tyr Ala Asp Met Leu Lys Arg
    3395                 3400                3405

Val Glu Pro Leu Arg Asn Glu Leu Gln Lys Leu Glu Asp Asp Ala
    3410                 3415                3420

Lys Asp Asn Gln Gln Lys Ala Asn Glu Val Glu Gln Met Ile Arg
    3425                 3430                3435

Asp Leu Glu Ala Ser Ile Ala Arg Tyr Lys Glu Glu Tyr Ala Val
    3440                 3445                3450

Leu Ile Ser Glu Ala Gln Ala Ile Lys Ala Asp Leu Ala Ala Val
    3455                 3460                3465

Glu Ala Lys Val Asn Arg Ser Thr Ala Leu Leu Lys Ser Leu Ser
    3470                 3475                3480

Ala Glu Arg Glu Arg Trp Glu Lys Thr Ser Glu Thr Phe Lys Asn
    3485                 3490                3495

Gln Met Ser Thr Ile Ala Gly Asp Cys Leu Leu Ser Ala Ala Phe
    3500                 3505                3510

Ile Ala Tyr Ala Gly Tyr Phe Asp Gln Gln Met Arg Gln Asn Leu
    3515                 3520                3525

Phe Thr Thr Trp Ser His His Leu Gln Gln Ala Asn Ile Gln Phe
    3530                 3535                3540

Arg Thr Asp Ile Ala Arg Thr Glu Tyr Leu Ser Asn Ala Asp Glu
    3545                 3550                3555

Arg Leu Arg Trp Gln Ala Ser Ser Leu Pro Ala Asp Asp Leu Cys
    3560                 3565                3570

Thr Glu Asn Ala Ile Met Leu Lys Arg Phe Asn Arg Tyr Pro Leu
    3575                 3580                3585

Ile Ile Asp Pro Ser Gly Gln Ala Thr Glu Phe Ile Met Asn Glu
    3590                 3595                3600

Tyr Lys Asp Arg Lys Ile Thr Arg Thr Ser Phe Leu Asp Asp Ala
    3605                 3610                3615

Phe Arg Lys Asn Leu Glu Ser Ala Leu Arg Phe Gly Asn Pro Leu
    3620                 3625                3630

Leu Val Gln Asp Val Glu Ser Tyr Asp Pro Val Leu Asn Pro Val
    3635                 3640                3645

Leu Asn Arg Glu Val Arg Arg Thr Gly Gly Arg Val Leu Ile Thr
    3650                 3655                3660

Leu Gly Asp Gln Asp Ile Asp Leu Ser Pro Ser Phe Val Ile Phe
    3665                 3670                3675

Leu Ser Thr Arg Asp Pro Thr Val Glu Phe Pro Pro Asp Leu Cys
    3680                 3685                3690

Ser Arg Val Thr Phe Val Asn Phe Thr Val Thr Arg Ser Ser Leu
    3695                 3700                3705

Gln Ser Gln Cys Leu Asn Glu Val Leu Lys Ala Glu Arg Pro Asp
    3710                 3715                3720

Val Asp Glu Lys Arg Ser Asp Leu Leu Lys Leu Gln Gly Glu Phe
    3725                 3730                3735

Gln Leu Arg Leu Arg Gln Leu Glu Lys Ser Leu Leu Gln Ala Leu
    3740                 3745                3750
```

-continued

```
Asn Glu  Val Lys Gly Arg Ile  Leu Asp Asp Asp Thr  Ile Ile Thr
    3755                 3760                 3765

Thr Leu  Glu Asn Leu Lys Arg  Glu Ala Ala Glu Val  Thr Arg Lys
    3770                 3775                 3780

Val Glu  Glu Thr Asp Ile Val  Met Gln Glu Val Glu  Thr Val Ser
    3785                 3790                 3795

Gln Gln  Tyr Leu Pro Leu Ser  Thr Ala Cys Ser Ser  Ile Tyr Phe
    3800                 3805                 3810

Thr Met  Glu Ser Leu Lys Gln  Ile His Phe Leu Tyr  Gln Tyr Ser
    3815                 3820                 3825

Leu Gln  Phe Phe Leu Asp Ile  Tyr His Asn Val Leu  Tyr Glu Asn
    3830                 3835                 3840

Pro Asn  Leu Lys Gly Val Thr  Asp His Thr Gln Arg  Leu Ser Ile
    3845                 3850                 3855

Ile Thr  Lys Asp Leu Phe Gln  Val Ala Phe Asn Arg  Val Ala Arg
    3860                 3865                 3870

Gly Met  Leu His Gln Asp His  Ile Thr Phe Ala Met  Leu Leu Ala
    3875                 3880                 3885

Arg Ile  Lys Leu Lys Gly Thr  Val Gly Glu Pro Thr  Tyr Asp Ala
    3890                 3895                 3900

Glu Phe  Gln His Phe Leu Arg  Gly Asn Glu Ile Val  Leu Ser Ala
    3905                 3910                 3915

Gly Ser  Thr Pro Arg Ile Gln  Gly Leu Thr Val Glu  Gln Ala Glu
    3920                 3925                 3930

Ala Val  Val Arg Leu Ser Cys  Leu Pro Ala Phe Lys  Asp Leu Ile
    3935                 3940                 3945

Ala Lys  Val Gln Ala Asp Glu  Gln Phe Gly Ile Trp  Leu Asp Ser
    3950                 3955                 3960

Ser Ser  Pro Glu Gln Thr Val  Pro Tyr Leu Trp Ser  Glu Glu Thr
    3965                 3970                 3975

Pro Ala  Thr Pro Ile Gly Gln  Ala Ile His Arg Leu  Leu Leu Ile
    3980                 3985                 3990

Gln Ala  Phe Arg Pro Asp Arg  Leu Leu Ala Met Ala  His Met Phe
    3995                 4000                 4005

Val Ser  Thr Asn Leu Gly Glu  Ser Phe Met Ser Ile  Met Glu Gln
    4010                 4015                 4020

Pro Leu  Asp Leu Thr His Ile  Val Gly Thr Glu Val  Lys Pro Asn
    4025                 4030                 4035

Thr Pro  Val Leu Met Cys Ser  Val Pro Gly Tyr Asp  Ala Ser Gly
    4040                 4045                 4050

His Val  Glu Asp Leu Ala Ala  Glu Gln Asn Thr Gln  Ile Thr Ser
    4055                 4060                 4065

Ile Ala  Ile Gly Ser Ala Glu  Gly Phe Asn Gln Ala  Asp Lys Ala
    4070                 4075                 4080

Ile Asn  Thr Ala Val Lys Ser  Gly Arg Trp Val Met  Leu Lys Asn
    4085                 4090                 4095

Val His  Leu Ala Pro Gly Trp  Leu Met Gln Leu Glu  Lys Lys Leu
    4100                 4105                 4110

His Ser  Leu Gln Pro His Ala  Cys Phe Arg Leu Phe  Leu Thr Met
    4115                 4120                 4125

Glu Ile  Asn Pro Lys Val Pro  Val Asn Leu Leu Arg  Ala Gly Arg
    4130                 4135                 4140

Ile Phe  Val Phe Glu Pro Pro  Pro Gly Val Lys Ala  Asn Met Leu
```

-continued

```
        4145                    4150                    4155

Arg Thr Phe Ser Ser Ile Pro Val Ser Arg Ile Cys Lys Ser Pro
    4160                    4165                    4170

Asn Glu Arg Ala Arg Leu Tyr Phe Leu Leu Ala Trp Phe His Ala
    4175                    4180                    4185

Ile Ile Gln Glu Arg Leu Arg Tyr Ala Pro Leu Gly Trp Ser Lys
    4190                    4195                    4200

Lys Tyr Glu Phe Gly Glu Ser Asp Leu Arg Ser Ala Cys Asp Thr
    4205                    4210                    4215

Val Asp Thr Trp Leu Asp Asp Thr Ala Lys Gly Arg Gln Asn Ile
    4220                    4225                    4230

Ser Pro Asp Lys Ile Pro Trp Ser Ala Leu Lys Thr Leu Met Ala
    4235                    4240                    4245

Gln Ser Ile Tyr Gly Gly Arg Val Asp Asn Glu Phe Asp Gln Arg
    4250                    4255                    4260

Leu Leu Asn Thr Phe Leu Glu Arg Leu Phe Thr Thr Arg Ser Phe
    4265                    4270                    4275

Asp Ser Glu Phe Lys Leu Ala Cys Lys Val Asp Gly His Lys Asp
    4280                    4285                    4290

Ile Gln Met Pro Asp Gly Ile Arg Arg Glu Glu Phe Val Gln Trp
    4295                    4300                    4305

Val Glu Leu Leu Pro Asp Thr Gln Thr Pro Ser Trp Leu Gly Leu
    4310                    4315                    4320

Pro Asn Asn Ala Glu Arg Val Leu Leu Thr Thr Gln Gly Val Asp
    4325                    4330                    4335

Met Ile Ser Lys Met Leu Lys Met Gln Met Leu Glu Asp Glu Asp
    4340                    4345                    4350

Asp Leu Ala Tyr Ala Glu Thr Glu Lys Lys Thr Arg Thr Asp Ser
    4355                    4360                    4365

Thr Ser Asp Gly Arg Pro Ala Trp Met Arg Thr Leu His Thr Thr
    4370                    4375                    4380

Ala Ser Asn Trp Leu His Leu Ile Pro Gln Thr Leu Ser His Leu
    4385                    4390                    4395

Lys Arg Thr Val Glu Asn Ile Lys Asp Pro Leu Phe Arg Phe Phe
    4400                    4405                    4410

Glu Arg Glu Val Lys Met Gly Ala Lys Leu Leu Gln Asp Val Arg
    4415                    4420                    4425

Gln Asp Leu Ala Asp Val Val Gln Val Cys Glu Gly Lys Lys Lys
    4430                    4435                    4440

Gln Thr Asn Tyr Leu Arg Thr Leu Ile Asn Glu Leu Val Lys Gly
    4445                    4450                    4455

Ile Leu Pro Arg Ser Trp Ser His Tyr Thr Val Pro Ala Gly Met
    4460                    4465                    4470

Thr Val Ile Gln Trp Val Ser Asp Phe Ser Glu Arg Ile Lys Gln
    4475                    4480                    4485

Leu Gln Asn Ile Ser Leu Ala Ala Ala Ser Gly Gly Ala Lys Glu
    4490                    4495                    4500

Leu Lys Asn Ile His Val Cys Leu Gly Gly Leu Phe Val Pro Glu
    4505                    4510                    4515

Ala Tyr Ile Thr Ala Thr Arg Gln Tyr Val Ala Gln Ala Asn Ser
    4520                    4525                    4530

Trp Ser Leu Glu Glu Leu Cys Leu Glu Val Asn Val Thr Thr Ser
    4535                    4540                    4545
```

-continued

Gln Gly Ala Thr Leu Asp Ala Cys Ser Phe Gly Val Thr Gly Leu
4550 4555 4560

Lys Leu Gln Gly Ala Thr Cys Asn Asn Asn Lys Leu Ser Leu Ser
4565 4570 4575

Asn Ala Ile Ser Thr Ala Leu Pro Leu Thr Gln Leu Arg Trp Val
4580 4585 4590

Lys Gln Thr Asn Thr Glu Lys Lys Ala Ser Val Val Thr Leu Pro
4595 4600 4605

Val Tyr Leu Asn Phe Thr Arg Ala Asp Leu Ile Phe Thr Val Asp
4610 4615 4620

Phe Glu Ile Ala Thr Lys Glu Asp Pro Arg Ser Phe Tyr Glu Arg
4625 4630 4635

Gly Val Ala Val Leu Cys Thr Glu
4640 4645

<210> SEQ ID NO 47
<211> LENGTH: 916
<212> TYPE: PRT
<213> ORGANISM: Artificial Sequence
<220> FEATURE:
<223> OTHER INFORMATION: Synthetic

<400> SEQUENCE: 47

Met Asp Cys Glu His Ser Leu Ser Leu Pro Cys Arg Gly Ala Glu Ala
1 5 10 15

Trp Glu Ile Gly Ile Asp Lys Tyr Leu Tyr Ala Met Arg Leu Ser Asp
20 25 30

Glu Thr Leu Ile Asp Ile Met Thr Arg Phe Arg Lys Glu Met Lys Asn
35 40 45

Gly Leu Ser Arg Asp Phe Asn Pro Thr Ala Thr Val Lys Met Leu Pro
50 55 60

Thr Phe Val Arg Ser Ile Pro Asp Gly Ser Glu Lys Gly Asp Phe Ile
65 70 75 80

Ala Leu Asp Leu Gly Gly Ser Ser Phe Arg Ile Leu Arg Val Gln Val
85 90 95

Asn His Glu Lys Asn Gln Asn Val His Met Glu Ser Glu Val Tyr Asp
100 105 110

Thr Pro Glu Asn Ile Val His Gly Ser Gly Ser Gln Leu Phe Asp His
115 120 125

Val Ala Glu Cys Leu Gly Asp Phe Met Glu Lys Arg Lys Ile Lys Asp
130 135 140

Lys Lys Leu Pro Val Gly Phe Thr Phe Ser Phe Pro Cys Gln Gln Ser
145 150 155 160

Lys Ile Asp Glu Ala Ile Leu Ile Thr Trp Thr Lys Arg Phe Lys Ala
165 170 175

Ser Gly Val Glu Gly Ala Asp Val Val Lys Leu Leu Asn Lys Ala Ile
180 185 190

Lys Lys Arg Gly Asp Tyr Asp Ala Asn Ile Val Ala Val Val Asn Asp
195 200 205

Thr Val Gly Thr Met Met Thr Cys Gly Tyr Asp Asp Gln His Cys Glu
210 215 220

Val Gly Leu Ile Ile Gly Thr Gly Thr Asn Ala Cys Tyr Met Glu Glu
225 230 235 240

Leu Arg His Ile Asp Leu Val Glu Gly Asp Glu Gly Arg Met Cys Ile
245 250 255

Asn Thr Glu Trp Gly Ala Phe Gly Asp Asp Gly Ser Leu Glu Asp Ile

-continued

```
            260                 265                 270

Arg Thr Glu Phe Asp Arg Glu Ile Asp Arg Gly Ser Leu Asn Pro Gly
        275                 280                 285

Lys Gln Leu Phe Glu Lys Met Val Ser Gly Met Tyr Leu Gly Glu Leu
    290                 295                 300

Val Arg Leu Ile Leu Val Lys Met Ala Lys Glu Gly Leu Leu Phe Glu
305                 310                 315                 320

Gly Arg Ile Thr Pro Glu Leu Leu Thr Arg Gly Lys Phe Asn Thr Ser
                325                 330                 335

Asp Val Ser Ala Ile Glu Lys Asn Lys Glu Gly Leu His Asn Ala Lys
            340                 345                 350

Glu Ile Leu Thr Arg Leu Gly Val Glu Pro Ser Asp Asp Asp Cys Val
        355                 360                 365

Ser Val Gln His Val Cys Thr Ile Val Ser Phe Arg Ser Ala Asn Leu
    370                 375                 380

Val Ala Ala Thr Leu Gly Ala Ile Leu Asn Arg Leu Arg Asp Asn Lys
385                 390                 395                 400

Gly Thr Pro Arg Leu Arg Thr Thr Val Gly Val Asp Gly Ser Leu Tyr
                405                 410                 415

Lys Thr His Pro Gln Tyr Ser Arg Arg Phe His Lys Thr Leu Arg Arg
            420                 425                 430

Leu Val Pro Asp Ser Asp Val Arg Phe Leu Leu Ser Glu Ser Gly Ser
        435                 440                 445

Gly Lys Gly Ala Ala Met Val Thr Ala Val Ala Tyr Arg Leu Ala Glu
    450                 455                 460

Gln His Arg Gln Ile Glu Glu Thr Leu Ala His Phe His Leu Thr Lys
465                 470                 475                 480

Asp Met Leu Leu Glu Val Lys Lys Arg Met Arg Ala Glu Met Glu Leu
                485                 490                 495

Gly Leu Arg Lys Gln Thr His Asn Asn Ala Val Val Lys Met Leu Pro
            500                 505                 510

Ser Phe Val Arg Arg Thr Pro Asp Gly Thr Glu Asn Gly Asp Phe Leu
        515                 520                 525

Ala Leu Asp Leu Gly Gly Thr Asn Phe Arg Val Leu Leu Val Lys Ile
    530                 535                 540

Arg Ser Gly Lys Lys Arg Thr Val Glu Met His Asn Lys Ile Tyr Ala
545                 550                 555                 560

Ile Pro Ile Glu Ile Met Gln Gly Thr Gly Glu Glu Leu Phe Asp His
                565                 570                 575

Ile Val Ser Cys Ile Ser Asp Phe Leu Asp Tyr Met Gly Ile Lys Gly
            580                 585                 590

Pro Arg Met Pro Leu Gly Phe Thr Phe Ser Phe Pro Cys Gln Gln Thr
        595                 600                 605

Ser Leu Asp Ala Gly Ile Leu Ile Thr Trp Thr Lys Gly Phe Lys Ala
    610                 615                 620

Thr Asp Cys Val Gly His Asp Val Val Thr Leu Leu Arg Asp Ala Ile
625                 630                 635                 640

Lys Arg Arg Glu Glu Phe Asp Leu Asp Val Val Ala Val Val Asn Asp
                645                 650                 655

Thr Val Gly Thr Met Met Thr Cys Ala Tyr Glu Glu Pro Thr Cys Glu
            660                 665                 670

Val Gly Leu Ile Val Gly Thr Gly Ser Asn Ala Cys Tyr Met Glu Glu
        675                 680                 685
```

Met Lys Asn Val Glu Met Val Glu Gly Asp Gln Gly Gln Met Cys Ile
690 695 700

Asn Met Glu Trp Gly Ala Phe Gly Asp Asn Gly Cys Leu Asp Asp Ile
705 710 715 720

Arg Thr His Tyr Asp Arg Leu Val Asp Glu Tyr Ser Leu Asn Ala Gly
725 730 735

Lys Gln Arg Tyr Glu Lys Met Ile Ser Gly Met Tyr Leu Gly Glu Ile
740 745 750

Val Arg Asn Ile Leu Ile Asp Phe Thr Lys Lys Gly Phe Leu Phe Arg
755 760 765

Gly Gln Ile Ser Glu Thr Leu Lys Thr Arg Gly Ile Phe Glu Thr Lys
770 775 780

Phe Leu Ser Gln Ile Glu Ser Asp Arg Leu Ala Leu Leu Gln Val Arg
785 790 795 800

Ala Ile Leu Gln Gln Leu Gly Leu Asn Ser Thr Cys Asp Asp Ser Ile
805 810 815

Leu Val Lys Thr Val Cys Gly Val Val Ser Arg Arg Ala Ala Gln Leu
820 825 830

Cys Gly Ala Gly Met Ala Ala Val Val Asp Lys Ile Arg Glu Asn Arg
835 840 845

Gly Leu Asp Arg Leu Asn Val Thr Val Gly Val Asp Gly Thr Leu Tyr
850 855 860

Lys Leu His Pro His Phe Ser Arg Ile Met His Gln Thr Val Lys Glu
865 870 875 880

Leu Ser Pro Lys Cys Asn Val Ser Phe Leu Leu Ser Glu Asp Gly Ser
885 890 895

Gly Lys Gly Ala Ala Leu Ile Thr Ala Val Gly Val Arg Leu Arg Thr
900 905 910

Glu Ala Ser Ser
915

<210> SEQ ID NO 48
<211> LENGTH: 1253
<212> TYPE: PRT
<213> ORGANISM: Artificial Sequence
<220> FEATURE:
<223> OTHER INFORMATION: Synthetic

<400> SEQUENCE: 48

Met Thr Thr His Val Thr Leu Glu Asp Ala Leu Ser Asn Val Asp Leu
1 5 10 15

Leu Glu Glu Leu Pro Leu Pro Asp Gln Gln Pro Cys Ile Glu Pro Pro
20 25 30

Pro Ser Ser Ile Met Tyr Gln Ala Asn Phe Asp Thr Asn Phe Glu Asp
35 40 45

Arg Asn Ala Phe Val Thr Gly Ile Ala Arg Tyr Ile Glu Gln Ala Thr
50 55 60

Val His Ser Ser Met Asn Glu Met Leu Glu Glu Gly His Glu Tyr Ala
65 70 75 80

Val Met Leu Tyr Thr Trp Arg Ser Cys Ser Arg Ala Ile Pro Gln Val
85 90 95

Lys Cys Asn Glu Gln Pro Asn Arg Val Glu Ile Tyr Glu Lys Thr Val
100 105 110

Glu Val Leu Glu Pro Glu Val Thr Lys Leu Met Lys Phe Met Tyr Phe
115 120 125

Gln Arg Lys Ala Ile Glu Arg Phe Cys Ser Glu Val Lys Arg Leu Cys

-continued

```
        130                 135                 140

His Ala Glu Arg Arg Lys Asp Phe Val Ser Glu Ala Tyr Leu Leu Thr
145                 150                 155                 160

Leu Gly Lys Phe Ile Asn Met Phe Ala Val Leu Asp Glu Leu Lys Asn
                165                 170                 175

Met Lys Cys Ser Val Lys Asn Asp His Ser Ala Tyr Lys Arg Ala Ala
            180                 185                 190

Gln Phe Leu Arg Lys Met Ala Asp Pro Gln Ser Ile Gln Glu Ser Gln
        195                 200                 205

Asn Leu Ser Met Phe Leu Ala Asn His Asn Arg Ile Thr Gln Cys Leu
    210                 215                 220

His Gln Gln Leu Glu Val Ile Pro Gly Tyr Glu Glu Leu Leu Ala Asp
225                 230                 235                 240

Ile Val Asn Ile Cys Val Asp Tyr Tyr Glu Asn Lys Met Tyr Leu Thr
                245                 250                 255

Pro Ser Glu Lys His Met Leu Leu Lys Val Met Gly Phe Gly Leu Tyr
            260                 265                 270

Leu Met Asp Gly Asn Val Ser Asn Ile Tyr Lys Leu Asp Ala Lys Lys
        275                 280                 285

Arg Ile Asn Leu Ser Lys Ile Asp Lys Phe Phe Lys Gln Leu Gln Val
    290                 295                 300

Val Pro Leu Phe Gly Asp Met Gln Ile Glu Leu Ala Arg Tyr Ile Lys
305                 310                 315                 320

Thr Ser Ala His Tyr Glu Glu Asn Lys Ser Lys Trp Thr Cys Thr Gln
                325                 330                 335

Ser Ser Ile Ser Pro Gln Tyr Asn Ile Cys Glu Gln Met Val Gln Ile
            340                 345                 350

Arg Asp Asp His Ile Arg Phe Ile Ser Glu Leu Ala Arg Tyr Ser Asn
        355                 360                 365

Ser Glu Val Val Thr Gly Ser Gly Leu Asp Ser Gln Lys Ser Asp Glu
    370                 375                 380

Glu Tyr Arg Glu Leu Phe Asp Leu Ala Leu Arg Gly Leu Gln Leu Leu
385                 390                 395                 400

Ser Lys Trp Ser Ala His Val Met Glu Val Tyr Ser Trp Lys Leu Val
                405                 410                 415

His Pro Thr Asp Lys Phe Cys Asn Lys Asp Cys Pro Gly Thr Ala Glu
            420                 425                 430

Glu Tyr Glu Arg Ala Thr Arg Tyr Asn Tyr Thr Ser Glu Glu Lys Phe
        435                 440                 445

Ala Phe Val Glu Val Ile Ala Met Ile Lys Gly Leu Gln Val Leu Met
    450                 455                 460

Gly Arg Met Glu Ser Val Phe Asn Gln Ala Ile Arg Asn Thr Ile Tyr
465                 470                 475                 480

Ala Ala Leu Gln Asp Phe Ala Gln Val Thr Leu Arg Glu Pro Leu Arg
                485                 490                 495

Gln Ala Val Arg Lys Lys Lys Asn Val Leu Ile Ser Val Leu Gln Ala
            500                 505                 510

Ile Arg Lys Thr Ile Cys Asp Trp Glu Gly Gly Arg Glu Pro Pro Asn
        515                 520                 525

Asp Pro Cys Leu Arg Gly Glu Lys Asp Pro Lys Gly Gly Phe Asp Ile
    530                 535                 540

Lys Val Pro Arg Arg Ala Val Gly Pro Ser Ser Thr Gln Leu Tyr Met
545                 550                 555                 560
```

```
Val Arg Thr Met Leu Glu Ser Leu Ile Ala Asp Lys Ser Gly Ser Lys
                565                 570                 575

Lys Thr Leu Arg Ser Ser Leu Asp Gly Pro Ile Val Leu Ala Ile Glu
            580                 585                 590

Asp Phe His Lys Gln Ser Phe Phe Phe Thr His Leu Leu Asn Ile Ser
        595                 600                 605

Glu Ala Leu Gln Gln Cys Cys Asp Leu Ser Gln Leu Trp Phe Arg Glu
    610                 615                 620

Phe Phe Leu Glu Leu Thr Met Gly Arg Arg Ile Gln Phe Pro Ile Glu
625                 630                 635                 640

Met Ser Met Pro Trp Ile Leu Thr Asp His Ile Leu Glu Thr Lys Glu
                645                 650                 655

Pro Ser Met Met Glu Tyr Val Leu Tyr Pro Leu Asp Leu Tyr Asn Asp
            660                 665                 670

Ser Ala Tyr Tyr Ala Leu Thr Lys Phe Lys Lys Gln Phe Leu Tyr Asp
        675                 680                 685

Glu Ile Glu Ala Glu Val Asn Leu Cys Phe Asp Gln Phe Val Tyr Lys
    690                 695                 700

Leu Ala Asp Gln Ile Phe Ala Tyr Tyr Lys Ala Met Ala Gly Ser Val
705                 710                 715                 720

Leu Leu Asp Lys Arg Phe Arg Ala Glu Cys Lys Asn Tyr Gly Val Ile
                725                 730                 735

Ile Pro Tyr Pro Pro Ser Asn Arg Tyr Glu Thr Leu Leu Lys Gln Arg
            740                 745                 750

His Val Gln Leu Leu Gly Arg Ser Ile Asp Leu Asn Arg Leu Ile Thr
        755                 760                 765

Gln Arg Ile Ser Ala Ala Met Tyr Lys Ser Leu Asp Gln Ala Ile Ser
    770                 775                 780

Arg Phe Glu Ser Glu Asp Leu Thr Ser Ile Val Glu Leu Glu Trp Leu
785                 790                 795                 800

Leu Glu Ile Asn Arg Leu Thr His Arg Leu Leu Cys Lys His Met Thr
                805                 810                 815

Leu Asp Ser Phe Asp Ala Met Phe Arg Glu Ala Asn His Asn Val Ser
            820                 825                 830

Ala Pro Tyr Gly Arg Ile Thr Leu His Val Phe Trp Glu Leu Asn Phe
        835                 840                 845

Asp Phe Leu Pro Asn Tyr Cys Tyr Asn Gly Ser Thr Asn Arg Phe Val
    850                 855                 860

Arg Thr Ala Ile Pro Phe Thr Gln Glu Pro Gln Arg Asp Lys Pro Ala
865                 870                 875                 880

Asn Val Gln Pro Tyr Tyr Leu Tyr Gly Ser Lys Pro Leu Asn Ile Ala
                885                 890                 895

Tyr Ser His Ile Tyr Ser Ser Tyr Arg Asn Phe Val Gly Pro Pro His
            900                 905                 910

Phe Lys Thr Ile Cys Arg Leu Leu Gly Tyr Gln Gly Ile Ala Val Val
        915                 920                 925

Met Glu Glu Leu Leu Lys Ile Val Lys Ser Leu Leu Gln Gly Thr Ile
    930                 935                 940

Leu Gln Tyr Val Lys Thr Leu Ile Glu Val Met Pro Lys Ile Cys Arg
945                 950                 955                 960

Leu Pro Arg His Glu Tyr Gly Ser Pro Gly Ile Leu Glu Phe Phe His
                965                 970                 975

His Gln Leu Lys Asp Ile Ile Glu Tyr Ala Glu Leu Lys Thr Asp Val
            980                 985                 990
```

```
Phe Gln Ser Leu Arg Glu Val Gly  Asn Ala Ile Leu Phe  Cys Leu Leu
        995                 1000                 1005

Ile Glu  Gln Ala Leu Ser Gln  Glu Glu Val Cys Asp  Leu Leu His
    1010                 1015                 1020

Ala Ala  Pro Phe Gln Asn Ile  Leu Pro Arg Val Tyr  Ile Lys Glu
    1025                 1030                 1035

Gly Glu  Arg Leu Glu Val Arg  Met Lys Arg Leu Glu  Ala Lys Tyr
    1040                 1045                 1050

Ala Pro  Leu His Leu Val Pro  Leu Ile Glu Arg Leu  Gly Thr Pro
    1055                 1060                 1065

Gln Gln  Ile Ala Ile Ala Arg  Glu Gly Asp Leu Leu  Thr Lys Glu
    1070                 1075                 1080

Arg Leu  Cys Cys Gly Leu Ser  Met Phe Glu Val Ile  Leu Thr Arg
    1085                 1090                 1095

Ile Arg  Ser Tyr Leu Gln Asp  Pro Ile Trp Arg Gly  Pro Pro Pro
    1100                 1105                 1110

Thr Asn  Gly Val Met His Val  Asp Glu Cys Val Glu  Phe His Arg
    1115                 1120                 1125

Leu Trp  Ser Ala Met Gln Phe  Val Tyr Cys Ile Pro  Val Gly Thr
    1130                 1135                 1140

Asn Glu  Phe Thr Ala Glu Gln  Cys Phe Gly Asp Gly  Leu Asn Trp
    1145                 1150                 1155

Ala Gly  Cys Ser Ile Ile Val  Leu Leu Gly Gln Gln  Arg Arg Phe
    1160                 1165                 1170

Asp Leu  Phe Asp Phe Cys Tyr  His Leu Leu Lys Val  Gln Arg Gln
    1175                 1180                 1185

Asp Gly  Lys Asp Glu Ile Ile  Lys Asn Val Pro Leu  Lys Lys Met
    1190                 1195                 1200

Ala Asp  Arg Ile Arg Lys Tyr  Gln Ile Leu Asn Asn  Glu Val Phe
    1205                 1210                 1215

Ala Ile  Leu Asn Lys Tyr Met  Lys Ser Val Glu Thr  Asp Ser Ser
    1220                 1225                 1230

Thr Val  Glu His Val Arg Cys  Phe Gln Pro Pro Ile  His Gln Ser
    1235                 1240                 1245

Leu Ala  Thr Thr Cys
    1250


<210> SEQ ID NO 49
<211> LENGTH: 285
<212> TYPE: PRT
<213> ORGANISM: Artificial Sequence
<220> FEATURE:
<223> OTHER INFORMATION: Synthetic

<400> SEQUENCE: 49

Met Ala Leu Val Ala Ser Val Arg Val Pro Ala Arg Val Leu Leu Arg
1               5                   10                  15

Ala Gly Ala Arg Leu Pro Gly Ala Ala Leu Gly Arg Thr Glu Arg Ala
            20                  25                  30

Ala Gly Gly Gly Asp Gly Ala Arg Arg Phe Gly Ser Gln Arg Val Leu
        35                  40                  45

Val Glu Pro Asp Ala Gly Ala Gly Val Ala Val Met Lys Phe Lys Asn
    50                  55                  60

Pro Pro Val Asn Ser Leu Ser Leu Glu Phe Leu Thr Glu Leu Val Ile
65                  70                  75                  80
```

Ser Leu Glu Lys Leu Glu Asn Asp Lys Ser Phe Arg Gly Val Ile Leu
85 90 95

Thr Ser Asp Arg Pro Gly Val Phe Ser Ala Gly Leu Asp Leu Thr Glu
100 105 110

Met Cys Gly Arg Ser Pro Ala His Tyr Ala Gly Tyr Trp Lys Ala Val
115 120 125

Gln Glu Leu Trp Leu Arg Leu Tyr Gln Ser Asn Leu Val Leu Val Ser
130 135 140

Ala Ile Asn Gly Ala Cys Pro Ala Gly Gly Cys Leu Val Ala Leu Thr
145 150 155 160

Cys Asp Tyr Arg Ile Leu Ala Asp Asn Pro Arg Leu Lys Asp Thr Leu
165 170 175

Glu Asn Thr Ile Gly His Arg Ala Ala Glu Arg Ala Leu Gln Leu Gly
180 185 190

Leu Leu Phe Pro Pro Ala Glu Ala Leu Gln Val Gly Ile Val Asp Gln
195 200 205

Val Val Pro Glu Glu Gln Val Gln Ser Thr Ala Leu Ser Ala Ile Ala
210 215 220

Gln Trp Met Ala Ile Pro Asp His Ala Arg Gln Leu Thr Lys Ala Met
225 230 235 240

Met Arg Lys Ala Thr Ala Ser Arg Leu Val Thr Gln Arg Asp Ala Asp
245 250 255

Val Gln Asn Phe Val Ser Phe Ile Ser Lys Asp Ser Ile Gln Lys Ser
260 265 270

Leu Gln Met Tyr Leu Glu Arg Leu Lys Glu Glu Lys Gly
275 280 285

<210> SEQ ID NO 50
<211> LENGTH: 108
<212> TYPE: PRT
<213> ORGANISM: Artificial Sequence
<220> FEATURE:
<223> OTHER INFORMATION: Synthetic

<400> SEQUENCE: 50

Met Ser Leu Thr Ser Ser Ser Ser Val Arg Val Glu Trp Ile Ala Ala
1 5 10 15

Val Thr Ile Ala Ala Gly Thr Ala Ala Ile Gly Tyr Leu Ala Tyr Lys
20 25 30

Arg Phe Tyr Val Lys Asp His Arg Asn Lys Ala Met Ile Asn Leu His
35 40 45

Ile Gln Lys Asp Asn Pro Lys Ile Val His Ala Phe Asp Met Glu Asp
50 55 60

Leu Gly Asp Lys Ala Val Tyr Cys Arg Cys Trp Arg Ser Lys Lys Phe
65 70 75 80

Pro Phe Cys Asp Gly Ala His Thr Lys His Asn Glu Glu Thr Gly Asp
85 90 95

Asn Val Gly Pro Leu Ile Ile Lys Lys Lys Glu Thr
100 105

<210> SEQ ID NO 51
<211> LENGTH: 893
<212> TYPE: PRT
<213> ORGANISM: Artificial Sequence
<220> FEATURE:
<223> OTHER INFORMATION: Synthetic

<400> SEQUENCE: 51

-continued

```
Met Thr Pro Pro Ser Arg Ala Glu Ala Gly Val Arg Arg Ser Arg Val
1               5                   10                  15

Pro Ser Glu Gly Arg Trp Arg Gly Ala Glu Pro Pro Gly Ile Ser Ala
            20                  25                  30

Ser Thr Gln Pro Ala Ser Ala Gly Arg Ala Ala Arg His Cys Gly Ala
        35                  40                  45

Met Ser Gly Ala Arg Gly Glu Gly Pro Glu Ala Gly Ala Gly Gly Ala
    50                  55                  60

Gly Gly Arg Ala Ala Pro Glu Asn Pro Gly Gly Val Leu Ser Val Glu
65                  70                  75                  80

Leu Pro Gly Leu Leu Ala Gln Leu Ala Arg Ser Phe Ala Leu Leu Leu
                85                  90                  95

Pro Val Tyr Ala Leu Gly Tyr Leu Gly Leu Ser Phe Ser Trp Val Leu
            100                 105                 110

Leu Ala Leu Ala Leu Leu Ala Trp Cys Arg Arg Ser Arg Gly Leu Lys
        115                 120                 125

Ala Leu Arg Leu Cys Arg Ala Leu Ala Leu Leu Glu Asp Glu Glu Arg
    130                 135                 140

Val Val Arg Leu Gly Val Arg Ala Cys Asp Leu Pro Ala Trp Val His
145                 150                 155                 160

Phe Pro Asp Thr Glu Arg Ala Glu Trp Leu Asn Lys Thr Val Lys His
                165                 170                 175

Met Trp Pro Phe Ile Cys Gln Phe Ile Glu Lys Leu Phe Arg Glu Thr
            180                 185                 190

Ile Glu Pro Ala Val Arg Gly Ala Asn Thr His Leu Ser Thr Phe Ser
        195                 200                 205

Phe Thr Lys Val Asp Val Gly Gln Gln Pro Leu Arg Ile Asn Gly Val
    210                 215                 220

Lys Val Tyr Thr Glu Asn Val Asp Lys Arg Gln Ile Ile Leu Asp Leu
225                 230                 235                 240

Gln Ile Ser Phe Val Gly Asn Cys Glu Ile Asp Leu Glu Ile Lys Arg
                245                 250                 255

Tyr Phe Cys Arg Ala Gly Val Lys Ser Ile Gln Ile His Gly Thr Met
            260                 265                 270

Arg Val Ile Leu Glu Pro Leu Ile Gly Asp Met Pro Leu Val Gly Ala
        275                 280                 285

Leu Ser Ile Phe Phe Leu Arg Lys Pro Leu Leu Glu Ile Asn Trp Thr
    290                 295                 300

Gly Leu Thr Asn Leu Leu Asp Val Pro Gly Leu Asn Gly Leu Ser Asp
305                 310                 315                 320

Thr Ile Ile Leu Asp Ile Ile Ser Asn Tyr Leu Val Leu Pro Asn Arg
                325                 330                 335

Ile Thr Val Pro Leu Val Ser Glu Val Gln Ile Ala Gln Leu Arg Phe
            340                 345                 350

Pro Val Pro Lys Gly Val Leu Arg Ile His Phe Ile Glu Ala Gln Asp
        355                 360                 365

Leu Gln Gly Lys Asp Thr Tyr Leu Lys Gly Leu Val Lys Gly Lys Ser
    370                 375                 380

Asp Pro Tyr Gly Ile Ile Arg Val Gly Asn Gln Ile Phe Gln Ser Arg
385                 390                 395                 400

Val Ile Lys Glu Asn Leu Ser Pro Lys Trp Asn Glu Val Tyr Glu Ala
                405                 410                 415

Leu Val Tyr Glu His Pro Gly Gln Glu Leu Glu Ile Glu Leu Phe Asp
            420                 425                 430
```

```
Glu Asp Pro Asp Lys Asp Asp Phe Leu Gly Ser Leu Met Ile Asp Leu
        435                 440                 445

Ile Glu Val Glu Lys Glu Arg Leu Leu Asp Glu Trp Phe Thr Leu Asp
    450                 455                 460

Glu Val Pro Lys Gly Lys Leu His Leu Arg Leu Glu Trp Leu Thr Leu
465                 470                 475                 480

Met Pro Asn Ala Ser Asn Leu Asp Lys Val Leu Thr Asp Ile Lys Ala
                485                 490                 495

Asp Lys Asp Gln Ala Asn Asp Gly Leu Ser Ser Ala Leu Leu Ile Leu
            500                 505                 510

Tyr Leu Asp Ser Ala Arg Asn Leu Pro Ser Gly Lys Lys Ile Ser Ser
        515                 520                 525

Asn Pro Asn Pro Val Val Gln Met Ser Val Gly His Lys Ala Gln Glu
    530                 535                 540

Ser Lys Ile Arg Tyr Lys Thr Asn Glu Pro Val Trp Glu Glu Asn Phe
545                 550                 555                 560

Thr Phe Phe Ile His Asn Pro Lys Arg Gln Asp Leu Glu Val Glu Val
                565                 570                 575

Arg Asp Glu Gln His Gln Cys Ser Leu Gly Asn Leu Lys Val Pro Leu
            580                 585                 590

Ser Gln Leu Leu Thr Ser Glu Asp Met Thr Val Ser Gln Arg Phe Gln
        595                 600                 605

Leu Ser Asn Ser Gly Pro Asn Ser Thr Ile Lys Met Lys Ile Ala Leu
    610                 615                 620

Arg Val Leu His Leu Glu Lys Arg Glu Arg Pro Pro Asp His Gln His
625                 630                 635                 640

Ser Ala Gln Val Lys Arg Pro Ser Val Ser Lys Glu Gly Arg Lys Thr
                645                 650                 655

Ser Ile Lys Ser His Met Ser Gly Ser Pro Gly Pro Gly Gly Ser Asn
            660                 665                 670

Thr Ala Pro Ser Thr Pro Val Ile Gly Gly Ser Asp Lys Pro Gly Met
        675                 680                 685

Glu Glu Lys Ala Gln Pro Pro Glu Ala Gly Pro Gln Gly Leu His Asp
    690                 695                 700

Leu Gly Arg Ser Ser Ser Ser Leu Leu Ala Ser Pro Gly His Ile Ser
705                 710                 715                 720

Val Lys Glu Pro Thr Pro Ser Ile Ala Ser Asp Ile Ser Leu Pro Ile
                725                 730                 735

Ala Thr Gln Glu Leu Arg Gln Arg Leu Arg Gln Leu Glu Asn Gly Thr
            740                 745                 750

Thr Leu Gly Gln Ser Pro Leu Gly Gln Ile Gln Leu Thr Ile Arg His
        755                 760                 765

Ser Ser Gln Arg Asn Lys Leu Ile Val Val Val His Ala Cys Arg Asn
    770                 775                 780

Leu Ile Ala Phe Ser Glu Asp Gly Ser Asp Pro Tyr Val Arg Met Tyr
785                 790                 795                 800

Leu Leu Pro Asp Lys Arg Arg Ser Gly Arg Arg Lys Thr His Val Ser
                805                 810                 815

Lys Lys Thr Leu Asn Pro Val Phe Asp Gln Ser Phe Asp Phe Ser Val
            820                 825                 830

Ser Leu Pro Glu Val Gln Arg Arg Thr Leu Asp Val Ala Val Lys Asn
        835                 840                 845

Ser Gly Gly Phe Leu Ser Lys Asp Lys Gly Leu Leu Gly Lys Val Leu
```

```
    850                 855                 860

Val Ala Leu Ala Ser Glu Glu Leu Ala Lys Gly Trp Thr Gln Trp Tyr
865                 870                 875                 880

Asp Leu Thr Glu Asp Gly Thr Arg Pro Gln Ala Met Thr
                885                 890


<210> SEQ ID NO 52
<211> LENGTH: 541
<212> TYPE: PRT
<213> ORGANISM: Artificial Sequence
<220> FEATURE:
<223> OTHER INFORMATION: Synthetic

<400> SEQUENCE: 52

Met Val Ala Asp Pro Pro Arg Asp Ser Lys Gly Leu Ala Ala Ala Glu
1               5                   10                  15

Pro Thr Ala Asn Gly Gly Leu Ala Leu Ala Ser Ile Glu Asp Gln Gly
            20                  25                  30

Ala Ala Ala Gly Gly Tyr Cys Gly Ser Arg Asp Gln Val Arg Arg Cys
        35                  40                  45

Leu Arg Ala Asn Leu Leu Val Leu Leu Thr Val Val Ala Val Val Ala
    50                  55                  60

Gly Val Ala Leu Gly Leu Gly Val Ser Gly Ala Gly Gly Ala Leu Ala
65                  70                  75                  80

Leu Gly Pro Glu Arg Leu Ser Ala Phe Val Phe Pro Gly Glu Leu Leu
                85                  90                  95

Leu Arg Leu Leu Arg Met Ile Ile Leu Pro Leu Val Val Cys Ser Leu
            100                 105                 110

Ile Gly Gly Ala Ala Ser Leu Asp Pro Gly Ala Leu Gly Arg Leu Gly
        115                 120                 125

Ala Trp Ala Leu Leu Phe Phe Leu Val Thr Thr Leu Leu Ala Ser Ala
    130                 135                 140

Leu Gly Val Gly Leu Ala Leu Ala Leu Gln Pro Gly Ala Ala Ser Ala
145                 150                 155                 160

Ala Ile Asn Ala Ser Val Gly Ala Ala Gly Ser Ala Glu Asn Ala Pro
                165                 170                 175

Ser Lys Glu Val Leu Asp Ser Phe Leu Asp Leu Ala Arg Asn Ile Phe
            180                 185                 190

Pro Ser Asn Leu Val Ser Ala Ala Phe Arg Ser Tyr Ser Thr Thr Tyr
        195                 200                 205

Glu Glu Arg Asn Ile Thr Gly Thr Arg Val Lys Val Pro Val Gly Gln
    210                 215                 220

Glu Val Glu Gly Met Asn Ile Leu Gly Leu Val Val Phe Ala Ile Val
225                 230                 235                 240

Phe Gly Val Ala Leu Arg Lys Leu Gly Pro Glu Gly Glu Leu Leu Ile
                245                 250                 255

Arg Phe Phe Asn Ser Phe Asn Glu Ala Thr Met Val Leu Val Ser Trp
            260                 265                 270

Ile Met Trp Tyr Ala Pro Val Gly Ile Met Phe Leu Val Ala Gly Lys
        275                 280                 285

Ile Val Glu Met Glu Asp Val Gly Leu Leu Phe Ala Arg Leu Gly Lys
    290                 295                 300

Tyr Ile Leu Cys Cys Leu Leu Gly His Ala Ile His Gly Leu Leu Val
305                 310                 315                 320

Leu Pro Leu Ile Tyr Phe Leu Phe Thr Arg Lys Asn Pro Tyr Arg Phe
                325                 330                 335
```

Leu Trp Gly Ile Val Thr Pro Leu Ala Thr Ala Phe Gly Thr Ser Ser
340 345 350

Ser Ser Ala Thr Leu Pro Leu Met Met Lys Cys Val Glu Glu Asn Asn
355 360 365

Gly Val Ala Lys His Ile Ser Arg Phe Ile Leu Pro Ile Gly Ala Thr
370 375 380

Val Asn Met Asp Gly Ala Ala Leu Phe Gln Cys Val Ala Ala Val Phe
385 390 395 400

Ile Ala Gln Leu Ser Gln Gln Ser Leu Asp Phe Val Lys Ile Ile Thr
405 410 415

Ile Leu Val Thr Ala Thr Ala Ser Ser Val Gly Ala Ala Gly Ile Pro
420 425 430

Ala Gly Gly Val Leu Thr Leu Ala Ile Ile Leu Glu Ala Val Asn Leu
435 440 445

Pro Val Asp His Ile Ser Leu Ile Leu Ala Val Asp Trp Leu Val Asp
450 455 460

Arg Ser Cys Thr Val Leu Asn Val Glu Gly Asp Ala Leu Gly Ala Gly
465 470 475 480

Leu Leu Gln Asn Tyr Val Asp Arg Thr Glu Ser Arg Ser Thr Glu Pro
485 490 495

Glu Leu Ile Gln Val Lys Ser Glu Leu Pro Leu Asp Pro Leu Pro Val
500 505 510

Pro Thr Glu Glu Gly Asn Pro Leu Leu Lys His Tyr Arg Gly Pro Ala
515 520 525

Gly Asp Ala Thr Val Ala Ser Glu Lys Glu Ser Val Met
530 535 540

<210> SEQ ID NO 53
<211> LENGTH: 489
<212> TYPE: PRT
<213> ORGANISM: Artificial Sequence
<220> FEATURE:
<223> OTHER INFORMATION: Synthetic

<400> SEQUENCE: 53

Met Glu Asp Ser Ala Ser Ala Ser Leu Ser Ser Ala Ala Ala Thr Gly
1 5 10 15

Thr Ser Thr Ser Thr Pro Ala Ala Pro Thr Ala Arg Lys Gln Leu Asp
20 25 30

Lys Glu Gln Val Arg Lys Ala Val Asp Ala Leu Leu Thr His Cys Lys
35 40 45

Ser Arg Lys Asn Asn Tyr Gly Leu Leu Leu Asn Glu Asn Glu Ser Leu
50 55 60

Phe Leu Met Val Val Leu Trp Lys Ile Pro Ser Lys Glu Leu Arg Val
65 70 75 80

Arg Leu Thr Leu Pro His Ser Ile Arg Ser Asp Ser Glu Asp Ile Cys
85 90 95

Leu Phe Thr Lys Asp Glu Pro Asn Ser Thr Pro Glu Lys Thr Glu Gln
100 105 110

Phe Tyr Arg Lys Leu Leu Asn Lys His Gly Ile Lys Thr Val Ser Gln
115 120 125

Ile Ile Ser Leu Gln Thr Leu Lys Lys Glu Tyr Lys Ser Tyr Glu Ala
130 135 140

Lys Leu Arg Leu Leu Ser Ser Phe Asp Phe Phe Leu Thr Asp Ala Arg
145 150 155 160

Ile Arg Arg Leu Leu Pro Ser Leu Ile Gly Arg His Phe Tyr Gln Arg
165 170 175

Lys Lys Val Pro Val Ser Val Asn Leu Leu Ser Lys Asn Leu Ser Arg
180 185 190

Glu Ile Asn Asp Cys Ile Gly Gly Thr Val Leu Asn Ile Ser Lys Ser
195 200 205

Gly Ser Cys Ser Ala Ile Arg Ile Gly His Val Gly Met Gln Ile Glu
210 215 220

His Ile Ile Glu Asn Ile Val Ala Val Thr Lys Gly Leu Ser Glu Lys
225 230 235 240

Leu Pro Glu Trp Glu Ser Val Lys Leu Leu Phe Val Lys Thr Glu Lys
245 250 255

Ser Ala Ala Leu Pro Ile Phe Ser Ser Phe Val Ser Asn Trp Asp Glu
260 265 270

Ala Thr Lys Arg Ser Leu Leu Asn Lys Lys Lys Lys Glu Ala Arg Arg
275 280 285

Lys Arg Arg Glu Arg Asn Phe Glu Lys Gln Lys Glu Arg Lys Lys Lys
290 295 300

Arg Gln Gln Ala Arg Lys Thr Ala Ser Val Leu Ser Lys Asp Asp Val
305 310 315 320

Ala Pro Glu Ser Gly Asp Thr Thr Val Lys Lys Pro Glu Ser Lys Lys
325 330 335

Glu Gln Thr Pro Glu His Gly Lys Lys Lys Arg Gly Arg Gly Lys Ala
340 345 350

Gln Val Lys Ala Thr Asn Glu Ser Glu Asp Glu Ile Pro Gln Leu Val
355 360 365

Pro Ile Gly Lys Lys Thr Pro Ala Asn Glu Lys Val Glu Ile Gln Lys
370 375 380

His Ala Thr Gly Lys Lys Ser Pro Ala Lys Ser Pro Asn Pro Ser Thr
385 390 395 400

Pro Arg Gly Lys Lys Arg Lys Ala Leu Pro Ala Ser Glu Thr Pro Lys
405 410 415

Ala Ala Glu Ser Glu Thr Pro Gly Lys Ser Pro Glu Lys Lys Pro Lys
420 425 430

Ile Lys Glu Glu Ala Val Lys Glu Lys Ser Pro Ser Leu Gly Lys Lys
435 440 445

Asp Ala Arg Gln Thr Pro Lys Lys Pro Glu Ala Lys Phe Phe Thr Thr
450 455 460

Pro Ser Lys Ser Val Arg Lys Ala Ser His Thr Pro Lys Lys Trp Pro
465 470 475 480

Lys Lys Pro Lys Val Pro Gln Ser Thr
485

<210> SEQ ID NO 54
<211> LENGTH: 148
<212> TYPE: PRT
<213> ORGANISM: Artificial Sequence
<220> FEATURE:
<223> OTHER INFORMATION: Synthetic

<400> SEQUENCE: 54

Met Lys Ala Leu Ile Val Leu Gly Leu Val Leu Leu Ser Val Thr Val
1 5 10 15

Gln Gly Lys Val Phe Glu Arg Cys Glu Leu Ala Arg Thr Leu Lys Arg
20 25 30

Leu Gly Met Asp Gly Tyr Arg Gly Ile Ser Leu Ala Asn Trp Met Cys

```
        35                  40                  45

Leu Ala Lys Trp Glu Ser Gly Tyr Asn Thr Arg Ala Thr Asn Tyr Asn
    50                  55                  60

Ala Gly Asp Arg Ser Thr Asp Tyr Gly Ile Phe Gln Ile Asn Ser Arg
65                  70                  75                  80

Tyr Trp Cys Asn Asp Gly Lys Thr Pro Gly Ala Val Asn Ala Cys His
                85                  90                  95

Leu Ser Cys Ser Ala Leu Leu Gln Asp Asn Ile Ala Asp Ala Val Ala
            100                 105                 110

Cys Ala Lys Arg Val Val Arg Asp Pro Gln Gly Ile Arg Ala Trp Val
        115                 120                 125

Ala Trp Arg Asn Arg Cys Gln Asn Arg Asp Val Arg Gln Tyr Val Gln
    130                 135                 140

Gly Cys Gly Val
145


<210> SEQ ID NO 55
<211> LENGTH: 1170
<212> TYPE: PRT
<213> ORGANISM: Artificial Sequence
<220> FEATURE:
<223> OTHER INFORMATION: Synthetic

<400> SEQUENCE: 55

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255
```

```
Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
    530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
    610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
```

-continued

```
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
    770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
    850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
        915                 920                 925

Ala Cys Lys Asp Asp Phe Asp His Asp Ser Val Pro Asp Ile Asp Asp
    930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
            980                 985                 990

Asp Pro Gly Leu Ala Val Gly Tyr  Asp Glu Phe Asn Ala  Val Asp Phe
        995                 1000                1005

Ser Gly  Thr Phe Phe Ile Asn  Thr Glu Arg Asp Asp  Asp Tyr Ala
    1010                1015                1020

Gly Phe  Val Phe Gly Tyr Gln  Ser Ser Ser Arg Phe  Tyr Val Val
    1025                1030                1035

Met Trp  Lys Gln Val Thr Gln  Ser Tyr Trp Asp Thr  Asn Pro Thr
    1040                1045                1050

Arg Ala  Gln Gly Tyr Ser Gly  Leu Ser Val Lys Val  Val Asn Ser
    1055                1060                1065

Thr Thr  Gly Pro Gly Glu His  Leu Arg Asn Ala Leu  Trp His Thr
    1070                1075                1080

Gly Asn  Thr Pro Gly Gln Val  Arg Thr Leu Trp His  Asp Pro Arg
    1085                1090                1095
```

-continued

```
His Ile  Gly Trp Lys Asp Phe  Thr Ala Tyr Arg Trp  Arg Leu Ser
    1100                 1105                 1110

His Arg  Pro Lys Thr Gly Phe  Ile Arg Val Val Met  Tyr Glu Gly
    1115                 1120                 1125

Lys Lys  Ile Met Ala Asp Ser  Gly Pro Ile Tyr Asp  Lys Thr Tyr
    1130                 1135                 1140

Ala Gly  Gly Arg Leu Gly Leu  Phe Val Phe Ser Gln  Glu Met Val
    1145                 1150                 1155

Phe Phe  Ser Asp Leu Lys Tyr  Glu Cys Arg Asp Pro
    1160                 1165                 1170


<210> SEQ ID NO 56
<211> LENGTH: 1349
<212> TYPE: PRT
<213> ORGANISM: Artificial Sequence
<220> FEATURE:
<223> OTHER INFORMATION: Synthetic

<400> SEQUENCE: 56

Met Lys Lys Ile Arg Ile Cys His Ile Phe Thr Phe Tyr Ser Trp Met
1               5                   10                  15

Ser Tyr Asp Val Leu Phe Gln Arg Thr Glu Leu Gly Ala Leu Glu Ile
            20                  25                  30

Trp Arg Gln Leu Ile Cys Ala His Val Cys Ile Cys Val Gly Trp Leu
        35                  40                  45

Tyr Leu Arg Asp Arg Val Cys Ser Lys Lys Asp Ile Ile Leu Arg Thr
    50                  55                  60

Glu Gln Asn Ser Gly Arg Thr Ile Leu Ile Lys Ala Val Thr Glu Lys
65                  70                  75                  80

Asn Phe Glu Thr Lys Asp Phe Arg Ala Ser Leu Glu Asn Gly Val Leu
                85                  90                  95

Leu Cys Asp Leu Ile Asn Lys Leu Lys Pro Gly Val Ile Lys Lys Ile
            100                 105                 110

Asn Arg Leu Ser Thr Pro Ile Ala Gly Leu Asp Asn Ile Asn Val Phe
        115                 120                 125

Leu Lys Ala Cys Glu Gln Ile Gly Leu Lys Glu Ala Gln Leu Phe His
    130                 135                 140

Pro Gly Asp Leu Gln Asp Leu Ser Asn Arg Val Thr Val Lys Gln Glu
145                 150                 155                 160

Glu Thr Asp Arg Arg Val Lys Asn Val Leu Ile Thr Leu Tyr Trp Leu
                165                 170                 175

Gly Arg Lys Ala Gln Ser Asn Pro Tyr Tyr Asn Gly Pro His Leu Asn
            180                 185                 190

Leu Lys Ala Phe Glu Asn Leu Leu Gly Gln Ala Leu Thr Lys Ala Leu
        195                 200                 205

Glu Asp Ser Ser Phe Leu Lys Arg Ser Gly Arg Asp Ser Gly Tyr Gly
    210                 215                 220

Asp Ile Trp Cys Pro Glu Arg Gly Glu Phe Leu Ala Pro Pro Arg His
225                 230                 235                 240

His Lys Arg Glu Asp Ser Phe Glu Ser Leu Asp Ser Leu Gly Ser Arg
                245                 250                 255

Ser Leu Thr Ser Cys Ser Ser Asp Ile Thr Leu Arg Gly Gly Arg Glu
            260                 265                 270

Gly Phe Glu Ser Asp Thr Asp Ser Glu Phe Thr Phe Lys Met Gln Asp
        275                 280                 285

Tyr Asn Lys Asp Asp Met Ser Tyr Arg Arg Ile Ser Ala Val Glu Pro
```

```
    290                 295                 300

Lys Thr Ala Leu Pro Phe Asn Arg Phe Leu Pro Asn Lys Ser Arg Gln
305                 310                 315                 320

Pro Ser Tyr Val Pro Ala Pro Leu Arg Lys Lys Lys Pro Asp Lys His
                325                 330                 335

Glu Asp Asn Arg Arg Ser Trp Ala Ser Pro Val Tyr Thr Glu Ala Asp
            340                 345                 350

Gly Thr Phe Ser Arg Leu Phe Gln Lys Ile Tyr Gly Glu Asn Gly Ser
        355                 360                 365

Lys Ser Met Ser Asp Val Ser Ala Glu Asp Val Gln Asn Leu Arg Gln
    370                 375                 380

Leu Arg Tyr Glu Glu Met Gln Lys Ile Lys Ser Gln Leu Lys Glu Gln
385                 390                 395                 400

Asp Gln Lys Trp Gln Asp Asp Leu Ala Lys Trp Lys Asp Arg Arg Lys
                405                 410                 415

Ser Tyr Thr Ser Asp Leu Gln Lys Lys Lys Glu Glu Arg Glu Glu Ile
            420                 425                 430

Glu Lys Gln Ala Leu Glu Lys Ser Lys Arg Ser Ser Lys Thr Phe Lys
        435                 440                 445

Glu Met Leu Gln Asp Arg Glu Ser Gln Asn Gln Lys Ser Thr Val Pro
    450                 455                 460

Ser Arg Arg Arg Met Tyr Ser Phe Asp Asp Val Leu Glu Glu Gly Lys
465                 470                 475                 480

Arg Pro Pro Thr Met Thr Val Ser Glu Ala Ser Tyr Gln Ser Glu Arg
                485                 490                 495

Val Glu Glu Lys Gly Ala Thr Tyr Pro Ser Glu Ile Pro Lys Glu Asp
            500                 505                 510

Ser Thr Thr Phe Ala Lys Arg Glu Asp Arg Val Thr Thr Glu Ile Gln
        515                 520                 525

Leu Pro Ser Gln Ser Pro Val Glu Glu Gln Ser Pro Ala Ser Leu Ser
    530                 535                 540

Ser Leu Arg Ser Arg Ser Thr Gln Met Glu Ser Thr Arg Val Ser Ala
545                 550                 555                 560

Ser Leu Pro Arg Ser Tyr Arg Lys Thr Asp Thr Val Arg Leu Thr Ser
                565                 570                 575

Val Val Thr Pro Arg Pro Phe Gly Ser Gln Thr Arg Gly Ile Ser Ser
            580                 585                 590

Leu Pro Arg Ser Tyr Thr Met Asp Asp Ala Trp Lys Tyr Asn Gly Asp
        595                 600                 605

Ile Glu Asp Ile Lys Arg Thr Pro Asn Asn Val Val Ser Thr Pro Ala
    610                 615                 620

Pro Ser Pro Asp Ala Ser Gln Leu Ala Ser Ser Leu Ser Ser Gln Lys
625                 630                 635                 640

Glu Val Ala Ala Thr Glu Glu Asp Val Thr Arg Leu Pro Ser Pro Thr
                645                 650                 655

Ser Pro Phe Ser Ser Leu Ser Gln Asp Gln Ala Ala Thr Ser Lys Ala
            660                 665                 670

Thr Leu Ser Ser Thr Ser Gly Leu Asp Leu Met Ser Glu Ser Gly Glu
        675                 680                 685

Gly Glu Ile Ser Pro Gln Arg Glu Val Ser Arg Ser Gln Asp Gln Phe
    690                 695                 700

Ser Asp Met Arg Ile Ser Ile Asn Gln Thr Pro Gly Lys Ser Leu Asp
705                 710                 715                 720
```

-continued

```
Phe Gly Phe Thr Ile Lys Trp Asp Ile Pro Gly Ile Phe Val Ala Ser
                725                 730                 735

Val Glu Ala Gly Ser Pro Ala Glu Phe Ser Gln Leu Gln Val Asp Asp
            740                 745                 750

Glu Ile Ile Ala Ile Asn Asn Thr Lys Phe Ser Tyr Asn Asp Ser Lys
        755                 760                 765

Glu Trp Glu Glu Ala Met Ala Lys Ala Gln Glu Thr Gly His Leu Val
    770                 775                 780

Met Asp Val Arg Arg Tyr Gly Lys Ala Gly Ser Pro Glu Thr Lys Trp
785                 790                 795                 800

Ile Asp Ala Thr Ser Gly Ile Tyr Asn Ser Glu Lys Ser Ser Asn Leu
                805                 810                 815

Ser Val Thr Thr Asp Phe Ser Glu Ser Leu Gln Ser Ser Asn Ile Glu
            820                 825                 830

Ser Lys Glu Ile Asn Gly Ile His Asp Glu Ser Asn Ala Phe Glu Ser
        835                 840                 845

Lys Ala Ser Glu Ser Ile Ser Leu Lys Asn Leu Lys Arg Arg Ser Gln
    850                 855                 860

Phe Phe Glu Gln Gly Ser Ser Asp Ser Val Val Pro Asp Leu Pro Val
865                 870                 875                 880

Pro Thr Ile Ser Ala Pro Ser Arg Trp Val Trp Asp Gln Glu Glu Glu
                885                 890                 895

Arg Lys Arg Gln Glu Arg Trp Gln Lys Glu Gln Asp Arg Leu Leu Gln
            900                 905                 910

Glu Lys Tyr Gln Arg Glu Gln Glu Lys Leu Arg Glu Glu Trp Gln Arg
        915                 920                 925

Ala Lys Gln Glu Ala Glu Arg Glu Asn Ser Lys Tyr Leu Asp Glu Glu
    930                 935                 940

Leu Met Val Leu Ser Ser Asn Ser Met Ser Leu Thr Thr Arg Glu Pro
945                 950                 955                 960

Ser Leu Ala Thr Trp Glu Ala Thr Trp Ser Glu Gly Ser Lys Ser Ser
                965                 970                 975

Asp Arg Glu Gly Thr Arg Ala Gly Glu Glu Glu Arg Arg Gln Pro Gln
            980                 985                 990

Glu Glu Val Val His Glu Asp Gln  Gly Lys Lys Pro Gln  Asp Gln Leu
        995                 1000                1005

Val Ile  Glu Arg Glu Arg Lys  Trp Glu Gln Gln Leu  Gln Glu Glu
    1010                1015                1020

Gln Glu  Gln Lys Arg Leu Gln  Ala Glu Ala Glu Glu  Gln Lys Arg
    1025                1030                1035

Pro Ala  Glu Glu Gln Lys Arg  Gln Ala Glu Ile Glu  Arg Glu Thr
    1040                1045                1050

Ser Val  Arg Ile Tyr Gln Tyr  Arg Arg Pro Val Asp  Ser Tyr Asp
    1055                1060                1065

Ile Pro  Lys Thr Glu Glu Ala  Ser Ser Gly Phe Leu  Pro Gly Asp
    1070                1075                1080

Arg Asn  Lys Ser Arg Ser Thr  Thr Glu Leu Asp Asp  Tyr Ser Thr
    1085                1090                1095

Asn Lys  Asn Gly Asn Asn Lys  Tyr Leu Asp Gln Ile  Gly Asn Met
    1100                1105                1110

Thr Ser  Ser Gln Arg Arg Ser  Lys Lys Glu Gln Val  Pro Ser Gly
    1115                1120                1125

Ala Glu  Leu Glu Arg Gln Gln  Ile Leu Gln Glu Met  Arg Lys Arg
    1130                1135                1140
```

Thr Pro Leu His Asn Asp Asn Ser Trp Ile Arg Gln Arg Ser Ala
1145 1150 1155

Ser Val Asn Lys Glu Pro Val Ser Leu Pro Gly Ile Met Arg Arg
1160 1165 1170

Gly Glu Ser Leu Asp Asn Leu Asp Ser Pro Arg Ser Asn Ser Trp
1175 1180 1185

Arg Gln Pro Pro Trp Leu Asn Gln Pro Thr Gly Phe Tyr Ala Ser
1190 1195 1200

Ser Ser Val Gln Asp Phe Ser Arg Pro Pro Pro Gln Leu Val Ser
1205 1210 1215

Thr Ser Asn Arg Ala Tyr Met Arg Asn Pro Ser Ser Ser Val Pro
1220 1225 1230

Pro Pro Ser Ala Gly Ser Val Lys Thr Ser Thr Thr Gly Val Ala
1235 1240 1245

Thr Thr Gln Ser Pro Thr Pro Arg Ser His Ser Pro Ser Ala Ser
1250 1255 1260

Gln Ser Gly Ser Gln Leu Arg Asn Arg Ser Val Ser Gly Lys Arg
1265 1270 1275

Ile Cys Ser Tyr Cys Asn Asn Ile Leu Gly Lys Gly Ala Ala Met
1280 1285 1290

Ile Ile Glu Ser Leu Gly Leu Cys Tyr His Leu His Cys Phe Lys
1295 1300 1305

Cys Val Ala Cys Glu Cys Asp Leu Gly Gly Ser Ser Ser Gly Ala
1310 1315 1320

Glu Val Arg Ile Arg Asn His Gln Leu Tyr Cys Asn Asp Cys Tyr
1325 1330 1335

Leu Arg Phe Lys Ser Gly Arg Pro Thr Ala Met
1340 1345

<210> SEQ ID NO 57
<211> LENGTH: 2201
<212> TYPE: PRT
<213> ORGANISM: Artificial Sequence
<220> FEATURE:
<223> OTHER INFORMATION: Synthetic

<400> SEQUENCE: 57

Met Gly Ala Met Thr Gln Leu Leu Ala Gly Val Phe Leu Ala Phe Leu
1 5 10 15

Ala Leu Ala Thr Glu Gly Gly Val Leu Lys Lys Val Ile Arg His Lys
20 25 30

Arg Gln Ser Gly Val Asn Ala Thr Leu Pro Glu Glu Asn Gln Pro Val
35 40 45

Val Phe Asn His Val Tyr Asn Ile Lys Leu Pro Val Gly Ser Gln Cys
50 55 60

Ser Val Asp Leu Glu Ser Ala Ser Gly Glu Lys Asp Leu Ala Pro Pro
65 70 75 80

Ser Glu Pro Ser Glu Ser Phe Gln Glu His Thr Val Asp Gly Glu Asn
85 90 95

Gln Ile Val Phe Thr His Arg Ile Asn Ile Pro Arg Arg Ala Cys Gly
100 105 110

Cys Ala Ala Ala Pro Asp Val Lys Glu Leu Leu Ser Arg Leu Glu Glu
115 120 125

Leu Glu Asn Leu Val Ser Ser Leu Arg Glu Gln Cys Thr Ala Gly Ala
130 135 140

-continued

```
Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Val Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575
```

```
Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp  Lys Thr Pro
```

-continued 995 1000 1005

Leu Ala Lys Phe Asp Arg Tyr Arg Leu Asn Tyr Ser Leu Pro Thr
1010 1015 1020

Gly Gln Trp Val Gly Val Gln Leu Pro Arg Asn Thr Thr Ser Tyr
1025 1030 1035

Val Leu Arg Gly Leu Glu Pro Gly Gln Glu Tyr Asn Val Leu Leu
1040 1045 1050

Thr Ala Glu Lys Gly Arg His Lys Ser Lys Pro Ala Arg Val Lys
1055 1060 1065

Ala Ser Thr Glu Gln Ala Pro Glu Leu Glu Asn Leu Thr Val Thr
1070 1075 1080

Glu Val Gly Trp Asp Gly Leu Arg Leu Asn Trp Thr Ala Ala Asp
1085 1090 1095

Gln Ala Tyr Glu His Phe Ile Ile Gln Val Gln Glu Ala Asn Lys
1100 1105 1110

Val Glu Ala Ala Arg Asn Leu Thr Val Pro Gly Ser Leu Arg Ala
1115 1120 1125

Val Asp Ile Pro Gly Leu Lys Ala Ala Thr Pro Tyr Thr Val Ser
1130 1135 1140

Ile Tyr Gly Val Ile Gln Gly Tyr Arg Thr Pro Val Leu Ser Ala
1145 1150 1155

Glu Ala Ser Thr Gly Glu Thr Pro Asn Leu Gly Glu Val Val Val
1160 1165 1170

Ala Glu Val Gly Trp Asp Ala Leu Lys Leu Asn Trp Thr Ala Pro
1175 1180 1185

Glu Gly Ala Tyr Glu Tyr Phe Phe Ile Gln Val Gln Glu Ala Asp
1190 1195 1200

Thr Val Glu Ala Ala Gln Asn Leu Thr Val Pro Gly Gly Leu Arg
1205 1210 1215

Ser Thr Asp Leu Pro Gly Leu Lys Ala Ala Thr His Tyr Thr Ile
1220 1225 1230

Thr Ile Arg Gly Val Thr Gln Asp Phe Ser Thr Thr Pro Leu Ser
1235 1240 1245

Val Glu Val Leu Thr Glu Glu Val Pro Asp Met Gly Asn Leu Thr
1250 1255 1260

Val Thr Glu Val Ser Trp Asp Ala Leu Arg Leu Asn Trp Thr Thr
1265 1270 1275

Pro Asp Gly Thr Tyr Asp Gln Phe Thr Ile Gln Val Gln Glu Ala
1280 1285 1290

Asp Gln Val Glu Glu Ala His Asn Leu Thr Val Pro Gly Ser Leu
1295 1300 1305

Arg Ser Met Glu Ile Pro Gly Leu Arg Ala Gly Thr Pro Tyr Thr
1310 1315 1320

Val Thr Leu His Gly Glu Val Arg Gly His Ser Thr Arg Pro Leu
1325 1330 1335

Ala Val Glu Val Val Thr Glu Asp Leu Pro Gln Leu Gly Asp Leu
1340 1345 1350

Ala Val Ser Glu Val Gly Trp Asp Gly Leu Arg Leu Asn Trp Thr
1355 1360 1365

Ala Ala Asp Asn Ala Tyr Glu His Phe Val Ile Gln Val Gln Glu
1370 1375 1380

Val Asn Lys Val Glu Ala Ala Gln Asn Leu Thr Leu Pro Gly Ser
1385 1390 1395

-continued

```
Leu Arg  Ala Val Asp Ile Pro  Gly Leu Glu Ala Ala  Thr Pro Tyr
    1400                 1405                 1410

Arg Val  Ser Ile Tyr Gly Val  Ile Arg Gly Tyr Arg  Thr Pro Val
    1415                 1420                 1425

Leu Ser  Ala Glu Ala Ser Thr  Ala Lys Glu Pro Glu  Ile Gly Asn
    1430                 1435                 1440

Leu Asn  Val Ser Asp Ile Thr  Pro Glu Ser Phe Asn  Leu Ser Trp
    1445                 1450                 1455

Met Ala  Thr Asp Gly Ile Phe  Glu Thr Phe Thr Ile  Glu Ile Ile
    1460                 1465                 1470

Asp Ser  Asn Arg Leu Leu Glu  Thr Val Glu Tyr Asn  Ile Ser Gly
    1475                 1480                 1485

Ala Glu  Arg Thr Ala His Ile  Ser Gly Leu Pro Pro  Ser Thr Asp
    1490                 1495                 1500

Phe Ile  Val Tyr Leu Ser Gly  Leu Ala Pro Ser Ile  Arg Thr Lys
    1505                 1510                 1515

Thr Ile  Ser Ala Thr Ala Thr  Thr Glu Ala Leu Pro  Leu Leu Glu
    1520                 1525                 1530

Asn Leu  Thr Ile Ser Asp Ile  Asn Pro Tyr Gly Phe  Thr Val Ser
    1535                 1540                 1545

Trp Met  Ala Ser Glu Asn Ala  Phe Asp Ser Phe Leu  Val Thr Val
    1550                 1555                 1560

Val Asp  Ser Gly Lys Leu Leu  Asp Pro Gln Glu Phe  Thr Leu Ser
    1565                 1570                 1575

Gly Thr  Gln Arg Lys Leu Glu  Leu Arg Gly Leu Ile  Thr Gly Ile
    1580                 1585                 1590

Gly Tyr  Glu Val Met Val Ser  Gly Phe Thr Gln Gly  His Gln Thr
    1595                 1600                 1605

Lys Pro  Leu Arg Ala Glu Ile  Val Thr Glu Ala Glu  Pro Glu Val
    1610                 1615                 1620

Asp Asn  Leu Leu Val Ser Asp  Ala Thr Pro Asp Gly  Phe Arg Leu
    1625                 1630                 1635

Ser Trp  Thr Ala Asp Glu Gly  Val Phe Asp Asn Phe  Val Leu Lys
    1640                 1645                 1650

Ile Arg  Asp Thr Lys Lys Gln  Ser Glu Pro Leu Glu  Ile Thr Leu
    1655                 1660                 1665

Leu Ala  Pro Glu Arg Thr Arg  Asp Ile Thr Gly Leu  Arg Glu Ala
    1670                 1675                 1680

Thr Glu  Tyr Glu Ile Glu Leu  Tyr Gly Ile Ser Lys  Gly Arg Arg
    1685                 1690                 1695

Ser Gln  Thr Val Ser Ala Ile  Ala Thr Thr Ala Met  Gly Ser Pro
    1700                 1705                 1710

Lys Glu  Val Ile Phe Ser Asp  Ile Thr Glu Asn Ser  Ala Thr Val
    1715                 1720                 1725

Ser Trp  Arg Ala Pro Thr Ala  Gln Val Glu Ser Phe  Arg Ile Thr
    1730                 1735                 1740

Tyr Val  Pro Ile Thr Gly Gly  Thr Pro Ser Met Val  Thr Val Asp
    1745                 1750                 1755

Gly Thr  Lys Thr Gln Thr Arg  Leu Val Lys Leu Ile  Pro Gly Val
    1760                 1765                 1770

Glu Tyr  Leu Val Ser Ile Ile  Ala Met Lys Gly Phe  Glu Glu Ser
    1775                 1780                 1785

Glu Pro  Val Ser Gly Ser Phe  Thr Thr Ala Leu Asp  Gly Pro Ser
    1790                 1795                 1800
```

```
Gly Leu  Val Thr Ala Asn Ile  Thr Asp Ser Glu Ala  Leu Ala Arg
    1805                 1810                 1815

Trp Gln  Pro Ala Ile Ala Thr  Val Asp Ser Tyr Val  Ile Ser Tyr
    1820                 1825                 1830

Thr Gly  Glu Lys Val Pro Glu  Ile Thr Arg Thr Val  Ser Gly Asn
    1835                 1840                 1845

Thr Val  Glu Tyr Ala Leu Thr  Asp Leu Glu Pro Ala  Thr Glu Tyr
    1850                 1855                 1860

Thr Leu  Arg Ile Phe Ala Glu  Lys Gly Pro Gln Lys  Ser Ser Thr
    1865                 1870                 1875

Ile Thr  Ala Lys Phe Thr Thr  Asp Leu Asp Ser Pro  Arg Asp Leu
    1880                 1885                 1890

Thr Ala  Thr Glu Val Gln Ser  Glu Thr Ala Leu Leu  Thr Trp Arg
    1895                 1900                 1905

Pro Pro  Arg Ala Ser Val Thr  Gly Tyr Leu Leu Val  Tyr Glu Ser
    1910                 1915                 1920

Val Asp  Gly Thr Val Lys Glu  Val Ile Val Gly Pro  Asp Thr Thr
    1925                 1930                 1935

Ser Tyr  Ser Leu Ala Asp Leu  Ser Pro Ser Thr His  Tyr Thr Ala
    1940                 1945                 1950

Lys Ile  Gln Ala Leu Asn Gly  Pro Leu Arg Ser Asn  Met Ile Gln
    1955                 1960                 1965

Thr Ile  Phe Thr Thr Ile Gly  Leu Leu Tyr Pro Phe  Pro Lys Asp
    1970                 1975                 1980

Cys Ser  Gln Ala Met Leu Asn  Gly Asp Thr Thr Ser  Gly Leu Tyr
    1985                 1990                 1995

Thr Ile  Tyr Leu Asn Gly Asp  Lys Ala Glu Ala Leu  Glu Val Phe
    2000                 2005                 2010

Cys Asp  Met Thr Ser Asp Gly  Gly Gly Trp Ile Val  Phe Leu Arg
    2015                 2020                 2025

Arg Lys  Asn Gly Arg Glu Asn  Phe Tyr Gln Asn Trp  Lys Ala Tyr
    2030                 2035                 2040

Ala Ala  Gly Phe Gly Asp Arg  Arg Glu Glu Phe Trp  Leu Gly Leu
    2045                 2050                 2055

Asp Asn  Leu Asn Lys Ile Thr  Ala Gln Gly Gln Tyr  Glu Leu Arg
    2060                 2065                 2070

Val Asp  Leu Arg Asp His Gly  Glu Thr Ala Phe Ala  Val Tyr Asp
    2075                 2080                 2085

Lys Phe  Ser Val Gly Asp Ala  Lys Thr Arg Tyr Lys  Leu Lys Val
    2090                 2095                 2100

Glu Gly  Tyr Ser Gly Thr Ala  Gly Asp Ser Met Ala  Tyr His Asn
    2105                 2110                 2115

Gly Arg  Ser Phe Ser Thr Phe  Asp Lys Asp Thr Asp  Ser Ala Ile
    2120                 2125                 2130

Thr Asn  Cys Ala Leu Ser Tyr  Lys Gly Ala Phe Trp  Tyr Arg Asn
    2135                 2140                 2145

Cys His  Arg Val Asn Leu Met  Gly Arg Tyr Gly Asp  Asn Asn His
    2150                 2155                 2160

Ser Gln  Gly Val Asn Trp Phe  His Trp Lys Gly His  Glu His Ser
    2165                 2170                 2175

Ile Gln  Phe Ala Glu Met Lys  Leu Arg Pro Ser Asn  Phe Arg Asn
    2180                 2185                 2190

Leu Glu  Gly Arg Arg Lys Arg  Ala
```

2195 2200

<210> SEQ ID NO 58
<211> LENGTH: 524
<212> TYPE: PRT
<213> ORGANISM: Artificial Sequence
<220> FEATURE:
<223> OTHER INFORMATION: Synthetic

<400> SEQUENCE: 58

Met Ala Asp Asp Ile Asp Ile Glu Ala Met Leu Glu Ala Pro Tyr Lys
1 5 10 15

Lys Asp Glu Asn Lys Leu Ser Ser Ala Asn Gly His Glu Glu Arg Ser
20 25 30

Lys Lys Arg Lys Lys Ser Lys Ser Arg Ser Arg Ser His Glu Arg Lys
35 40 45

Arg Ser Lys Ser Lys Glu Arg Lys Arg Ser Arg Asp Arg Glu Arg Lys
50 55 60

Lys Ser Lys Ser Arg Glu Arg Lys Arg Ser Arg Ser Lys Glu Arg Arg
65 70 75 80

Arg Ser Arg Ser Arg Ser Arg Asp Arg Arg Phe Arg Gly Arg Tyr Arg
85 90 95

Ser Pro Tyr Ser Gly Pro Lys Phe Asn Ser Ala Ile Arg Gly Lys Ile
100 105 110

Gly Leu Pro His Ser Ile Lys Leu Ser Arg Arg Arg Ser Arg Ser Lys
115 120 125

Ser Pro Phe Arg Lys Asp Lys Ser Pro Val Arg Glu Pro Ile Asp Asn
130 135 140

Leu Thr Pro Glu Glu Arg Asp Ala Arg Thr Val Phe Cys Met Gln Leu
145 150 155 160

Ala Ala Arg Ile Arg Pro Arg Asp Leu Glu Glu Phe Phe Ser Thr Val
165 170 175

Gly Lys Val Arg Asp Val Arg Met Ile Ser Asp Arg Asn Ser Arg Arg
180 185 190

Ser Lys Gly Ile Ala Tyr Val Glu Phe Val Asp Val Ser Ser Val Pro
195 200 205

Leu Ala Ile Gly Leu Thr Gly Gln Arg Val Leu Gly Val Pro Ile Ile
210 215 220

Val Gln Ala Ser Gln Ala Glu Lys Asn Arg Ala Ala Ala Met Ala Asn
225 230 235 240

Asn Leu Gln Lys Gly Ser Ala Gly Pro Met Arg Leu Tyr Val Gly Ser
245 250 255

Leu His Phe Asn Ile Thr Glu Asp Met Leu Arg Gly Ile Phe Glu Pro
260 265 270

Phe Gly Arg Ile Glu Ser Ile Gln Leu Met Met Asp Ser Glu Thr Gly
275 280 285

Arg Ser Lys Gly Tyr Gly Phe Ile Thr Phe Ser Asp Ser Glu Cys Ala
290 295 300

Lys Lys Ala Leu Glu Gln Leu Asn Gly Phe Glu Leu Ala Gly Arg Pro
305 310 315 320

Met Lys Val Gly His Val Thr Glu Arg Thr Asp Ala Ser Ser Ala Ser
325 330 335

Ser Phe Leu Asp Ser Asp Glu Leu Glu Arg Thr Gly Ile Asp Leu Gly
340 345 350

Thr Thr Gly Arg Leu Gln Leu Met Ala Arg Leu Ala Glu Gly Thr Gly
355 360 365

```
Leu Gln Ile Pro Pro Ala Ala Gln Gln Ala Leu Gln Met Ser Gly Ser
    370                 375                 380

Leu Ala Phe Gly Ala Val Ala Asp Leu Gln Thr Arg Leu Ser Gln Gln
385                 390                 395                 400

Thr Glu Ala Ser Ala Leu Ala Ala Ala Ala Ser Val Gln Pro Leu Ala
                405                 410                 415

Thr Gln Cys Phe Gln Leu Ser Asn Met Phe Asn Pro Gln Thr Glu Glu
            420                 425                 430

Glu Val Gly Trp Asp Thr Glu Ile Lys Asp Asp Val Ile Glu Glu Cys
        435                 440                 445

Asn Lys His Gly Gly Val Ile His Ile Tyr Val Asp Lys Asn Ser Ala
    450                 455                 460

Gln Gly Asn Val Tyr Val Lys Cys Pro Ser Ile Ala Ala Ala Ile Ala
465                 470                 475                 480

Ala Val Asn Ala Leu His Gly Arg Trp Phe Ala Gly Lys Met Ile Thr
                485                 490                 495

Ala Ala Tyr Val Pro Leu Pro Thr Tyr His Asn Leu Phe Pro Asp Ser
            500                 505                 510

Met Thr Ala Thr Gln Leu Leu Val Pro Ser Arg Arg
        515                 520


<210> SEQ ID NO 59
<211> LENGTH: 632
<212> TYPE: PRT
<213> ORGANISM: Artificial Sequence
<220> FEATURE:
<223> OTHER INFORMATION: Synthetic

<400> SEQUENCE: 59

Met Glu Thr Pro Ala Ala Ala Ala Pro Ala Gly Ser Leu Phe Pro Ser
1               5                   10                  15

Phe Leu Leu Leu Ala Cys Gly Thr Leu Val Ala Ala Leu Leu Gly Ala
            20                  25                  30

Ala His Arg Leu Gly Leu Phe Tyr Gln Leu Leu His Lys Val Asp Lys
        35                  40                  45

Ala Ser Val Arg His Gly Gly Glu Asn Val Ala Ala Val Leu Arg Ala
    50                  55                  60

His Gly Val Arg Phe Ile Phe Thr Leu Val Gly Gly His Ile Ser Pro
65                  70                  75                  80

Leu Leu Val Ala Cys Glu Lys Leu Gly Ile Arg Val Val Asp Thr Arg
                85                  90                  95

His Glu Val Thr Ala Val Phe Ala Ala Asp Ala Met Ala Arg Leu Ser
            100                 105                 110

Gly Thr Val Gly Val Ala Ala Val Thr Ala Gly Pro Gly Leu Thr Asn
        115                 120                 125

Thr Val Thr Ala Val Lys Asn Ala Gln Met Ala Gln Ser Pro Ile Leu
    130                 135                 140

Leu Leu Gly Gly Ala Ala Ser Thr Leu Leu Gln Asn Arg Gly Ala Leu
145                 150                 155                 160

Gln Ala Val Asp Gln Leu Ser Leu Phe Arg Pro Leu Cys Lys Phe Cys
                165                 170                 175

Val Ser Val Arg Arg Val Arg Asp Ile Val Pro Thr Leu Arg Ala Ala
            180                 185                 190

Met Ala Ala Ala Gln Ser Gly Thr Pro Gly Pro Val Phe Val Glu Leu
        195                 200                 205
```

-continued

```
Pro Val Asp Val Leu Tyr Pro Tyr Phe Met Val Gln Lys Glu Met Val
    210                 215                 220

Pro Ala Lys Pro Pro Lys Gly Leu Val Gly Arg Val Val Ser Trp Tyr
225                 230                 235                 240

Leu Glu Asn Tyr Leu Ala Asn Leu Phe Ala Gly Ala Trp Glu Pro Gln
                245                 250                 255

Pro Glu Gly Pro Leu Pro Leu Asp Ile Pro Gln Ala Ser Pro Gln Gln
            260                 265                 270

Val Gln Arg Cys Val Glu Ile Leu Ser Arg Ala Lys Arg Pro Leu Met
        275                 280                 285

Val Leu Gly Ser Gln Ala Leu Leu Thr Pro Thr Ser Ala Asp Lys Leu
    290                 295                 300

Arg Ala Ala Val Glu Thr Leu Gly Val Pro Cys Phe Leu Gly Gly Met
305                 310                 315                 320

Ala Arg Gly Leu Leu Gly Arg Asn His Pro Leu His Ile Arg Glu Asn
                325                 330                 335

Arg Ser Ala Ala Leu Lys Lys Ala Asp Val Ile Val Leu Ala Gly Thr
            340                 345                 350

Val Cys Asp Phe Arg Leu Ser Tyr Gly Arg Val Leu Ser His Ser Ser
        355                 360                 365

Lys Ile Ile Ile Val Asn Arg Asn Arg Glu Glu Met Leu Leu Asn Ser
    370                 375                 380

Asp Ile Phe Trp Lys Pro Gln Glu Ala Val Gln Gly Asp Val Gly Ser
385                 390                 395                 400

Phe Val Leu Lys Leu Val Glu Gly Leu Gln Gly Gln Thr Trp Ala Pro
                405                 410                 415

Asp Trp Val Glu Glu Leu Arg Glu Ala Asp Arg Gln Lys Glu Gln Thr
            420                 425                 430

Phe Arg Glu Lys Ala Ala Met Pro Val Ala Gln His Leu Asn Pro Val
        435                 440                 445

Gln Val Leu Gln Leu Val Glu Glu Thr Leu Pro Asp Asn Ser Ile Leu
    450                 455                 460

Val Val Asp Gly Gly Asp Phe Val Gly Thr Ala Ala His Leu Val Gln
465                 470                 475                 480

Pro Arg Gly Pro Leu Arg Trp Leu Asp Pro Gly Ala Phe Gly Thr Leu
                485                 490                 495

Gly Val Gly Ala Gly Phe Ala Leu Gly Ala Lys Leu Cys Arg Pro Asp
            500                 505                 510

Ala Glu Val Trp Cys Leu Phe Gly Asp Gly Ala Phe Gly Tyr Ser Leu
        515                 520                 525

Ile Glu Phe Asp Thr Phe Val Arg His Lys Ile Pro Val Met Ala Leu
    530                 535                 540

Val Gly Asn Asp Ala Gly Trp Thr Gln Ile Ser Arg Glu Gln Val Pro
545                 550                 555                 560

Ser Leu Gly Ser Asn Val Ala Cys Gly Leu Ala Tyr Thr Asp Tyr His
                565                 570                 575

Lys Ala Ala Met Gly Leu Gly Ala Arg Gly Leu Leu Leu Ser Arg Glu
            580                 585                 590

Asn Glu Asp Gln Val Val Lys Val Leu His Asp Ala Gln Gln Gln Cys
        595                 600                 605

Arg Asp Gly His Pro Val Val Val Asn Ile Leu Ile Gly Arg Thr Asp
    610                 615                 620

Phe Arg Asp Gly Ser Ile Ala Val
625                 630
```

<210> SEQ ID NO 60
<211> LENGTH: 468
<212> TYPE: PRT
<213> ORGANISM: Artificial Sequence
<220> FEATURE:
<223> OTHER INFORMATION: Synthetic

<400> SEQUENCE: 60

```
Met Gly Arg Gly Trp Gly Phe Leu Phe Gly Leu Leu Gly Ala Val Trp
1               5                   10                  15

Leu Leu Ser Ser Gly His Gly Glu Glu Gln Pro Pro Glu Thr Ala Ala
            20                  25                  30

Gln Arg Cys Phe Cys Gln Val Ser Gly Tyr Leu Asp Asp Cys Thr Cys
        35                  40                  45

Asp Val Glu Thr Ile Asp Arg Phe Asn Asn Tyr Arg Leu Phe Pro Arg
    50                  55                  60

Leu Gln Lys Leu Leu Glu Ser Asp Tyr Phe Arg Tyr Tyr Lys Val Asn
65                  70                  75                  80

Leu Lys Arg Pro Cys Pro Phe Trp Asn Asp Ile Ser Gln Cys Gly Arg
                85                  90                  95

Arg Asp Cys Ala Val Lys Pro Cys Gln Ser Asp Glu Val Pro Asp Gly
            100                 105                 110

Ile Lys Ser Ala Ser Tyr Lys Tyr Ser Glu Glu Ala Asn Asn Leu Ile
        115                 120                 125

Glu Glu Cys Glu Gln Ala Glu Arg Leu Gly Ala Val Asp Glu Ser Leu
    130                 135                 140

Ser Glu Glu Thr Gln Lys Ala Val Leu Gln Trp Thr Lys His Asp Asp
145                 150                 155                 160

Ser Ser Asp Asn Phe Cys Glu Ala Asp Asp Ile Gln Ser Pro Glu Ala
                165                 170                 175

Glu Tyr Val Asp Leu Leu Leu Asn Pro Glu Arg Tyr Thr Gly Tyr Lys
            180                 185                 190

Gly Pro Asp Ala Trp Lys Ile Trp Asn Val Ile Tyr Glu Glu Asn Cys
        195                 200                 205

Phe Lys Pro Gln Thr Ile Lys Arg Pro Leu Asn Pro Leu Ala Ser Gly
    210                 215                 220

Gln Gly Thr Ser Glu Glu Asn Thr Phe Tyr Ser Trp Leu Glu Gly Leu
225                 230                 235                 240

Cys Val Glu Lys Arg Ala Phe Tyr Arg Leu Ile Ser Gly Leu His Ala
                245                 250                 255

Ser Ile Asn Val His Leu Ser Ala Arg Tyr Leu Leu Gln Glu Thr Trp
            260                 265                 270

Leu Glu Lys Lys Trp Gly His Asn Ile Thr Glu Phe Gln Gln Arg Phe
        275                 280                 285

Asp Gly Ile Leu Thr Glu Gly Glu Gly Pro Arg Arg Leu Lys Asn Leu
    290                 295                 300

Tyr Phe Leu Tyr Leu Ile Glu Leu Arg Ala Leu Ser Lys Val Leu Pro
305                 310                 315                 320

Phe Phe Glu Arg Pro Asp Phe Gln Leu Phe Thr Gly Asn Lys Ile Gln
                325                 330                 335

Asp Glu Glu Asn Lys Met Leu Leu Leu Glu Ile Leu His Glu Ile Lys
            340                 345                 350

Ser Phe Pro Leu His Phe Asp Glu Asn Ser Phe Phe Ala Gly Asp Lys
        355                 360                 365
```

Lys Glu Ala His Lys Leu Lys Glu Asp Phe Arg Leu His Phe Arg Asn
    370                 375                 380

Ile Ser Arg Ile Met Asp Cys Val Gly Cys Phe Lys Cys Arg Leu Trp
385                 390                 395                 400

Gly Lys Leu Gln Thr Gln Gly Leu Gly Thr Ala Leu Lys Ile Leu Phe
                405                 410                 415

Ser Glu Lys Leu Ile Ala Asn Met Pro Glu Ser Gly Pro Ser Tyr Glu
            420                 425                 430

Phe His Leu Thr Arg Gln Glu Ile Val Ser Leu Phe Asn Ala Phe Gly
        435                 440                 445

Arg Ile Ser Thr Ser Val Lys Glu Leu Glu Asn Phe Arg Asn Leu Leu
    450                 455                 460

Gln Asn Ile His
465

<210> SEQ ID NO 61
<211> LENGTH: 568
<212> TYPE: PRT
<213> ORGANISM: Artificial Sequence
<220> FEATURE:
<223> OTHER INFORMATION: Synthetic

<400> SEQUENCE: 61

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Gly Thr Met Ser Gln Asp Thr Glu Val Asp Met
        35                  40                  45

Lys Glu Val Glu Leu Asn Glu Leu Glu Pro Glu Lys Gln Pro Met Asn
    50                  55                  60

Ala Ala Ser Gly Ala Ala Met Ser Leu Ala Gly Ala Glu Lys Asn Gly
65                  70                  75                  80

Leu Val Lys Ile Lys Val Ala Glu Asp Glu Ala Glu Ala Ala Ala Ala
                85                  90                  95

Ala Lys Phe Thr Gly Leu Ser Lys Glu Glu Leu Leu Lys Val Ala Gly
            100                 105                 110

Ser Pro Gly Trp Val Arg Thr Arg Trp Ala Leu Leu Leu Leu Phe Trp
        115                 120                 125

Leu Gly Trp Leu Gly Met Leu Ala Gly Ala Val Val Ile Ile Val Arg
    130                 135                 140

Ala Pro Arg Cys Arg Glu Leu Pro Ala Gln Lys Trp Trp His Thr Gly
145                 150                 155                 160

Ala Leu Tyr Arg Ile Gly Asp Leu Gln Ala Phe Gln Gly His Gly Ala
                165                 170                 175

Gly Asn Leu Ala Gly Leu Lys Gly Arg Leu Asp Tyr Leu Ser Ser Leu
            180                 185                 190

Lys Val Lys Gly Leu Val Leu Gly Pro Ile His Lys Asn Gln Lys Asp
        195                 200                 205

Asp Val Ala Gln Thr Asp Leu Leu Gln Ile Asp Pro Asn Phe Gly Ser
    210                 215                 220

Lys Glu Asp Phe Asp Ser Leu Leu Gln Ser Ala Lys Lys Lys Ser Ile
225                 230                 235                 240

Arg Val Ile Leu Asp Leu Thr Pro Asn Tyr Arg Gly Glu Asn Ser Trp
                245                 250                 255

Phe Ser Thr Gln Val Asp Thr Val Ala Thr Lys Val Lys Asp Ala Leu 260 265 270

Glu Phe Trp Leu Gln Ala Gly Val Asp Gly Phe Gln Val Arg Asp Ile
275 280 285

Glu Asn Leu Lys Asp Ala Ser Ser Phe Leu Ala Glu Trp Gln Asn Ile
290 295 300

Thr Lys Gly Phe Ser Glu Asp Arg Leu Leu Ile Ala Gly Thr Asn Ser
305 310 315 320

Ser Asp Leu Gln Gln Ile Leu Ser Leu Leu Glu Ser Asn Lys Asp Leu
325 330 335

Leu Leu Thr Ser Ser Tyr Leu Ser Asp Ser Gly Ser Thr Gly Glu His
340 345 350

Thr Lys Ser Leu Val Thr Gln Tyr Leu Asn Ala Thr Gly Asn Arg Trp
355 360 365

Cys Ser Trp Ser Leu Ser Gln Ala Arg Leu Leu Thr Ser Phe Leu Pro
370 375 380

Ala Gln Leu Leu Arg Leu Tyr Gln Leu Met Leu Phe Thr Leu Pro Gly
385 390 395 400

Thr Pro Val Phe Ser Tyr Gly Asp Glu Ile Gly Leu Asp Ala Ala Ala
405 410 415

Leu Pro Gly Gln Pro Met Glu Ala Pro Val Met Leu Trp Asp Glu Ser
420 425 430

Ser Phe Pro Asp Ile Pro Gly Ala Val Ser Ala Asn Met Thr Val Lys
435 440 445

Gly Gln Ser Glu Asp Pro Gly Ser Leu Leu Ser Leu Phe Arg Arg Leu
450 455 460

Ser Asp Gln Arg Ser Lys Glu Arg Ser Leu Leu His Gly Asp Phe His
465 470 475 480

Ala Phe Ser Ala Gly Pro Gly Leu Phe Ser Tyr Ile Arg His Trp Asp
485 490 495

Gln Asn Glu Arg Phe Leu Val Val Leu Asn Phe Gly Asp Val Gly Leu
500 505 510

Ser Ala Gly Leu Gln Ala Ser Asp Leu Pro Ala Ser Ala Ser Leu Pro
515 520 525

Ala Lys Ala Asp Leu Leu Leu Ser Thr Gln Pro Gly Arg Glu Glu Gly
530 535 540

Ser Pro Leu Glu Leu Glu Arg Leu Lys Leu Glu Pro His Glu Gly Leu
545 550 555 560

Leu Leu Arg Phe Pro Tyr Ala Ala
565

<210> SEQ ID NO 62
<211> LENGTH: 1412
<212> TYPE: PRT
<213> ORGANISM: Artificial Sequence
<220> FEATURE:
<223> OTHER INFORMATION: Synthetic

<400> SEQUENCE: 62

Met Ala Glu Ala Arg Lys Arg Arg Glu Leu Leu Pro Leu Ile Tyr His
1 5 10 15

His Leu Leu Arg Ala Gly Tyr Val Arg Ala Ala Arg Glu Val Lys Glu
20 25 30

Gln Ser Gly Gln Lys Cys Phe Leu Ala Gln Pro Val Thr Leu Leu Asp
35 40 45

Ile Tyr Thr His Trp Gln Gln Thr Ser Glu Leu Gly Arg Lys Arg Lys
50 55 60

-continued

```
Ala Glu Glu Asp Ala Ala Leu Gln Ala Lys Lys Thr Arg Val Ser Asp
65                  70                  75                  80

Pro Ile Ser Thr Ser Glu Ser Ser Glu Glu Glu Glu Glu Ala Glu Ala
                85                  90                  95

Glu Thr Ala Lys Ala Thr Pro Arg Leu Ala Ser Thr Asn Ser Ser Val
            100                 105                 110

Leu Gly Ala Asp Leu Pro Ser Ser Met Lys Glu Lys Ala Lys Ala Glu
        115                 120                 125

Thr Glu Lys Ala Gly Lys Thr Gly Asn Ser Met Pro His Pro Ala Thr
    130                 135                 140

Gly Lys Thr Val Ala Asn Leu Leu Ser Gly Lys Ser Pro Arg Lys Ser
145                 150                 155                 160

Ala Glu Pro Ser Ala Asn Thr Thr Leu Val Ser Glu Thr Glu Glu Glu
                165                 170                 175

Gly Ser Val Pro Ala Phe Gly Ala Ala Ala Lys Pro Gly Met Val Ser
            180                 185                 190

Ala Gly Gln Ala Asp Ser Ser Ser Glu Asp Thr Ser Ser Ser Ser Asp
        195                 200                 205

Glu Thr Asp Val Glu Val Lys Ala Ser Glu Lys Ile Leu Gln Val Arg
    210                 215                 220

Ala Ala Ser Ala Pro Ala Lys Gly Thr Pro Gly Lys Gly Ala Thr Pro
225                 230                 235                 240

Ala Pro Pro Gly Lys Ala Gly Ala Val Ala Ser Gln Thr Lys Ala Gly
                245                 250                 255

Lys Pro Glu Glu Asp Ser Glu Ser Ser Ser Glu Glu Ser Ser Asp Ser
            260                 265                 270

Glu Glu Glu Thr Pro Ala Ala Lys Ala Leu Leu Gln Ala Lys Ala Ser
        275                 280                 285

Gly Lys Thr Ser Gln Val Gly Ala Ala Ser Ala Pro Ala Lys Glu Ser
    290                 295                 300

Pro Arg Lys Gly Ala Ala Pro Ala Pro Pro Gly Lys Thr Gly Pro Ala
305                 310                 315                 320

Val Ala Lys Ala Gln Ala Gly Lys Arg Glu Glu Asp Ser Gln Ser Ser
                325                 330                 335

Ser Glu Glu Ser Asp Ser Glu Glu Glu Ala Pro Ala Gln Ala Lys Pro
            340                 345                 350

Ser Gly Lys Ala Pro Gln Val Arg Ala Ala Ser Ala Pro Ala Lys Glu
        355                 360                 365

Ser Pro Arg Lys Gly Ala Ala Pro Ala Pro Pro Arg Lys Thr Gly Pro
    370                 375                 380

Ala Ala Ala Gln Val Gln Val Gly Lys Gln Glu Glu Asp Ser Arg Ser
385                 390                 395                 400

Ser Ser Glu Glu Ser Asp Ser Asp Arg Glu Ala Leu Ala Ala Met Asn
                405                 410                 415

Ala Ala Gln Val Lys Pro Leu Gly Lys Ser Pro Gln Val Lys Pro Ala
            420                 425                 430

Ser Thr Met Gly Met Gly Pro Leu Gly Lys Gly Ala Gly Pro Val Pro
        435                 440                 445

Pro Gly Lys Val Gly Pro Ala Thr Pro Ser Ala Gln Val Gly Lys Trp
    450                 455                 460

Glu Glu Asp Ser Glu Ser Ser Ser Glu Glu Ser Ser Asp Ser Ser Asp
465                 470                 475                 480

Gly Glu Val Pro Thr Ala Val Ala Pro Ala Gln Glu Lys Ser Leu Gly
```

```
                485                 490                 495

Asn Ile Leu Gln Ala Lys Pro Thr Ser Ser Pro Ala Lys Gly Pro Pro
            500                 505                 510

Gln Lys Ala Gly Pro Val Ala Val Gln Val Lys Ala Glu Lys Pro Met
        515                 520                 525

Asp Asn Ser Glu Ser Ser Glu Glu Ser Ser Asp Ser Ala Asp Ser Glu
    530                 535                 540

Glu Ala Pro Ala Ala Met Thr Ala Ala Gln Ala Lys Pro Ala Leu Lys
545                 550                 555                 560

Ile Pro Gln Thr Lys Ala Cys Pro Lys Lys Thr Asn Thr Thr Ala Ser
                565                 570                 575

Ala Lys Val Ala Pro Val Arg Val Gly Thr Gln Pro Pro Arg Lys Ala
            580                 585                 590

Gly Thr Ala Thr Ser Pro Ala Gly Ser Ser Pro Ala Val Ala Gly Gly
        595                 600                 605

Thr Gln Arg Pro Ala Glu Asp Ser Ser Ser Ser Glu Glu Ser Asp Ser
    610                 615                 620

Glu Glu Glu Lys Thr Gly Leu Ala Val Thr Val Gly Gln Ala Lys Ser
625                 630                 635                 640

Val Gly Lys Gly Leu Gln Val Lys Ala Ala Ser Val Pro Val Lys Gly
                645                 650                 655

Ser Leu Gly Gln Gly Thr Ala Pro Val Leu Pro Gly Lys Thr Gly Pro
            660                 665                 670

Thr Val Thr Gln Val Lys Ala Glu Lys Gln Glu Asp Ser Glu Ser Ser
        675                 680                 685

Glu Glu Glu Ser Asp Ser Glu Glu Ala Ala Ala Ser Pro Ala Gln Val
    690                 695                 700

Lys Thr Ser Val Lys Lys Thr Gln Ala Lys Ala Asn Pro Ala Ala Ala
705                 710                 715                 720

Arg Ala Pro Ser Ala Lys Gly Thr Ile Ser Ala Pro Gly Lys Val Val
                725                 730                 735

Thr Ala Ala Ala Gln Ala Lys Gln Arg Ser Pro Ser Lys Val Lys Pro
            740                 745                 750

Pro Val Arg Asn Pro Gln Asn Ser Thr Val Leu Ala Arg Gly Pro Ala
        755                 760                 765

Ser Val Pro Ser Val Gly Lys Ala Val Ala Thr Ala Ala Gln Ala Gln
    770                 775                 780

Thr Gly Pro Glu Glu Asp Ser Gly Ser Ser Glu Glu Glu Ser Asp Ser
785                 790                 795                 800

Glu Glu Glu Ala Glu Thr Leu Ala Gln Ala Lys Pro Ser Gly Lys Thr
                805                 810                 815

His Gln Ile Arg Ala Ala Leu Ala Pro Ala Lys Glu Ser Pro Arg Lys
            820                 825                 830

Gly Ala Ala Pro Thr Pro Pro Gly Lys Thr Gly Pro Ser Ala Ala Gln
        835                 840                 845

Ala Gly Lys Gln Asp Asp Ser Gly Ser Ser Ser Glu Glu Ser Asp Ser
    850                 855                 860

Asp Gly Glu Ala Pro Ala Ala Val Thr Ser Ala Gln Val Ile Lys Pro
865                 870                 875                 880

Pro Leu Ile Phe Val Asp Pro Asn Arg Ser Pro Ala Gly Pro Ala Ala
                885                 890                 895

Thr Pro Ala Gln Ala Gln Ala Ala Ser Thr Pro Arg Lys Ala Arg Ala
            900                 905                 910
```

Ser Glu Ser Thr Ala Arg Ser Ser Ser Ser Glu Ser Glu Asp Glu Asp
915 920 925

Val Ile Pro Ala Thr Gln Cys Leu Thr Pro Gly Ile Arg Thr Asn Val
930 935 940

Val Thr Met Pro Thr Ala His Pro Arg Ile Ala Pro Lys Ala Ser Met
945 950 955 960

Ala Gly Ala Ser Ser Ser Lys Glu Ser Ser Arg Ile Ser Asp Gly Lys
965 970 975

Lys Gln Glu Gly Pro Ala Thr Gln Val Ser Lys Lys Asn Pro Ala Ser
980 985 990

Leu Pro Leu Thr Gln Ala Ala Leu Lys Val Leu Ala Gln Lys Ala Ser
995 1000 1005

Glu Ala Gln Pro Pro Val Ala Arg Thr Gln Pro Ser Ser Gly Val
1010 1015 1020

Asp Ser Ala Val Gly Thr Leu Pro Ala Thr Ser Pro Gln Ser Thr
1025 1030 1035

Ser Val Gln Ala Lys Gly Thr Asn Lys Leu Arg Lys Pro Lys Leu
1040 1045 1050

Pro Glu Val Gln Gln Ala Thr Lys Ala Pro Glu Ser Ser Asp Asp
1055 1060 1065

Ser Glu Asp Ser Ser Asp Ser Ser Ser Gly Ser Glu Glu Asp Gly
1070 1075 1080

Glu Gly Pro Gln Gly Ala Lys Ser Ala His Thr Leu Val Gly Pro
1085 1090 1095

Thr Pro Ser Arg Thr Glu Thr Leu Val Glu Glu Thr Ala Ala Glu
1100 1105 1110

Ser Ser Glu Asp Asp Val Val Ala Pro Ser Gln Ser Leu Leu Ser
1115 1120 1125

Gly Tyr Met Thr Pro Gly Leu Thr Pro Ala Asn Ser Gln Ala Ser
1130 1135 1140

Lys Ala Thr Pro Lys Leu Asp Ser Ser Pro Ser Val Ser Ser Thr
1145 1150 1155

Leu Ala Ala Lys Asp Asp Pro Asp Gly Lys Gln Glu Ala Lys Pro
1160 1165 1170

Gln Gln Ala Ala Gly Met Leu Ser Pro Lys Thr Gly Gly Lys Glu
1175 1180 1185

Ala Ala Ser Gly Thr Thr Pro Gln Lys Ser Arg Lys Pro Lys Lys
1190 1195 1200

Gly Ala Gly Asn Pro Gln Ala Ser Thr Leu Ala Leu Gln Ser Asn
1205 1210 1215

Ile Thr Gln Cys Leu Leu Gly Gln Pro Trp Pro Leu Asn Glu Ala
1220 1225 1230

Gln Val Gln Ala Ser Val Val Lys Val Leu Thr Glu Leu Leu Glu
1235 1240 1245

Gln Glu Arg Lys Lys Val Val Asp Thr Thr Lys Glu Ser Ser Arg
1250 1255 1260

Lys Gly Trp Glu Ser Arg Lys Arg Lys Leu Ser Gly Asp Gln Pro
1265 1270 1275

Ala Ala Arg Thr Pro Arg Ser Lys Lys Lys Lys Lys Leu Gly Ala
1280 1285 1290

Gly Glu Gly Gly Glu Ala Ser Val Ser Pro Glu Lys Thr Ser Thr
1295 1300 1305

Thr Ser Lys Gly Lys Ala Lys Arg Asp Lys Ala Ser Gly Asp Val
1310 1315 1320

-continued

```
Lys Glu  Lys Lys Gly Lys Gly  Ser Leu Gly Ser Gln  Gly Ala Lys
    1325                 1330                 1335

Asp Glu  Pro Glu Glu Glu Leu  Gln Lys Gly Met Gly  Thr Val Glu
    1340                 1345                 1350

Gly Gly  Asp Gln Ser Asn Pro  Lys Ser Lys Lys Glu  Lys Lys Lys
    1355                 1360                 1365

Ser Asp  Lys Arg Lys Lys Asp  Lys Glu Lys Lys Glu  Lys Lys Lys
    1370                 1375                 1380

Lys Ala  Lys Lys Ala Ser Thr  Lys Asp Ser Glu Ser  Pro Ser Gln
    1385                 1390                 1395

Lys Lys  Lys Lys Lys Lys Lys  Lys Thr Ala Glu Gln  Thr Val
    1400                 1405                 1410


<210> SEQ ID NO 63
<211> LENGTH: 376
<212> TYPE: PRT
<213> ORGANISM: Artificial Sequence
<220> FEATURE:
<223> OTHER INFORMATION: Synthetic

<400> SEQUENCE: 63

Met Glu Thr Leu Ser Asn Ala Ser Gly Thr Phe Ala Ile Arg Leu Leu
1               5                   10                  15

Lys Ile Leu Cys Gln Asp Asn Pro Ser His Asn Val Phe Cys Ser Pro
            20                  25                  30

Val Ser Ile Ser Ser Ala Leu Ala Met Val Leu Leu Gly Ala Lys Gly
        35                  40                  45

Asn Thr Ala Thr Gln Met Ala Gln Ala Leu Ser Leu Asn Thr Glu Glu
    50                  55                  60

Asp Ile His Arg Ala Phe Gln Ser Leu Leu Thr Glu Val Asn Lys Ala
65                  70                  75                  80

Gly Thr Gln Tyr Leu Leu Arg Thr Ala Asn Arg Leu Phe Gly Glu Lys
                85                  90                  95

Thr Cys Gln Phe Leu Ser Thr Phe Lys Glu Ser Cys Leu Gln Phe Tyr
            100                 105                 110

His Ala Glu Leu Lys Glu Leu Ser Phe Ile Arg Ala Ala Glu Glu Ser
        115                 120                 125

Arg Lys His Ile Asn Thr Trp Val Ser Lys Lys Thr Glu Gly Lys Ile
    130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
            180                 185                 190

Arg Pro Val Gln Met Met Tyr Gln Glu Ala Thr Phe Lys Leu Ala His
        195                 200                 205

Val Gly Glu Val Arg Ala Gln Leu Leu Glu Leu Pro Tyr Ala Arg Lys
    210                 215                 220

Glu Leu Ser Leu Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
                245                 250                 255

Pro Asp Cys Met Lys Ser Thr Glu Val Glu Val Leu Leu Pro Lys Phe
            260                 265                 270
```

```
Lys Leu Gln Glu Asp Tyr Asp Met Glu Ser Val Leu Arg His Leu Gly
        275                 280                 285

Ile Val Asp Ala Phe Gln Gln Gly Lys Ala Asp Leu Ser Ala Met Ser
    290                 295                 300

Ala Glu Arg Asp Leu Cys Leu Ser Lys Phe Val His Lys Ser Phe Val
305                 310                 315                 320

Glu Val Asn Glu Glu Gly Thr Glu Ala Ala Ala Ala Ser Ser Cys Phe
                325                 330                 335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
        355                 360                 365

Phe Cys Gly Arg Phe Ser Ser Pro
    370                 375


<210> SEQ ID NO 64
<211> LENGTH: 418
<212> TYPE: PRT
<213> ORGANISM: Artificial Sequence
<220> FEATURE:
<223> OTHER INFORMATION: Synthetic

<400> SEQUENCE: 64

Met Leu Pro Asn Thr Gly Arg Leu Ala Gly Cys Thr Val Phe Ile Thr
1               5                   10                  15

Gly Ala Ser Arg Gly Ile Gly Lys Ala Ile Ala Leu Lys Ala Ala Lys
            20                  25                  30

Asp Gly Ala Asn Ile Val Ile Ala Ala Lys Thr Ala Gln Pro His Pro
        35                  40                  45

Lys Leu Leu Gly Thr Ile Tyr Thr Ala Ala Glu Glu Ile Glu Ala Val
    50                  55                  60

Gly Gly Lys Ala Leu Pro Cys Ile Val Asp Val Arg Asp Glu Gln Gln
65                  70                  75                  80

Ile Ser Ala Ala Val Glu Lys Ala Ile Lys Lys Phe Gly Gly Ile Asp
                85                  90                  95

Ile Leu Val Asn Asn Ala Ser Ala Ile Ser Leu Thr Asn Thr Leu Asp
            100                 105                 110

Thr Pro Thr Lys Arg Leu Asp Leu Met Met Asn Val Asn Thr Arg Gly
        115                 120                 125

Thr Tyr Leu Ala Ser Lys Ala Cys Ile Pro Tyr Leu Lys Lys Ser Lys
    130                 135                 140

Val Ala His Ile Leu Asn Ile Ser Pro Pro Leu Asn Leu Asn Pro Val
145                 150                 155                 160

Trp Phe Lys Gln His Cys Ala Tyr Thr Ile Ala Lys Tyr Gly Met Ser
                165                 170                 175

Met Tyr Val Leu Gly Met Ala Glu Glu Phe Lys Gly Glu Ile Ala Val
            180                 185                 190

Asn Ala Leu Trp Pro Lys Thr Ala Ile His Thr Ala Ala Met Asp Met
        195                 200                 205

Leu Gly Gly Pro Gly Ile Glu Ser Gln Cys Arg Lys Val Asp Ile Ile
    210                 215                 220

Ala Asp Ala Ala Tyr Ser Ile Phe Gln Lys Pro Lys Ser Phe Thr Gly
225                 230                 235                 240

Asn Phe Val Ile Asp Glu Asn Ile Leu Lys Glu Glu Gly Ile Glu Asn
                245                 250                 255

Phe Asp Val Tyr Ala Ile Lys Pro Gly His Pro Leu Gln Pro Asp Phe
```

```
            260                 265                 270

Phe Leu Asp Glu Tyr Pro Glu Ala Val Ser Lys Lys Val Glu Ser Thr
        275                 280                 285

Gly Ala Val Pro Glu Phe Lys Glu Glu Lys Leu Gln Leu Gln Pro Lys
    290                 295                 300

Pro Arg Ser Gly Ala Val Glu Glu Thr Phe Arg Ile Val Lys Asp Ser
305                 310                 315                 320

Leu Ser Asp Asp Val Val Lys Ala Thr Gln Ala Ile Tyr Leu Phe Glu
                325                 330                 335

Leu Ser Gly Glu Asp Gly Gly Thr Trp Phe Leu Asp Leu Lys Ser Lys
            340                 345                 350

Gly Gly Asn Val Gly Tyr Gly Glu Pro Ser Asp Gln Ala Asp Val Val
        355                 360                 365

Met Ser Met Thr Thr Asp Asp Phe Val Lys Met Phe Ser Gly Lys Leu
    370                 375                 380

Lys Pro Thr Met Ala Phe Met Ser Gly Lys Leu Lys Ile Lys Gly Asn
385                 390                 395                 400

Met Ala Leu Ala Ile Lys Leu Glu Lys Leu Met Asn Gln Met Asn Ala
                405                 410                 415

Arg Leu


<210> SEQ ID NO 65
<211> LENGTH: 470
<212> TYPE: PRT
<213> ORGANISM: Artificial Sequence
<220> FEATURE:
<223> OTHER INFORMATION: Synthetic

<400> SEQUENCE: 65

Met Leu Arg Gly Ile Ser Gln Leu Pro Ala Val Ala Thr Met Ser Trp
1               5                   10                  15

Val Leu Leu Pro Val Leu Trp Leu Ile Val Gln Thr Gln Ala Ile Ala
            20                  25                  30

Ile Lys Gln Thr Pro Glu Leu Thr Leu His Glu Ile Val Cys Pro Lys
        35                  40                  45

Lys Leu His Ile Leu His Lys Arg Glu Ile Lys Asn Asn Gln Thr Glu
    50                  55                  60

Lys His Gly Lys Glu Glu Arg Tyr Glu Pro Glu Val Gln Tyr Gln Met
65                  70                  75                  80

Ile Leu Asn Gly Glu Glu Ile Ile Leu Ser Leu Gln Lys Thr Lys His
                85                  90                  95

Leu Leu Gly Pro Asp Tyr Thr Glu Thr Leu Tyr Ser Pro Arg Gly Glu
            100                 105                 110

Glu Ile Thr Thr Lys Pro Glu Asn Met Glu His Cys Tyr Tyr Lys Gly
        115                 120                 125

Asn Ile Leu Asn Glu Lys Asn Ser Val Ala Ser Ile Ser Thr Cys Asp
    130                 135                 140

Gly Leu Arg Gly Tyr Phe Thr His His His Gln Arg Tyr Gln Ile Lys
145                 150                 155                 160

Pro Leu Lys Ser Thr Asp Glu Lys Glu His Ala Val Phe Thr Ser Asn
                165                 170                 175

Gln Glu Glu Gln Asp Pro Ala Asn His Thr Cys Gly Val Lys Ser Thr
            180                 185                 190

Asp Gly Lys Gln Gly Pro Ile Arg Ile Ser Arg Ser Leu Lys Ser Pro
        195                 200                 205
```

Glu Lys Glu Asp Phe Leu Arg Ala Gln Lys Tyr Ile Asp Leu Tyr Leu
210 215 220

Val Leu Asp Asn Ala Phe Tyr Lys Asn Tyr Asn Glu Asn Leu Thr Leu
225 230 235 240

Ile Arg Ser Phe Val Phe Asp Val Met Asn Leu Leu Asn Val Ile Tyr
245 250 255

Asn Thr Ile Asp Val Gln Val Ala Leu Val Gly Met Glu Ile Trp Ser
260 265 270

Asp Gly Asp Lys Ile Lys Val Val Pro Ser Ala Ser Thr Thr Phe Asp
275 280 285

Asn Phe Leu Arg Trp His Ser Ser Asn Leu Gly Lys Lys Ile His Asp
290 295 300

His Ala Gln Leu Leu Ser Gly Ile Ser Phe Asn Asn Arg Arg Val Gly
305 310 315 320

Leu Ala Ala Ser Asn Ser Leu Cys Ser Pro Ser Ser Val Ala Val Ile
325 330 335

Glu Ala Lys Lys Lys Asn Asn Val Ala Leu Val Gly Val Met Ser His
340 345 350

Glu Leu Gly His Val Leu Gly Met Pro Asp Val Pro Phe Asn Thr Lys
355 360 365

Cys Pro Ser Gly Ser Cys Val Met Asn Gln Tyr Leu Ser Ser Lys Phe
370 375 380

Pro Lys Asp Phe Ser Thr Ser Cys Arg Ala His Phe Glu Arg Tyr Leu
385 390 395 400

Leu Ser Gln Lys Pro Lys Cys Leu Leu Gln Ala Pro Ile Pro Thr Asn
405 410 415

Ile Met Thr Thr Pro Val Cys Gly Asn His Leu Leu Glu Val Gly Glu
420 425 430

Asp Cys Asp Cys Gly Ser Pro Lys Glu Cys Thr Asn Leu Cys Cys Glu
435 440 445

Ala Leu Thr Cys Lys Leu Lys Pro Gly Thr Asp Cys Gly Gly Asp Ala
450 455 460

Pro Asn His Thr Thr Glu
465 470

<210> SEQ ID NO 66
<211> LENGTH: 394
<212> TYPE: PRT
<213> ORGANISM: Artificial Sequence
<220> FEATURE:
<223> OTHER INFORMATION: Synthetic

<400> SEQUENCE: 66

Met Ala Leu Gln Gly Ile Ser Val Val Glu Leu Ser Gly Leu Ala Pro
1 5 10 15

Gly Pro Phe Cys Ala Met Val Leu Ala Asp Phe Gly Ala Arg Val Val
20 25 30

Arg Val Asp Arg Pro Gly Ser Arg Tyr Asp Val Ser Arg Leu Gly Arg
35 40 45

Gly Lys Arg Ser Leu Val Leu Asp Leu Lys Gln Pro Arg Gly Ala Ala
50 55 60

Val Leu Arg Arg Leu Cys Lys Arg Ser Asp Val Leu Leu Glu Pro Phe
65 70 75 80

Arg Arg Gly Val Met Glu Lys Leu Gln Leu Gly Pro Glu Ile Leu Gln
85 90 95

Arg Glu Asn Pro Arg Leu Ile Tyr Ala Arg Leu Ser Gly Phe Gly Gln

```
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Gly Leu Met Cys
145                 150                 155                 160

Ala Leu Gly Ile Ile Met Ala Leu Phe Asp Arg Thr Arg Thr Gly Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Leu Ser Leu Trp Glu Ala Pro Arg
        195                 200                 205

Gly Gln Asn Met Leu Asp Gly Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270

Asp Val Phe Ala Glu Lys Thr Lys Ala Glu Trp Cys Gln Ile Phe Asp
        275                 280                 285

Gly Thr Asp Ala Cys Val Thr Pro Val Leu Thr Phe Glu Glu Val Val
    290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
                325                 330                 335

Ile Pro Ser Phe Lys Arg Asp Pro Phe Ile Gly Glu His Thr Glu Glu
            340                 345                 350

Ile Leu Glu Glu Phe Gly Phe Ser Arg Glu Glu Ile Tyr Gln Leu Asn
        355                 360                 365

Ser Asp Lys Ile Ile Glu Ser Asn Lys Ala Gly Ser Lys Phe Trp Ile
    370                 375                 380

Leu Tyr Pro Thr His Ser Asn Ile Gln Lys
385                 390


<210> SEQ ID NO 67
<211> LENGTH: 394
<212> TYPE: PRT
<213> ORGANISM: Artificial Sequence
<220> FEATURE:
<223> OTHER INFORMATION: Synthetic

<400> SEQUENCE: 67

Met Ala Leu Gln Gly Ile Ser Val Val Glu Leu Ser Gly Leu Ala Pro
1               5                   10                  15

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80
```

Arg Arg Gly Val Met Glu Lys Leu Gln Leu Gly Pro Glu Ile Leu Gln
85 90 95

Arg Glu Asn Pro Arg Leu Ile Tyr Ala Arg Leu Ser Gly Phe Gly Gln
100 105 110

Ser Gly Ser Phe Cys Arg Leu Ala Gly His Asp Ile Asn Tyr Leu Ala
115 120 125

Leu Ser Gly Val Leu Ser Lys Ile Gly Arg Ser Gly Glu Asn Pro Tyr
130 135 140

Ala Pro Leu Asn Leu Leu Ala Asp Phe Ala Gly Gly Gly Leu Met Cys
145 150 155 160

Ala Leu Gly Ile Ile Met Ala Leu Phe Asp Arg Thr Arg Thr Gly Lys
165 170 175

Gly Gln Val Ile Asp Ala Asn Met Val Glu Gly Thr Ala Tyr Leu Ser
180 185 190

Ser Phe Leu Trp Lys Thr Gln Lys Leu Ser Leu Trp Glu Ala Pro Arg
195 200 205

Gly Gln Asn Met Leu Asp Gly Gly Ala Pro Phe Tyr Thr Thr Tyr Arg
210 215 220

Thr Ala Asp Gly Glu Phe Met Ala Val Gly Ala Ile Glu Pro Gln Phe
225 230 235 240

Tyr Glu Leu Leu Ile Lys Gly Leu Gly Leu Lys Ser Asp Glu Leu Pro
245 250 255

Asn Gln Met Ser Met Asp Asp Trp Pro Glu Met Lys Lys Lys Phe Ala
260 265 270

Asp Val Phe Ala Glu Lys Thr Lys Ala Glu Trp Cys Gln Ile Phe Asp
275 280 285

Gly Thr Asp Ala Cys Val Thr Pro Val Leu Thr Phe Glu Glu Val Val
290 295 300

His His Asp His Asn Lys Glu Arg Gly Ser Phe Ile Thr Ser Glu Glu
305 310 315 320

Gln Asp Val Ser Pro Arg Pro Ala Pro Leu Leu Leu Asn Thr Pro Ala
325 330 335

Ile Pro Ser Phe Lys Arg Asp Pro Phe Ile Gly Glu His Thr Glu Glu
340 345 350

Ile Leu Glu Glu Phe Gly Phe Ser Arg Glu Glu Ile Tyr Gln Leu Asn
355 360 365

Ser Asp Lys Ile Ile Glu Ser Asn Lys Ala Gly Ser Lys Phe Trp Ile
370 375 380

Leu Tyr Pro Thr His Ser Asn Ile Gln Lys
385 390

<210> SEQ ID NO 68
<211> LENGTH: 2285
<212> TYPE: PRT
<213> ORGANISM: Artificial Sequence
<220> FEATURE:
<223> OTHER INFORMATION: Synthetic

<400> SEQUENCE: 68

Met Ala Ala Gln Val Ala Pro Ala Ala Ala Ser Ser Leu Gly Asn Pro
1 5 10 15

Pro Pro Pro Pro Pro Ser Glu Leu Lys Lys Ala Glu Gln Gln Gln Arg
20 25 30

Glu Glu Ala Gly Gly Glu Ala Ala Ala Ala Ala Ala Ala Glu Arg Gly
35 40 45

-continued

```
Glu Met Lys Ala Ala Ala Gly Gln Glu Ser Glu Gly Pro Ala Val Gly
    50                  55                  60

Pro Pro Gln Pro Leu Gly Lys Glu Leu Gln Asp Gly Ala Glu Ser Asn
65                  70                  75                  80

Gly Gly Gly Gly Gly Gly Gly Ala Gly Ser Gly Gly Gly Pro Gly Ala
                85                  90                  95

Glu Pro Asp Leu Lys Asn Ser Asn Gly Asn Ala Gly Pro Arg Pro Ala
            100                 105                 110

Leu Asn Asn Asn Leu Thr Glu Pro Pro Gly Gly Gly Gly Gly Gly Ser
        115                 120                 125

Ser Asp Gly Val Gly Ala Pro Pro His Ser Ala Ala Ala Ala Leu Pro
    130                 135                 140

Pro Pro Ala Tyr Gly Phe Gly Gln Pro Tyr Gly Arg Ser Pro Ser Ala
145                 150                 155                 160

Val Ala Ala Ala Ala Ala Ala Val Phe His Gln Gln His Gly Gly Gln
                165                 170                 175

Gln Ser Pro Gly Leu Ala Ala Leu Gln Ser Gly Gly Gly Gly Gly Leu
            180                 185                 190

Glu Pro Tyr Ala Gly Pro Gln Gln Asn Ser His Asp His Gly Phe Pro
        195                 200                 205

Asn His Gln Tyr Asn Ser Tyr Tyr Pro Asn Arg Ser Ala Tyr Pro Pro
    210                 215                 220

Pro Ala Pro Ala Tyr Ala Leu Ser Ser Pro Arg Gly Gly Thr Pro Gly
225                 230                 235                 240

Ser Gly Ala Ala Ala Ala Ala Gly Ser Lys Pro Pro Pro Ser Ser Ser
                245                 250                 255

Ala Ser Ala Ser Ser Ser Ser Ser Ser Phe Ala Gln Gln Arg Phe Gly
            260                 265                 270

Ala Met Gly Gly Gly Gly Pro Ser Ala Ala Gly Gly Gly Thr Pro Gln
        275                 280                 285

Pro Thr Ala Thr Pro Thr Leu Asn Gln Leu Leu Thr Ser Pro Ser Ser
    290                 295                 300

Ala Arg Gly Tyr Gln Gly Tyr Pro Gly Gly Asp Tyr Ser Gly Gly Pro
305                 310                 315                 320

Gln Asp Gly Gly Ala Gly Lys Gly Pro Ala Asp Met Ala Ser Gln Cys
                325                 330                 335

Trp Gly Ala Ala Ala Ala Ala Ala Ala Ala Ala Ala Ala Ser Gly Gly
            340                 345                 350

Ala Gln Gln Arg Ser His His Ala Pro Met Ser Pro Gly Ser Ser Gly
        355                 360                 365

Gly Gly Gly Gln Pro Leu Ala Arg Thr Pro Gln Pro Ser Ser Pro Met
    370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415

Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
        435                 440                 445

Gln Gln Ile Pro Pro Tyr Gly Gln Gln Gly Pro Ser Gly Tyr Gly Gln
    450                 455                 460

Gln Gly Gln Thr Pro Tyr Tyr Asn Gln Gln Ser Pro His Pro Gln Gln
465                 470                 475                 480
```

-continued

```
Gln Gln Pro Pro Tyr Ser Gln Gln Pro Pro Ser Gln Thr Pro His Ala
                485                 490                 495

Gln Pro Ser Tyr Gln Gln Gln Pro Gln Ser Gln Pro Pro Gln Leu Gln
            500                 505                 510

Ser Ser Gln Pro Pro Tyr Ser Gln Gln Pro Ser Gln Pro Pro His Gln
        515                 520                 525

Gln Ser Pro Ala Pro Tyr Pro Ser Gln Gln Ser Thr Thr Gln Gln His
    530                 535                 540

Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Gln Thr Ala Tyr
            580                 585                 590

Ser Gln Gln Arg Phe Pro Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
    690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gly Gln Ile His Thr Gly
    770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
```

-continued

```
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
    930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
            980                 985                 990

Ser Lys Ser Lys Lys Ser Ser Ser  Ser Thr Thr Thr Asn  Glu Lys Ile
        995                 1000                1005

Thr Lys  Leu Tyr Glu Leu Gly  Gly Glu Pro Glu Arg  Lys Met Trp
    1010                 1015                 1020

Val Asp  Arg Tyr Leu Ala Phe  Thr Glu Glu Lys Ala  Met Gly Met
    1025                 1030                 1035

Thr Asn  Leu Pro Ala Val Gly  Arg Lys Pro Leu Asp  Leu Tyr Arg
    1040                 1045                 1050

Leu Tyr  Val Ser Val Lys Glu  Ile Gly Gly Leu Thr  Gln Val Asn
    1055                 1060                 1065

Lys Asn  Lys Lys Trp Arg Glu  Leu Ala Thr Asn Leu  Asn Val Gly
    1070                 1075                 1080

Thr Ser  Ser Ser Ala Ala Ser  Ser Leu Lys Lys Gln  Tyr Ile Gln
    1085                 1090                 1095

Cys Leu  Tyr Ala Phe Glu Cys  Lys Ile Glu Arg Gly  Glu Asp Pro
    1100                 1105                 1110

Pro Pro  Asp Ile Phe Ala Ala  Ala Asp Ser Lys Lys  Ser Gln Pro
    1115                 1120                 1125

Lys Ile  Gln Pro Pro Ser Pro  Ala Gly Ser Gly Ser  Met Gln Gly
    1130                 1135                 1140

Pro Gln  Thr Pro Gln Ser Thr  Ser Ser Ser Met Ala  Glu Gly Gly
    1145                 1150                 1155

Asp Leu  Lys Pro Pro Thr Pro  Ala Ser Thr Pro His  Ser Gln Ile
    1160                 1165                 1170

Pro Pro  Leu Pro Gly Met Ser  Arg Ser Asn Ser Val  Gly Ile Gln
    1175                 1180                 1185

Asp Ala  Phe Asn Asp Gly Ser  Asp Ser Thr Phe Gln  Lys Arg Asn
    1190                 1195                 1200

Ser Met  Thr Pro Asn Pro Gly  Tyr Gln Pro Ser Met  Asn Thr Ser
    1205                 1210                 1215

Asp Met  Met Gly Arg Met Ser  Tyr Glu Pro Asn Lys  Asp Pro Tyr
    1220                 1225                 1230

Gly Ser  Met Arg Lys Ala Pro  Gly Ser Asp Pro Phe  Met Ser Ser
    1235                 1240                 1245

Gly Gln  Gly Pro Asn Gly Gly  Met Gly Asp Pro Tyr  Ser Arg Ala
    1250                 1255                 1260

Ala Gly  Pro Gly Leu Gly Asn  Val Ala Met Gly Pro  Arg Gln His
    1265                 1270                 1275

Tyr Pro  Tyr Gly Gly Pro Tyr  Asp Arg Val Arg Thr  Glu Pro Gly
    1280                 1285                 1290

Ile Gly  Pro Glu Gly Asn Met  Ser Thr Gly Ala Pro  Gln Pro Asn
    1295                 1300                 1305
```

```
Leu Met  Pro Ser Asn Pro Asp  Ser Gly Met Tyr Ser  Pro Ser Arg
    1310                 1315                 1320

Tyr Pro  Pro Gln Gln Gln Gln  Gln Gln Gln Gln Arg  His Asp Ser
    1325                 1330                 1335

Tyr Gly  Asn Gln Phe Ser Thr  Gln Gly Thr Pro Ser  Gly Ser Pro
    1340                 1345                 1350

Phe Pro  Ser Gln Gln Thr Thr  Met Tyr Gln Gln Gln  Gln Gln Asn
    1355                 1360                 1365

Tyr Lys  Arg Pro Met Asp Gly  Thr Tyr Gly Pro Pro  Ala Lys Arg
    1370                 1375                 1380

His Glu  Gly Glu Met Tyr Ser  Val Pro Tyr Ser Thr  Gly Gln Gly
    1385                 1390                 1395

Gln Pro  Gln Gln Gln Gln Leu  Pro Pro Ala Gln Pro  Gln Pro Ala
    1400                 1405                 1410

Ser Gln  Gln Gln Ala Ala Gln  Pro Ser Pro Gln Gln  Asp Val Tyr
    1415                 1420                 1425

Asn Gln  Tyr Gly Asn Ala Tyr  Pro Ala Thr Ala Thr  Ala Ala Thr
    1430                 1435                 1440

Glu Arg  Arg Pro Ala Gly Gly  Pro Gln Asn Gln Phe  Pro Phe Gln
    1445                 1450                 1455

Phe Gly  Arg Asp Arg Val Ser  Ala Pro Pro Gly Thr  Asn Ala Gln
    1460                 1465                 1470

Gln Asn  Met Pro Pro Gln Met  Met Gly Gly Pro Ile  Gln Ala Ser
    1475                 1480                 1485

Ala Glu  Val Ala Gln Gln Gly  Thr Met Trp Gln Gly  Arg Asn Asp
    1490                 1495                 1500

Met Thr  Tyr Asn Tyr Ala Asn  Arg Gln Ser Thr Gly  Ser Ala Pro
    1505                 1510                 1515

Gln Gly  Pro Ala Tyr His Gly  Val Asn Arg Thr Asp  Glu Met Leu
    1520                 1525                 1530

His Thr  Asp Gln Arg Ala Asn  His Glu Gly Ser Trp  Pro Ser His
    1535                 1540                 1545

Gly Thr  Arg Gln Pro Pro Tyr  Gly Pro Ser Ala Pro  Val Pro Pro
    1550                 1555                 1560

Met Thr  Arg Pro Pro Pro Ser  Asn Tyr Gln Pro Pro  Pro Ser Met
    1565                 1570                 1575

Gln Asn  His Ile Pro Gln Val  Ser Ser Pro Ala Pro  Leu Pro Arg
    1580                 1585                 1590

Pro Met  Glu Asn Arg Thr Ser  Pro Ser Lys Ser Pro  Phe Leu His
    1595                 1600                 1605

Ser Gly  Met Lys Met Gln Lys  Ala Gly Pro Pro Val  Pro Ala Ser
    1610                 1615                 1620

His Ile  Ala Pro Ala Pro Val  Gln Pro Pro Met Ile  Arg Arg Asp
    1625                 1630                 1635

Ile Thr  Phe Pro Pro Gly Ser  Val Glu Ala Thr Gln  Pro Val Leu
    1640                 1645                 1650

Lys Gln  Arg Arg Arg Leu Thr  Met Lys Asp Ile Gly  Thr Pro Glu
    1655                 1660                 1665

Ala Trp  Arg Val Met Met Ser  Leu Lys Ser Gly Leu  Leu Ala Glu
    1670                 1675                 1680

Ser Thr  Trp Ala Leu Asp Thr  Ile Asn Ile Leu Leu  Tyr Asp Asp
    1685                 1690                 1695

Asn Ser  Ile Met Thr Phe Asn  Leu Ser Gln Leu Pro  Gly Leu Leu
    1700                 1705                 1710
```

```
Glu Leu  Leu Val Glu Tyr Phe  Arg Arg Cys Leu Ile  Glu Ile Phe
    1715                 1720                 1725

Gly Ile  Leu Lys Glu Tyr Glu  Val Gly Asp Pro Gly  Gln Arg Thr
    1730                 1735                 1740

Leu Leu  Asp Pro Gly Arg Phe  Ser Lys Val Ser Ser  Pro Ala Pro
    1745                 1750                 1755

Met Glu  Gly Gly Glu Glu Glu  Glu Glu Leu Leu Gly  Pro Lys Leu
    1760                 1765                 1770

Glu Glu  Glu Glu Glu Glu Glu  Val Val Glu Asn Asp  Glu Glu Ile
    1775                 1780                 1785

Ala Phe  Ser Gly Lys Asp Lys  Pro Ala Ser Glu Asn  Ser Glu Glu
    1790                 1795                 1800

Lys Leu  Ile Ser Lys Phe Asp  Lys Leu Pro Val Lys  Ile Val Gln
    1805                 1810                 1815

Lys Asn  Asp Pro Phe Val Val  Asp Cys Ser Asp Lys  Leu Gly Arg
    1820                 1825                 1830

Val Gln  Glu Phe Asp Ser Gly  Leu Leu His Trp Arg  Ile Gly Gly
    1835                 1840                 1845

Gly Asp  Thr Thr Glu His Ile  Gln Thr His Phe Glu  Ser Lys Thr
    1850                 1855                 1860

Glu Leu  Leu Pro Ser Arg Pro  His Ala Pro Cys Pro  Pro Ala Pro
    1865                 1870                 1875

Arg Lys  His Val Thr Thr Ala  Glu Gly Thr Pro Gly  Thr Thr Asp
    1880                 1885                 1890

Gln Glu  Gly Pro Pro Pro Asp  Gly Pro Pro Glu Lys  Arg Ile Thr
    1895                 1900                 1905

Ala Thr  Met Asp Asp Met Leu  Ser Thr Arg Ser Ser  Thr Leu Thr
    1910                 1915                 1920

Glu Asp  Gly Ala Lys Ser Ser  Glu Ala Ile Lys Glu  Ser Ser Lys
    1925                 1930                 1935

Phe Pro  Phe Gly Ile Ser Pro  Ala Gln Ser His Arg  Asn Ile Lys
    1940                 1945                 1950

Ile Leu  Glu Asp Glu Pro His  Ser Lys Asp Glu Thr  Pro Leu Cys
    1955                 1960                 1965

Thr Leu  Leu Asp Trp Gln Asp  Ser Leu Ala Lys Arg  Cys Val Cys
    1970                 1975                 1980

Val Ser  Asn Thr Ile Arg Ser  Leu Ser Phe Val Pro  Gly Asn Asp
    1985                 1990                 1995

Phe Glu  Met Ser Lys His Pro  Gly Leu Leu Leu Ile  Leu Gly Lys
    2000                 2005                 2010

Leu Ile  Leu Leu His His Lys  His Pro Glu Arg Lys  Gln Ala Pro
    2015                 2020                 2025

Leu Thr  Tyr Glu Lys Glu Glu  Glu Gln Asp Gln Gly  Val Ser Cys
    2030                 2035                 2040

Asn Lys  Val Glu Trp Trp Trp  Asp Cys Leu Glu Met  Leu Arg Glu
    2045                 2050                 2055

Asn Thr  Leu Val Thr Leu Ala  Asn Ile Ser Gly Gln  Leu Asp Leu
    2060                 2065                 2070

Ser Pro  Tyr Pro Glu Ser Ile  Cys Leu Pro Val Leu  Asp Gly Leu
    2075                 2080                 2085

Leu His  Trp Ala Val Cys Pro  Ser Ala Glu Ala Gln  Asp Pro Phe
    2090                 2095                 2100

Ser Thr  Leu Gly Pro Asn Ala  Val Leu Ser Pro Gln  Arg Leu Val
```

2105 2110 2115

Leu Glu Thr Leu Ser Lys Leu Ser Ile Gln Asp Asn Asn Val Asp
2120 2125 2130

Leu Ile Leu Ala Thr Pro Pro Phe Ser Arg Leu Glu Lys Leu Tyr
2135 2140 2145

Ser Thr Met Val Arg Phe Leu Ser Asp Arg Lys Asn Pro Val Cys
2150 2155 2160

Arg Glu Met Ala Val Val Leu Leu Ala Asn Leu Ala Gln Gly Asp
2165 2170 2175

Ser Leu Ala Ala Arg Ala Ile Ala Val Gln Lys Gly Ser Ile Gly
2180 2185 2190

Asn Leu Leu Gly Phe Leu Glu Asp Ser Leu Ala Ala Thr Gln Phe
2195 2200 2205

Gln Gln Ser Gln Ala Ser Leu Leu His Met Gln Asn Pro Pro Phe
2210 2215 2220

Glu Pro Thr Ser Val Asp Met Met Arg Arg Ala Ala Arg Ala Leu
2225 2230 2235

Leu Ala Leu Ala Lys Val Asp Glu Asn His Ser Glu Phe Thr Leu
2240 2245 2250

Tyr Glu Ser Arg Leu Leu Asp Ile Ser Val Ser Pro Leu Met Asn
2255 2260 2265

Ser Leu Val Ser Gln Val Ile Cys Asp Val Leu Phe Leu Ile Gly
2270 2275 2280

Gln Ser
2285

<210> SEQ ID NO 69
<211> LENGTH: 1054
<212> TYPE: PRT
<213> ORGANISM: Artificial Sequence
<220> FEATURE:
<223> OTHER INFORMATION: Synthetic

<400> SEQUENCE: 69

Met Ala Ala Val Lys Glu Pro Leu Glu Phe His Ala Lys Arg Pro Trp
1 5 10 15

Arg Pro Glu Glu Ala Val Glu Asp Pro Asp Glu Glu Asp Glu Asp Asn
20 25 30

Thr Ser Glu Ala Glu Asn Gly Phe Ser Leu Glu Glu Val Leu Arg Leu
35 40 45

Gly Gly Thr Lys Gln Asp Tyr Leu Met Leu Ala Thr Leu Asp Glu Asn
50 55 60

Glu Glu Val Ile Asp Gly Gly Lys Lys Gly Ala Ile Asp Asp Leu Gln
65 70 75 80

Gln Gly Glu Leu Glu Ala Phe Ile Gln Asn Leu Asn Leu Ala Lys Tyr
85 90 95

Thr Lys Ala Ser Leu Ile Glu Glu Asp Glu Pro Ala Glu Lys Glu Asn
100 105 110

Ser Ser Lys Lys Glu Val Lys Ile Pro Lys Ile Asn Asn Lys Asn Thr
115 120 125

Ala Glu Ser Gln Arg Thr Ser Val Asn Lys Val Lys Asn Lys Asn Arg
130 135 140

Pro Glu Pro His Ser Asp Glu Asn Gly Ser Thr Thr Pro Lys Val Lys
145 150 155 160

Lys Asp Lys Gln Asn Ile Phe Glu Phe Phe Glu Arg Gln Thr Leu Leu
165 170 175

-continued

```
Leu Arg Pro Gly Gly Lys Trp Tyr Asp Leu Glu Tyr Ser Asn Glu Tyr
            180                 185                 190

Ser Leu Lys Pro Gln Pro Gln Asp Val Val Ser Lys Tyr Lys Thr Leu
        195                 200                 205

Ala Gln Lys Leu Tyr Gln His Glu Ile Asn Leu Phe Lys Ser Lys Thr
    210                 215                 220

Asn Ser Gln Lys Gly Ala Ser Ser Thr Trp Met Lys Ala Ile Val Ser
225                 230                 235                 240

Ser Gly Thr Leu Gly Asp Arg Met Ala Ala Met Ile Leu Leu Ile Gln
                245                 250                 255

Asp Asp Ala Val His Thr Leu Gln Phe Val Glu Thr Leu Val Asn Leu
            260                 265                 270

Val Lys Lys Lys Gly Ser Lys Gln Gln Cys Leu Met Ala Leu Asp Thr
        275                 280                 285

Phe Lys Glu Leu Leu Ile Thr Asp Leu Leu Pro Asp Asn Arg Lys Leu
    290                 295                 300

Arg Ile Phe Ser Gln Arg Pro Phe Asp Lys Leu Glu Gln Leu Ser Ser
305                 310                 315                 320

Gly Asn Lys Asp Ser Arg Asp Arg Arg Leu Ile Leu Trp Tyr Phe Glu
                325                 330                 335

His Gln Leu Lys His Leu Val Ala Glu Phe Val Gln Val Leu Glu Thr
            340                 345                 350

Leu Ser His Asp Thr Leu Val Thr Thr Lys Thr Arg Ala Leu Thr Val
        355                 360                 365

Ala His Glu Leu Leu Cys Asn Lys Pro Glu Glu Glu Lys Ala Leu Leu
    370                 375                 380

Val Gln Val Val Asn Lys Leu Gly Asp Pro Gln Asn Arg Ile Ala Thr
385                 390                 395                 400

Lys Ala Ser His Leu Leu Glu Thr Leu Leu Cys Lys His Pro Asn Met
                405                 410                 415

Lys Gly Val Val Ser Gly Glu Val Glu Arg Leu Leu Phe Arg Ser Asn
            420                 425                 430

Ile Ser Ser Lys Ala Gln Tyr Tyr Ala Ile Cys Phe Leu Asn Gln Met
        435                 440                 445

Ala Leu Ser His Glu Glu Ser Glu Leu Ala Asn Lys Leu Ile Thr Val
    450                 455                 460

Tyr Phe Cys Phe Phe Arg Thr Cys Val Lys Lys Lys Asp Val Glu Ser
465                 470                 475                 480

Lys Met Leu Ser Ala Leu Leu Thr Gly Val Asn Arg Ala Tyr Pro Tyr
                485                 490                 495

Ser Gln Thr Gly Asp Asp Lys Val Arg Glu Gln Ile Asp Thr Leu Phe
            500                 505                 510

Lys Val Leu His Ile Val Asn Phe Asn Thr Ser Val Gln Ala Leu Met
        515                 520                 525

Leu Leu Phe Gln Val Met Asn Ser Gln Gln Thr Ile Ser Asp Arg Tyr
    530                 535                 540

Tyr Thr Ala Leu Tyr Arg Lys Met Leu Asp Pro Gly Leu Met Thr Cys
545                 550                 555                 560

Ser Lys Gln Ala Met Phe Leu Asn Leu Val Tyr Lys Ser Leu Lys Ala
                565                 570                 575

Asp Ile Val Leu Arg Arg Val Lys Ala Phe Val Lys Arg Leu Leu Gln
            580                 585                 590

Val Thr Cys Gln Gln Met Pro Pro Phe Ile Cys Gly Ala Leu Tyr Leu
```

-continued

```
        595                 600                 605

Val Ser Glu Ile Leu Lys Ala Lys Pro Gly Leu Arg Ser Gln Leu Asp
    610                 615                 620

Asp His Pro Glu Ser Asp Asp Glu Glu Asn Phe Ile Asp Ala Asn Asp
625                 630                 635                 640

Asp Glu Asp Met Glu Lys Phe Thr Asp Ala Asp Lys Glu Thr Glu Ile
                645                 650                 655

Val Lys Lys Leu Glu Thr Glu Glu Thr Val Pro Glu Thr Asp Val Glu
            660                 665                 670

Thr Lys Lys Pro Glu Val Ala Ser Trp Val His Phe Asp Asn Leu Lys
        675                 680                 685

Gly Gly Lys Gln Leu Asn Lys Tyr Asp Pro Phe Ser Arg Asn Pro Leu
    690                 695                 700

Phe Cys Gly Ala Glu Asn Thr Ser Leu Trp Glu Leu Lys Lys Leu Ser
705                 710                 715                 720

Val His Phe His Pro Ser Val Ala Leu Phe Ala Lys Thr Ile Leu Gln
                725                 730                 735

Gly Asn Tyr Ile Gln Tyr Ser Gly Asp Pro Leu Gln Asp Phe Thr Leu
            740                 745                 750

Met Arg Phe Leu Asp Arg Phe Val Tyr Arg Asn Pro Lys Pro His Lys
        755                 760                 765

Gly Lys Glu Asn Thr Asp Ser Val Val Met Gln Pro Lys Arg Lys His
    770                 775                 780

Phe Ile Lys Asp Ile Arg His Leu Pro Val Asn Ser Lys Glu Phe Leu
785                 790                 795                 800

Ala Lys Glu Glu Ser Gln Ile Pro Val Asp Glu Val Phe Phe His Arg
                805                 810                 815

Tyr Tyr Lys Lys Val Ala Val Lys Glu Lys Gln Lys Arg Asp Ala Asp
            820                 825                 830

Glu Glu Ser Ile Glu Asp Val Asp Asp Glu Glu Phe Glu Glu Leu Ile
        835                 840                 845

Asp Thr Phe Glu Asp Asp Asn Cys Phe Ser Ser Gly Lys Asp Asp Met
    850                 855                 860

Asp Phe Ala Gly Asn Val Lys Lys Arg Thr Lys Gly Ala Lys Asp Asn
865                 870                 875                 880

Thr Leu Asp Glu Asp Ser Glu Gly Ser Asp Asp Glu Leu Gly Asn Leu
                885                 890                 895

Asp Asp Asp Glu Val Ser Leu Gly Ser Met Asp Asp Glu Glu Phe Ala
            900                 905                 910

Glu Val Asp Glu Asp Gly Gly Thr Phe Met Asp Val Leu Asp Asp Glu
        915                 920                 925

Ser Glu Ser Val Pro Glu Leu Glu Val His Ser Lys Val Ser Thr Lys
    930                 935                 940

Lys Ser Lys Arg Lys Gly Thr Asp Asp Phe Asp Phe Ala Gly Ser Phe
945                 950                 955                 960

Gln Gly Pro Arg Lys Lys Lys Arg Asn Leu Asn Asp Ser Ser Leu Phe
                965                 970                 975

Val Ser Ala Glu Glu Phe Gly His Leu Leu Asp Glu Asn Met Gly Ser
            980                 985                 990

Lys Phe Asp Asn Ile Gly Met Asn  Ala Met Ala Asn Lys  Asp Asn Ala
        995                 1000                1005

Ser Leu  Lys Gln Leu Arg Trp  Glu Ala Glu Arg Asp  Asp Trp Leu
    1010                1015                1020
```

His Asn Arg Asp Ala Lys Ser Ile Ile Lys Lys Lys Lys His Phe
1025 1030 1035

Lys Lys Lys Arg Ile Lys Thr Thr Gln Lys Thr Lys Lys Gln Arg
1040 1045 1050

Lys

<210> SEQ ID NO 70
<211> LENGTH: 1838
<212> TYPE: PRT
<213> ORGANISM: Artificial Sequence
<220> FEATURE:
<223> OTHER INFORMATION: Synthetic

<400> SEQUENCE: 70

Met Asp Val His Thr Arg Trp Lys Ala Arg Ser Ala Leu Arg Pro Gly
1 5 10 15

Ala Pro Leu Leu Pro Pro Leu Leu Leu Leu Leu Leu Trp Ala Pro Pro
20 25 30

Pro Ser Arg Ala Ala Gln Pro Ala Asp Leu Leu Lys Val Leu Asp Phe
35 40 45

His Asn Leu Pro Asp Gly Ile Thr Lys Thr Thr Gly Phe Cys Ala Thr
50 55 60

Arg Arg Ser Ser Lys Gly Pro Asp Val Ala Tyr Arg Val Thr Lys Asp
65 70 75 80

Ala Gln Leu Ser Ala Pro Thr Lys Gln Leu Tyr Pro Ala Ser Ala Phe
85 90 95

Pro Glu Asp Phe Ser Ile Leu Thr Thr Val Lys Ala Lys Lys Gly Ser
100 105 110

Gln Ala Phe Leu Val Ser Ile Tyr Asn Glu Gln Gly Ile Gln Gln Ile
115 120 125

Gly Leu Glu Leu Gly Arg Ser Pro Val Phe Leu Tyr Glu Asp His Thr
130 135 140

Gly Lys Pro Gly Pro Glu Asp Tyr Pro Leu Phe Arg Gly Ile Asn Leu
145 150 155 160

Ser Asp Gly Lys Trp His Arg Ile Ala Leu Ser Val His Lys Lys Asn
165 170 175

Val Thr Leu Ile Leu Asp Cys Lys Lys Lys Thr Thr Lys Phe Leu Asp
180 185 190

Arg Ser Asp His Pro Met Ile Asp Ile Asn Gly Ile Ile Val Phe Gly
195 200 205

Thr Arg Ile Leu Asp Glu Glu Val Phe Glu Gly Asp Ile Gln Gln Leu
210 215 220

Leu Phe Val Ser Asp His Arg Ala Ala Tyr Asp Tyr Cys Glu His Tyr
225 230 235 240

Ser Pro Asp Cys Asp Thr Ala Val Pro Asp Thr Pro Gln Ser Gln Asp
245 250 255

Pro Asn Pro Asp Glu Tyr Tyr Thr Glu Gly Asp Gly Glu Gly Glu Thr
260 265 270

Tyr Tyr Tyr Glu Tyr Pro Tyr Tyr Glu Asp Pro Glu Asp Leu Gly Lys
275 280 285

Glu Pro Thr Pro Ser Lys Lys Pro Val Glu Ala Ala Lys Glu Thr Thr
290 295 300

Glu Val Pro Glu Glu Leu Thr Pro Thr Pro Thr Glu Ala Ala Pro Met
305 310 315 320

Pro Glu Thr Ser Glu Gly Ala Gly Lys Glu Glu Asp Val Gly Ile Gly
325 330 335

```
Asp Tyr Asp Tyr Val Pro Ser Glu Asp Tyr Tyr Thr Pro Ser Pro Tyr
            340                 345                 350

Asp Asp Leu Thr Tyr Gly Glu Gly Glu Glu Asn Pro Asp Gln Pro Thr
        355                 360                 365

Asp Pro Gly Ala Gly Ala Glu Ile Pro Thr Ser Thr Ala Asp Thr Ser
    370                 375                 380

Asn Ser Ser Asn Pro Ala Pro Pro Pro Gly Glu Gly Ala Asp Asp Leu
385                 390                 395                 400

Glu Gly Glu Phe Thr Glu Glu Thr Ile Arg Asn Leu Asp Glu Asn Tyr
                405                 410                 415

Tyr Asp Pro Tyr Tyr Asp Pro Thr Ser Ser Pro Ser Glu Ile Gly Pro
            420                 425                 430

Gly Met Pro Ala Asn Gln Asp Thr Ile Tyr Glu Gly Ile Gly Gly Pro
        435                 440                 445

Arg Gly Glu Lys Gly Gln Lys Gly Glu Pro Ala Ile Ile Glu Pro Gly
    450                 455                 460

Met Leu Ile Glu Gly Pro Pro Gly Pro Glu Gly Pro Ala Gly Leu Pro
465                 470                 475                 480

Gly Pro Pro Gly Thr Met Gly Pro Thr Gly Gln Val Gly Asp Pro Gly
                485                 490                 495

Glu Arg Gly Pro Pro Gly Arg Pro Gly Leu Pro Gly Ala Asp Gly Leu
            500                 505                 510

Pro Gly Pro Pro Gly Thr Met Leu Met Leu Pro Phe Arg Phe Gly Gly
        515                 520                 525

Gly Gly Asp Ala Gly Ser Lys Gly Pro Met Val Ser Ala Gln Glu Ser
    530                 535                 540

Gln Ala Gln Ala Ile Leu Gln Gln Ala Arg Leu Ala Leu Arg Gly Pro
545                 550                 555                 560

Ala Gly Pro Met Gly Leu Thr Gly Arg Pro Gly Pro Val Gly Pro Pro
                565                 570                 575

Gly Ser Gly Gly Leu Lys Gly Glu Pro Gly Asp Val Gly Pro Gln Gly
            580                 585                 590

Pro Arg Gly Val Gln Gly Pro Pro Gly Pro Ala Gly Lys Pro Gly Arg
        595                 600                 605

Arg Gly Arg Ala Gly Ser Asp Gly Ala Arg Gly Met Pro Gly Gln Thr
    610                 615                 620

Gly Pro Lys Gly Asp Arg Gly Phe Asp Gly Leu Ala Gly Leu Pro Gly
625                 630                 635                 640

Glu Lys Gly His Arg Gly Asp Pro Gly Pro Ser Gly Pro Pro Gly Pro
                645                 650                 655

Pro Gly Asp Asp Gly Glu Arg Gly Asp Asp Gly Glu Val Gly Pro Arg
            660                 665                 670

Gly Leu Pro Gly Glu Pro Gly Pro Arg Gly Leu Leu Gly Pro Lys Gly
        675                 680                 685

Pro Pro Gly Pro Pro Gly Pro Pro Gly Val Thr Gly Met Asp Gly Gln
    690                 695                 700

Pro Gly Pro Lys Gly Asn Val Gly Pro Gln Gly Glu Pro Gly Pro Pro
705                 710                 715                 720

Gly Gln Gln Gly Asn Pro Gly Ala Gln Gly Leu Pro Gly Pro Gln Gly
                725                 730                 735

Ala Ile Gly Pro Pro Gly Glu Lys Gly Pro Leu Gly Lys Pro Gly Leu
            740                 745                 750

Pro Gly Met Pro Gly Ala Asp Gly Pro Pro Gly His Pro Gly Lys Glu
```

```
        755                 760                 765

Gly Pro Pro Gly Glu Lys Gly Gly Gln Gly Pro Pro Gly Pro Gln Gly
    770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
                805                 810                 815

Gly Phe Lys Gly Asp Met Gly Ile Lys Gly Asp Arg Gly Glu Ile Gly
            820                 825                 830

Pro Pro Gly Pro Arg Gly Glu Asp Gly Pro Glu Gly Pro Lys Gly Arg
        835                 840                 845

Gly Gly Pro Asn Gly Asp Pro Gly Pro Leu Gly Pro Pro Gly Glu Lys
    850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
                885                 890                 895

Lys Gly Gly Arg Gly Thr Pro Gly Lys Pro Gly Pro Arg Gly Gln Arg
            900                 905                 910

Gly Pro Thr Gly Pro Arg Gly Glu Arg Gly Pro Arg Gly Ile Thr Gly
        915                 920                 925

Lys Pro Gly Pro Lys Gly Asn Ser Gly Gly Asp Gly Pro Ala Gly Pro
    930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Pro Gly Lys Asp Gly Leu Pro Gly
                965                 970                 975

His Pro Gly Gln Arg Gly Glu Thr Gly Phe Gln Gly Lys Thr Gly Pro
            980                 985                 990

Pro Gly Pro Pro Gly Val Val Gly  Pro Gln Gly Pro Thr  Gly Glu Thr
        995                 1000                 1005

Gly Pro  Met Gly Glu Arg Gly  His Pro Gly Pro Pro  Gly Pro Pro
    1010                 1015                 1020

Gly Glu  Gln Gly Leu Pro Gly  Leu Ala Gly Lys Glu  Gly Thr Lys
    1025                 1030                 1035

Gly Asp  Pro Gly Pro Ala Gly  Leu Pro Gly Lys Asp  Gly Pro Pro
    1040                 1045                 1050

Gly Leu  Arg Gly Phe Pro Gly  Asp Arg Gly Leu Pro  Gly Pro Val
    1055                 1060                 1065

Gly Ala  Leu Gly Leu Lys Gly  Asn Glu Gly Pro Pro  Gly Pro Pro
    1070                 1075                 1080

Gly Pro  Ala Gly Ser Pro Gly  Glu Arg Gly Pro Ala  Gly Ala Ala
    1085                 1090                 1095

Gly Pro  Ile Gly Ile Pro Gly  Arg Pro Gly Pro Gln  Gly Pro Pro
    1100                 1105                 1110

Gly Pro  Ala Gly Glu Lys Gly  Ala Pro Gly Glu Lys  Gly Pro Gln
    1115                 1120                 1125

Gly Pro  Ala Gly Arg Asp Gly  Leu Gln Gly Pro Val  Gly Leu Pro
    1130                 1135                 1140

Gly Pro  Ala Gly Pro Val Gly  Pro Pro Gly Glu Asp  Gly Asp Lys
    1145                 1150                 1155

Gly Glu  Ile Gly Glu Pro Gly  Gln Lys Gly Ser Lys  Gly Asp Lys
    1160                 1165                 1170
```

-continued

```
Gly Glu  Gln Gly Pro Pro Gly  Pro Thr Gly Pro Gln  Gly Pro Ile
    1175                 1180                 1185

Gly Gln  Pro Gly Pro Ser Gly  Ala Asp Gly Glu Pro  Gly Pro Arg
    1190                 1195                 1200

Gly Gln  Gln Gly Leu Phe Gly  Gln Lys Gly Asp Glu  Gly Pro Arg
    1205                 1210                 1215

Gly Phe  Pro Gly Pro Pro Gly  Pro Val Gly Leu Gln  Gly Leu Pro
    1220                 1225                 1230

Gly Pro  Pro Gly Glu Lys Gly  Glu Thr Gly Asp Val  Gly Gln Met
    1235                 1240                 1245

Gly Pro  Pro Gly Pro Pro Gly  Pro Arg Gly Pro Ser  Gly Ala Pro
    1250                 1255                 1260

Gly Ala  Asp Gly Pro Gln Gly  Pro Pro Gly Gly Ile  Gly Asn Pro
    1265                 1270                 1275

Gly Ala  Val Gly Glu Lys Gly  Glu Pro Gly Glu Ala  Gly Glu Pro
    1280                 1285                 1290

Gly Leu  Pro Gly Glu Gly Gly  Pro Pro Gly Pro Lys  Gly Glu Arg
    1295                 1300                 1305

Gly Glu  Lys Gly Glu Ser Gly  Pro Ser Gly Ala Ala  Gly Pro Pro
    1310                 1315                 1320

Gly Pro  Lys Gly Pro Pro Gly  Asp Asp Gly Pro Lys  Gly Ser Pro
    1325                 1330                 1335

Gly Pro  Val Gly Phe Pro Gly  Asp Pro Gly Pro Pro  Gly Glu Pro
    1340                 1345                 1350

Gly Pro  Ala Gly Gln Asp Gly  Pro Pro Gly Asp Lys  Gly Asp Asp
    1355                 1360                 1365

Gly Glu  Pro Gly Gln Thr Gly  Ser Pro Gly Pro Thr  Gly Glu Pro
    1370                 1375                 1380

Gly Pro  Ser Gly Pro Pro Gly  Lys Arg Gly Pro Pro  Gly Pro Ala
    1385                 1390                 1395

Gly Pro  Glu Gly Arg Gln Gly  Glu Lys Gly Ala Lys  Gly Glu Ala
    1400                 1405                 1410

Gly Leu  Glu Gly Pro Pro Gly  Lys Thr Gly Pro Ile  Gly Pro Gln
    1415                 1420                 1425

Gly Ala  Pro Gly Lys Pro Gly  Pro Asp Gly Leu Arg  Gly Ile Pro
    1430                 1435                 1440

Gly Pro  Val Gly Glu Gln Gly  Leu Pro Gly Ser Pro  Gly Pro Asp
    1445                 1450                 1455

Gly Pro  Pro Gly Pro Met Gly  Pro Pro Gly Leu Pro  Gly Leu Lys
    1460                 1465                 1470

Gly Asp  Ser Gly Pro Lys Gly  Glu Lys Gly His Pro  Gly Leu Ile
    1475                 1480                 1485

Gly Leu  Ile Gly Pro Pro Gly  Glu Gln Gly Glu Lys  Gly Asp Arg
    1490                 1495                 1500

Gly Leu  Pro Gly Pro Gln Gly  Ser Ser Gly Pro Lys  Gly Glu Gln
    1505                 1510                 1515

Gly Ile  Thr Gly Pro Ser Gly  Pro Ile Gly Pro Pro  Gly Pro Pro
    1520                 1525                 1530

Gly Leu  Pro Gly Pro Pro Gly  Pro Lys Gly Ala Lys  Gly Ser Ser
    1535                 1540                 1545

Gly Pro  Thr Gly Pro Lys Gly  Glu Ala Gly His Pro  Gly Pro Pro
    1550                 1555                 1560

Gly Pro  Pro Gly Pro Pro Gly  Glu Val Ile Gln Pro  Leu Pro Ile
    1565                 1570                 1575
```

Gln Ala Ser Arg Thr Arg Arg Asn Ile Asp Ala Ser Gln Leu Leu
1580 1585 1590

Asp Asp Gly Asn Gly Glu Asn Tyr Val Asp Tyr Ala Asp Gly Met
1595 1600 1605

Glu Glu Ile Phe Gly Ser Leu Asn Ser Leu Lys Leu Glu Ile Glu
1610 1615 1620

Gln Met Lys Arg Pro Leu Gly Thr Gln Gln Asn Pro Ala Arg Thr
1625 1630 1635

Cys Lys Asp Leu Gln Leu Cys His Pro Asp Phe Pro Asp Gly Glu
1640 1645 1650

Tyr Trp Val Asp Pro Asn Gln Gly Cys Ser Arg Asp Ser Phe Lys
1655 1660 1665

Val Tyr Cys Asn Phe Thr Ala Gly Gly Ser Thr Cys Val Phe Pro
1670 1675 1680

Asp Lys Lys Ser Glu Gly Ala Arg Ile Thr Ser Trp Pro Lys Glu
1685 1690 1695

Asn Pro Gly Ser Trp Phe Ser Glu Phe Lys Arg Gly Lys Leu Leu
1700 1705 1710

Ser Tyr Val Asp Ala Glu Gly Asn Pro Val Gly Val Val Gln Met
1715 1720 1725

Thr Phe Leu Arg Leu Leu Ser Ala Ser Ala His Gln Asn Val Thr
1730 1735 1740

Tyr His Cys Tyr Gln Ser Val Ala Trp Gln Asp Ala Ala Thr Gly
1745 1750 1755

Ser Tyr Asp Lys Ala Leu Arg Phe Leu Gly Ser Asn Asp Glu Glu
1760 1765 1770

Met Ser Tyr Asp Asn Asn Pro Tyr Ile Arg Ala Leu Val Asp Gly
1775 1780 1785

Cys Ala Thr Lys Lys Gly Tyr Gln Lys Thr Val Leu Glu Ile Asp
1790 1795 1800

Thr Pro Lys Val Glu Gln Val Pro Ile Val Asp Ile Met Phe Asn
1805 1810 1815

Asp Phe Gly Glu Ala Ser Gln Lys Phe Gly Phe Glu Val Gly Pro
1820 1825 1830

Ala Cys Phe Met Gly
1835

<210> SEQ ID NO 71
<211> LENGTH: 620
<212> TYPE: PRT
<213> ORGANISM: Artificial Sequence
<220> FEATURE:
<223> OTHER INFORMATION: Synthetic

<400> SEQUENCE: 71

Leu Val Glu Gln Ser Gly Lys Ala Leu Leu Gly Pro His Ile Ser Glu
1 5 10 15

Lys Ala Glu Leu Gly Ser Cys Leu Arg Ser Leu Gln Gly Gln Pro Arg
20 25 30

Arg Leu Ala Val Pro Ser Arg Pro Leu Ser Ala Asp Val Asn Glu Cys
35 40 45

Leu Thr Ile Pro Glu Ala Cys Lys Gly Glu Met Lys Cys Ile Asn His
50 55 60

Tyr Gly Gly Tyr Leu Cys Leu Pro Arg Ser Ala Ala Val Ile Asn Asp
65 70 75 80

-continued

```
Leu His Gly Glu Gly Pro Pro Pro Pro Val Pro Pro Ala Gln His Pro
                85                  90                  95

Asn Pro Cys Pro Pro Gly Tyr Glu Pro Asp Asp Gln Asp Ser Cys Val
            100                 105                 110

Gly Glu Trp Gly Leu Leu Trp Cys Leu Ala Ser Ser Pro Leu Thr Arg
        115                 120                 125

Arg Leu Lys Leu Arg Pro His Val Pro Pro Gln Leu Lys Arg Ala Thr
    130                 135                 140

Gly Asp Val His Thr Leu Ile Gln Thr Leu Met Leu Phe Arg Thr Cys
145                 150                 155                 160

Arg Arg Trp Pro Gln Leu Val Cys His Cys Ser Ser Gln Leu Arg Ala
                165                 170                 175

Pro Pro Leu Gly Cys Cys Arg Asp Thr Ala Gly Ser Leu Pro Ser Ser
            180                 185                 190

Val Cys Pro Leu Gly Ala Thr Gly Leu Gly Gly Arg Thr Val Gln Glu
        195                 200                 205

Ser Val Leu Leu Gly Met Phe Gly Gln Asp Leu Ile Ser Cys Ala Thr
    210                 215                 220

Pro Asn Met Trp Phe Val Pro Ala Gly Ser Ser Pro Pro Ala Leu Cys
225                 230                 235                 240

Pro Leu Pro Ser Ala Leu Leu Leu Leu Pro Leu Ser Leu Asp Ile Asp
                245                 250                 255

Glu Cys Arg Tyr Arg Tyr Cys Gln His Arg Cys Val Asn Leu Pro Gly
            260                 265                 270

Ser Phe Arg Cys Gln Cys Glu Pro Gly Phe Gln Leu Gly Pro Asn Asn
        275                 280                 285

Arg Ser Cys Val Asp Val Asn Glu Cys Asp Met Gly Ala Pro Cys Glu
    290                 295                 300

Gln Arg Cys Phe Asn Ser Tyr Gly Thr Phe Leu Cys Arg Cys His Gln
305                 310                 315                 320

Gly Tyr Glu Leu His Arg Asp Gly Phe Ser Cys Ser Gly Glu Ser Ser
                325                 330                 335

Ile Pro Ala Val Tyr Ser Ser Val Asp Pro Gln Ala Leu Ala Met Pro
            340                 345                 350

Cys Leu Leu Pro His Ser Ser Pro Phe Glu Ala Ser Ala Ser Cys His
        355                 360                 365

Cys Ala Pro Ser Cys Leu Leu Gly Thr Arg Pro Arg Leu Ala Val Glu
    370                 375                 380

His Ser Gln Ala Ser Gly Gly Gly Thr Arg Arg Gly Ser Tyr Val Leu
385                 390                 395                 400

Thr Glu Ala Tyr Trp Gly Met Pro Leu Thr Arg Gly Pro His Pro His
                405                 410                 415

Ala Ser Ser Asp Ile Asp Glu Cys Ser Tyr Ser Ser Tyr Leu Cys Gln
            420                 425                 430

Tyr Arg Cys Val Asn Glu Pro Gly Arg Phe Ser Cys His Cys Pro Gln
        435                 440                 445

Gly Tyr Gln Leu Leu Ala Thr Arg Leu Cys Gln Asp Ile Asp Glu Cys
    450                 455                 460

Glu Ser Gly Ala His Gln Cys Ser Glu Ala Gln Thr Cys Val Asn Phe
465                 470                 475                 480

His Gly Gly Tyr Arg Cys Val Asp Thr Asn Arg Cys Val Glu Pro Tyr
                485                 490                 495

Ile Gln Val Ser Glu Asn Arg Cys Leu Cys Pro Ala Ser Asn Pro Leu
            500                 505                 510
```

```
Cys Arg Glu Gln Pro Ser Ser Ile Val His Arg Tyr Met Thr Ile Thr
        515                 520                 525

Ser Glu Arg Ser Val Pro Ala Asp Val Phe Gln Ile Gln Ala Thr Ser
    530                 535                 540

Val Tyr Pro Gly Ala Tyr Asn Ala Phe Gln Ile Arg Ala Gly Asn Ser
545                 550                 555                 560

Gln Gly Asp Phe Tyr Ile Arg Gln Ile Asn Asn Val Ser Ala Met Leu
                565                 570                 575

Val Leu Ala Arg Pro Val Thr Gly Pro Arg Glu Tyr Val Leu Asp Leu
            580                 585                 590

Glu Met Val Thr Met Asn Ser Leu Met Ser Tyr Arg Ala Ser Ser Val
        595                 600                 605

Leu Arg Leu Thr Val Phe Val Gly Ala Tyr Thr Phe
    610                 615                 620


<210> SEQ ID NO 72
<211> LENGTH: 310
<212> TYPE: PRT
<213> ORGANISM: Artificial Sequence
<220> FEATURE:
<223> OTHER INFORMATION: Synthetic

<400> SEQUENCE: 72

Met Gly Asn Gln Val Glu Lys Leu Thr His Leu Ser Tyr Lys Glu Val
1               5                   10                  15

Pro Thr Ala Asp Pro Thr Gly Val Asp Arg Asp Asp Gly Pro Arg Ile
            20                  25                  30

Gly Val Ser Tyr Ile Phe Ser Asn Asp Asp Glu Asp Val Glu Pro Gln
        35                  40                  45

Pro Pro Pro Gln Gly Pro Asp Gly Gly Gly Leu Pro Asp Gly Gly Asp
    50                  55                  60

Gly Pro Pro Pro Pro Gln Pro Gln Pro Tyr Asp Pro Arg Leu His Glu
65                  70                  75                  80

Val Glu Cys Ser Val Phe Tyr Arg Asp Glu Cys Ile Tyr Gln Lys Ser
                85                  90                  95

Phe Ala Pro Gly Ser Ala Ala Leu Ser Thr Tyr Thr Pro Glu Asn Leu
            100                 105                 110

Leu Asn Lys Cys Lys Pro Gly Asp Leu Val Glu Phe Val Ser Gln Ala
        115                 120                 125

Gln Tyr Pro His Trp Ala Val Tyr Val Gly Asn Phe Gln Val Val His
    130                 135                 140

Leu His Arg Leu Glu Val Ile Asn Ser Phe Leu Thr Asp Ala Ser Gln
145                 150                 155                 160

Gly Arg Arg Gly Arg Val Val Asn Asp Leu Tyr Arg Tyr Lys Pro Leu
                165                 170                 175

Ser Ser Ser Ala Val Val Arg Asn Ala Leu Ala His Val Gly Ala Lys
            180                 185                 190

Glu Arg Glu Leu Ser Trp Arg Asn Ser Glu Ser Phe Ala Ala Trp Cys
        195                 200                 205

Arg Tyr Gly Lys Arg Glu Phe Lys Ile Gly Gly Glu Leu Arg Ile Gly
    210                 215                 220

Lys Gln Pro Tyr Arg Leu Gln Ile Gln Leu Ser Ala Gln Arg Ser His
225                 230                 235                 240

Thr Leu Glu Phe Gln Ser Leu Glu Asp Leu Ile Met Glu Lys Arg Arg
                245                 250                 255
```

Asn Asp Gln Ile Gly Arg Ala Ala Val Leu Gln Glu Leu Ala Thr His
260 265 270

Leu His Pro Ala Glu Pro Glu Glu Gly Asp Ser Asn Val Ala Arg Thr
275 280 285

Thr Pro Pro Pro Gly Arg Pro Pro Ala Pro Ser Ser Glu Glu Glu Asp
290 295 300

Gly Glu Ala Val Ala His
305 310

<210> SEQ ID NO 73
<211> LENGTH: 582
<212> TYPE: PRT
<213> ORGANISM: Artificial Sequence
<220> FEATURE:
<223> OTHER INFORMATION: Synthetic

<400> SEQUENCE: 73

Met Phe Pro Ala Gly Pro Pro Ser His Ser Leu Leu Arg Leu Pro Leu
1 5 10 15

Leu Gln Leu Leu Leu Leu Val Val Gln Ala Val Gly Arg Gly Leu Gly
20 25 30

Arg Ala Ser Pro Ala Gly Gly Pro Leu Glu Asp Val Val Ile Glu Arg
35 40 45

Tyr His Ile Pro Arg Ala Cys Pro Arg Glu Val Gln Met Gly Asp Phe
50 55 60

Val Arg Tyr His Tyr Asn Gly Thr Phe Glu Asp Gly Lys Lys Phe Asp
65 70 75 80

Ser Ser Tyr Asp Arg Asn Thr Leu Val Ala Ile Val Val Gly Val Gly
85 90 95

Arg Leu Ile Thr Gly Met Asp Arg Gly Leu Met Gly Met Cys Val Asn
100 105 110

Glu Arg Arg Arg Leu Ile Val Pro Pro His Leu Gly Tyr Gly Ser Ile
115 120 125

Gly Leu Ala Gly Leu Ile Pro Pro Asp Ala Thr Leu Tyr Phe Asp Val
130 135 140

Val Leu Leu Asp Val Trp Asn Lys Glu Asp Thr Val Gln Val Ser Thr
145 150 155 160

Leu Leu Arg Pro Pro His Cys Pro Arg Met Val Gln Asp Gly Asp Phe
165 170 175

Val Arg Tyr His Tyr Asn Gly Thr Leu Leu Asp Gly Thr Ser Phe Asp
180 185 190

Thr Ser Tyr Ser Lys Gly Gly Thr Tyr Asp Thr Tyr Val Gly Ser Gly
195 200 205

Trp Leu Ile Lys Gly Met Asp Gln Gly Leu Leu Gly Met Cys Pro Gly
210 215 220

Glu Arg Arg Lys Ile Ile Ile Pro Pro Phe Leu Ala Tyr Gly Glu Lys
225 230 235 240

Gly Tyr Gly Thr Val Ile Pro Pro Gln Ala Ser Leu Val Phe His Val
245 250 255

Leu Leu Ile Asp Val His Asn Pro Lys Asp Ala Val Gln Leu Glu Thr
260 265 270

Leu Glu Leu Pro Pro Gly Cys Val Arg Arg Ala Gly Ala Gly Asp Phe
275 280 285

Met Arg Tyr His Tyr Asn Gly Ser Leu Met Asp Gly Thr Leu Phe Asp
290 295 300

Ser Ser Tyr Ser Arg Asn His Thr Tyr Asn Thr Tyr Ile Gly Gln Gly

```
305                 310                 315                 320

Tyr Ile Ile Pro Gly Met Asp Gln Gly Leu Gln Gly Ala Cys Met Gly
                325                 330                 335

Glu Arg Arg Arg Ile Thr Ile Pro Pro His Leu Ala Tyr Gly Glu Asn
            340                 345                 350

Gly Thr Gly Asp Lys Ile Pro Gly Ser Ala Val Leu Ile Phe Asn Val
        355                 360                 365

His Val Ile Asp Phe His Asn Pro Ala Asp Val Val Glu Ile Arg Thr
    370                 375                 380

Leu Ser Arg Pro Ser Glu Thr Cys Asn Glu Thr Thr Lys Leu Gly Asp
385                 390                 395                 400

Phe Val Arg Tyr His Tyr Asn Cys Ser Leu Leu Asp Gly Thr Gln Leu
                405                 410                 415

Phe Thr Ser His Asp Tyr Gly Ala Pro Gln Glu Ala Thr Leu Gly Ala
            420                 425                 430

Asn Lys Val Ile Glu Gly Leu Asp Thr Gly Leu Gln Gly Met Cys Val
        435                 440                 445

Gly Glu Arg Arg Gln Leu Ile Val Pro Pro His Leu Ala His Gly Glu
    450                 455                 460

Ser Gly Ala Arg Gly Val Pro Gly Ser Ala Val Leu Leu Phe Glu Val
465                 470                 475                 480

Glu Leu Val Ser Arg Glu Asp Gly Leu Pro Thr Gly Tyr Leu Phe Val
                485                 490                 495

Trp His Lys Asp Pro Pro Ala Asn Leu Phe Glu Asp Met Asp Leu Asn
            500                 505                 510

Lys Asp Gly Glu Val Pro Pro Glu Glu Phe Ser Thr Phe Ile Lys Ala
        515                 520                 525

Gln Val Ser Glu Gly Lys Gly Arg Leu Met Pro Gly Gln Asp Pro Glu
    530                 535                 540

Lys Thr Ile Gly Asp Met Phe Gln Asn Gln Asp Arg Asn Gln Asp Gly
545                 550                 555                 560

Lys Ile Thr Val Asp Glu Leu Lys Leu Lys Ser Asp Glu Asp Glu Glu
                565                 570                 575

Arg Val His Glu Glu Leu
            580


<210> SEQ ID NO 74
<211> LENGTH: 570
<212> TYPE: PRT
<213> ORGANISM: Artificial Sequence
<220> FEATURE:
<223> OTHER INFORMATION: Synthetic

<400> SEQUENCE: 74

Met Ala Phe Arg Gly Trp Arg Pro Pro Pro Pro Pro Leu Leu Leu Leu
1               5                   10                  15

Leu Leu Trp Val Thr Gly Gln Ala Ala Pro Val Ala Gly Leu Gly Ser
            20                  25                  30

Asp Ala Glu Leu Gln Ile Glu Arg Arg Phe Val Pro Asp Glu Cys Pro
        35                  40                  45

Arg Thr Val Arg Ser Gly Asp Phe Val Arg Tyr His Tyr Val Gly Thr
    50                  55                  60

Phe Pro Asp Gly Gln Lys Phe Asp Ser Ser Tyr Asp Arg Asp Ser Thr
65                  70                  75                  80

Phe Asn Val Phe Val Gly Lys Gly Gln Leu Ile Thr Gly Met Asp Gln
                85                  90                  95
```

```
Ala Leu Val Gly Met Cys Val Asn Glu Arg Arg Phe Val Lys Ile Pro
            100                 105                 110

Pro Lys Leu Ala Tyr Gly Asn Glu Gly Val Ser Gly Val Ile Pro Pro
        115                 120                 125

Asn Ser Val Leu His Phe Asp Val Leu Leu Met Asp Ile Trp Asn Ser
    130                 135                 140

Glu Asp Gln Val Gln Ile His Thr Tyr Phe Lys Pro Pro Ser Cys Pro
145                 150                 155                 160

Arg Thr Ile Gln Val Ser Asp Phe Val Arg Tyr His Tyr Asn Gly Thr
                165                 170                 175

Phe Leu Asp Gly Thr Leu Phe Asp Ser Ser His Asn Arg Met Lys Thr
            180                 185                 190

Tyr Asp Thr Tyr Val Gly Ile Gly Trp Leu Ile Pro Gly Met Asp Lys
        195                 200                 205

Gly Leu Leu Gly Met Cys Val Gly Glu Lys Arg Ile Ile Thr Ile Pro
    210                 215                 220

Pro Phe Leu Ala Tyr Gly Glu Asp Gly Asp Gly Lys Asp Ile Pro Gly
225                 230                 235                 240

Gln Ala Ser Leu Val Phe Asp Val Ala Leu Leu Asp Leu His Asn Pro
                245                 250                 255

Lys Asp Ser Ile Ser Ile Glu Asn Lys Val Val Pro Glu Asn Cys Glu
            260                 265                 270

Arg Ile Ser Gln Ser Gly Asp Phe Leu Arg Tyr His Tyr Asn Gly Thr
        275                 280                 285

Leu Leu Asp Gly Thr Leu Phe Asp Ser Ser Tyr Ser Arg Asn Arg Thr
    290                 295                 300

Phe Asp Thr Tyr Ile Gly Gln Gly Tyr Val Ile Pro Gly Met Asp Glu
305                 310                 315                 320

Gly Leu Leu Gly Val Cys Ile Gly Glu Lys Arg Arg Ile Val Val Pro
                325                 330                 335

Pro His Leu Gly Tyr Gly Glu Glu Gly Arg Gly Asn Ile Pro Gly Ser
            340                 345                 350

Ala Val Leu Val Phe Asp Ile His Val Ile Asp Phe His Asn Pro Ser
        355                 360                 365

Asp Ser Ile Ser Ile Thr Ser His Tyr Lys Pro Pro Asp Cys Ser Val
    370                 375                 380

Leu Ser Lys Lys Gly Asp Tyr Leu Lys Tyr His Tyr Asn Ala Ser Leu
385                 390                 395                 400

Leu Asp Gly Thr Leu Leu Asp Ser Thr Trp Asn Leu Gly Lys Thr Tyr
                405                 410                 415

Asn Ile Val Leu Gly Ser Gly Gln Val Val Leu Gly Met Asp Met Gly
            420                 425                 430

Leu Arg Glu Met Cys Val Gly Glu Lys Arg Thr Val Ile Ile Pro Pro
        435                 440                 445

His Leu Gly Tyr Gly Glu Ala Gly Val Asp Gly Glu Val Pro Gly Ser
    450                 455                 460

Ala Val Leu Val Phe Asp Ile Glu Leu Leu Glu Leu Val Ala Gly Leu
465                 470                 475                 480

Pro Glu Gly Tyr Met Phe Ile Trp Asn Gly Glu Val Ser Pro Asn Leu
                485                 490                 495

Phe Glu Glu Ile Asp Lys Asp Gly Asn Gly Glu Val Leu Leu Glu Glu
            500                 505                 510

Phe Ser Glu Tyr Ile His Ala Gln Val Ala Ser Gly Lys Gly Lys Leu
```

515 520 525

Ala Pro Gly Phe Asp Ala Glu Leu Ile Val Lys Asn Met Phe Thr Asn
530 535 540

Gln Asp Arg Asn Gly Asp Gly Lys Val Thr Ala Glu Glu Phe Lys Leu
545 550 555 560

Lys Asp Gln Glu Ala Lys His Asp Glu Leu
565 570

<210> SEQ ID NO 75
<211> LENGTH: 357
<212> TYPE: PRT
<213> ORGANISM: Artificial Sequence
<220> FEATURE:
<223> OTHER INFORMATION: Synthetic

<400> SEQUENCE: 75

Met Ala Thr Thr Val Pro Asp Gly Cys Arg Asn Gly Leu Lys Ser Lys
1 5 10 15

Tyr Tyr Arg Leu Cys Asp Lys Ala Glu Ala Trp Gly Ile Val Leu Glu
20 25 30

Thr Val Ala Thr Ala Gly Val Val Thr Ser Val Ala Phe Met Leu Thr
35 40 45

Leu Pro Ile Leu Val Cys Lys Val Gln Asp Ser Asn Arg Arg Lys Met
50 55 60

Leu Pro Thr Gln Phe Leu Phe Leu Leu Gly Val Leu Gly Ile Phe Gly
65 70 75 80

Leu Thr Phe Ala Phe Ile Ile Gly Leu Asp Gly Ser Thr Gly Pro Thr
85 90 95

Arg Phe Phe Leu Phe Gly Ile Leu Phe Ser Ile Cys Phe Ser Cys Leu
100 105 110

Leu Ala His Ala Val Ser Leu Thr Lys Leu Val Arg Gly Arg Lys Pro
115 120 125

Leu Ser Leu Leu Val Ile Leu Gly Leu Ala Val Gly Phe Ser Leu Val
130 135 140

Gln Asp Val Ile Ala Ile Glu Tyr Ile Val Leu Thr Met Asn Arg Thr
145 150 155 160

Asn Val Asn Val Phe Ser Glu Leu Ser Ala Pro Arg Arg Asn Glu Asp
165 170 175

Phe Val Leu Leu Leu Thr Tyr Val Leu Phe Leu Met Ala Leu Thr Phe
180 185 190

Leu Met Ser Ser Phe Thr Phe Cys Gly Ser Phe Thr Gly Trp Lys Arg
195 200 205

His Gly Ala His Ile Tyr Leu Thr Met Leu Leu Ser Ile Ala Ile Trp
210 215 220

Val Ala Trp Ile Thr Leu Leu Met Leu Pro Asp Phe Asp Arg Arg Trp
225 230 235 240

Asp Asp Thr Ile Leu Ser Ser Ala Leu Ala Ala Asn Gly Trp Val Phe
245 250 255

Leu Leu Ala Tyr Val Ser Pro Glu Phe Trp Leu Leu Thr Lys Gln Arg
260 265 270

Asn Pro Met Asp Tyr Pro Val Glu Asp Ala Phe Cys Lys Pro Gln Leu
275 280 285

Val Lys Lys Ser Tyr Gly Val Glu Asn Arg Ala Tyr Ser Gln Glu Glu
290 295 300

Ile Thr Gln Gly Phe Glu Glu Thr Gly Asp Thr Leu Tyr Ala Pro Tyr
305 310 315 320

-continued

```
Ser Thr His Phe Gln Leu Gln Asn Gln Pro Pro Gln Lys Glu Phe Ser
                325                 330                 335

Ile Pro Arg Ala His Ala Trp Pro Ser Pro Tyr Lys Asp Tyr Glu Val
            340                 345                 350

Lys Lys Glu Gly Ser
        355
```

<210> SEQ ID NO 76
<211> LENGTH: 529
<212> TYPE: PRT
<213> ORGANISM: Artificial Sequence
<220> FEATURE:
<223> OTHER INFORMATION: Synthetic

<400> SEQUENCE: 76

```
Met Ser Thr Asn Glu Asn Ala Asn Thr Pro Ala Ala Arg Leu His Arg
1               5                   10                  15

Phe Lys Asn Lys Gly Lys Asp Ser Thr Glu Met Arg Arg Arg Arg Ile
            20                  25                  30

Glu Val Asn Val Glu Leu Arg Lys Ala Lys Lys Asp Asp Gln Met Leu
        35                  40                  45

Lys Arg Arg Asn Val Ser Ser Phe Pro Asp Asp Ala Thr Ser Pro Leu
    50                  55                  60

Gln Glu Asn Arg Asn Asn Gln Gly Thr Val Asn Trp Ser Val Asp Asp
65                  70                  75                  80

Ile Val Lys Gly Ile Asn Ser Ser Asn Val Glu Asn Gln Leu Gln Ala
                85                  90                  95

Thr Gln Ala Ala Arg Lys Leu Leu Ser Arg Glu Lys Gln Pro Pro Ile
            100                 105                 110

Asp Asn Ile Ile Arg Ala Gly Leu Ile Pro Lys Phe Val Ser Phe Leu
        115                 120                 125

Gly Arg Thr Asp Cys Ser Pro Ile Gln Phe Glu Ser Ala Trp Ala Leu
    130                 135                 140

Thr Asn Ile Ala Ser Gly Thr Ser Glu Gln Thr Lys Ala Val Val Asp
145                 150                 155                 160

Gly Gly Ala Ile Pro Ala Phe Ile Ser Leu Leu Ala Ser Pro His Ala
                165                 170                 175

His Ile Ser Glu Gln Ala Val Trp Ala Leu Gly Asn Ile Ala Gly Asp
            180                 185                 190

Gly Ser Val Phe Arg Asp Leu Val Ile Lys Tyr Gly Ala Val Asp Pro
        195                 200                 205

Leu Leu Ala Leu Leu Ala Val Pro Glu Met Ser Ser Leu Ala Cys Gly
    210                 215                 220

Tyr Leu Arg Asn Leu Thr Trp Thr Leu Ser Asn Leu Cys Arg Asn Lys
225                 230                 235                 240

Asn Pro Ala Pro Pro Ile Asp Ala Val Glu Gln Ile Leu Pro Thr Leu
                245                 250                 255

Val Arg Leu Leu His His Asp Asp Pro Glu Val Leu Ala Asp Thr Cys
            260                 265                 270

Trp Ala Ile Ser Tyr Leu Thr Asp Gly Pro Asn Glu Arg Ile Gly Met
        275                 280                 285

Val Val Lys Thr Gly Val Val Pro Gln Leu Val Lys Leu Leu Gly Ala
    290                 295                 300

Ser Glu Leu Pro Ile Val Thr Pro Ala Leu Arg Ala Ile Gly Asn Ile
305                 310                 315                 320
```

Val Thr Gly Thr Asp Glu Gln Thr Gln Val Val Ile Asp Ala Gly Ala
325 330 335

Leu Ala Val Phe Pro Ser Leu Leu Thr Asn Pro Lys Thr Asn Ile Gln
340 345 350

Lys Glu Ala Thr Trp Thr Met Ser Asn Ile Thr Ala Gly Arg Gln Asp
355 360 365

Gln Ile Gln Gln Val Val Asn His Gly Leu Val Pro Phe Leu Val Ser
370 375 380

Val Leu Ser Lys Ala Asp Phe Lys Thr Gln Lys Glu Ala Val Trp Ala
385 390 395 400

Val Thr Asn Tyr Thr Ser Gly Gly Thr Val Glu Gln Ile Val Tyr Leu
405 410 415

Val His Cys Gly Ile Ile Glu Pro Leu Met Asn Leu Leu Thr Ala Lys
420 425 430

Asp Thr Lys Ile Ile Leu Val Ile Leu Asp Ala Ile Ser Asn Ile Phe
435 440 445

Gln Ala Ala Glu Lys Leu Gly Glu Thr Glu Lys Leu Ser Ile Met Ile
450 455 460

Glu Glu Cys Gly Gly Leu Asp Lys Ile Glu Ala Leu Gln Asn His Glu
465 470 475 480

Asn Glu Ser Val Tyr Lys Ala Ser Leu Ser Leu Ile Glu Lys Tyr Phe
485 490 495

Ser Val Glu Glu Glu Glu Asp Gln Asn Val Val Pro Glu Thr Thr Ser
500 505 510

Glu Gly Tyr Thr Phe Gln Val Gln Asp Gly Ala Pro Gly Thr Phe Asn
515 520 525

Phe

<210> SEQ ID NO 77
<211> LENGTH: 469
<212> TYPE: PRT
<213> ORGANISM: Artificial Sequence
<220> FEATURE:
<223> OTHER INFORMATION: Synthetic

<400> SEQUENCE: 77

Met His Ser Phe Pro Pro Leu Leu Leu Leu Leu Phe Trp Gly Val Val
1 5 10 15

Ser His Ser Phe Pro Ala Thr Leu Glu Thr Gln Glu Gln Asp Val Asp
20 25 30

Leu Val Gln Lys Tyr Leu Glu Lys Tyr Tyr Asn Leu Lys Asn Asp Gly
35 40 45

Arg Gln Val Glu Lys Arg Arg Asn Ser Gly Pro Val Val Glu Lys Leu
50 55 60

Lys Gln Met Gln Glu Phe Phe Gly Leu Lys Val Thr Gly Lys Pro Asp
65 70 75 80

Ala Glu Thr Leu Lys Val Met Lys Gln Pro Arg Cys Gly Val Pro Asp
85 90 95

Val Ala Gln Phe Val Leu Thr Glu Gly Asn Pro Arg Trp Glu Gln Thr
100 105 110

His Leu Thr Tyr Arg Ile Glu Asn Tyr Thr Pro Asp Leu Pro Arg Ala
115 120 125

Asp Val Asp His Ala Ile Glu Lys Ala Phe Gln Leu Trp Ser Asn Val
130 135 140

Thr Pro Leu Thr Phe Thr Lys Val Ser Glu Gly Gln Ala Asp Ile Met
145 150 155 160

```
Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Arg
        195                 200                 205

Glu Tyr Asn Leu His Arg Val Ala Ala His Glu Leu Gly His Ser Leu
    210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
        275                 280                 285

Thr Ile Arg Gly Glu Val Met Phe Phe Lys Asp Arg Phe Tyr Met Arg
    290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365

Gly Phe Pro Arg Thr Val Lys His Ile Asp Ala Ala Leu Ser Glu Glu
    370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
        435                 440                 445

Pro Lys Thr Lys Arg Ile Leu Thr Leu Gln Lys Ala Asn Ser Trp Phe
    450                 455                 460

Asn Cys Arg Lys Asn
465


<210> SEQ ID NO 78
<211> LENGTH: 448
<212> TYPE: PRT
<213> ORGANISM: Artificial Sequence
<220> FEATURE:
<223> OTHER INFORMATION: Synthetic

<400> SEQUENCE: 78

Met Ala Leu Thr Leu Leu Glu Asp Trp Cys Lys Gly Met Asp Met Asp
1               5                   10                  15

Pro Arg Lys Ala Leu Leu Ile Val Gly Ile Pro Met Glu Cys Ser Glu
            20                  25                  30

Val Glu Ile Gln Asp Thr Val Lys Ala Gly Leu Gln Pro Leu Cys Ala
        35                  40                  45
```

```
Tyr Arg Val Leu Gly Arg Met Phe Arg Arg Glu Asp Asn Ala Lys Ala
    50                  55                  60

Val Phe Ile Glu Leu Ala Asp Thr Val Asn Tyr Thr Thr Leu Pro Ser
65                  70                  75                  80

His Ile Pro Gly Lys Gly Gly Ser Trp Glu Val Val Val Lys Pro Arg
                85                  90                  95

Asn Pro Asp Asp Glu Phe Leu Ser Arg Leu Asn Tyr Phe Leu Lys Asp
            100                 105                 110

Glu Gly Arg Ser Met Thr Asp Val Ala Arg Ala Leu Gly Cys Cys Ser
        115                 120                 125

Leu Pro Ala Glu Ser Leu Asp Ala Glu Val Met Pro Gln Val Arg Ser
    130                 135                 140

Pro Pro Leu Glu Pro Pro Lys Glu Ser Met Trp Tyr Arg Lys Leu Lys
145                 150                 155                 160

Val Phe Ser Gly Thr Ala Ser Pro Ser Pro Gly Glu Glu Thr Phe Glu
                165                 170                 175

Asp Trp Leu Glu Gln Val Thr Glu Ile Met Pro Ile Trp Gln Val Ser
            180                 185                 190

Glu Val Glu Lys Arg Arg Arg Leu Leu Glu Ser Leu Arg Gly Pro Ala
        195                 200                 205

Leu Ser Ile Met Arg Val Leu Gln Ala Asn Asn Asp Ser Ile Thr Val
    210                 215                 220

Glu Gln Cys Leu Asp Ala Leu Lys Gln Ile Phe Gly Asp Lys Glu Asp
225                 230                 235                 240

Phe Arg Ala Ser Gln Phe Arg Phe Leu Gln Thr Ser Pro Lys Ile Gly
                245                 250                 255

Glu Lys Val Ser Thr Phe Leu Leu Arg Leu Glu Pro Leu Leu Gln Lys
            260                 265                 270

Ala Val His Lys Ser Pro Leu Ser Val Arg Ser Thr Asp Met Ile Arg
        275                 280                 285

Leu Lys His Leu Leu Ala Arg Val Ala Met Thr Pro Ala Leu Arg Gly
    290                 295                 300

Lys Leu Glu Leu Leu Asp Gln Arg Gly Cys Pro Pro Asn Phe Leu Glu
305                 310                 315                 320

Leu Met Lys Leu Ile Arg Asp Glu Glu Glu Trp Glu Asn Thr Glu Ala
                325                 330                 335

Val Met Lys Asn Lys Glu Lys Pro Ser Gly Arg Gly Arg Gly Ala Ser
            340                 345                 350

Gly Arg Gln Ala Arg Ala Glu Ala Ser Val Ser Ala Pro Gln Ala Thr
        355                 360                 365

Val Gln Ala Arg Ser Phe Ser Asp Ser Ser Pro Gln Thr Ile Gln Gly
    370                 375                 380

Gly Leu Pro Pro Leu Val Lys Arg Arg Arg Leu Leu Gly Ser Glu Ser
385                 390                 395                 400

Thr Arg Gly Glu Asp His Gly Gln Ala Thr Tyr Pro Lys Ala Glu Asn
                405                 410                 415

Gln Thr Pro Gly Arg Glu Gly Pro Gln Ala Ala Gly Glu Glu Leu Gly
            420                 425                 430

Asn Glu Ala Gly Ala Gly Ala Met Ser His Pro Lys Pro Trp Glu Thr
        435                 440                 445
```

<210> SEQ ID NO 79
<211> LENGTH: 346
<212> TYPE: PRT
<213> ORGANISM: Artificial Sequence
<220> FEATURE:
<223> OTHER INFORMATION: Synthetic

<400> SEQUENCE: 79

Met Ala Ala Ser Gln Ala Val Glu Glu Met Arg Ser Arg Val Val Leu
1               5                   10                  15

Gly Glu Phe Gly Val Arg Asn Val His Thr Thr Asp Phe Pro Gly Asn
            20                  25                  30

Tyr Ser Gly Tyr Asp Asp Ala Trp Asp Gln Asp Arg Phe Glu Lys Asn
        35                  40                  45

Phe Arg Val Asp Val Val His Met Asp Glu Asn Ser Leu Glu Phe Asp
    50                  55                  60

Met Val Gly Ile Asp Ala Ala Ile Ala Asn Ala Phe Arg Arg Ile Leu
65                  70                  75                  80

Leu Ala Glu Val Pro Thr Met Ala Val Glu Lys Val Leu Val Tyr Asn
                85                  90                  95

Asn Thr Ser Ile Val Gln Asp Glu Ile Leu Ala His Arg Leu Gly Leu
            100                 105                 110

Ile Pro Ile His Ala Asp Pro Arg Leu Phe Glu Tyr Arg Asn Gln Gly
        115                 120                 125

Asp Glu Glu Gly Thr Glu Ile Asp Thr Leu Gln Phe Arg Leu Gln Val
    130                 135                 140

Arg Cys Thr Arg Asn Pro His Ala Ala Lys Asp Ser Ser Asp Pro Asn
145                 150                 155                 160

Glu Leu Tyr Val Asn His Lys Val Tyr Thr Arg His Met Thr Trp Ile
                165                 170                 175

Pro Leu Gly Asn Gln Ala Asp Leu Phe Pro Glu Gly Thr Ile Arg Pro
            180                 185                 190

Val His Asp Asp Ile Leu Ile Ala Gln Leu Arg Pro Gly Gln Glu Ile
        195                 200                 205

Asp Leu Leu Met His Cys Val Lys Gly Ile Gly Lys Asp His Ala Lys
    210                 215                 220

Phe Ser Pro Val Ala Thr Ala Ser Tyr Arg Leu Leu Pro Asp Ile Thr
225                 230                 235                 240

Leu Leu Glu Pro Val Glu Gly Glu Ala Ala Glu Glu Leu Ser Arg Cys
                245                 250                 255

Phe Ser Pro Gly Val Ile Glu Val Gln Glu Val Gln Gly Lys Lys Val
            260                 265                 270

Ala Arg Val Ala Asn Pro Arg Leu Asp Thr Phe Ser Arg Glu Ile Phe
        275                 280                 285

Arg Asn Glu Lys Leu Lys Lys Val Val Arg Leu Ala Arg Val Arg Asp
    290                 295                 300

His Tyr Ile Phe Ser Val Glu Ser Thr Gly Val Leu Pro Pro Asp Val
305                 310                 315                 320

Leu Val Ser Glu Ala Ile Lys Val Leu Met Gly Lys Cys Arg Arg Phe
                325                 330                 335

Leu Asp Glu Leu Asp Ala Val Gln Met Asp
            340                 345

<210> SEQ ID NO 80
<211> LENGTH: 315
<212> TYPE: PRT
<213> ORGANISM: Artificial Sequence
<220> FEATURE:
<223> OTHER INFORMATION: Synthetic

<400> SEQUENCE: 80

Met His Phe Met Cys Asp Leu Arg Val Pro Ser Thr Met Arg Ala Trp
1 5 10 15

Ile Phe Phe Leu Leu Cys Leu Ala Gly Arg Ala Leu Ala Ala Pro Gln
20 25 30

Gln Glu Ala Leu Pro Asp Glu Thr Glu Val Val Glu Glu Thr Val Ala
35 40 45

Glu Val Thr Glu Val Ser Val Gly Ala Asn Pro Val Gln Val Glu Val
50 55 60

Gly Glu Phe Asp Asp Gly Ala Glu Glu Thr Glu Glu Glu Val Val Ala
65 70 75 80

Glu Asn Pro Cys Gln Asn His His Cys Lys His Gly Lys Val Cys Glu
85 90 95

Leu Asp Glu Asn Asn Thr Pro Met Cys Val Cys Gln Asp Pro Thr Ser
100 105 110

Cys Pro Ala Pro Ile Gly Glu Phe Glu Lys Val Cys Ser Asn Asp Asn
115 120 125

Lys Thr Phe Asp Ser Ser Cys His Phe Phe Ala Thr Lys Cys Thr Leu
130 135 140

Glu Gly Thr Lys Lys Gly His Lys Leu His Leu Asp Tyr Ile Gly Pro
145 150 155 160

Cys Lys Tyr Ile Pro Pro Cys Leu Asp Ser Glu Leu Thr Glu Phe Pro
165 170 175

Leu Arg Met Arg Asp Trp Leu Lys Asn Val Leu Val Thr Leu Tyr Glu
180 185 190

Arg Asp Glu Asp Asn Asn Leu Leu Thr Glu Lys Gln Lys Leu Arg Val
195 200 205

Lys Lys Ile His Glu Asn Glu Lys Arg Leu Glu Ala Gly Asp His Pro
210 215 220

Val Glu Leu Leu Ala Arg Asp Phe Glu Lys Asn Tyr Asn Met Tyr Ile
225 230 235 240

Phe Pro Val His Trp Gln Phe Gly Gln Leu Asp Gln His Pro Ile Asp
245 250 255

Gly Tyr Leu Ser His Thr Glu Leu Ala Pro Leu Arg Ala Pro Leu Ile
260 265 270

Pro Met Glu His Cys Thr Thr Arg Phe Phe Glu Thr Cys Asp Leu Asp
275 280 285

Asn Asp Lys Tyr Ile Ala Leu Asp Glu Trp Ala Gly Cys Phe Gly Ile
290 295 300

Lys Gln Lys Asp Ile Asp Lys Asp Leu Val Ile
305 310 315

<210> SEQ ID NO 81
<211> LENGTH: 1119
<212> TYPE: PRT
<213> ORGANISM: Artificial Sequence
<220> FEATURE:
<223> OTHER INFORMATION: Synthetic

<400> SEQUENCE: 81

Met Met Thr Ser Val Ser Ser Asp His Cys Arg Gly Ala Arg Glu Lys
1 5 10 15

Pro Gln Ile Ser Ala Ala Gln Ser Thr Gln Pro Gln Lys Gln Val Val
20 25 30

Gln Ala Thr Ala Glu Gln Met Arg Leu Ala Gln Val Ile Phe Asp Lys
35 40 45

```
Asn Asp Ser Asp Phe Glu Ala Lys Val Lys Gln Leu Met Glu Val Thr
    50                  55                  60

Gly Lys Asn Gln Asp Glu Cys Ile Val Ala Leu His Asp Cys Asn Gly
65                  70                  75                  80

Asp Val Asn Lys Ala Ile Asn Ile Leu Leu Glu Gly Asn Ser Asp Thr
                85                  90                  95

Thr Ser Trp Glu Thr Val Gly Cys Lys Lys Lys Asn Phe Ala Lys Glu
            100                 105                 110

Asn Ser Glu Asn Lys Glu Asn Arg Glu Lys Lys Ser Glu Lys Glu Ser
        115                 120                 125

Ser Arg Gly Arg Gly Asn Asn Asn Arg Lys Gly Arg Gly Gly Asn Arg
    130                 135                 140

Gly Arg Glu Phe Arg Gly Glu Glu Asn Gly Ile Asp Cys Asn Gln Val
145                 150                 155                 160

Asp Lys Pro Ser Asp Arg Gly Lys Arg Ala Arg Gly Arg Gly Phe Gly
                165                 170                 175

Arg Gly Arg Gly Arg Gly Ala Gly Arg Phe Ser Thr Gln Gly Met Gly
            180                 185                 190

Thr Phe Asn Pro Ala Asp Tyr Ser Asp Ser Thr Ser Thr Asp Val Cys
        195                 200                 205

Gly Thr Lys Leu Val Val Trp Glu Ala Ala Gln Asn Gly Ala Asp Glu
    210                 215                 220

Gly Thr Glu Leu Ala Ser Asn Thr His Asn Ile Ala Gln Asp Leu Ser
225                 230                 235                 240

Asn Lys Ser Ser Tyr Gly Leu Lys Gly Ala Trp Lys Asn Ser Val Glu
                245                 250                 255

Glu Trp Thr Thr Glu Asp Trp Thr Glu Asp Leu Ser Glu Thr Lys Val
            260                 265                 270

Phe Thr Ala Ser Ser Ala Pro Ala Glu Asn His Ile Leu Pro Gly Gln
        275                 280                 285

Ser Ile Asp Leu Val Ala Leu Leu Gln Lys Pro Val Pro His Ser Gln
    290                 295                 300

Ala Ser Glu Ala Asn Ser Phe Glu Thr Ser Gln Gln Gln Gly Phe Gly
305                 310                 315                 320

Gln Ala Leu Val Phe Thr Asn Ser Gln His Asn Asn Gln Met Ala Pro
                325                 330                 335

Gly Thr Gly Ser Ser Thr Ala Val Asn Ser Cys Ser Pro Gln Ser Leu
            340                 345                 350

Ser Ser Val Leu Gly Ser Gly Phe Gly Glu Leu Ala Pro Pro Lys Met
        355                 360                 365

Ala Asn Ile Thr Ser Ser Gln Ile Leu Asp Gln Leu Lys Ala Pro Ser
    370                 375                 380

Leu Gly Gln Phe Thr Thr Thr Pro Ser Thr Gln Gln Asn Ser Thr Ser
385                 390                 395                 400

His Pro Thr Thr Thr Thr Ser Trp Asp Leu Lys Pro Pro Thr Ser Gln
                405                 410                 415

Ser Ser Val Leu Ser His Leu Asp Phe Lys Ser Gln Pro Glu Pro Ser
            420                 425                 430

Pro Val Leu Ser Gln Leu Ser Gln Arg Gln Gln His Gln Ser Gln Ala
        435                 440                 445

Val Thr Val Pro Pro Pro Gly Leu Glu Ser Phe Pro Ser Gln Ala Lys
    450                 455                 460

Leu Arg Glu Ser Thr Pro Gly Asp Ser Pro Ser Thr Val Asn Lys Leu
465                 470                 475                 480
```

```
Leu Gln Leu Pro Ser Thr Thr Ile Glu Asn Ile Ser Val Ser Val His
                485                 490                 495

Gln Pro Gln Pro Lys His Ile Lys Leu Ala Lys Arg Arg Ile Pro Pro
            500                 505                 510

Ala Ser Lys Ile Pro Ala Ser Ala Val Glu Met Pro Gly Ser Ala Asp
        515                 520                 525

Val Thr Gly Leu Asn Val Gln Phe Gly Ala Leu Glu Phe Gly Ser Glu
    530                 535                 540

Pro Ser Leu Ser Glu Phe Gly Ser Ala Pro Ser Ser Glu Asn Ser Asn
545                 550                 555                 560

Gln Ile Pro Ile Ser Leu Tyr Ser Lys Ser Leu Ser Glu Pro Leu Asn
                565                 570                 575

Thr Ser Leu Ser Met Thr Ser Ala Val Gln Asn Ser Thr Tyr Thr Thr
            580                 585                 590

Ser Val Ile Thr Ser Cys Ser Leu Thr Ser Ser Ser Leu Asn Ser Ala
        595                 600                 605

Ser Pro Val Ala Met Ser Ser Ser Tyr Asp Gln Ser Ser Val His Asn
    610                 615                 620

Arg Ile Pro Tyr Gln Ser Pro Val Ser Ser Ser Glu Ser Ala Pro Gly
625                 630                 635                 640

Thr Ile Met Asn Gly His Gly Gly Gly Arg Ser Gln Gln Thr Leu Asp
                645                 650                 655

Thr Pro Lys Thr Thr Gly Pro Pro Ser Ala Leu Pro Ser Val Ser Ser
            660                 665                 670

Leu Pro Ser Thr Thr Ser Cys Thr Ala Leu Leu Pro Ser Thr Ser Gln
        675                 680                 685

His Thr Gly Asp Leu Thr Ser Ser Pro Leu Ser Gln Leu Ser Ser Ser
    690                 695                 700

Leu Ser Ser His Gln Ser Ser Leu Ser Ala His Ala Ala Leu Ser Ser
705                 710                 715                 720

Ser Thr Ser His Thr His Ala Ser Val Glu Ser Ala Ser Ser His Gln
                725                 730                 735

Ser Ser Ala Thr Phe Ser Thr Ala Ala Thr Ser Val Ser Ser Ser Ala
            740                 745                 750

Ser Ser Gly Ala Ser Leu Ser Ser Ser Met Asn Thr Ala Asn Ser Leu
        755                 760                 765

Cys Leu Gly Gly Thr Pro Ala Ser Ala Ser Ser Ser Ser Ser Arg Ala
    770                 775                 780

Ala Pro Leu Val Thr Ser Gly Lys Ala Pro Pro Asn Leu Pro Gln Gly
785                 790                 795                 800

Val Pro Pro Leu Leu His Asn Gln Tyr Leu Val Gly Pro Gly Gly Leu
                805                 810                 815

Leu Pro Ala Tyr Pro Ile Tyr Gly Tyr Asp Glu Leu Gln Met Leu Gln
            820                 825                 830

Ser Arg Leu Pro Val Asp Tyr Tyr Gly Ile Pro Phe Ala Ala Pro Thr
        835                 840                 845

Ala Leu Ala Ser Arg Asp Gly Ser Leu Ala Asn Asn Pro Tyr Pro Gly
    850                 855                 860

Asp Val Thr Lys Phe Gly Arg Gly Asp Ser Ala Ser Pro Ala Pro Ala
865                 870                 875                 880

Thr Thr Pro Ala Gln Pro Gln Gln Ser Gln Ser Gln Thr His His Thr
                885                 890                 895

Ala Gln Gln Pro Phe Val Asn Pro Ala Leu Pro Pro Gly Tyr Ser Tyr
```

```
            900                 905                 910

Thr Gly Leu Pro Tyr Tyr Thr Gly Met Pro Ser Ala Phe Gln Tyr Gly
        915                 920                 925

Pro Thr Met Phe Val Pro Pro Ala Ser Ala Lys Gln His Gly Val Asn
    930                 935                 940

Leu Ser Thr Pro Thr Pro Pro Phe Gln Gln Ala Ser Gly Tyr Gly Gln
945                 950                 955                 960

His Gly Tyr Ser Thr Gly Tyr Asp Asp Leu Thr Gln Gly Thr Ala Ala
                965                 970                 975

Gly Asp Tyr Ser Lys Gly Gly Tyr Ala Gly Ser Ser Gln Ala Pro Asn
            980                 985                 990

Lys Ser Ala Gly Ser Gly Pro Gly  Lys Gly Val Ser Val  Ser Ser Ser
        995                 1000                1005

Thr Thr  Gly Leu Pro Asp Met  Thr Gly Ser Val Tyr  Asn Lys Thr
    1010                1015                1020

Gln Thr  Phe Asp Lys Gln Gly  Phe His Ala Gly Thr  Pro Pro Pro
    1025                1030                1035

Phe Ser  Leu Pro Ser Val Leu  Gly Ser Thr Gly Pro  Leu Ala Ser
    1040                1045                1050

Gly Ala  Ala Pro Gly Tyr Ala  Pro Pro Pro Phe Leu  His Ile Leu
    1055                1060                1065

Pro Ala  His Gln Gln Pro His  Ser Gln Leu Leu His  His His Leu
    1070                1075                1080

Pro Gln  Asp Ala Gln Ser Gly  Ser Gly Gln Arg Ser  Gln Pro Ser
    1085                1090                1095

Ser Leu  Gln Pro Lys Ser Gln  Ala Ser Lys Pro Ala  Tyr Gly Asn
    1100                1105                1110

Ser Pro  Tyr Trp Thr Asn
    1115


<210> SEQ ID NO 82
<211> LENGTH: 261
<212> TYPE: PRT
<213> ORGANISM: Artificial Sequence
<220> FEATURE:
<223> OTHER INFORMATION: Synthetic

<400> SEQUENCE: 82

Met Ala Gly Asp Ser Glu Gln Thr Leu Gln Asn His Gln Gln Pro Asn
1               5                   10                  15

Gly Gly Glu Pro Phe Leu Ile Gly Val Ser Gly Gly Thr Ala Ser Gly
            20                  25                  30

Lys Ser Ser Val Cys Ala Lys Ile Val Gln Leu Leu Gly Gln Asn Glu
        35                  40                  45

Val Asp Tyr Arg Gln Lys Gln Val Val Ile Leu Ser Gln Asp Ser Phe
    50                  55                  60

Tyr Arg Val Leu Thr Ser Glu Gln Lys Ala Lys Ala Leu Lys Gly Gln
65                  70                  75                  80

Phe Asn Phe Asp His Pro Asp Ala Phe Asp Asn Glu Leu Ile Leu Lys
                85                  90                  95

Thr Leu Lys Glu Ile Thr Glu Gly Lys Thr Val Gln Ile Pro Val Tyr
            100                 105                 110

Asp Phe Val Ser His Ser Arg Lys Glu Glu Thr Val Thr Val Tyr Pro
        115                 120                 125

Ala Asp Val Val Leu Phe Glu Gly Ile Leu Ala Phe Tyr Ser Gln Glu
    130                 135                 140
```

```
Val Arg Asp Leu Phe Gln Met Lys Leu Phe Val Asp Thr Asp Ala Asp
145                 150                 155                 160

Thr Arg Leu Ser Arg Arg Val Leu Arg Asp Ile Ser Glu Arg Gly Arg
                165                 170                 175

Asp Leu Glu Gln Ile Leu Ser Gln Tyr Ile Thr Phe Val Lys Pro Ala
            180                 185                 190

Phe Glu Glu Phe Cys Leu Pro Thr Lys Lys Tyr Ala Asp Val Ile Ile
        195                 200                 205

Pro Arg Gly Ala Asp Asn Leu Val Ala Ile Asn Leu Ile Val Gln His
    210                 215                 220

Ile Gln Asp Ile Leu Asn Gly Gly Pro Ser Lys Arg Gln Thr Asn Gly
225                 230                 235                 240

Cys Leu Asn Gly Tyr Thr Pro Ser Arg Lys Arg Gln Ala Ser Glu Ser
                245                 250                 255

Ser Ser Arg Pro His
            260


<210> SEQ ID NO 83
<211> LENGTH: 385
<212> TYPE: PRT
<213> ORGANISM: Artificial Sequence
<220> FEATURE:
<223> OTHER INFORMATION: Synthetic

<400> SEQUENCE: 83

Met Ala Ala Ala Ala Ala Arg Trp Asn His Val Trp Val Gly Thr Glu
1               5                   10                  15

Thr Gly Ile Leu Lys Gly Val Asn Leu Gln Arg Lys Gln Ala Ala Asn
            20                  25                  30

Phe Thr Ala Gly Gly Gln Pro Arg Arg Glu Glu Ala Val Ser Ala Leu
        35                  40                  45

Cys Trp Gly Thr Gly Gly Glu Thr Gln Met Leu Val Gly Cys Ala Asp
    50                  55                  60

Arg Thr Val Lys His Phe Ser Thr Glu Asp Gly Ile Phe Gln Gly Gln
65                  70                  75                  80

Arg His Cys Pro Gly Gly Glu Gly Met Phe Arg Gly Leu Ala Gln Ala
                85                  90                  95

Asp Gly Thr Leu Ile Thr Cys Val Asp Ser Gly Ile Leu Arg Val Trp
            100                 105                 110

His Asp Lys Asp Lys Asp Thr Ser Ser Asp Pro Leu Leu Glu Leu Arg
        115                 120                 125

Val Gly Pro Gly Val Cys Arg Met Arg Gln Asp Pro Ala His Pro His
    130                 135                 140

Val Val Ala Thr Gly Gly Lys Glu Asn Ala Leu Lys Ile Trp Asp Leu
145                 150                 155                 160

Gln Gly Ser Glu Glu Pro Val Phe Arg Ala Lys Asn Val Arg Asn Asp
                165                 170                 175

Trp Leu Asp Leu Arg Val Pro Ile Trp Asp Gln Asp Ile Gln Phe Leu
            180                 185                 190

Pro Gly Ser Gln Lys Leu Val Thr Cys Thr Gly Tyr His Gln Val Arg
        195                 200                 205

Val Tyr Asp Pro Ala Ser Pro Gln Arg Arg Pro Val Leu Glu Thr Thr
    210                 215                 220

Tyr Gly Glu Tyr Pro Leu Thr Ala Met Thr Leu Thr Pro Gly Gly Asn
225                 230                 235                 240
```

```
Ser Val Ile Val Gly Asn Thr His Gly Gln Leu Ala Glu Ile Asp Leu
                245                 250                 255

Arg Gln Gly Arg Leu Leu Gly Cys Leu Lys Gly Leu Ala Gly Ser Val
            260                 265                 270

Arg Gly Leu Gln Cys His Pro Ser Lys Pro Leu Leu Ala Ser Cys Gly
        275                 280                 285

Leu Asp Arg Val Leu Arg Ile His Arg Ile Gln Asn Pro Arg Gly Leu
    290                 295                 300

Glu His Lys Val Tyr Leu Lys Ser Gln Leu Asn Cys Leu Leu Leu Ser
305                 310                 315                 320

Gly Arg Asp Asn Trp Glu Asp Glu Pro Gln Glu Pro Gln Glu Pro Asn
                325                 330                 335

Lys Val Pro Leu Glu Asp Thr Glu Thr Asp Glu Leu Trp Ala Ser Leu
            340                 345                 350

Glu Ala Ala Ala Lys Arg Lys Leu Ser Gly Leu Glu Gln Pro Gln Gly
        355                 360                 365

Ala Leu Gln Thr Arg Arg Arg Lys Lys Lys Arg Pro Gly Ser Thr Ser
    370                 375                 380

Pro
385


<210> SEQ ID NO 84
<211> LENGTH: 2413
<212> TYPE: PRT
<213> ORGANISM: Artificial Sequence
<220> FEATURE:
<223> OTHER INFORMATION: Synthetic

<400> SEQUENCE: 84

Met Gly Ile Ser Thr Val Ile Leu Glu Met Cys Leu Leu Trp Gly Gln
1               5                   10                  15

Val Leu Ser Thr Gly Gly Trp Ile Pro Arg Thr Thr Asp Tyr Ala Ser
            20                  25                  30

Leu Ile Pro Ser Glu Val Pro Leu Asp Pro Thr Val Ala Glu Gly Ser
        35                  40                  45

Pro Phe Pro Ser Glu Ser Thr Leu Glu Ser Thr Val Ala Glu Gly Ser
    50                  55                  60

Pro Ile Ser Leu Glu Ser Thr Leu Glu Ser Thr Val Ala Glu Gly Ser
65                  70                  75                  80

Leu Ile Pro Ser Glu Ser Thr Leu Glu Ser Thr Val Ala Glu Gly Ser
                85                  90                  95

Asp Ser Gly Leu Ala Leu Arg Leu Val Asn Gly Asp Gly Arg Cys Gln
            100                 105                 110

Gly Arg Val Glu Ile Leu Tyr Arg Gly Ser Trp Gly Thr Val Cys Asp
        115                 120                 125

Asp Ser Trp Asp Thr Asn Asp Ala Asn Val Val Cys Arg Gln Leu Gly
    130                 135                 140

Cys Gly Trp Ala Met Ser Ala Pro Gly Asn Ala Trp Phe Gly Gln Gly
145                 150                 155                 160

Ser Gly Pro Ile Ala Leu Asp Asp Val Arg Cys Ser Gly His Glu Ser
                165                 170                 175

Tyr Leu Trp Ser Cys Pro His Asn Gly Trp Leu Ser His Asn Cys Gly
            180                 185                 190

His Gly Glu Asp Ala Gly Val Ile Cys Ser Ala Ala Gln Pro Gln Ser
        195                 200                 205

Thr Leu Arg Pro Glu Ser Trp Pro Val Arg Ile Ser Pro Pro Val Pro
```

```
    210                 215                 220

Thr Glu Gly Ser Glu Ser Ser Leu Ala Leu Arg Leu Val Asn Gly Gly
225                 230                 235                 240

Asp Arg Cys Arg Gly Arg Val Glu Val Leu Tyr Arg Gly Ser Trp Gly
                245                 250                 255

Thr Val Cys Asp Asp Tyr Trp Asp Thr Asn Asp Ala Asn Val Val Cys
            260                 265                 270

Arg Gln Leu Gly Cys Gly Trp Ala Met Ser Ala Pro Gly Asn Ala Gln
        275                 280                 285

Phe Gly Gln Gly Ser Gly Pro Ile Val Leu Asp Asp Val Arg Cys Ser
    290                 295                 300

Gly His Glu Ser Tyr Leu Trp Ser Cys Pro His Asn Gly Trp Leu Thr
305                 310                 315                 320

His Asn Cys Gly His Ser Glu Asp Ala Gly Val Ile Cys Ser Ala Pro
                325                 330                 335

Gln Ser Arg Pro Thr Pro Ser Pro Asp Thr Trp Pro Thr Ser His Ala
            340                 345                 350

Ser Thr Ala Gly Pro Glu Ser Ser Leu Ala Leu Arg Leu Val Asn Gly
        355                 360                 365

Gly Asp Arg Cys Gln Gly Arg Val Glu Val Leu Tyr Arg Gly Ser Trp
    370                 375                 380

Gly Thr Val Cys Asp Asp Ser Trp Asp Thr Ser Asp Ala Asn Val Val
385                 390                 395                 400

Cys Arg Gln Leu Gly Cys Gly Trp Ala Thr Ser Ala Pro Gly Asn Ala
                405                 410                 415

Arg Phe Gly Gln Gly Ser Gly Pro Ile Val Leu Asp Asp Val Arg Cys
            420                 425                 430

Ser Gly Tyr Glu Ser Tyr Leu Trp Ser Cys Pro His Asn Gly Trp Leu
        435                 440                 445

Ser His Asn Cys Gln His Ser Glu Asp Ala Gly Val Ile Cys Ser Ala
    450                 455                 460

Ala His Ser Trp Ser Thr Pro Ser Pro Asp Thr Leu Pro Thr Ile Thr
465                 470                 475                 480

Leu Pro Ala Ser Thr Val Gly Ser Glu Ser Ser Leu Ala Leu Arg Leu
                485                 490                 495

Val Asn Gly Gly Asp Arg Cys Gln Gly Arg Val Glu Val Leu Tyr Arg
            500                 505                 510

Gly Ser Trp Gly Thr Val Cys Asp Asp Ser Trp Asp Thr Asn Asp Ala
        515                 520                 525

Asn Val Val Cys Arg Gln Leu Gly Cys Gly Trp Ala Met Leu Ala Pro
    530                 535                 540

Gly Asn Ala Arg Phe Gly Gln Gly Ser Gly Pro Ile Val Leu Asp Asp
545                 550                 555                 560

Val Arg Cys Ser Gly Asn Glu Ser Tyr Leu Trp Ser Cys Pro His Asn
                565                 570                 575

Gly Trp Leu Ser His Asn Cys Gly His Ser Glu Asp Ala Gly Val Ile
            580                 585                 590

Cys Ser Gly Pro Glu Ser Ser Leu Ala Leu Arg Leu Val Asn Gly Gly
        595                 600                 605

Asp Arg Cys Gln Gly Arg Val Glu Val Leu Tyr Arg Gly Ser Trp Gly
    610                 615                 620

Thr Val Cys Asp Asp Ser Trp Asp Thr Asn Asp Ala Asn Val Val Cys
625                 630                 635                 640
```

```
Arg Gln Leu Gly Cys Gly Trp Ala Thr Ser Ala Pro Gly Asn Ala Arg
                645                 650                 655

Phe Gly Gln Gly Ser Gly Pro Ile Val Leu Asp Asp Val Arg Cys Ser
            660                 665                 670

Gly His Glu Ser Tyr Leu Trp Ser Cys Pro Asn Asn Gly Trp Leu Ser
        675                 680                 685

His Asn Cys Gly His His Glu Asp Ala Gly Val Ile Cys Ser Ala Ala
    690                 695                 700

Gln Ser Arg Ser Thr Pro Arg Pro Asp Thr Leu Ser Thr Ile Thr Leu
705                 710                 715                 720

Pro Pro Ser Thr Val Gly Ser Glu Ser Ser Leu Thr Leu Arg Leu Val
                725                 730                 735

Asn Gly Ser Asp Arg Cys Gln Gly Arg Val Glu Val Leu Tyr Arg Gly
            740                 745                 750

Ser Trp Gly Thr Val Cys Asp Asp Ser Trp Asp Thr Asn Asp Ala Asn
        755                 760                 765

Val Val Cys Arg Gln Leu Gly Cys Gly Trp Ala Thr Ser Ala Pro Gly
    770                 775                 780

Asn Ala Arg Phe Gly Gln Gly Ser Gly Pro Ile Val Leu Asp Asp Val
785                 790                 795                 800

Arg Cys Ser Gly His Glu Ser Tyr Leu Trp Ser Cys Pro His Asn Gly
                805                 810                 815

Trp Leu Ser His Asn Cys Gly His His Glu Asp Ala Gly Val Ile Cys
            820                 825                 830

Ser Val Ser Gln Ser Arg Pro Thr Pro Ser Pro Asp Thr Trp Pro Thr
        835                 840                 845

Ser His Ala Ser Thr Ala Gly Pro Glu Ser Ser Leu Ala Leu Arg Leu
    850                 855                 860

Val Asn Gly Gly Asp Arg Cys Gln Gly Arg Val Glu Val Leu Tyr Arg
865                 870                 875                 880

Gly Ser Trp Gly Thr Val Cys Asp Asp Ser Trp Asp Thr Ser Asp Ala
                885                 890                 895

Asn Val Val Cys Arg Gln Leu Gly Cys Gly Trp Ala Thr Ser Ala Pro
            900                 905                 910

Gly Asn Ala Arg Phe Gly Gln Gly Ser Gly Pro Ile Val Leu Asp Asp
        915                 920                 925

Val Arg Cys Ser Gly Tyr Glu Ser Tyr Leu Trp Ser Cys Pro His Asn
    930                 935                 940

Gly Trp Leu Ser His Asn Cys Gln His Ser Glu Asp Ala Gly Val Ile
945                 950                 955                 960

Cys Ser Ala Ala His Ser Trp Ser Thr Pro Ser Pro Asp Thr Leu Pro
                965                 970                 975

Thr Ile Thr Leu Pro Ala Ser Thr Val Gly Ser Glu Ser Ser Leu Ala
            980                 985                 990

Leu Arg Leu Val Asn Gly Gly Asp  Arg Cys Gln Gly Arg  Val Glu Val
        995                 1000                 1005

Leu Tyr  Gln Gly Ser Trp Gly  Thr Val Cys Asp Asp  Ser Trp Asp
    1010                 1015                 1020

Thr Asn  Asp Ala Asn Val Val  Cys Arg Gln Leu Gly  Cys Gly Trp
    1025                 1030                 1035

Ala Met  Ser Ala Pro Gly Asn  Ala Arg Phe Gly Gln  Gly Ser Gly
    1040                 1045                 1050

Pro Ile  Val Leu Asp Asp Val  Arg Cys Ser Gly His  Glu Ser Tyr
    1055                 1060                 1065
```

-continued

```
Leu Trp Ser Cys Pro His Asn Gly Trp Leu Ser His Asn Cys Gly
    1070                1075                1080

His Ser Glu Asp Ala Gly Val Ile Cys Ser Ala Ser Gln Ser Arg
    1085                1090                1095

Pro Thr Pro Ser Pro Asp Thr Trp Pro Thr Ser His Ala Ser Thr
    1100                1105                1110

Ala Gly Ser Glu Ser Ser Leu Ala Leu Arg Leu Val Asn Gly Gly
    1115                1120                1125

Asp Arg Cys Gln Gly Arg Val Glu Val Leu Tyr Arg Gly Ser Trp
    1130                1135                1140

Gly Thr Val Cys Asp Asp Tyr Trp Asp Thr Asn Asp Ala Asn Val
    1145                1150                1155

Val Cys Arg Gln Leu Gly Cys Gly Trp Ala Met Ser Ala Pro Gly
    1160                1165                1170

Asn Ala Arg Phe Gly Gln Gly Ser Gly Pro Ile Val Leu Asp Asp
    1175                1180                1185

Val Arg Cys Ser Gly His Glu Ser Tyr Leu Trp Ser Cys Pro His
    1190                1195                1200

Asn Gly Trp Leu Ser His Asn Cys Gly His His Glu Asp Ala Gly
    1205                1210                1215

Val Ile Cys Ser Ala Ser Gln Ser Gln Pro Thr Pro Ser Pro Asp
    1220                1225                1230

Thr Trp Pro Thr Ser His Ala Ser Thr Ala Gly Ser Glu Ser Ser
    1235                1240                1245

Leu Ala Leu Arg Leu Val Asn Gly Gly Asp Arg Cys Gln Gly Arg
    1250                1255                1260

Val Glu Val Leu Tyr Arg Gly Ser Trp Gly Thr Val Cys Asp Asp
    1265                1270                1275

Tyr Trp Asp Thr Asn Asp Ala Asn Val Val Cys Arg Gln Leu Gly
    1280                1285                1290

Cys Gly Trp Ala Thr Ser Ala Pro Gly Asn Ala Arg Phe Gly Gln
    1295                1300                1305

Gly Ser Gly Pro Ile Val Leu Asp Asp Val Arg Cys Ser Gly His
    1310                1315                1320

Glu Ser Tyr Leu Trp Ser Cys Pro His Asn Gly Trp Leu Ser His
    1325                1330                1335

Asn Cys Gly His His Glu Asp Ala Gly Val Ile Cys Ser Ala Ser
    1340                1345                1350

Gln Ser Gln Pro Thr Pro Ser Pro Asp Thr Trp Pro Thr Ser His
    1355                1360                1365

Ala Ser Thr Ala Gly Ser Glu Ser Ser Leu Ala Leu Arg Leu Val
    1370                1375                1380

Asn Gly Gly Asp Arg Cys Gln Gly Arg Val Glu Val Leu Tyr Arg
    1385                1390                1395

Gly Ser Trp Gly Thr Val Cys Asp Asp Tyr Trp Asp Thr Asn Asp
    1400                1405                1410

Ala Asn Val Val Cys Arg Gln Leu Gly Cys Gly Trp Ala Thr Ser
    1415                1420                1425

Ala Pro Gly Asn Ala Arg Phe Gly Gln Gly Ser Gly Pro Ile Val
    1430                1435                1440

Leu Asp Asp Val Arg Cys Ser Gly His Glu Ser Tyr Leu Trp Ser
    1445                1450                1455

Cys Pro His Asn Gly Trp Leu Ser His Asn Cys Gly His His Glu
```

-continued

```
                1460                1465                1470
Asp Ala Gly Val Ile Cys Ser Ala Ser Gln Ser Gln Pro Thr Pro
    1475                1480                1485

Ser Pro Asp Thr Trp Pro Thr Ser Arg Ala Ser Thr Ala Gly Ser
    1490                1495                1500

Glu Ser Thr Leu Ala Leu Arg Leu Val Asn Gly Gly Asp Arg Cys
    1505                1510                1515

Arg Gly Arg Val Glu Val Leu Tyr Gln Gly Ser Trp Gly Thr Val
    1520                1525                1530

Cys Asp Asp Tyr Trp Asp Thr Asn Asp Ala Asn Val Val Cys Arg
    1535                1540                1545

Gln Leu Gly Cys Gly Trp Ala Met Ser Ala Pro Gly Asn Ala Gln
    1550                1555                1560

Phe Gly Gln Gly Ser Gly Pro Ile Val Leu Asp Asp Val Arg Cys
    1565                1570                1575

Ser Gly His Glu Ser Tyr Leu Trp Ser Cys Pro His Asn Gly Trp
    1580                1585                1590

Leu Ser His Asn Cys Gly His His Glu Asp Ala Gly Val Ile Cys
    1595                1600                1605

Ser Ala Ala Gln Ser Gln Ser Thr Pro Arg Pro Asp Thr Trp Leu
    1610                1615                1620

Thr Thr Asn Leu Pro Ala Leu Thr Val Gly Ser Glu Ser Ser Leu
    1625                1630                1635

Ala Leu Arg Leu Val Asn Gly Gly Asp Arg Cys Arg Gly Arg Val
    1640                1645                1650

Glu Val Leu Tyr Arg Gly Ser Trp Gly Thr Val Cys Asp Asp Ser
    1655                1660                1665

Trp Asp Thr Asn Asp Ala Asn Val Val Cys Arg Gln Leu Gly Cys
    1670                1675                1680

Gly Trp Ala Met Ser Ala Pro Gly Asn Ala Arg Phe Gly Gln Gly
    1685                1690                1695

Ser Gly Pro Ile Val Leu Asp Asp Val Arg Cys Ser Gly Asn Glu
    1700                1705                1710

Ser Tyr Leu Trp Ser Cys Pro His Lys Gly Trp Leu Thr His Asn
    1715                1720                1725

Cys Gly His His Glu Asp Ala Gly Val Ile Cys Ser Ala Thr Gln
    1730                1735                1740

Ile Asn Ser Thr Thr Thr Asp Trp Trp His Pro Thr Thr Thr Thr
    1745                1750                1755

Thr Ala Arg Pro Ser Ser Asn Cys Gly Gly Phe Leu Phe Tyr Ala
    1760                1765                1770

Ser Gly Thr Phe Ser Ser Pro Ser Tyr Pro Ala Tyr Tyr Pro Asn
    1775                1780                1785

Asn Ala Lys Cys Val Trp Glu Ile Glu Val Asn Ser Gly Tyr Arg
    1790                1795                1800

Ile Asn Leu Gly Phe Ser Asn Leu Lys Leu Glu Ala His His Asn
    1805                1810                1815

Cys Ser Phe Asp Tyr Val Glu Ile Phe Asp Gly Ser Leu Asn Ser
    1820                1825                1830

Ser Leu Leu Leu Gly Lys Ile Cys Asn Asp Thr Arg Gln Ile Phe
    1835                1840                1845

Thr Ser Ser Tyr Asn Arg Met Thr Ile His Phe Arg Ser Asp Ile
    1850                1855                1860
```

-continued

Ser Phe Gln Asn Thr Gly Phe Leu Ala Trp Tyr Asn Ser Phe Pro
1865 1870 1875

Ser Asp Ala Thr Leu Arg Leu Val Asn Leu Asn Ser Ser Tyr Gly
1880 1885 1890

Leu Cys Ala Gly Arg Val Glu Ile Tyr His Gly Gly Thr Trp Gly
1895 1900 1905

Thr Val Cys Asp Asp Ser Trp Thr Ile Gln Glu Ala Glu Val Val
1910 1915 1920

Cys Arg Gln Leu Gly Cys Gly Arg Ala Val Ser Ala Leu Gly Asn
1925 1930 1935

Ala Tyr Phe Gly Ser Gly Ser Gly Pro Ile Thr Leu Asp Asp Val
1940 1945 1950

Glu Cys Ser Gly Thr Glu Ser Thr Leu Trp Gln Cys Arg Asn Arg
1955 1960 1965

Gly Trp Phe Ser His Asn Cys Asn His Arg Glu Asp Ala Gly Val
1970 1975 1980

Ile Cys Ser Gly Asn His Leu Ser Thr Pro Ala Pro Phe Leu Asn
1985 1990 1995

Ile Thr Arg Pro Asn Thr Asp Tyr Ser Cys Gly Gly Phe Leu Ser
2000 2005 2010

Gln Pro Ser Gly Asp Phe Ser Ser Pro Phe Tyr Pro Gly Asn Tyr
2015 2020 2025

Pro Asn Asn Ala Lys Cys Val Trp Asp Ile Glu Val Gln Asn Asn
2030 2035 2040

Tyr Arg Val Thr Val Ile Phe Arg Asp Val Gln Leu Glu Gly Gly
2045 2050 2055

Cys Asn Tyr Asp Tyr Ile Glu Val Phe Asp Gly Pro Tyr Arg Ser
2060 2065 2070

Ser Pro Leu Ile Ala Arg Val Cys Asp Gly Ala Arg Gly Ser Phe
2075 2080 2085

Thr Ser Ser Ser Asn Phe Met Ser Ile Arg Phe Ile Ser Asp His
2090 2095 2100

Ser Ile Thr Arg Arg Gly Phe Arg Ala Glu Tyr Tyr Ser Ser Pro
2105 2110 2115

Ser Asn Asp Ser Thr Asn Leu Leu Cys Leu Pro Asn His Met Gln
2120 2125 2130

Ala Ser Val Ser Arg Ser Tyr Leu Gln Ser Leu Gly Phe Ser Ala
2135 2140 2145

Ser Asp Leu Val Ile Ser Thr Trp Asn Gly Tyr Tyr Glu Cys Arg
2150 2155 2160

Pro Gln Ile Thr Pro Asn Leu Val Ile Phe Thr Ile Pro Tyr Ser
2165 2170 2175

Gly Cys Gly Thr Phe Lys Gln Ala Asp Asn Asp Thr Ile Asp Tyr
2180 2185 2190

Ser Asn Phe Leu Thr Ala Ala Val Ser Gly Gly Ile Ile Lys Arg
2195 2200 2205

Arg Thr Asp Leu Arg Ile His Val Ser Cys Arg Met Leu Gln Asn
2210 2215 2220

Thr Trp Val Asp Thr Met Tyr Ile Ala Asn Asp Thr Ile His Val
2225 2230 2235

Ala Asn Asn Thr Ile Gln Val Glu Glu Val Gln Tyr Gly Asn Phe
2240 2245 2250

Asp Val Asn Ile Ser Phe Tyr Thr Ser Ser Ser Phe Leu Tyr Pro
2255 2260 2265

Val Thr Ser Arg Pro Tyr Tyr Val Asp Leu Asn Gln Asp Leu Tyr
2270 2275 2280

Val Gln Ala Glu Ile Leu His Ser Asp Ala Val Leu Thr Leu Phe
2285 2290 2295

Val Asp Thr Cys Val Ala Ser Pro Tyr Ser Asn Asp Phe Thr Ser
2300 2305 2310

Leu Thr Tyr Asp Leu Ile Arg Ser Gly Cys Val Arg Asp Asp Thr
2315 2320 2325

Tyr Gly Pro Tyr Ser Ser Pro Ser Leu Arg Ile Ala Arg Phe Arg
2330 2335 2340

Phe Arg Ala Phe His Phe Leu Asn Arg Phe Pro Ser Val Tyr Leu
2345 2350 2355

Arg Cys Lys Met Val Val Cys Arg Ala Tyr Asp Pro Ser Ser Arg
2360 2365 2370

Cys Tyr Arg Gly Cys Val Leu Arg Ser Lys Arg Asp Val Gly Ser
2375 2380 2385

Tyr Gln Glu Lys Val Asp Val Val Leu Gly Pro Ile Gln Leu Gln
2390 2395 2400

Thr Pro Pro Arg Arg Glu Glu Glu Pro Arg
2405 2410

<210> SEQ ID NO 85
<211> LENGTH: 461
<212> TYPE: PRT
<213> ORGANISM: Artificial Sequence
<220> FEATURE:
<223> OTHER INFORMATION: Synthetic

<400> SEQUENCE: 85

Met Pro Pro Ser Gly Pro Arg Gly Thr Leu Leu Leu Leu Pro Leu Leu
1 5 10 15

Leu Leu Leu Leu Leu Arg Ala Val Leu Ala Val Pro Leu Glu Arg Gly
20 25 30

Ala Pro Asn Lys Glu Glu Thr Pro Ala Thr Glu Ser Pro Asp Thr Gly
35 40 45

Leu Tyr Tyr His Arg Tyr Leu Gln Glu Val Ile Asp Val Leu Glu Thr
50 55 60

Asp Gly His Phe Arg Glu Lys Leu Gln Ala Ala Asn Ala Glu Asp Ile
65 70 75 80

Lys Ser Gly Lys Leu Ser Arg Glu Leu Asp Phe Val Ser His His Val
85 90 95

Arg Thr Lys Leu Asp Glu Leu Lys Arg Gln Glu Val Ser Arg Leu Arg
100 105 110

Met Leu Leu Lys Ala Lys Met Asp Ala Glu Gln Asp Pro Asn Val Gln
115 120 125

Val Asp His Leu Asn Leu Leu Lys Gln Phe Glu His Leu Asp Pro Gln
130 135 140

Asn Gln His Thr Phe Glu Ala Arg Asp Leu Glu Leu Leu Ile Gln Thr
145 150 155 160

Ala Thr Arg Asp Leu Ala Gln Tyr Asp Ala Ala His His Glu Glu Phe
165 170 175

Lys Arg Tyr Glu Met Leu Lys Glu His Glu Arg Arg Arg Tyr Leu Glu
180 185 190

Ser Leu Gly Glu Glu Gln Arg Lys Glu Ala Glu Arg Lys Leu Glu Glu
195 200 205

-continued

Gln Gln Arg Arg His Arg Glu His Pro Lys Val Asn Val Pro Gly Ser
    210                 215                 220

Gln Ala Gln Leu Lys Glu Val Trp Glu Glu Leu Asp Gly Leu Asp Pro
225                 230                 235                 240

Asn Arg Phe Asn Pro Lys Thr Phe Phe Ile Leu His Asp Ile Asn Ser
                245                 250                 255

Asp Gly Val Leu Asp Glu Gln Glu Leu Glu Ala Leu Phe Thr Lys Glu
            260                 265                 270

Leu Glu Lys Val Tyr Asp Pro Lys Asn Glu Glu Asp Asp Met Arg Glu
        275                 280                 285

Met Glu Glu Glu Arg Leu Arg Met Arg Glu His Val Met Lys Asn Val
    290                 295                 300

Asp Thr Asn Gln Asp Arg Leu Val Thr Leu Glu Glu Phe Leu Ala Ser
305                 310                 315                 320

Thr Gln Arg Lys Glu Phe Gly Asp Thr Gly Glu Gly Trp Glu Thr Val
                325                 330                 335

Glu Met His Pro Ala Tyr Thr Glu Glu Glu Leu Arg Arg Phe Glu Glu
            340                 345                 350

Glu Leu Ala Ala Arg Glu Ala Glu Leu Asn Ala Lys Ala Gln Arg Leu
        355                 360                 365

Ser Gln Glu Thr Glu Ala Leu Gly Arg Ser Gln Gly Arg Leu Glu Ala
    370                 375                 380

Gln Lys Arg Glu Leu Gln Gln Ala Val Leu His Met Glu Gln Arg Lys
385                 390                 395                 400

Gln Gln Gln Gln Gln Gln Gln Gly His Lys Ala Pro Ala Ala His Pro
                405                 410                 415

Glu Gly Gln Leu Lys Phe His Pro Asp Thr Asp Asp Val Pro Val Pro
            420                 425                 430

Ala Pro Ala Gly Asp Gln Lys Glu Val Asp Thr Ser Glu Lys Lys Leu
        435                 440                 445

Leu Glu Arg Leu Pro Glu Val Glu Val Pro Gln His Leu
    450                 455                 460

<210> SEQ ID NO 86
<211> LENGTH: 318
<212> TYPE: PRT
<213> ORGANISM: Artificial Sequence
<220> FEATURE:
<223> OTHER INFORMATION: Synthetic

<400> SEQUENCE: 86

Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
        35                  40                  45

Lys Asn Tyr Gly Arg Tyr Tyr Ile Ala Ala Ser Tyr Val Lys Tyr Leu
    50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

Gly Gly Ser Val Asp Leu Arg Arg Ser Asp Tyr Ala Lys Val Ala Lys
            100                 105                 110

Ile Phe Tyr Asn Leu Ser Ile Gln Ser Phe Asp Asp Gly Asp Tyr Phe

```
        115                 120                 125

Pro Val Trp Gly Thr Cys Leu Gly Phe Glu Glu Leu Ser Leu Leu Ile
    130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
            180                 185                 190

Asn Phe His Lys Trp Ser Leu Ser Val Lys Asn Phe Thr Met Asn Glu
        195                 200                 205

Lys Leu Lys Lys Phe Phe Asn Val Leu Thr Thr Asn Thr Asp Gly Lys
    210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
                245                 250                 255

Gly Ile Ser His Ala Pro Asn Ala Val Lys Thr Ala Phe Tyr Leu Ala
            260                 265                 270

Glu Phe Phe Val Asn Glu Ala Arg Lys Asn Asn His His Phe Lys Ser
        275                 280                 285

Glu Ser Glu Glu Glu Lys Ala Leu Ile Tyr Gln Phe Ser Pro Ile Tyr
    290                 295                 300

Thr Gly Asn Ile Ser Ser Phe Gln Gln Cys Tyr Ile Phe Asp
305                 310                 315


<210> SEQ ID NO 87
<211> LENGTH: 166
<212> TYPE: PRT
<213> ORGANISM: Artificial Sequence
<220> FEATURE:
<223> OTHER INFORMATION: Synthetic

<400> SEQUENCE: 87

Met Met Leu His Ser Ala Leu Gly Leu Cys Leu Leu Leu Val Thr Val
1               5                   10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
        115                 120                 125

Arg Ala Asp Ile Ala Gly Arg Tyr Ser Asn Arg Leu Tyr Thr Tyr Glu
    130                 135                 140

Pro Arg Asp Leu Pro Leu Leu Ile Glu Asn Met Lys Lys Ala Leu Arg
145                 150                 155                 160

Leu Ile Gln Ser Glu Leu
                165
```

<210> SEQ ID NO 88
<211> LENGTH: 663
<212> TYPE: PRT
<213> ORGANISM: Artificial Sequence
<220> FEATURE:
<223> OTHER INFORMATION: Synthetic

<400> SEQUENCE: 88

```
Met Ser Ala Arg Leu Pro Val Leu Ser Pro Pro Arg Trp Pro Arg Leu
1               5                   10                  15

Leu Leu Leu Ser Leu Leu Leu Leu Gly Ala Val Pro Gly Pro Arg Arg
            20                  25                  30

Ser Gly Ala Phe Tyr Leu Pro Gly Leu Ala Pro Val Asn Phe Cys Asp
        35                  40                  45

Glu Glu Lys Lys Ser Asp Glu Cys Lys Ala Glu Ile Glu Leu Phe Val
    50                  55                  60

Asn Arg Leu Asp Ser Val Glu Ser Val Leu Pro Tyr Glu Tyr Thr Ala
65                  70                  75                  80

Phe Asp Phe Cys Gln Ala Ser Glu Gly Lys Arg Pro Ser Glu Asn Leu
                85                  90                  95

Gly Gln Val Leu Phe Gly Glu Arg Ile Glu Pro Ser Pro Tyr Lys Phe
            100                 105                 110

Thr Phe Asn Lys Lys Glu Thr Cys Lys Leu Val Cys Thr Lys Thr Tyr
        115                 120                 125

His Thr Glu Lys Ala Glu Asp Lys Gln Lys Leu Glu Phe Leu Lys Lys
    130                 135                 140

Ser Met Leu Leu Asn Tyr Gln His His Trp Ile Val Asp Asn Met Pro
145                 150                 155                 160

Val Thr Trp Cys Tyr Asp Val Glu Asp Gly Gln Arg Phe Cys Asn Pro
                165                 170                 175

Gly Phe Pro Ile Gly Cys Tyr Ile Thr Asp Lys Gly His Ala Lys Asp
            180                 185                 190

Ala Cys Val Ile Ser Ser Asp Phe His Glu Arg Asp Thr Phe Tyr Ile
        195                 200                 205

Phe Asn His Val Asp Ile Lys Ile Tyr Tyr His Val Val Glu Thr Gly
    210                 215                 220

Ser Met Gly Ala Arg Leu Val Ala Ala Lys Leu Glu Pro Lys Ser Phe
225                 230                 235                 240

Lys His Thr His Ile Asp Lys Pro Asp Cys Ser Gly Pro Pro Met Asp
                245                 250                 255

Ile Ser Asn Lys Ala Ser Gly Glu Ile Lys Ile Ala Tyr Thr Tyr Ser
            260                 265                 270

Val Ser Phe Glu Glu Asp Asp Lys Ile Arg Trp Ala Ser Arg Trp Asp
        275                 280                 285

Tyr Ile Leu Glu Ser Met Pro His Thr His Ile Gln Trp Phe Ser Ile
    290                 295                 300

Met Asn Ser Leu Val Ile Val Leu Phe Leu Ser Gly Met Val Ala Met
305                 310                 315                 320

Ile Met Leu Arg Thr Leu His Lys Asp Ile Ala Arg Tyr Asn Gln Met
                325                 330                 335

Asp Ser Thr Glu Asp Ala Gln Glu Glu Phe Gly Trp Lys Leu Val His
            340                 345                 350

Gly Asp Ile Phe Arg Pro Pro Arg Lys Gly Met Leu Leu Ser Val Phe
        355                 360                 365
```

-continued

```
Leu Gly Ser Gly Thr Gln Ile Leu Ile Met Thr Phe Val Thr Leu Phe
    370                 375                 380

Phe Ala Cys Leu Gly Phe Leu Ser Pro Ala Asn Arg Gly Ala Leu Met
385                 390                 395                 400

Thr Cys Ala Val Val Leu Trp Val Leu Leu Gly Thr Pro Ala Gly Tyr
                405                 410                 415

Val Ala Ala Arg Phe Tyr Lys Ser Phe Gly Gly Glu Lys Trp Lys Thr
            420                 425                 430

Asn Val Leu Leu Thr Ser Phe Leu Cys Pro Gly Ile Val Phe Ala Asp
        435                 440                 445

Phe Phe Ile Met Asn Leu Ile Leu Trp Gly Glu Gly Ser Ser Ala Ala
    450                 455                 460

Ile Pro Phe Gly Thr Leu Val Ala Ile Leu Ala Leu Trp Phe Cys Ile
465                 470                 475                 480

Ser Val Pro Leu Thr Phe Ile Gly Ala Tyr Phe Gly Phe Lys Lys Asn
                485                 490                 495

Ala Ile Glu His Pro Val Arg Thr Asn Gln Ile Pro Arg Gln Ile Pro
            500                 505                 510

Glu Gln Ser Phe Tyr Thr Lys Pro Leu Pro Gly Ile Ile Met Gly Gly
        515                 520                 525

Ile Leu Pro Phe Gly Cys Ile Phe Ile Gln Leu Phe Phe Ile Leu Asn
    530                 535                 540

Ser Ile Trp Ser His Gln Met Tyr Tyr Met Phe Gly Phe Leu Phe Leu
545                 550                 555                 560

Val Phe Ile Ile Leu Val Ile Thr Cys Ser Glu Ala Thr Ile Leu Leu
                565                 570                 575

Cys Tyr Phe His Leu Cys Ala Glu Asp Tyr His Trp Gln Trp Arg Ser
            580                 585                 590

Phe Leu Thr Ser Gly Phe Thr Ala Val Tyr Phe Leu Ile Tyr Ala Val
        595                 600                 605

His Tyr Phe Phe Ser Lys Leu Gln Ile Thr Gly Thr Ala Ser Thr Ile
    610                 615                 620

Leu Tyr Phe Gly Tyr Thr Met Ile Met Val Leu Ile Phe Phe Leu Phe
625                 630                 635                 640

Thr Gly Thr Ile Gly Phe Phe Ala Cys Phe Trp Phe Val Thr Lys Ile
                645                 650                 655

Tyr Ser Val Val Lys Val Asp
            660
```

<210> SEQ ID NO 89
<211> LENGTH: 635
<212> TYPE: PRT
<213> ORGANISM: Artificial Sequence
<220> FEATURE:
<223> OTHER INFORMATION: Synthetic

<400> SEQUENCE: 89

```
Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
```

-continued

```
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
        275                 280                 285

Ile Ile Ser Arg Ile Lys Ser Tyr Ser Phe Pro Lys Pro Gly His Arg
    290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
            340                 345                 350

Ala Asp Pro Glu Glu Ile Arg Pro Lys Glu Val Tyr Leu Asp Arg Lys
        355                 360                 365

Leu Leu Thr Leu Glu Asp Lys Glu Leu Gly Ser Gly Asn Phe Gly Thr
    370                 375                 380

Val Lys Lys Gly Tyr Tyr Gln Met Lys Lys Val Val Lys Thr Val Ala
385                 390                 395                 400

Val Lys Ile Leu Lys Asn Glu Ala Asn Asp Pro Ala Leu Lys Asp Glu
                405                 410                 415

Leu Leu Ala Glu Ala Asn Val Met Gln Gln Leu Asp Asn Pro Tyr Ile
            420                 425                 430

Val Arg Met Ile Gly Ile Cys Glu Ala Glu Ser Trp Met Leu Val Met
        435                 440                 445

Glu Met Ala Glu Leu Gly Pro Leu Asn Lys Tyr Leu Gln Gln Asn Arg
    450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                485                 490                 495
```

```
Ala Arg Asn Val Leu Leu Val Thr Gln His Tyr Ala Lys Ile Ser Asp
            500                 505                 510

Phe Gly Leu Ser Lys Ala Leu Arg Ala Asp Glu Asn Tyr Tyr Lys Ala
        515                 520                 525

Gln Thr His Gly Lys Trp Pro Val Lys Trp Tyr Ala Pro Glu Cys Ile
    530                 535                 540

Asn Tyr Tyr Lys Phe Ser Ser Lys Ser Asp Val Trp Ser Phe Gly Val
545                 550                 555                 560

Leu Met Trp Glu Ala Phe Ser Tyr Gly Gln Lys Pro Tyr Arg Gly Met
                565                 570                 575

Lys Gly Ser Glu Val Thr Ala Met Leu Glu Lys Gly Glu Arg Met Gly
            580                 585                 590

Cys Pro Ala Gly Cys Pro Arg Glu Met Tyr Asp Leu Met Asn Leu Cys
        595                 600                 605

Trp Thr Tyr Asp Val Glu Asn Arg Pro Gly Phe Ala Ala Val Glu Leu
    610                 615                 620

Arg Leu Arg Asn Tyr Tyr Tyr Asp Val Val Asn
625                 630                 635


<210> SEQ ID NO 90
<211> LENGTH: 217
<212> TYPE: PRT
<213> ORGANISM: Artificial Sequence
<220> FEATURE:
<223> OTHER INFORMATION: Synthetic

<400> SEQUENCE: 90

Met Ala Tyr Pro Gly Tyr Gly Gly Gly Phe Gly Asn Phe Ser Ile Gln
1               5                   10                  15

Val Pro Gly Met Gln Met Gly Gln Pro Val Pro Glu Thr Gly Pro Ala
            20                  25                  30

Ile Leu Leu Asp Gly Tyr Ser Gly Pro Ala Tyr Ser Asp Thr Tyr Ser
        35                  40                  45

Ser Ala Gly Asp Ser Val Tyr Thr Tyr Phe Ser Ala Val Ala Gly Gln
    50                  55                  60

Asp Gly Glu Val Asp Ala Glu Glu Leu Gln Arg Cys Leu Thr Gln Ser
65                  70                  75                  80

Gly Ile Asn Gly Thr Tyr Ser Pro Phe Ser Leu Glu Thr Cys Arg Ile
                85                  90                  95

Met Ile Ala Met Leu Asp Arg Asp His Thr Gly Lys Met Gly Phe Asn
            100                 105                 110

Ala Phe Lys Glu Leu Trp Ala Ala Leu Asn Ala Trp Lys Glu Asn Phe
        115                 120                 125

Met Thr Val Asp Gln Asp Gly Ser Gly Thr Val Glu His His Glu Leu
    130                 135                 140

Arg Gln Ala Ile Gly Leu Met Gly Tyr Arg Leu Ser Pro Gln Thr Leu
145                 150                 155                 160

Thr Thr Ile Val Lys Arg Tyr Ser Lys Asn Gly Arg Ile Phe Phe Asp
                165                 170                 175

Asp Tyr Val Ala Cys Cys Val Lys Leu Arg Ala Leu Thr Asp Phe Phe
            180                 185                 190

Arg Lys Arg Asp His Leu Gln Gln Gly Ser Ala Asn Phe Ile Tyr Asp
        195                 200                 205

Asp Phe Leu Gln Gly Thr Met Ala Ile
    210                 215
```

<210> SEQ ID NO 91
<211> LENGTH: 1268
<212> TYPE: PRT
<213> ORGANISM: Artificial Sequence
<220> FEATURE:
<223> OTHER INFORMATION: Synthetic

<400> SEQUENCE: 91

```
Met Ser Ser Val Ala Val Leu Thr Gln Glu Ser Phe Ala Glu His Arg
1               5                   10                  15

Ser Gly Leu Val Pro Gln Gln Ile Lys Val Ala Thr Leu Asn Ser Glu
            20                  25                  30

Glu Glu Ser Asp Pro Pro Thr Tyr Lys Asp Ala Phe Pro Pro Leu Pro
        35                  40                  45

Glu Lys Ala Ala Cys Leu Glu Ser Ala Gln Glu Pro Ser Gly Ala Trp
    50                  55                  60

Gly Asn Lys Ile Arg Pro Ile Lys Ala Ser Val Ile Thr Gln Val Phe
65                  70                  75                  80

His Val Pro Leu Glu Glu Arg Lys Tyr Lys Asp Met Asn Gln Phe Gly
                85                  90                  95

Glu Gly Glu Gln Ala Lys Ile Cys Leu Glu Ile Met Gln Arg Thr Gly
            100                 105                 110

Ala His Leu Glu Leu Ser Leu Ala Lys Asp Gln Gly Leu Ser Ile Met
        115                 120                 125

Val Ser Gly Lys Leu Asp Ala Val Met Lys Ala Arg Lys Asp Ile Val
    130                 135                 140

Ala Arg Leu Gln Thr Gln Ala Ser Ala Thr Val Ala Ile Pro Lys Glu
145                 150                 155                 160

His His Arg Phe Val Ile Gly Lys Asn Gly Glu Lys Leu Gln Asp Leu
                165                 170                 175

Glu Leu Lys Thr Ala Thr Lys Ile Gln Ile Pro Arg Pro Asp Asp Pro
            180                 185                 190

Ser Asn Gln Ile Lys Ile Thr Gly Thr Lys Glu Gly Ile Glu Lys Ala
        195                 200                 205

Arg His Glu Val Leu Leu Ile Ser Ala Glu Gln Asp Lys Arg Ala Val
    210                 215                 220

Glu Arg Leu Glu Val Glu Lys Ala Phe His Pro Phe Ile Ala Gly Pro
225                 230                 235                 240

Tyr Asn Arg Leu Val Gly Glu Ile Met Gln Glu Thr Gly Thr Arg Ile
                245                 250                 255

Asn Ile Pro Pro Pro Ser Val Asn Arg Thr Glu Ile Val Phe Thr Gly
            260                 265                 270

Glu Lys Glu Gln Leu Ala Gln Ala Val Ala Arg Ile Lys Lys Ile Tyr
        275                 280                 285

Glu Glu Lys Lys Lys Lys Thr Thr Thr Ile Ala Val Glu Val Lys Lys
    290                 295                 300

Ser Gln His Lys Tyr Val Ile Gly Pro Lys Gly Asn Ser Leu Gln Glu
305                 310                 315                 320

Ile Leu Glu Arg Thr Gly Val Ser Val Glu Ile Pro Pro Ser Asp Ser
                325                 330                 335

Ile Ser Glu Thr Val Ile Leu Arg Gly Glu Pro Glu Lys Leu Gly Gln
            340                 345                 350

Ala Leu Thr Glu Val Tyr Ala Lys Ala Asn Ser Phe Thr Val Ser Ser
        355                 360                 365

Val Ala Ala Pro Ser Trp Leu His Arg Phe Ile Ile Gly Lys Lys Gly
    370                 375                 380
```

Gln Asn Leu Ala Lys Ile Thr Gln Gln Met Pro Lys Val His Ile Glu
385 390 395 400

Phe Thr Glu Gly Glu Asp Lys Ile Thr Leu Glu Gly Pro Thr Glu Asp
405 410 415

Val Asn Val Ala Gln Glu Gln Ile Glu Gly Met Val Lys Asp Leu Ile
420 425 430

Asn Arg Met Asp Tyr Val Glu Ile Asn Ile Asp His Lys Phe His Arg
435 440 445

His Leu Ile Gly Lys Ser Gly Ala Asn Ile Asn Arg Ile Lys Asp Gln
450 455 460

Tyr Lys Val Ser Val Arg Ile Pro Pro Asp Ser Glu Lys Ser Asn Leu
465 470 475 480

Ile Arg Ile Glu Gly Asp Pro Gln Gly Val Gln Gln Ala Lys Arg Glu
485 490 495

Leu Leu Glu Leu Ala Ser Arg Met Glu Asn Glu Arg Thr Lys Asp Leu
500 505 510

Ile Ile Glu Gln Arg Phe His Arg Thr Ile Ile Gly Gln Lys Gly Glu
515 520 525

Arg Ile Arg Glu Ile Arg Asp Lys Phe Pro Glu Val Ile Ile Asn Phe
530 535 540

Pro Asp Pro Ala Gln Lys Ser Asp Ile Val Gln Leu Arg Gly Pro Lys
545 550 555 560

Asn Glu Val Glu Lys Cys Thr Lys Tyr Met Gln Lys Met Val Ala Asp
565 570 575

Leu Val Glu Asn Ser Tyr Ser Ile Ser Val Pro Ile Phe Lys Gln Phe
580 585 590

His Lys Asn Ile Ile Gly Lys Gly Gly Ala Asn Ile Lys Lys Ile Arg
595 600 605

Glu Glu Ser Asn Thr Lys Ile Asp Leu Pro Ala Glu Asn Ser Asn Ser
610 615 620

Glu Thr Ile Ile Ile Thr Gly Lys Arg Ala Asn Cys Glu Ala Ala Arg
625 630 635 640

Ser Arg Ile Leu Ser Ile Gln Lys Asp Leu Ala Asn Ile Ala Glu Val
645 650 655

Glu Val Ser Ile Pro Ala Lys Leu His Asn Ser Leu Ile Gly Thr Lys
660 665 670

Gly Arg Leu Ile Arg Ser Ile Met Glu Glu Cys Gly Gly Val His Ile
675 680 685

His Phe Pro Val Glu Gly Ser Gly Ser Asp Thr Val Val Ile Arg Gly
690 695 700

Pro Ser Ser Asp Val Glu Lys Ala Lys Lys Gln Leu Leu His Leu Ala
705 710 715 720

Glu Glu Lys Gln Thr Lys Ser Phe Thr Val Asp Ile Arg Ala Lys Pro
725 730 735

Glu Tyr His Lys Phe Leu Ile Gly Lys Gly Gly Gly Lys Ile Arg Lys
740 745 750

Val Arg Asp Ser Thr Gly Ala Arg Val Ile Phe Pro Ala Ala Glu Asp
755 760 765

Lys Asp Gln Asp Leu Ile Thr Ile Ile Gly Lys Glu Asp Ala Val Arg
770 775 780

Glu Ala Gln Lys Glu Leu Glu Ala Leu Ile Gln Asn Leu Asp Asn Val
785 790 795 800

Val Glu Asp Ser Met Leu Val Asp Pro Lys His His Arg His Phe Val

```
                805                 810                 815

Ile Arg Arg Gly Gln Val Leu Arg Glu Ile Ala Glu Glu Tyr Gly Gly
            820                 825                 830

Val Met Val Ser Phe Pro Arg Ser Gly Thr Gln Ser Asp Lys Val Thr
        835                 840                 845

Leu Lys Gly Ala Lys Asp Cys Val Glu Ala Ala Lys Lys Arg Ile Gln
    850                 855                 860

Glu Ile Ile Glu Asp Leu Glu Ala Gln Val Thr Leu Glu Cys Ala Ile
865                 870                 875                 880

Pro Gln Lys Phe His Arg Ser Val Met Gly Pro Lys Gly Ser Arg Ile
                885                 890                 895

Gln Gln Ile Thr Arg Asp Phe Ser Val Gln Ile Lys Phe Pro Asp Arg
            900                 905                 910

Glu Glu Asn Ala Val His Ser Thr Glu Pro Val Val Gln Glu Asn Gly
        915                 920                 925

Asp Glu Ala Gly Glu Gly Arg Glu Ala Lys Asp Cys Asp Pro Gly Ser
    930                 935                 940

Pro Arg Arg Cys Asp Ile Ile Ile Ile Ser Gly Arg Lys Glu Lys Cys
945                 950                 955                 960

Glu Ala Ala Lys Glu Ala Leu Glu Ala Leu Val Pro Val Thr Ile Glu
                965                 970                 975

Val Glu Val Pro Phe Asp Leu His Arg Tyr Val Ile Gly Gln Lys Gly
            980                 985                 990

Ser Gly Ile Arg Lys Met Met Asp  Glu Phe Glu Val Asn  Ile His Val
        995                 1000                 1005

Pro Ala  Pro Glu Leu Gln Ser  Asp Ile Ile Ala Ile  Thr Gly Leu
    1010                 1015                 1020

Ala Ala  Asn Leu Asp Arg Ala  Lys Ala Gly Leu Leu  Glu Arg Val
    1025                 1030                 1035

Lys Glu  Leu Gln Ala Glu Gln  Glu Asp Arg Ala Leu  Arg Ser Phe
    1040                 1045                 1050

Lys Leu  Ser Val Thr Val Asp  Pro Lys Tyr His Pro  Lys Ile Ile
    1055                 1060                 1065

Gly Arg  Lys Gly Ala Val Ile  Thr Gln Ile Arg Leu  Glu His Asp
    1070                 1075                 1080

Val Asn  Ile Gln Phe Pro Asp  Lys Asp Asp Gly Asn  Gln Pro Gln
    1085                 1090                 1095

Asp Gln  Ile Thr Ile Thr Gly  Tyr Glu Lys Asn Thr  Glu Ala Ala
    1100                 1105                 1110

Arg Asp  Ala Ile Leu Arg Ile  Val Gly Glu Leu Glu  Gln Met Val
    1115                 1120                 1125

Ser Glu  Asp Val Pro Leu Asp  His Arg Val His Ala  Arg Ile Ile
    1130                 1135                 1140

Gly Ala  Arg Gly Lys Ala Ile  Arg Lys Ile Met Asp  Glu Phe Lys
    1145                 1150                 1155

Val Asp  Ile Arg Phe Pro Gln  Ser Gly Ala Pro Asp  Pro Asn Cys
    1160                 1165                 1170

Val Thr  Val Thr Gly Leu Pro  Glu Asn Val Glu Glu  Ala Ile Asp
    1175                 1180                 1185

His Ile  Leu Asn Leu Glu Glu  Glu Tyr Leu Ala Asp  Val Val Asp
    1190                 1195                 1200

Ser Glu  Ala Leu Gln Val Tyr  Met Lys Pro Pro Ala  His Glu Glu
    1205                 1210                 1215
```

Ala Lys Ala Pro Ser Arg Gly Phe Val Val Arg Asp Ala Pro Trp
1220 1225 1230

Thr Ala Ser Ser Ser Glu Lys Ala Pro Asp Met Ser Ser Ser Glu
1235 1240 1245

Glu Phe Pro Ser Phe Gly Ala Gln Val Ala Pro Lys Thr Leu Pro
1250 1255 1260

Trp Gly Pro Lys Arg
1265

<210> SEQ ID NO 92
<211> LENGTH: 282
<212> TYPE: PRT
<213> ORGANISM: Artificial Sequence
<220> FEATURE:
<223> OTHER INFORMATION: Synthetic

<400> SEQUENCE: 92

Met Leu Pro Leu Leu Arg Cys Val Pro Arg Val Leu Gly Ser Ser Val
1 5 10 15

Ala Gly Leu Arg Ala Ala Ala Pro Ala Ser Pro Phe Arg Gln Leu Leu
20 25 30

Gln Pro Ala Pro Arg Leu Cys Thr Arg Pro Phe Gly Leu Leu Ser Val
35 40 45

Arg Ala Gly Ser Glu Arg Arg Pro Gly Leu Leu Arg Pro Arg Gly Pro
50 55 60

Cys Ala Cys Gly Cys Gly Cys Gly Ser Leu His Thr Asp Gly Asp Lys
65 70 75 80

Ala Phe Val Asp Phe Leu Ser Asp Glu Ile Lys Glu Glu Arg Lys Ile
85 90 95

Gln Lys His Lys Thr Leu Pro Lys Met Ser Gly Gly Trp Glu Leu Glu
100 105 110

Leu Asn Gly Thr Glu Ala Lys Leu Val Arg Lys Val Ala Gly Glu Lys
115 120 125

Ile Thr Val Thr Phe Asn Ile Asn Asn Ser Ile Pro Pro Thr Phe Asp
130 135 140

Gly Glu Glu Glu Pro Ser Gln Gly Gln Lys Val Glu Glu Gln Glu Pro
145 150 155 160

Glu Leu Thr Ser Thr Pro Asn Phe Val Val Glu Val Ile Lys Asn Asp
165 170 175

Asp Gly Lys Lys Ala Leu Val Leu Asp Cys His Tyr Pro Glu Asp Glu
180 185 190

Val Gly Gln Glu Asp Glu Ala Glu Ser Asp Ile Phe Ser Ile Arg Glu
195 200 205

Val Ser Phe Gln Ser Thr Gly Glu Ser Glu Trp Lys Asp Thr Asn Tyr
210 215 220

Thr Leu Asn Thr Asp Ser Leu Asp Trp Ala Leu Tyr Asp His Leu Met
225 230 235 240

Asp Phe Leu Ala Asp Arg Gly Val Asp Asn Thr Phe Ala Asp Glu Leu
245 250 255

Val Glu Leu Ser Thr Ala Leu Glu His Gln Glu Tyr Ile Thr Phe Leu
260 265 270

Glu Asp Leu Lys Ser Phe Val Lys Ser Gln
275 280

<210> SEQ ID NO 93
<211> LENGTH: 241
<212> TYPE: PRT

-continued

```
<213> ORGANISM: Artificial Sequence
<220> FEATURE:
<223> OTHER INFORMATION: Synthetic

<400> SEQUENCE: 93

Met Ala Glu Glu Gln Pro Gln Val Glu Leu Phe Val Lys Ala Gly Ser
1               5                   10                  15

Asp Gly Ala Lys Ile Gly Asn Cys Pro Phe Ser Gln Arg Leu Phe Met
            20                  25                  30

Val Leu Trp Leu Lys Gly Val Thr Phe Asn Val Thr Thr Val Asp Thr
        35                  40                  45

Lys Arg Arg Thr Glu Thr Val Gln Lys Leu Cys Pro Gly Gly Gln Leu
    50                  55                  60

Pro Phe Leu Leu Tyr Gly Thr Glu Val His Thr Asp Thr Asn Lys Ile
65                  70                  75                  80

Glu Glu Phe Leu Glu Ala Val Leu Cys Pro Pro Arg Tyr Pro Lys Leu
                85                  90                  95

Ala Ala Leu Asn Pro Glu Ser Asn Thr Ala Gly Leu Asp Ile Phe Ala
            100                 105                 110

Lys Phe Ser Ala Tyr Ile Lys Asn Ser Asn Pro Ala Leu Asn Asp Asn
        115                 120                 125

Leu Glu Lys Gly Leu Leu Lys Ala Leu Lys Val Leu Asp Asn Tyr Leu
    130                 135                 140

Thr Ser Pro Leu Pro Glu Glu Val Asp Glu Thr Ser Ala Glu Asp Glu
145                 150                 155                 160

Gly Val Ser Gln Arg Lys Phe Leu Asp Gly Asn Glu Leu Thr Leu Ala
                165                 170                 175

Asp Cys Asn Leu Leu Pro Lys Leu His Ile Val Gln Val Val Cys Lys
            180                 185                 190

Lys Tyr Arg Gly Phe Thr Ile Pro Glu Ala Phe Arg Gly Val His Arg
        195                 200                 205

Tyr Leu Ser Asn Ala Tyr Ala Arg Glu Glu Phe Ala Ser Thr Cys Pro
    210                 215                 220

Asp Asp Glu Glu Ile Glu Leu Ala Tyr Glu Gln Val Ala Lys Ala Leu
225                 230                 235                 240

Lys
```